US012448395B2

(12) United States Patent
Kumar et al.

(10) Patent No.: US 12,448,395 B2
(45) Date of Patent: Oct. 21, 2025

(54) SUBSTITUTED BICYCLIC HETEROARYL COMPOUNDS

(71) Applicant: BRISTOL-MYERS SQUIBB COMPANY, Princeton, NJ (US)

(72) Inventors: Sreekantha Ratna Kumar, Bangalore (IN); Laxman Pasunoori, Warangal (IN); Subramanya Hegde, Bangalore (IN); Anupame Kandhi Ramachandra Reddy, Chitradurga (IN); Durga Buchi Raju Barre, East Godavari District (IN); Alaric J. Dyckman, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 869 days.

(21) Appl. No.: 17/766,198

(22) PCT Filed: Sep. 30, 2020

(86) PCT No.: PCT/US2020/053358
§ 371 (c)(1),
(2) Date: Apr. 1, 2022

(87) PCT Pub. No.: WO2021/067326
PCT Pub. Date: Apr. 8, 2021

(65) Prior Publication Data

US 2024/0124489 A1 Apr. 18, 2024

Related U.S. Application Data

(60) Provisional application No. 62/908,840, filed on Oct. 1, 2019.

(51) Int. Cl.
*C07D 513/04* (2006.01)
*C07D 519/00* (2006.01)

(52) U.S. Cl.
CPC ......... *C07D 513/04* (2013.01); *C07D 519/00* (2013.01)

(58) Field of Classification Search
CPC ............................ C07D 513/04; C07D 519/00
USPC ..................................................... 514/210.21
See application file for complete search history.

(56) References Cited

U.S. PATENT DOCUMENTS 6,187,777 B1 2/2001 Norman et al.
6,306,874 B1 10/2001 Fraley et al.
6,867,200 B1 3/2005 Allen et al.
7,410,975 B2 8/2008 Lipford et al.
8,138,187 B2 3/2012 Zemolka et al.
8,354,400 B2 1/2013 Zheng et al.
9,126,996 B2 9/2015 Lipford et al.
9,126,999 B2 9/2015 Bolvin et al.
9,241,991 B2 1/2016 Ji et al.
9,353,115 B2 5/2016 Lipford et al.
9,376,398 B2 6/2016 Hori et al.
9,428,495 B2 8/2016 Carlson et al.
9,643,967 B2 5/2017 Koul et al.
2004/0014802 A1 1/2004 Dutruc-Rosset et al.
2006/0235037 A1 10/2006 Purandare et al.
2010/0160314 A1 6/2010 Lipford et al.
2010/0197657 A1 8/2010 Chang et al.
2011/0015219 A1 1/2011 Trawick et al.
2011/0071150 A1 3/2011 Alam et al.
2011/0105427 A1 5/2011 Daun et al.
2011/0183967 A1 7/2011 Zheng et al.
2011/0275631 A1 11/2011 Abeywardane et al.
2012/0252759 A1 10/2012 Heinrich et al.
2013/0045986 A1 2/2013 Nagarathnam et al.
2013/0324547 A1 12/2013 Boivin et al.
2014/0066432 A1 3/2014 Howbert et al.
2014/0088085 A1 3/2014 Burgess et al.
2014/0242121 A1 8/2014 Lipford et al.
2015/0214490 A1 7/2015 Kim et al.
2015/0231142 A1 8/2015 Van Goor et al.
2017/0008885 A1 1/2017 Koul et al.

(Continued)

FOREIGN PATENT DOCUMENTS

EP 2738172 A1 6/2014
WO 03057696 A1 7/2003
WO 2006113458 A1 10/2006

(Continued)

OTHER PUBLICATIONS

International Preliminary Report on Patentability for No. PCT/US2020/053358, issued Apr. 5, 2022.

(Continued)

*Primary Examiner* — Kahsay Habte

(74) *Attorney, Agent, or Firm* — Gary Greenblatt

(57) ABSTRACT

Disclosed are compounds of Formula (I)

(I)

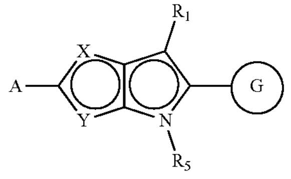

N-oxides, or salts thereof, wherein X, Y, A, G, $R_1$, and $R_5$ are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

13 Claims, No Drawings

(56) References Cited

U.S. PATENT DOCUMENTS

| | | | |
|---|---|---|---|
| 2017/0273983 | A1 | 9/2017 | Ding et al. |
| 2018/0000790 | A1 | 1/2018 | Dyckman et al. |

FOREIGN PATENT DOCUMENTS

| | | | |
|---|---|---|---|
| WO | 2007000241 | A1 | 1/2007 |
| WO | 2007115306 | A2 | 10/2007 |
| WO | 2008065198 | A1 | 6/2008 |
| WO | 2008152471 | A1 | 12/2008 |
| WO | 2009030996 | A1 | 3/2009 |
| WO | 2010149769 | A1 | 12/2010 |
| WO | 2013010904 | A1 | 1/2013 |
| WO | 2013181579 | A2 | 12/2013 |
| WO | 2015088045 | A1 | 6/2015 |
| WO | 2016029077 | A1 | 2/2016 |
| WO | 20170205633 | A1 | 11/2017 |
| WO | 2018005586 | A1 | 1/2018 |
| WO | 2018026620 | A1 | 2/2018 |
| WO | 2018049089 | A1 | 3/2018 |
| WO | 2019125977 | A1 | 6/2019 |
| WO | 2019126253 | A1 | 6/2019 |

OTHER PUBLICATIONS

Kawal, T., et al., "The Role of Pattern-Recognition Receptors in Innate Immunity: Update on Toll-like Receptors", Nature Immunol., 2011, 11, 373-384.

Koolman et al., Novel Syntheses of Variably Substituted Pyrrolo[2,3-d]thiazoles, Synthesis, 2010, No. 18, pp. 3152-3162.

Kutchukian, Peter S. et al., "Chemistry Informer Libraries: a chemoinformatics enabled approach to evaluate and advance synthetic methods", Chemical Science, 2016, vol. 7(4), pp. 2604-2613.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

Nozaki, M., et al. 1995, Medicinal Chemistry (1st ed.), pp. 98-99, Kagaku-Dojin Publishing Co., Inc.

SUBSTITUTED BICYCLIC HETEROARYL COMPOUNDS

CROSS REFERENCE

This application is a national phase application under 35 U.S.C. § 371 of International Patent Application No. PCT/US2020/053358, filed Sep. 30, 2020, which claims priority to U.S. Provisional Application Serial 62/908,840, filed Oct. 1, 2019, the contents of which are specifically incorporated fully herein by reference.

DESCRIPTION

The present invention generally relates to substituted bicyclic heteroaryl compounds useful as inhibitors of signaling through Toll-like receptor 7, 8, or 9 (TLR7, TLR8, TLR9) or combinations thereof. Provided herein are substituted bicyclic heteroaryl compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.,* 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.,* 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7/8/9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

SUMMARY OF THE INVENTION

The present invention relates to a new class of substituted bicyclic heteroaryl compounds found to be effective inhibitors of signaling through TLR7/8/9. These compounds are provided to be useful as pharmaceuticals with desirable stability, bioavailability, therapeutic index, and toxicity values that are important to their drugability.

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof. The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

(I)
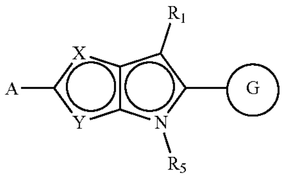
N-oxide, or a salt thereof, wherein:
X is N and Y is S; or X is S and Y is N or CH;
$R_1$ is H, F, Cl, —CN, $C_{1-4}$ alkyl, $C_{1-3}$ fluoroalkyl, —$OCH_3$, or —$S(O)_2(C_{1-3}$ alkyl);
G is:
(i)
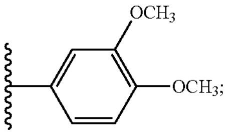 [SMILES: *c1ccc(OC)c(OC)c1]
(ii)
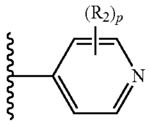
or
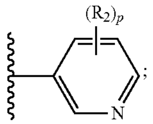
(iii)
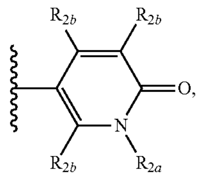
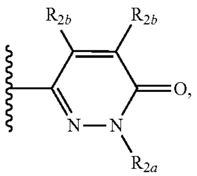
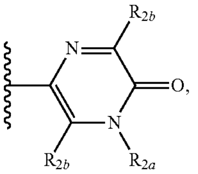
or
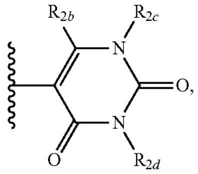
(iv) a 9-membered heterocyclic ring selected from:
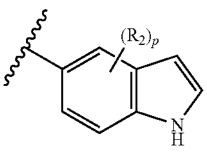
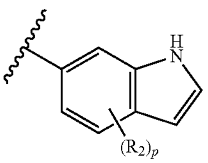
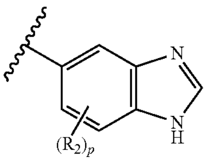
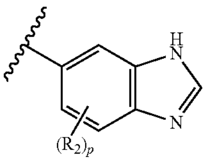
-continued
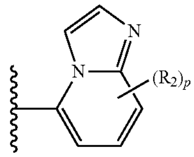
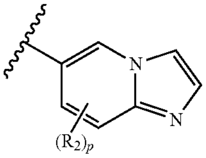
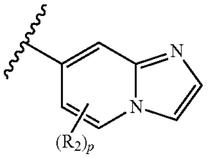
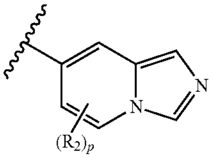
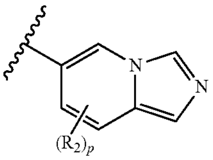
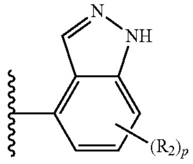
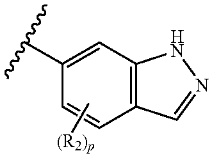
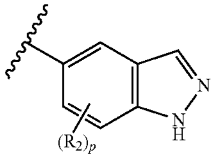
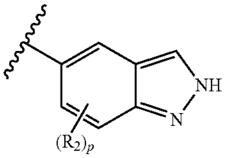
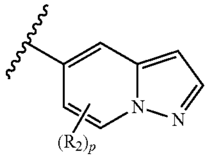
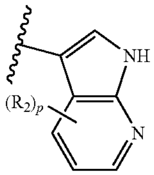
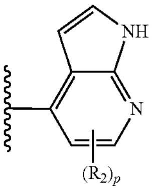
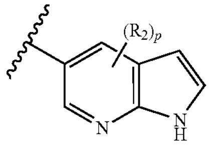
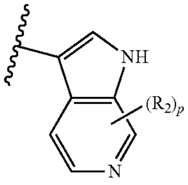
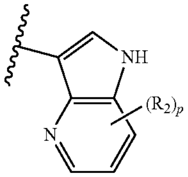
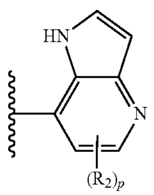
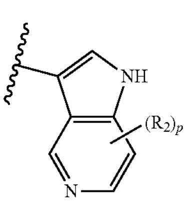
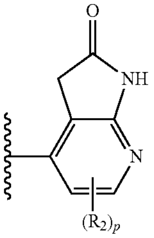
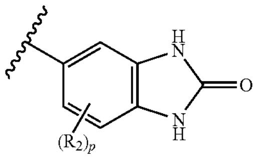
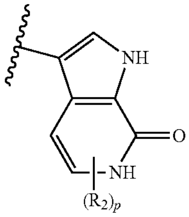

-continued
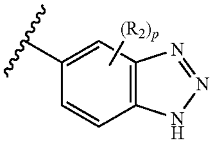
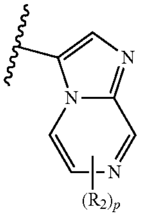
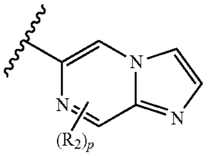
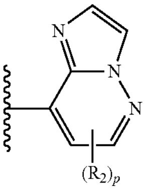
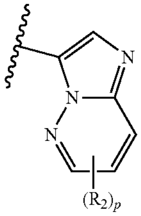
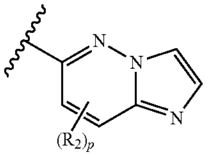
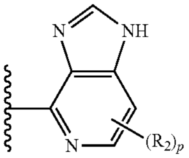
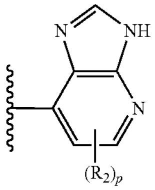
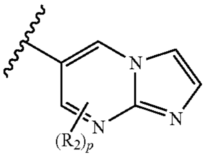
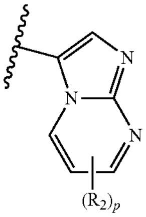
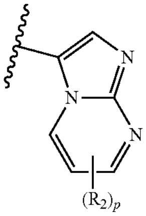
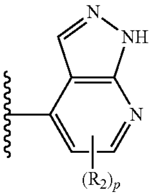
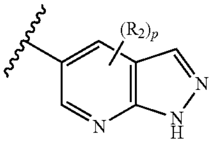
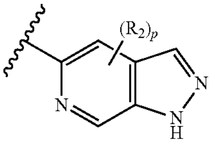
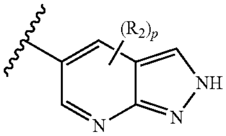
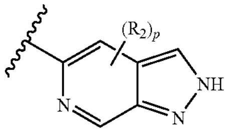
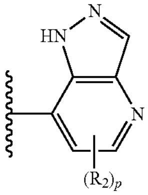
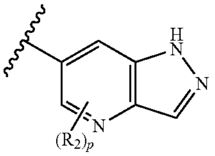
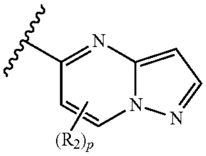
-continued
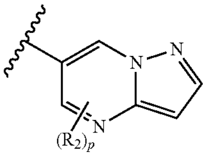
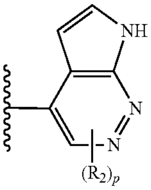
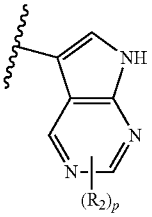
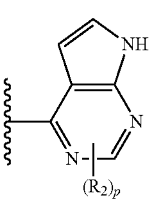
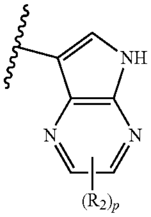
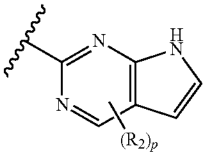
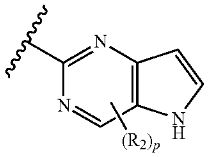
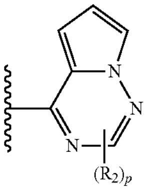
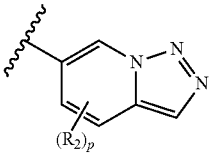
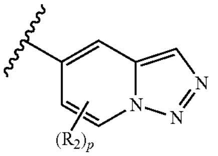
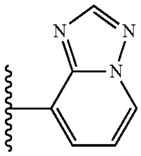
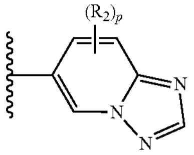
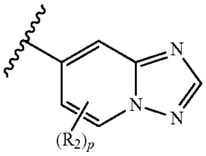
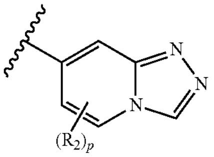
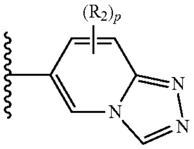
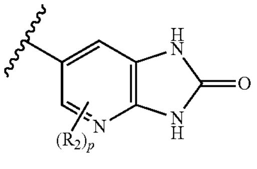
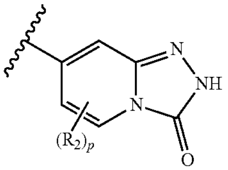
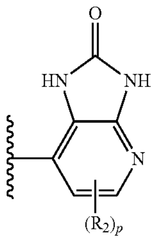
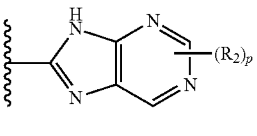
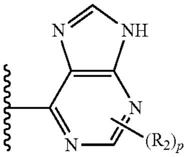
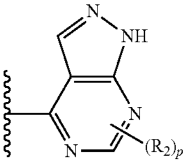

-continued
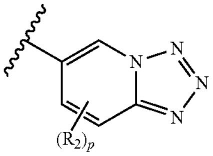
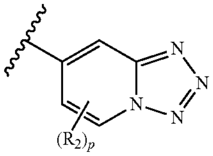
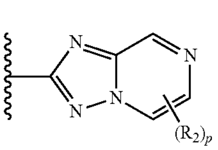
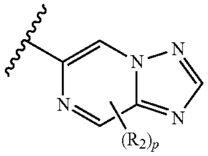
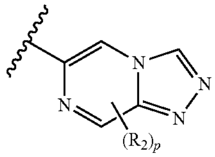
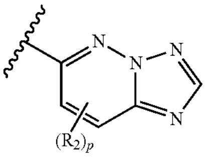
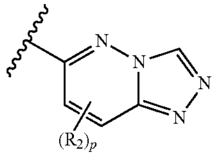
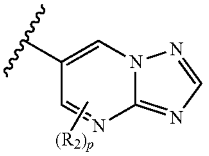
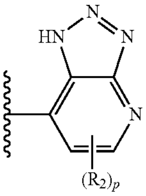
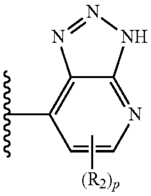
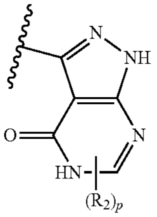
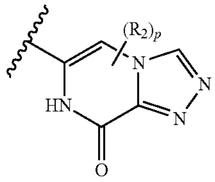
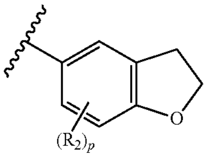
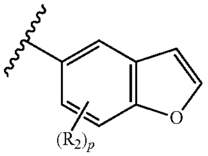
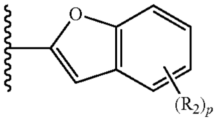
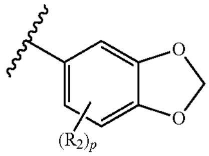
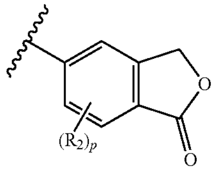
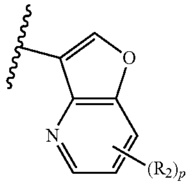
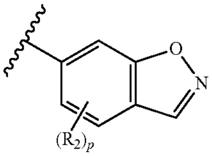
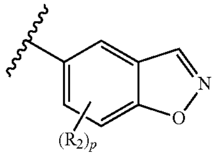
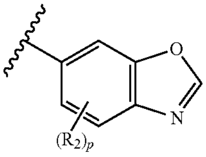
-continued
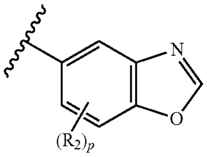
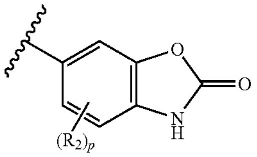
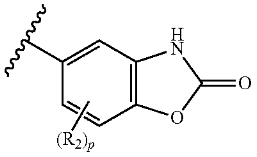
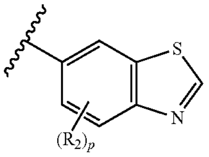
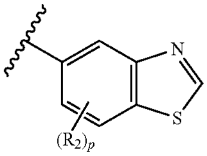
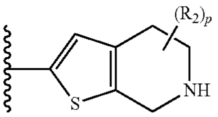
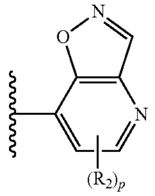
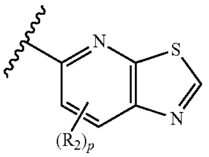
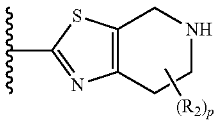
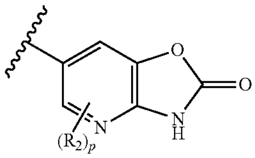 and
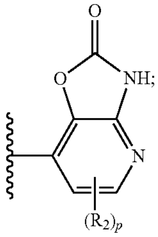
or
(v) 10-membered heterocyclic ring selected from:
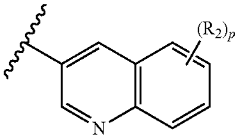
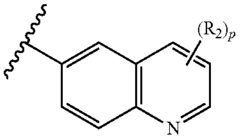
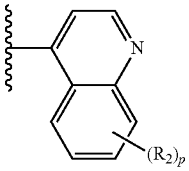
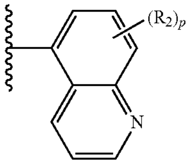
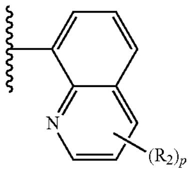
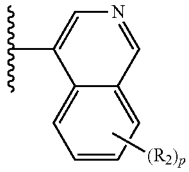

-continued

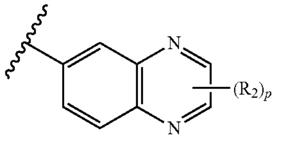
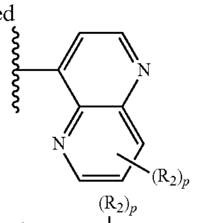
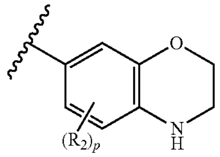
and
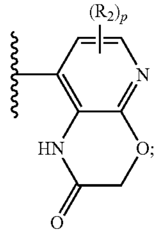
;

cyanoalkyl, $C_{1-3}$ hydroxyalkyl, $C_{1-3}$ aminoalkyl, $—O(CH_2)_{1-2}OH$, $—(CH_2)_{0-4}O(C_{1-4}$ alkyl), $C_{1-3}$ fluoroalkoxy, $—(CH_2)_{1-4}O(C_{1-3}$ alkyl), $—O(CH_2)_{1-2}OC(O)(C_{1-3}$ alkyl), $—O(CH_2)_{1-2}NR_xR_x$, $—C(O)O(C_{1-3}$ alkyl), $—(CH_2)_{0-2}C(O)NR_yR_y$, $—C(O)NR_x(C_{1-5}$ hydroxyalkyl), $—C(O)NR_x(C_{2-6}$ alkoxyalkyl), $—C(O)NR_x(C_{3-6}$ cycloalkyl), $—NR_yR_y$, $—NR_y(C_{1-3}$ fluoroalkyl), $—NR_y(C_{1-4}$ hydroxyalkyl), $—NR_xCH_2$(phenyl), $—NR_xS(O)_2(C_{3-6}$ cycloalkyl), $—NR_xC(O)(C_{1-3}$ alkyl), $—NR_xCH_2(C_{3-6}$ cycloalkyl), $—(CH_2)_{0-2}S(O)_2(C_{1-3}$ alkyl), $—(CH_2)_{0-2}(C_{3-6}$ cycloalkyl), $—(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, pyrimidinyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, $—(CH_2)_{0-4}O(C_{1-3}$ alkyl), $C_{3-6}$ cycloalkyl, $—(CH_2)_{1-3}C(O)NR_yR_y$, $—CH_2(C_{3-6}$ cycloalkyl), $—CH_2$(phenyl), tetrahydrofuranyl, tetrahydropyranyl, or phenyl;

each $R_{2b}$ is independently H, halo, —CN, $—NR_xR_x$, $C_{1-6}$ alkyl, $C_{1-3}$ fluoroalkyl, $C_{1-3}$ hydroxyalkyl, $C_{1-3}$ fluoroalkoxy, $—(CH_2)_{0-2}O(C_{1-3}$ alkyl), $—(CH_2)_{0-3}C(O)NR_xR_x$, $—(CH_2)_{1-3}(C_{3-6}$ cycloalkyl), $—C(O)O(C_{1-3}$ alkyl), $—C(O)NR_x(C_{1-3}$ alkyl), $—CR_x{=}CR_xR_x$, or $—CR_x{=}CH(C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_2$ is $R_{2b}$;

A is:

(i) H, $—NR_yR_y$, or $—CH_2NHCH_2C(O)NR_xR_x$;

(ii) $—CR_xR_xR_3$, $—CR_xR_xNR_xR_3$, $—CR_xR_xNR_xCH_2R_3$, $—C(O)NR_xR_3$, $—C(O)NR_xR_4$, $—C(O)R_3$, or $—NR_xC(O)R_3$; or (iii) $R_3$;

$R_3$ is:

(i) $C_{3-5}$ cycloalkyl, azetidinyl, oxetanyl, pyrrolidinyl, pyrrolidinonyl, piperidinyl, piperazinyl, piperazinonyl, morpholinyl, dioxidothiomorpholinyl, oxazepanyl, diazaspiro[3.3]heptanyl, dioxidothiaazaspiro[3.3]heptanyl, oxaazaspiro[3.3]heptanyl, or oxaazaspiro[3.5]nonanyl, each substituted with zero to 2 $R_{3a}$ and zero to 2 $R_{3b}$;

(ii) cyclohexyl substituted with $—NR_yR_y$, $—NR_x(C_{1-6}$ hydroxyalkyl), $—NR_x(CR_xR_x)_{1-2}O(C_{1-3}$ alkyl), $—NR_x(C_{1-6}$ hydroxy-fluoroalkyl), $—NR_xCH_2C(O)NR_xR_x$, $—NR_x(CH_2)_{1-2}S(O)_2(C_{1-3}$ alkyl), $—NR_xC(O)(C_{1-3}$ alkyl), $—NR_xC(O)CH_2NR_xR_x$, $—NR_xC(O)CH_2NR_xR_y$, $—NR_x(CH_2)_{1-2}C(O)NR_xR_x$, $—NR_x(CH_2)_{1-2}NR_xR_x$, $—NR_xS(O)_2(C_{1-3}$ alkyl), $—S(O)_2(C_{1-3}$ alkyl); $—NR_x$(cyanocyclopropyl), $—NR_x$(azetidinyl), $—NR_x$(oxetanyl), $—NR_x$(methyloxetanyl), $—NR_x$(ethyloxetanyl), $—NR_x$(isopropyloxetanyl), $—NR_x$(tetrahydropyranyl), $—NR_x$(bicyclo[1.1.1]pentyl), $—NR_x(CH_2$(methyloxetanyl)), $—NR_x$(dioxidotetrahydrothiophenyl), $—NR_xCH_2$(hydroxymethylcyclopropyl), $—NR_xCH_2$(methylsulfonylcyclopropyl), $—NR_xCH_2$(methylcyclobutyl), $—NR_xHCH_2C(O)$(morpholinyl), azetidinyl, fluoroazetidinyl, hydroxyazetidinyl, methoxyazetidinyl, hydroxy(trifluoromethyl)azetidinyl, bis(hydroxymethyl)azetidinyl, pyrrolidinyl, piperazinonyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl; or (iii) diazaspiro[3.3]heptanyl substituted with $C_{1-6}$ alkyl, $C_{1-6}$ hydroxyalkyl, $—(CH_2)_{1-3}S(O)_2(C_{1-6}$ alkyl), oxetanyl, or $—CH_2$(tetrahydropyranyl);

each $R_{3a}$ is independently F, Cl, $C_{1-6}$ alkyl, $C_{1-6}$ cyanoalkyl, $C_{1-6}$ fluoroalkyl, $C_{1-6}$ hydroxyalkyl, $—(CH_2)_{1-3}O(C_{1-3}$ alkyl), $—C(O)(C_{1-6}$ alkyl), $—CH_2C(O)NR_yR_y$, $—NR_yR_y$, $—NR_x(C_{1-4}$ hydroxyalkyl), $—C(O)(CH_2)_{1-3}NR_yR_y$, $—C(O)(C_{1-6}$ alkyl), $—(CH_2)_{0-2}S(O)_2(C_{1-3}$ alkyl), $—(CH_2)_{1-2}NR_xS(O)_2(C_{1-3}$ alkyl), $—NR_xCH_2C(O)NR_yR_y$, $—NR_x(CH_2)_{1-3}S(O)_2(C_{1-3}$ alkyl), $—NR_x(C_{3-6}$ cycloalkyl), $—NR_x$(oxetanyl), $—CH_2$(methyltriazolyl), $C_{3-6}$ cycloalkyl, oxetanyl, oxetanyl, pyrrolidinyl, morpholinyl, tetrahydropyranyl, $—CH_2(C_{3-6}$ cycloalkyl), $—CH_2$(oxetanyl), $—CH_2$(methyloxetanyl), $—CH_2$(tetrahydropyranyl), $—NR_x(C_{3-6}$ cycloalkyl), $—NR_x$(oxetanyl), $—NR_x$(methyloxetanyl), $—NR_xCH_2$(methyloxetanyl), or —C(O)(dioxidotetrahydrothiopyranyl);

each $R_{3b}$ is $—CH_3$;

$R_4$ is H, $C_{1-2}$ fluoroalkyl, $—(CR_xR_x)_{1-2}NR_yR_y$, or $—(CR_xR_x)_{1-3}R_3$;

$R_5$ is H, $C_{1-3}$ alkyl, or $C_{1-3}$ fluoroalkyl;

each $R_x$ is independently H or $—CH_3$;

each $R_y$ is independently H or $C_{1-6}$ alkyl; and p is zero, 1, or 2.

One embodiment provides a compound of Formula (I), N-oxide, or a salt thereof wherein X is N and Y is S. The compounds of this embodiment have the structure of Formula (II):

(II)

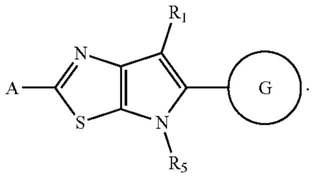

One embodiment provides a compound of Formula (I), N-oxide, or a salt thereof wherein X is S and Y is N. The compounds of this embodiment have the structure of Formula (III):

(III)
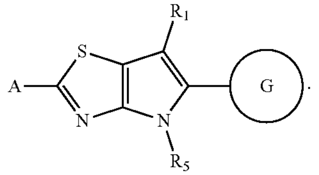
One embodiment provides a compound of Formula (I), N-oxide, or a salt thereof wherein X is S and Y is CH. The compounds of this embodiment have the structure of Formula (IV):
(IV)
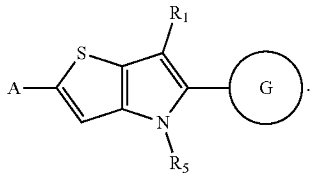
One embodiment provides a compound of Formula (I), N-oxide, or a salt thereof wherein:
$R_1$ is H, —$CH_3$, —$CH_2CH_3$, —$CH(CH_3)_2$, —$CF_3$, —$OCH_3$, or —$S(O)_2(C_{1-2}$ alkyl);
G is:
(i)
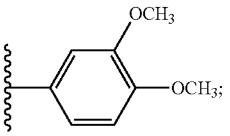 [SMILES: *c1ccc(OC)c(OC)c1]
(ii)
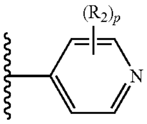
or
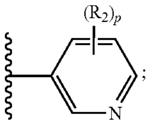
(iii)
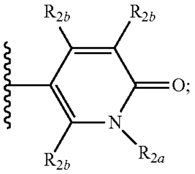
(iv) a 9-membered heterocyclic ring selected from:
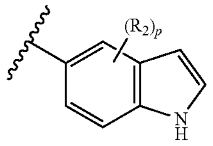
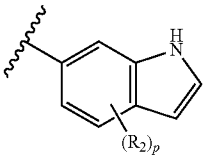
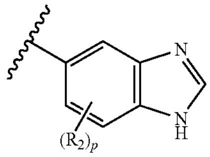
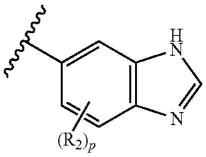
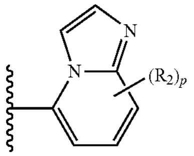
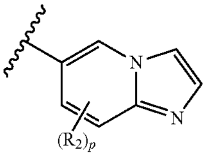
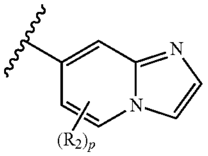
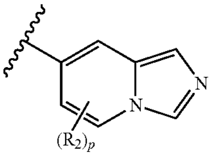
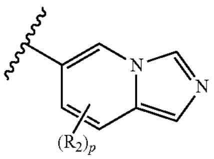
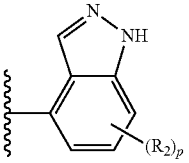
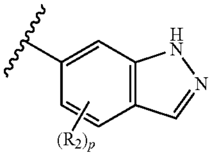
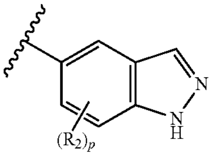
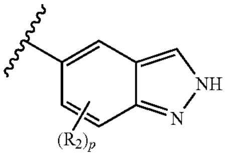
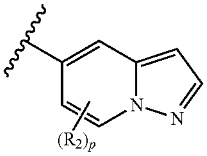
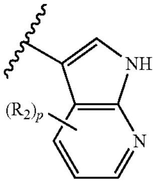
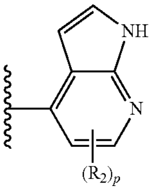
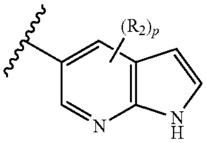
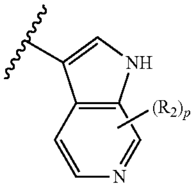
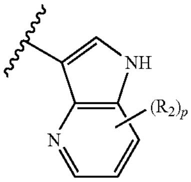
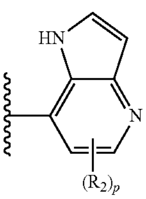
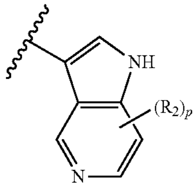
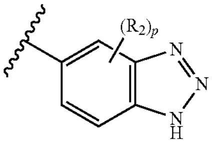

-continued
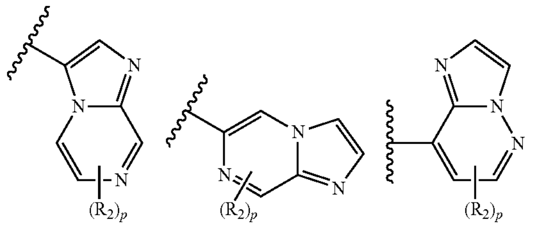
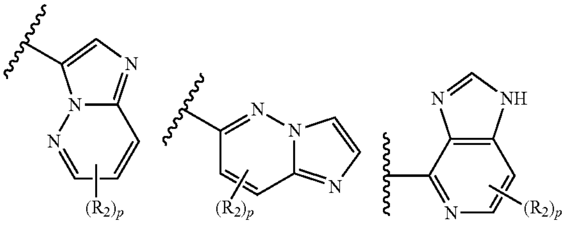
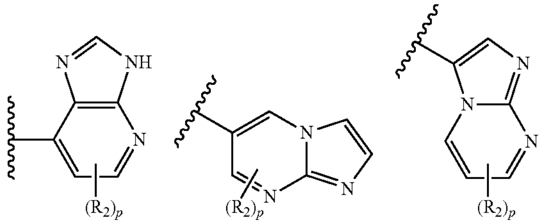
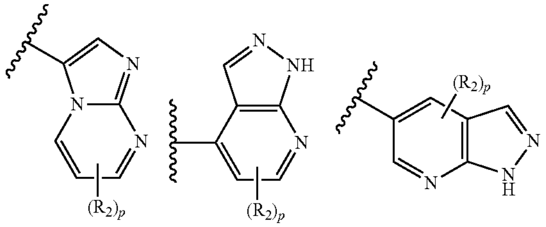
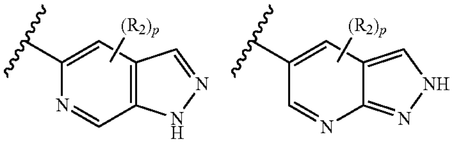
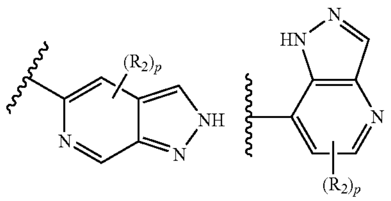
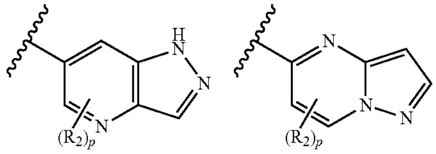
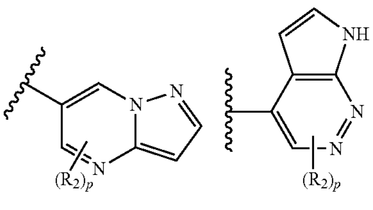
-continued
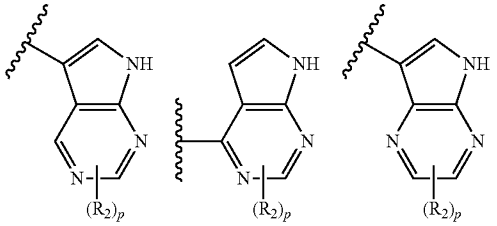
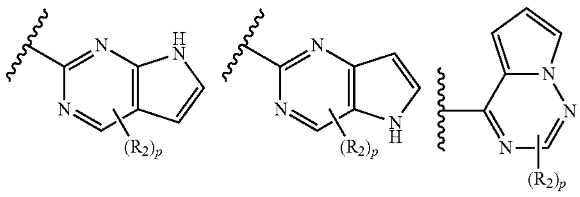
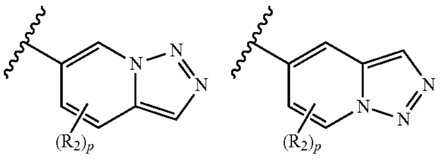
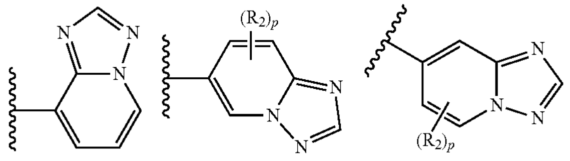
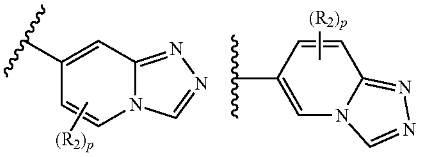
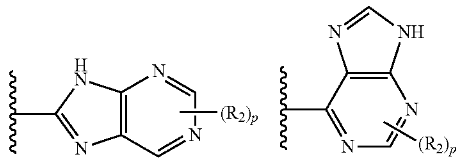
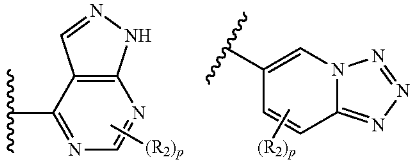
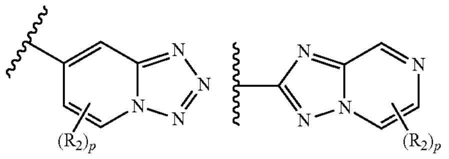
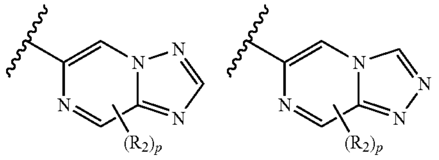
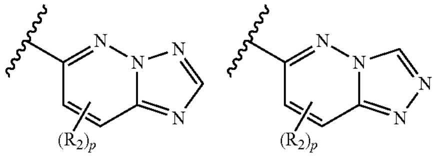

-continued

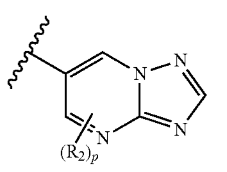
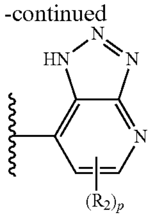
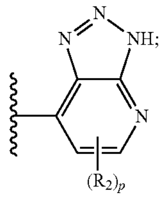

(v) 10-membered heterocyclic ring selected from:

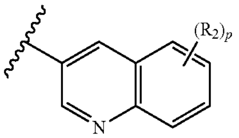
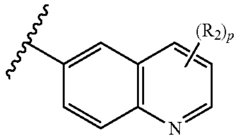
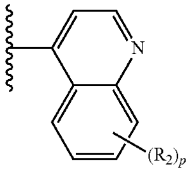
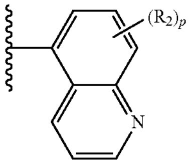
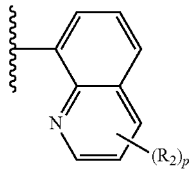
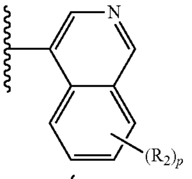
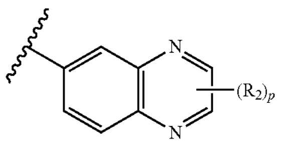
or
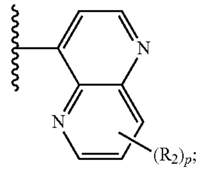

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, $-(CH_2)_{0-2}O(C_{1-3}$ alkyl), $C_{3-6}$ cycloalkyl, $-NR_xR_x$, $-(CH_2)_{0-2}C(O)NR_xR_x$, $-(CH_2)_{0-2}S(O)_2(C_{1-3}$ alkyl), $-CH_2(C_{3-6}$ cycloalkyl), $-CH_2$(phenyl), phenyl, pyrimidinyl, or triazolyl; $R_{2a}$ is $C_{1-4}$ alkyl, $C_{1-2}$ fluoroalkyl, $C_{1-4}$ hydroxyalkyl, $-(CH_2)_{1-3}OCH_3$, $C_{3-6}$ cycloalkyl, $-CH_2C(O)NR_xR_x$, $-CH_2(C_{3-6}$ cycloalkyl), $-CH_2$(phenyl), tetrahydrofuranyl, or phenyl;

each $R_{2b}$ is independently H, F, Cl, —CN, $-NR_xR_x$, $C_{1-6}$ alkyl, $C_{1-2}$ fluoroalkyl, $C_{1-3}$ hydroxyalkyl, $-(CH_2)_{0-2}O(C_{1-2}$ alkyl), $-(CH_2)_{0-2}C(O)NR_xR_x$, $-(CH_2)_{1-3}$(cyclopropyl), $-C(O)O(C_{1-2}$ alkyl), or $-C(O)NR_x(C_{1-3}$ alkyl);

A is:

(i) $-CH_2NHCH_2C(O)NR_xR_x$;

(ii) $-CR_xR_xR_3$, $-CH_2NR_xR_3$, $-CH_2NR_xCH_2R_3$, $-C(O)NR_xR_3$, $-C(O)NR_xR_4$, $-C(O)R_3$, or $-NR_xC(O)R_3$; or (iii) $R_3$; and $R_3$ is:

(i) azetidinyl, oxetanyl, cyclopropyl, pyrrolidinyl, pyrrolidinonyl, piperidinyl, piperazinyl, piperazinonyl, morpholinyl, dioxidothiomorpholinyl, oxazepanyl, diazaspiro[3.3]heptanyl, dioxidothiaazaspiro[3.3]heptanyl, oxaazaspiro[3.3]heptanyl, or oxaazaspiro[3.5]nonanyl, each substituted with zero to 1 $R_{3a}$ and zero to 2 $R_{3b}$;

(ii) cyclohexyl substituted with $-NR_yR_y$, $-NR_x(C_{1-4}$ hydroxyalkyl), $-NR_x(CR_xR_x)_{1-2}O(C_{1-2}$ alkyl), $-NR_x(C_{1-6}$ hydroxy-fluoroalkyl), $-NR_xCH_2C(O)NR_xR_x$, $-NR_x(CH_2)_{1-2}S(O)_2(C_{1-2}$ alkyl), $-NR_xC(O)(C_{1-2}$ alkyl), $-NR_xC(O)CH_2NR_xR_x$, $-NR_xC(O)CH_2NR_xR_y$, $-NR_x(CH_2)_{1-2}C(O)NR_xR_x$, $-NR_x(CH_2)_{1-2}NR_xR_x$, $-NR_xS(O)_2(C_{1-2}$ alkyl), $-S(O)_2(C_{1-2}$ alkyl); $-NR_x$(cyanocyclopropyl), $-NR_x$(azetidinyl), $-NR_x$(oxetanyl), $-NR_x$(methyloxetanyl), $-NR_x$(ethyloxetanyl), $-NR_x$(isopropyloxetanyl), $-NR_x$(tetrahydropyranyl), $-NR_x$(bicyclo[1.1.1]pentyl), $-NR_x(CH_2$(methyloxetanyl)), $-NR_x$(dioxidotetrahydrothiophenyl), $-NR_xCH_2$(hydroxymethylcyclopropyl), $-NR_xCH_2$(methylsulfonylcyclopropyl), $-NR_xCH_2$(methylcyclobutyl), $-NR_xHCH_2C(O)$(morpholinyl), azetidinyl, fluoroazetidinyl, hydroxyazetidinyl, methoxyazetidinyl, hydroxy(trifluoromethyl)azetidinyl, bis(hydroxymethyl)azetidinyl, pyrrolidinyl, piperazinonyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl; or (iii) diazaspiro[3.3]heptanyl substituted with $C_{1-4}$ alkyl, $C_{1-4}$ hydroxyalkyl, $-(CH_2)_{1-2}S(O)_2(C_{1-3}$ alkyl), oxetanyl, or $-CH_2$(tetrahydropyranyl);

each $R_{3a}$ is independently F, Cl, $C_{1-5}$ alkyl, $C_{1-3}$ cyanoalkyl, $C_{1-3}$ fluoroalkyl, $C_{1-4}$ hydroxyalkyl, $-(CH_2)_{1-2}O(C_{1-2}$ alkyl), $-C(O)(C_{1-3}$ alkyl), $-CH_2C(O)NR_xR_x$, $-NR_yR_y$, $-NH(C_{1-4}$ hydroxyalkyl), $-C(O)(CH_2)_{1-3}NR_xR_x$, $-C(O)(C_{1-3}$ alkyl), $-(CH_2)_{0-2}S(O)_2(C_{1-2}$ alkyl), $-(CH_2)_{1-2}NR_xS(O)_2(C_{1-2}$ alkyl), $-NR_xCH_2C(O)NR_yR_y$, $-NR_xCH_2CH_2S(O)_2(C_{1-2}$ alkyl), $-NR_x(C_{3-6}$ cycloalkyl), $-NR_x$(oxetanyl), $-CH_2$(methyltriazolyl), cyclobutyl, oxetanyl, pyrrolidinyl, morpholinyl, tetrahydropyranyl, $-CH_2(C_{3-4}$ cycloalkyl), $-CH_2$(oxetanyl), $-CH_2$(methyloxetanyl), $-CH_2$(tetrahydropyranyl), $-NR_x$(cyclobutyl), $-NR_x$(oxetanyl), $-NR_x$(methyloxetanyl), $-NR_xCH_2$(methyloxetanyl), or $-C(O)$(dioxidotetrahydrothiopyranyl);

each $R_{3b}$ is $-CH_3$; and $R_5$ is H, $-CH_3$, $-CH_2CH_3$, $-CF_3$, $-CH_2CHF_2$, or $-CH_2CF_3$.

Included in this embodiment are compounds in which X is N and Y is S. Also included in this embodiment are compounds in which X is S and Y is N. Additionally, included in this embodiment are compounds in which X is S and Y is CH.

One embodiment provides a compound of Formula (I), N-oxide, or a salt thereof wherein:

$R_1$ is independently $-CH_3$, $-CH_2CH_3$, or $-CH(CH_3)_2$;

G is:

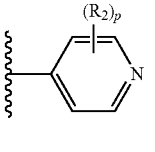
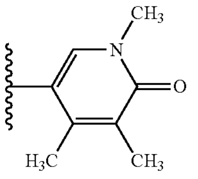

-continued

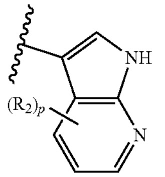

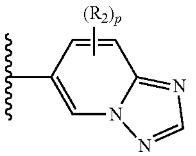

or

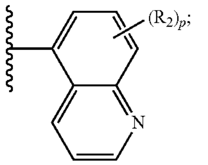

each $R_2$ is independently —CN, —$CH_3$, or —$OCH_3$;

A is:

(i) —$CH_2NHCH_2C(O)NH_2$;

(ii) —$CH_2R_3$, —$CH_2NHR_3$, —$CH_2NHCH_2R_3$, —C(O)$NHR_3$, —C(O)$NR_xR_4$, or —C(O)$R_3$; or (iii) cyclohexyl, piperidinyl, piperazinyl, methylpiperazinyl, dimethylpiperazinyl, or diazaspiro[3.3]heptanyl, each substituted with zero to 1 $R_{3a}$;

$R_3$ is azetidinyl, oxetanyl, cyclopropyl, cyclobutyl, pyrrolidinyl, pyrrolidinonyl, piperidinyl, piperazinyl, piperazinonyl, morpholinyl, dioxidothiomorpholinyl, oxazepanyl, diazaspiro[3.3]heptanyl, dioxidothiaazaspiro[3.3]heptanyl, oxaazaspiro[3.3]heptanyl, or oxaazaspiro[3.5]nonanyl, each substituted with zero to 1 $R_{3a}$ and zero to 2 $R_{3b}$;

$R_{3a}$ is F —$CH_3$, —$CH_2CH_3$, —$CH_2CH_2CH_3$, —$CH(CH_3)_2$, —$CH_2CH(CH_3)_2$, —$CH_2C(CH_3)_3$, —$CH_2CH(CH_2CH_3)_2$, —$CH_2CF_3$, —$CH_2CN$, —$CH_2C(CH_3)_2OH$, —$CH_2CH_2OCH_3$, —$CH_2CH_2S(O)_2CH_3$, —$CH_2C(O)NR_xR_x$, —$OCH_3$, —$C(O)CH_3$, —$C(O)CH_2N(CH_3)_2$, —$NH_2$, —$NH(CH_3)$, —$NH(CH(CH_3)_2)$, —$NH(CH_2C(CH_3)_3)$, —$NH(CH_2C(CH_3)_2OH)$, —$NH(CH_2CHFC(CH_3)_2OH)$, —$NH(CH_2C(CH_3)_2OCH_3)$, —$N(CH_3)(CH_2CH_3)$, —$N(CH_3)(CH(CH_3)_2)$, —$N(CH_3)CH_2CH(CH_3)_2$, —$N(CH_3)CH_2C(O)N(CH_3)_2$, —$N(CH_3)CH_2CH_2S(O)_2CH_3$, —$NHC(O)CH_2N(CH_3)_2$, —$NHC(O)CH_2N(CH_3)(CH_2CH_3)$, —$NHC(O)CH_2NH(CH_2CH(CH_3)_2)$, —$NHCH_2C(O)NH_2$, —$NHCH_2C(O)NH(CH_3)$, —$NHCH_2C(O)N(CH_3)_2$, —$NHCH_2CH_2NH(CH_3)$, —$NHS(O)_2CH_3$, —$S(O)_2CH_3$, —$CH_2$(cyclopropyl), —$CH_2$(methyloxetanyl), —$CH_2$(tetrahydropyranyl), —C(O)(dioxidotetrahydrothiopyranyl), —NH(cyanocyclopropyl), —NH(cyclobutyl), —NH(methylcyclobutyl), —NH(oxetanyl), —NH(methyloxetanyl), —NH(ethyloxetanyl), —NH(isopropylpiperidinyl), —NH(tetrahydropyranyl), —NH(bicyclo[1.1.1]pentyl), —$NHCH_2$(methyloxetanyl), —NH(dioxidotetrahydrothiophenyl), —$NHCH_2$(hydroxymethylcyclopropyl), —$NHCH_2$(methylsulfonylcyclopropyl), —$NHCH_2$(methylcyclobutyl), —$NHCH_2C(O)$(morpholinyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, piperazinonyl, tetrahydropyranyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl;

each $R_{3b}$ is —$CH_3$;

$R_4$ is H, —$CH_2CHF_2$, —$CH_2CF_3$, —$CH_2CH_2N(CH_3)_2$, —$CH_2R_3$, —$CH_2CR_xR_xR_3$, or —$(CH_2)_3R_3$;

$R_5$ is H or —$CH_2CF_3$; and p is zero, 1, or 2.

Included in this embodiment are compounds in which X is N and Y is S. Also included in this embodiment are compounds in which X is S and Y is N. Additionally, included in this embodiment are compounds in which X is S and Y is CH.

One embodiment provides a compound of Formula (I), N-oxide, or a salt thereof wherein A is cyclohexyl substituted with zero to 1 $R_{3a}$. Compounds of this embodiment have the structure:

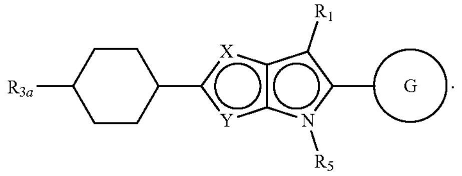

Included in this embodiment are compounds in which X is N and Y is S. Also included in this embodiment are compounds in which X is S and Y is N. Additionally, included in this embodiment are compounds in which X is S and Y is CH.

One embodiment provides a compound of Formula (I), N-oxide, or a salt thereof wherein A is cyclohexyl substituted with zero to 1 $R_{3a}$. Compounds of this embodiment have the structure:

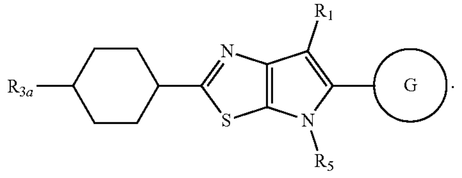

Included in this embodiment are compounds in which G is:

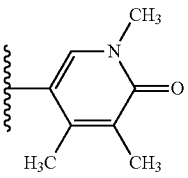

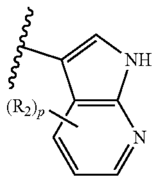

or

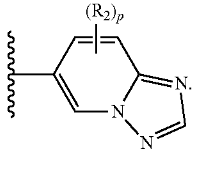

Also included in this embodiment are compounds in which $R_{3a}$ is F —$CH_3$, —$CH_2CH_3$, —$CH_2CH_2CH_3$, —$CH(CH_3)_2$, —$CH_2CH(CH_3)_2$, —$CH_2C(CH_3)_3$, —$CH_2CH(CH_2CH_3)_2$, —$CH_2CF_3$, —$CH_2CN$, —$CH_2C(CH_3)_2OH$, —$CH_2CH_2OCH_3$, —$CH_2CH_2S(O)_2CH_3$, —$CH_2C(O)NR_xR_x$, —$OCH_3$, —$C(O)CH_3$, —$C(O)CH_2N(CH_3)_2$, —$NH_2$, —$NH(CH_3)$, —$NH(CH(CH_3)_2)$, —NH(CH$_2$C $(CH_3)_3)$, $—NH(CH_2C(CH_3)_2OH)$, $—NH(CH_2CHFC(CH_3)_2OH)$, $—NH(CH_2C(CH_3)_2OCH_3)$, $—N(CH_3)(CH_2CH_3)$, $—N(CH_3)(CH(CH_3)_2)$, $—N(CH_3)CH_2CH(CH_3)_2$, $—N(CH_3)CH_2C(O)N(CH_3)_2$, $—N(CH_3)CH_2CH_2S(O)_2CH_3$, $—NHC(O)CH_2N(CH_3)_2$, $—NHC(O)CH_2N(CH_3)(CH_2CH_3)$, $—NHC(O)CH_2NH(CH_2CH(CH_3)_2)$, $—NHCH_2C(O)NH_2$, $—NHCH_2C(O)NH(CH_3)$, $—NHCH_2C(O)N(CH_3)_2$, $—NHCH_2CH_2NH(CH_3)$, $—NHS(O)_2CH_3$, $—S(O)_2CH_3$, $—CH_2$(cyclopropyl), $—CH_2$(methyloxetanyl), $—CH_2$(tetrahydropyranyl), —C(O)(dioxidotetrahydrothiopyranyl), —NH(cyanocyclopropyl), —NH(cyclobutyl), —NH(methylcyclobutyl), —NH(oxetanyl), —NH(methyloxetanyl), —NH(ethyloxetanyl), —NH(isopropylpiperidinyl), —NH(tetrahydropyranyl), —NH(bicyclo[1.1.1]pentyl), $—NHCH_2$(methyloxetanyl), —NH(dioxidotetrahydrothiophenyl), $—NHCH_2$(hydroxymethylcyclopropyl), $—NHCH_2$(methylsulfonylcyclopropyl), $—NHCH_2$(methylcyclobutyl), $—NHCH_2C(O)$(morpholinyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, piperazinonyl, tetrahydropyranyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl.

One embodiment provides a compound of Formula (I), N-oxide, or a salt thereof wherein A is 1-piperidinyl substituted with zero to 1 $R_{3a}$. Compounds of this embodiment have the structure:

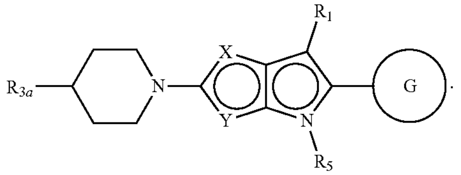

Included in this embodiment are compounds in which X is N and Y is S. Also included in this embodiment are compounds in which X is S and Y is N. Additionally, included in this embodiment are compounds in which X is S and Y is CH.

One embodiment provides a compound of Formula (I), N-oxide, or a salt thereof wherein A is 1-piperidinyl substituted with zero to 1 $R_{3a}$. Compounds of this embodiment have the structure:

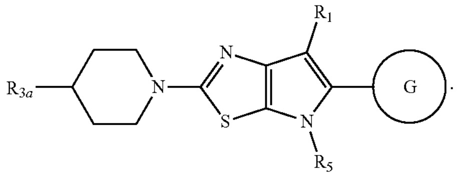

Included in this embodiment are compounds in which G is:

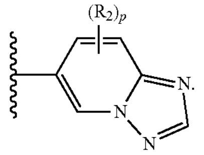

Also included in this embodiment are compounds in which $R_{3a}$ is F $—CH_3$, $—CH_2CH_3$, $—CH_2CH_2CH_3$, $—CH(CH_3)_2$, $—CH_2CH(CH_3)_2$, $—CH_2C(CH_3)_3$, $—CH_2CH(CH_2CH_3)_2$, $—CH_2CF_3$, $—CH_2CN$, $—CH_2C(CH_3)_2OH$, $—CH_2CH_2OCH_3$, $—CH_2CH_2S(O)_2CH_3$, $—CH_2C(O)NR_xR_x$, $—OCH_3$, $—C(O)CH_3$, $—C(O)CH_2N(CH_3)_2$, $—NH_2$, $—NH(CH_3)$, $—NH(CH(CH_3)_2)$, $—NH(CH_2C(CH_3)_3)$, $—NH(CH_2C(CH_3)_2OH)$, $—NH(CH_2CHFC(CH_3)_2OH)$, $—NH(CH_2C(CH_3)_2OCH_3)$, $—N(CH_3)(CH_2CH_3)$, $—N(CH_3)(CH(CH_3)_2)$, $—N(CH_3)CH_2CH(CH_3)_2$, $—N(CH_3)CH_2C(O)N(CH_3)_2$, $—N(CH_3)CH_2CH_2S(O)_2CH_3$, $—NHC(O)CH_2N(CH_3)_2$, $—NHC(O)CH_2N(CH_3)(CH_2CH_3)$, $—NHC(O)CH_2NH(CH_2CH(CH_3)_2)$, $—NHCH_2C(O)NH_2$, $—NHCH_2C(O)NH(CH_3)$, $—NHCH_2C(O)N(CH_3)_2$, $—NHCH_2CH_2NH(CH_3)$, $—NHS(O)_2CH_3$, $—S(O)_2CH_3$, $—CH_2$(cyclopropyl), $—CH_2$(methyloxetanyl), $—CH_2$(tetrahydropyranyl), —C(O)(dioxidotetrahydrothiopyranyl), —NH(cyanocyclopropyl), —NH(cyclobutyl), —NH(methylcyclobutyl), —NH(oxetanyl), —NH(methyloxetanyl), —NH(ethyloxetanyl), —NH(isopropylpiperidinyl), —NH(tetrahydropyranyl), —NH(bicyclo[1.1.1]pentyl), $—NHCH_2$(methyloxetanyl), —NH(dioxidotetrahydrothiophenyl), $—NHCH_2$(hydroxymethylcyclopropyl), $—NHCH_2$(methylsulfonylcyclopropyl), $—NHCH_2$(methylcyclobutyl), $—NHCH_2C(O)$(morpholinyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, piperazinonyl, tetrahydropyranyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl.

One embodiment provides a compound of Formula (I), N-oxide, or a salt thereof wherein A is 4-piperidinyl substituted with zero to 1 $R_{3a}$. Compounds of this embodiment have the structure:

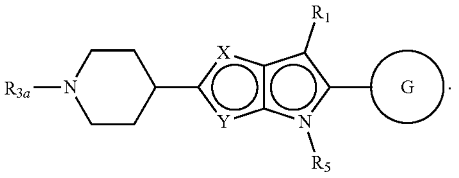

Included in this embodiment are compounds in which X is N and Y is S. Also included in this embodiment are compounds in which X is S and Y is N. Additionally, included in this embodiment are compounds in which X is S and Y is CH.

One embodiment provides a compound of Formula (I), N-oxide, or a salt thereof wherein A is 4-piperidinyl substituted with zero to 1 $R_{3a}$. Compounds of this embodiment have the structure:

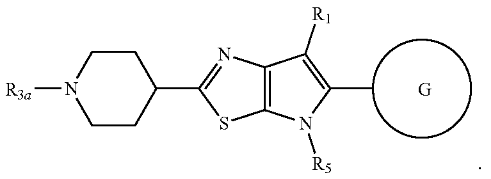

Included in this embodiment are compounds in which G is:

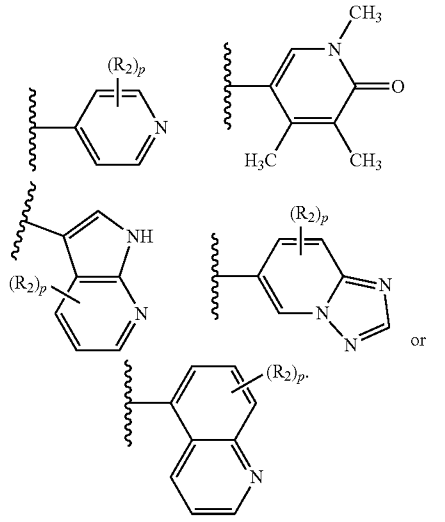

Included in this embodiment are compounds in which $R_{3a}$ is —$CH_3$, —$CH_2CH_3$, —$CH_2CH_2CH_3$, —$CH(CH_3)_2$, —$CH_2CH(CH_3)_2$, —$CH_2C(CH_3)_3$, —$CH_2CH(CH_2CH_3)_2$, —$CH_2CF_3$, —$CH_2CN$, —$CH_2C(CH_3)_2OH$, —$CH_2CH_2OCH_3$, —$CH_2CH_2S(O)_2CH_3$, —$CH_2C(O)NR_xR_x$, —$C(O)CH_3$, —$C(O)CH_2N(CH_3)_2$, —$S(O)_2CH_3$, —$CH_2$(cyclopropyl), —$CH_2$(methyloxetanyl), —$CH_2$(tetrahydropyranyl), —C(O)(dioxidotetrahydrothiopyranyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, tetrahydropyranyl, oxazepanyl, or bicyclo[1.1.1]pentanyl.

One embodiment provides a compound of Formula (I), N-oxide, or a salt thereof wherein A is piperazinyl substituted with zero to 1 $R_{3a}$ and zero to 2 $R_{3b}$. Compounds of this embodiment have the structure:

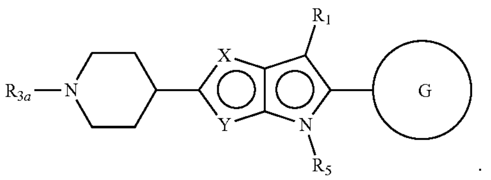

Included in this embodiment are compounds in which X is N and Y is S. Also included in this embodiment are compounds in which X is S and Y is N. Additionally, included in this embodiment are compounds in which X is S and Y is CH.

One embodiment provides a compound of Formula (I), N-oxide, or a salt thereof wherein A is piperazinyl substituted with zero to 1 $R_{3a}$ and zero to 2 $R_{3b}$. Compounds of this embodiment have the structure:

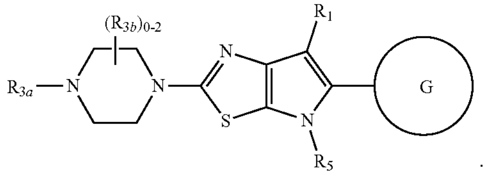

Included in this embodiment are compounds in which G is:

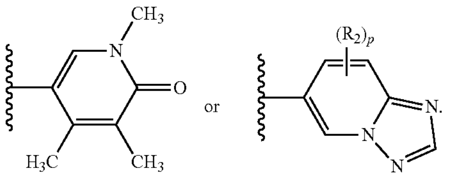

Also included in this embodiment are compounds in which $R_{3a}$ is —$CH_3$, —$CH_2CH_3$, —$CH_2CH_2CH_3$, —$CH(CH_3)_2$, —$CH_2CH(CH_3)_2$, —$CH_2C(CH_3)_3$, —$CH_2CH(CH_2CH_3)_2$, —$CH_2CF_3$, —$CH_2CN$, —$CH_2C(CH_3)_2OH$, —$CH_2CH_2OCH_3$, —$CH_2CH_2S(O)_2CH_3$, —$CH_2C(O)NR_xR_x$, —$C(O)CH_3$, —$C(O)CH_2N(CH_3)_2$, —$S(O)_2CH_3$, —$CH_2$(cyclopropyl), —$CH_2$(methyloxetanyl), —$CH_2$(tetrahydropyranyl), —C(O)(dioxidotetrahydrothiopyranyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, tetrahydropyranyl, oxazepanyl, or bicyclo[1.1.1]pentanyl.

One embodiment provides a compound of Formula (I), N-oxide, or a salt thereof wherein A is diazaspiro[3.3]heptanyl substituted with zero to 1 $R_{3a}$. Compounds of this embodiment have the structure:

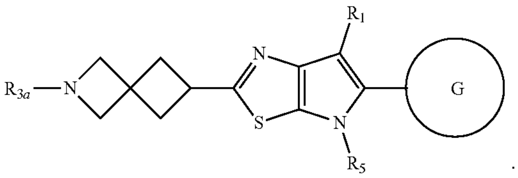

Included in this embodiment are compounds in which G is:

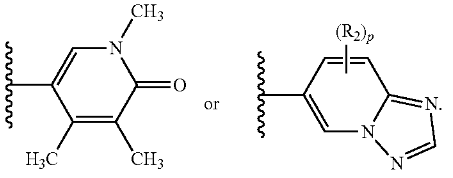

Also included in this embodiment are compounds in which $R_{3a}$ is —$CH_3$, —$CH_2CH_3$, —$CH_2CH_2CH_3$, —$CH(CH_3)_2$, —$CH_2CH(CH_3)_2$, —$CH_2C(CH_3)_3$, —$CH_2CH(CH_2CH_3)_2$, —$CH_2CF_3$, —$CH_2CN$, —$CH_2C(CH_3)_2OH$, —$CH_2CH_2OCH_3$, —$CH_2CH_2S(O)_2CH_3$, —$CH_2C(O)NR_xR_x$, —$C(O)CH_3$, —$C(O)CH_2N(CH_3)_2$, —$S(O)_2CH_3$, —$CH_2$(cyclopropyl), —$CH_2$(methyloxetanyl), —$CH_2$(tetrahydropyranyl), —C(O)(dioxidotetrahydrothiopyranyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, tetrahydropyranyl, oxazepanyl, or bicyclo[1.1.1]pentanyl.

One embodiment provides a compound of Formula (I), N-oxide, or a salt thereof wherein A is H, —$NR_yR_y$, or —$CH_2NHCH_2C(O)NR_xR_x$. Included in this embodiment are compounds in which A is H. Also included in this embodiment are compounds in which A is —$NR_yR_y$. Further, included in this embodiment are compound in which A is —$CH_2NHCH_2C(O)NR_xR_x$.

One embodiment provides a compound of Formula (I), N-oxide, or a salt thereof wherein A is —$CH_2R_3$, —$CH_2NHR_3$, or —$CH_2NHCH_2R_3$. Included in this embodiment are compounds in which G is:

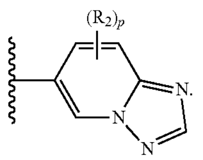

Also included in this embodiment are compounds in which $R_3$ is isopropylpiperidinyl, dioxidothiaazaspiro[3.3]heptanyl, oxaazaspiro[3.5]nonanyl, methylsulfonylcyclopropyl, piperazinonyl, morpholinyl, oxaazaspiro[3.3]heptanyl, or diazaspiro[3.3]heptanyl.

One embodiment provides a compound of Formula (I), N-oxide, or a salt thereof wherein A is —$C(O)NHR_3$ or —$C(O)NR_xR_4$. Included in this embodiment are compounds in which G is:

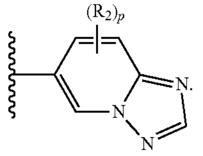

Also included in this embodiment are compounds in which $R_3$ is dimethylaminocyclohexyl, pyrrolidinyl, pyrrolidinonyl, morpholinyl, methylpiperidinyl, morpholinyl, or methylsulfonylcyclopropyl; and $R_4$ is H, —$CH_2CHF_2$, —$CH_2CF_3$, —$CH_2CH_2N(CH_3)_2$, —$CH_2R_3$, —$CH_2CR_xR_xR_3$, or —$(CH_2)_3R_3$.

One embodiment provides a compound of Formula (I), N-oxide, or a salt thereof wherein A is —$C(O)R_3$. Included in this embodiment are compounds in which G is:

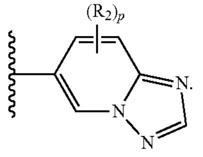

Also included in this embodiment are compounds in which $R_3$ is azetidinyl, fluoroazetidinyl, dimethylaminoazetidinyl, dioxidothiomorpholinyl, morpholinyl, oxazepanyl, oxetanyl, piperazinonyl, acetylpiperazinyl, isopropylpiperazinyl, methylsulfonylpiperazinyl, dimethylaminopiperidinyl, or pyrrolidinyl.

One embodiment provides a compound of Formula (I), N-oxide, or a salt thereof wherein A is cyclohexyl, piperidinyl, piperazinyl, methylpiperazinyl, dimethylpiperazinyl, or diazaspiro[3.3]heptanyl, each substituted with zero to 1 $R_{3a}$.

One embodiment provides a compound of Formula (I), N-oxide, or a salt thereof wherein:

G is:

(i)

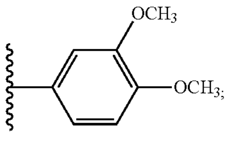 [SMILES: *c1ccc(OC)c(OC)c1]

(ii)

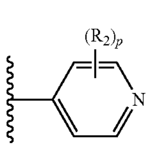

or

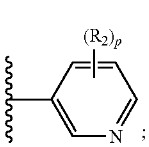

;

(iii)

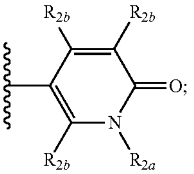

(iv) a 9-membered heterocyclic ring selected from:

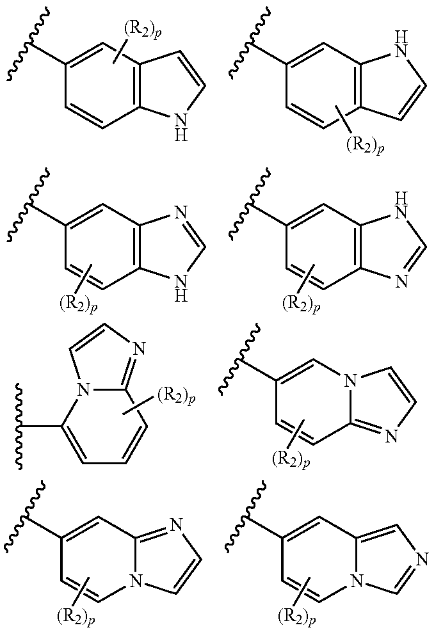

-continued
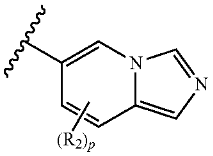 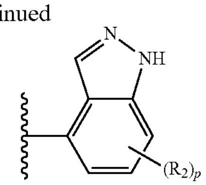
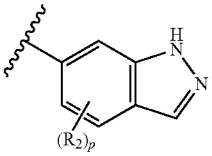 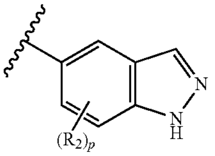
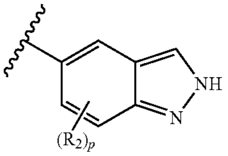 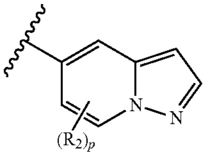
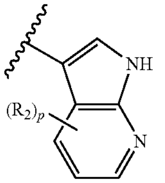 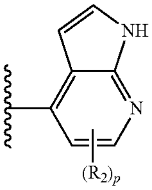 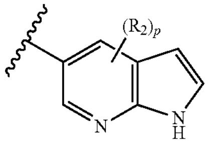
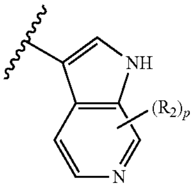 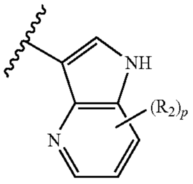 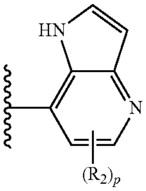
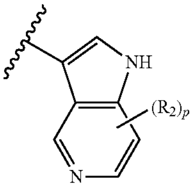 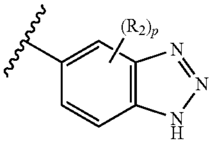
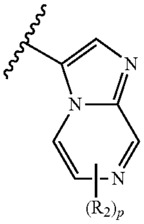 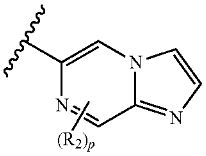 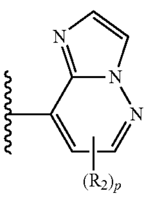
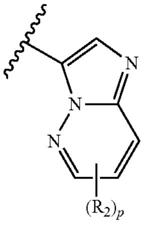 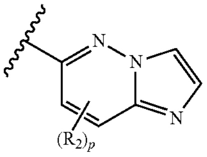 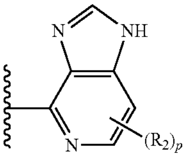
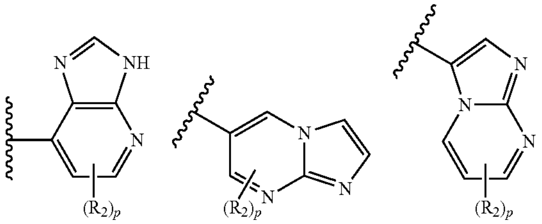
-continued
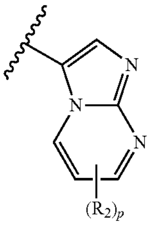 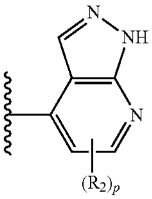 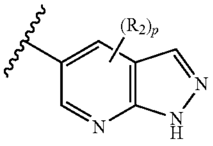
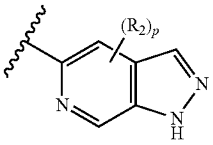 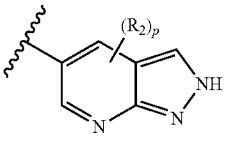
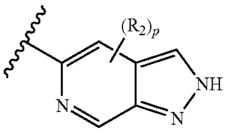 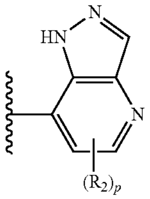
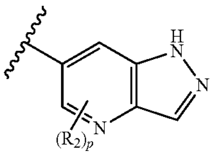 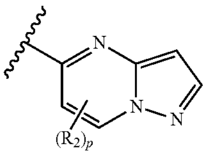
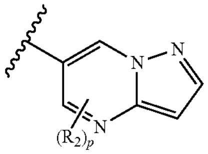 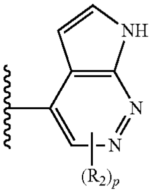
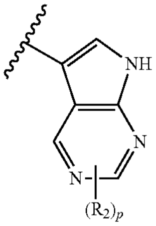 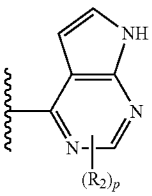 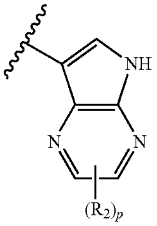
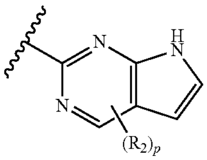 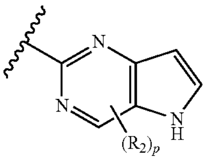 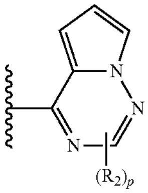
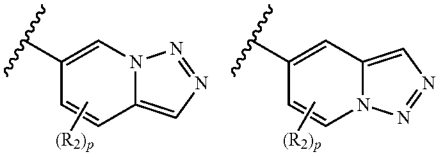
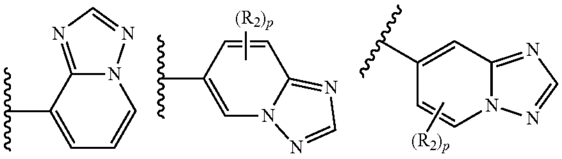

-continued

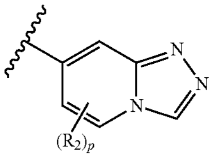 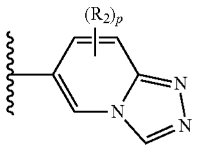

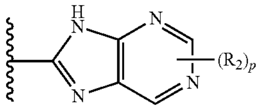 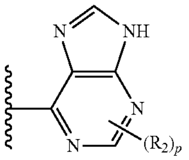

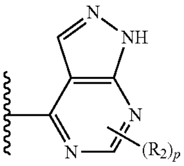 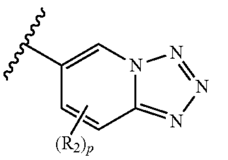

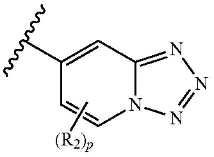 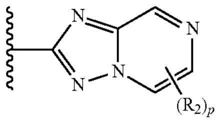

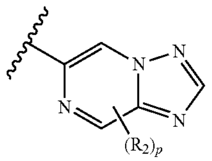 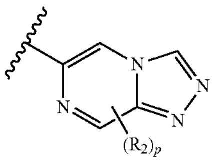

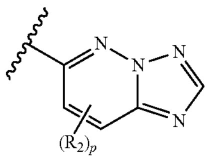 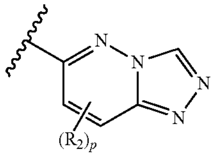

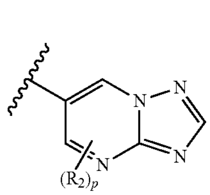 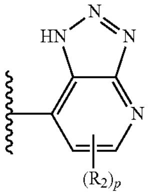 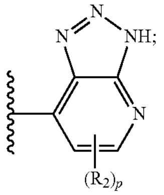

or (v) 10-membered heterocyclic ring selected from:

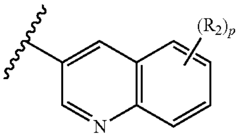 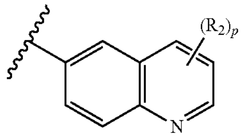

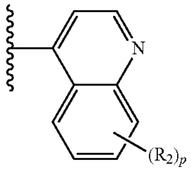 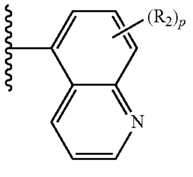

-continued

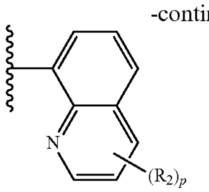 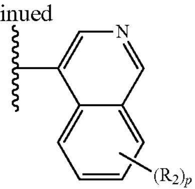

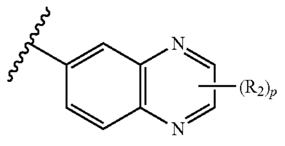 or 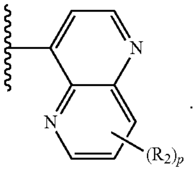 .

Included in this embodiment are compounds in which G is:

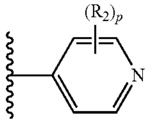 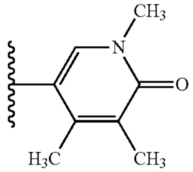 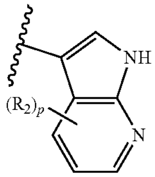

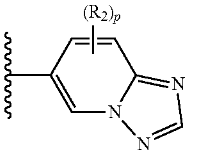 or 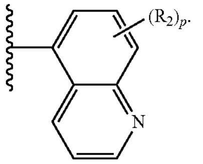

Also included in this embodiment are compounds in which G is

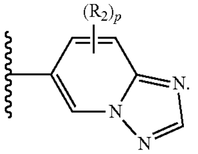

One embodiment provides a compound of Formula (I), N-oxide, or a salt thereof wherein each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, $—(CH_2)_{0-2}O(C_{1-3}$ alkyl), $C_{3-6}$ cycloalkyl, $—NR_xR_x$, $—(CH_2)_{0-2}C(O)NR_xR_x$, $—(CH_2)_{0-2}S(O)_2(C_{1-3}$ alkyl), $—CH_2(C_{3-6}$ cycloalkyl), $—CH_2$(phenyl), phenyl, pyrimidinyl, or triazolyl. Included in this embodiment are compounds in which each $R_2$ is independently —CN, $—CH_3$, or $—OCH_3$.

One embodiment provides a compound of Formula (I), N-oxide, or a salt thereof wherein $R_5$ is H, $—CH_3$, $—CH_2CH_3$, $—CF_3$, $—CH_2CHF_2$, or $—CH_2CF_3$. Included in this embodiment are compounds in which $R_5$ is H or $—CH_2CF_3$.

One embodiment provides a compound of Formula (I), N-oxide, or a salt thereof wherein $R_1$ is H, $—CH_3$, $—CH_2CH_3$, $—CH(CH_3)_2$, $—CF_3$, $—OCH_3$, or $—S(O)_2(C_{1-2}$ alkyl). Included in this embodiment are compounds in which $R_1$ is independently $—CH_3$, $—CH_2CH_3$, or $—CH(CH_3)_2$. Also included in this embodiment are compounds in which $R_1$ is $—CH(CH_3)_2$.

One embodiment provides a compound of Formula (I), N-oxide, or a salt thereof wherein $R_1$ is H, $—CH_3$, —$CH_2CH_3$, —$CH(CH_3)_2$, —$CF_3$, —$OCH_3$, or —$S(O)_2$ ($C_{1-2}$ alkyl); each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$(CH_2)_{0-2}S(O)_2(C_{1-3}$ alkyl), —$CH_2(C_{3-6}$ cycloalkyl), —$CH_2$(phenyl), phenyl, pyrimidinyl, or triazolyl; and $R_5$ is H, —$CH_3$, —$CH_2CH_3$, —$CF_3$, —$CH_2CHF_2$, or —$CH_2CF_3$.

One embodiment provides a compound of Formula (I), N-oxide, or a salt thereof wherein $R_1$ is independently —$CH_3$, —$CH_2CH_3$, or —$CH(CH_3)_2$; each $R_2$ is independently —CN, —$CH_3$, or —$OCH_3$; $R_5$ is H or —$CH_2CF_3$; and p is zero, 1, or 2.

One embodiment provides a compound of Formula (I), N-oxide, or a salt thereof wherein said compound is: 6-isopropyl-5-(8-methoxy-[1,2,4]triazolo[1,5-a]pyridin-6-yl)-2-(piperidin-4-yl)-4H-pyrrolo[3,2-d]thiazole (1); 6-isopropyl-5-(8-methyl-[1,2,4]triazolo[1,5-a]pyridin-6-yl)-2-(piperidin-4-yl)-4H-pyrrolo[3,2-d]thiazole (2); 6-isopropyl-5-(1-methyl-1H-pyrrolo[2,3-b]pyridin-3-yl)-2-(piperidin-4-yl)-4H-pyrrolo[3,2-d]thiazole (3); 5-(2,6-dimethylpyridin-4-yl)-6-isopropyl-2-(piperidin-4-yl)-4H-pyrrolo[3,2-d]thiazole (4); 5-(6-isopropyl-2-(piperidin-4-yl)-4H-pyrrolo[3,2-d]thiazol-5-yl)quinoline-8-carbonitrile (5); 2-(dimethylamino)-1-(4-(6-isopropyl-5-(8-methoxy-[1,2,4]triazolo[1,5-a]pyridin-6-yl)-4H-pyrrolo[3,2-d]thiazol-2-yl)piperidin-1-yl)ethan-1-one (6); 2-(4-(6-isopropyl-5-(8-methoxy-[1,2,4]triazolo[1,5-a]pyridin-6-yl)-4H-pyrrolo[3,2-d]thiazol-2-yl)piperidin-1-yl)-N,N-dimethylacetamide (7); 2-(4-(6-isopropyl-5-(8-methoxy-[1,2,4]triazolo[1,5-a]pyridin-6-yl)-4H-pyrrolo[3,2-d]thiazol-2-yl)piperidin-1-yl)-N-methylacetamide (8); 6-isopropyl-5-(8-methoxy-[1,2,4]triazolo[1,5-a]pyridin-6-yl)-4-(2,2,2-trifluoroethyl)-2-(1-(2,2,2-trifluoroethyl)piperidin-4-yl)-4H-pyrrolo[3,2-d]thiazole (9); 6-isopropyl-2-(1-isopropylpiperidin-4-yl)-5-(8-methoxy-[1,2,4]triazolo[1,5-a]pyridin-6-yl)-4H-pyrrolo[3,2-d]thiazole (10); 6-isopropyl-5-(8-methoxy-[1,2,4]triazolo[1,5-a]pyridin-6-yl)-2-(1-(oxetan-3-yl)piperidin-4-yl)-4H-pyrrolo[3,2-d]thiazole (11); 6-isopropyl-5-(8-methoxy-[1,2,4]triazolo[1,5-a]pyridin-6-yl)-2-(1-(tetrahydro-2H-pyran-4-yl)piperidin-4-yl)-4H-pyrrolo[3,2-d]thiazole (12); 6-isopropyl-5-(8-methoxy-[1,2,4]triazolo[1,5-a]pyridin-6-yl)-2-(1-neopentylpiperidin-4-yl)-4H-pyrrolo[3,2-d]thiazole (13); 6-isopropyl-5-(8-methoxy-[1,2,4]triazolo[1,5-a]pyridin-6-yl)-2-(1-((3-methyloxetan-3-yl)methyl) piperidin-4-yl)-4H-pyrrolo[3,2-d]thiazole (14); 1-(4-(6-isopropyl-5-(8-methoxy-[1,2,4]triazolo[1,5-a]pyridin-6-yl)-4H-pyrrolo[3,2-d]thiazol-2-yl)piperidin-1-yl)-2-methylpropan-2-ol (15); 6-isopropyl-5-(8-methoxy-[1,2,4]triazolo[1,5-a]pyridin-6-yl)-2-(1-(2-(methylsulfonyl)ethyl)piperidin-4-yl)-4H-pyrrolo[3,2-d]thiazole (16); 2-(4-(6-isopropyl-5-(8-methyl-[1,2,4]triazolo[1,5-a]pyridin-6-yl)-4H-pyrrolo[3,2-d]thiazol-2-yl) piperidin-1-yl)-N,N-dimethylacetamide (17); 1-(4-(6-isopropyl-5-(8-methyl-[1,2,4]triazolo[1,5-a]pyridin-6-yl)-4H-pyrrolo[3,2-d]thiazol-2-yl) piperidin-1-yl)-2-methylpropan-2-ol (18); 2-(dimethylamino)-1-(4-(6-isopropyl-5-(8-methyl-[1,2,4]triazolo[1,5-a]pyridin-6-yl)-4H-pyrrolo[3,2-d]thiazol-2-yl)piperidin-1-yl)ethan-1-one (19); 6-isopropyl-5-(8-methyl-[1,2,4]triazolo[1,5-a]pyridin-6-yl)-2-(1-(oxetan-3-yl) piperidin-4-yl)-4H-pyrrolo[3,2-d]thiazole (20); 6-isopropyl-2-(1-isopropylpiperidin-4-yl)-5-(8-methyl-[1,2,4]triazolo[1,5-a]pyridin-6-yl)-4H-pyrrolo[3,2-d]thiazole (21); 6-isopropyl-5-(8-methyl-[1,2,4]triazolo[1,5-a]pyridin-6-yl)-2-(1-(tetrahydro-2H-pyran-4-yl)piperidin-4-yl)-4H-pyrrolo[3,2-d]thiazole (22); 6-isopropyl-5-(8-methyl-[1,2,4]triazolo[1,5-a]pyridin-6-yl)-2-(1-((3-methyloxetan-3-yl)methyl)piperidin-4-yl)-4H-pyrrolo[3,2-d]thiazole (23); 2-(4-(5-(2,6-dimethylpyridin-4-yl)-6-isopropyl-4H-pyrrolo[3,2-d]thiazol-2-yl)piperidin-1-yl)-N,N-dimethylacetamide (24); 5-(2,6-dimethylpyridin-4-yl)-6-isopropyl-2-(1-isopropylpiperidin-4-yl)-4H-pyrrolo[3,2-d]thiazole (25); 5-(2,6-dimethylpyridin-4-yl)-6-isopropyl-2-(1-(tetrahydro-2H-pyran-4-yl) piperidin-4-yl)-4H-pyrrolo[3,2-d]thiazole (26); 5-(2,6-dimethylpyridin-4-yl)-6-isopropyl-2-(1-((3-methyloxetan-3-yl)methyl)piperidin-4-yl)-4H-pyrrolo[3,2-d]thiazole (27); 2-(dimethylamino)-1-(4-(5-(2,6-dimethylpyridin-4-yl)-6-isopropyl-4H-pyrrolo[3,2-d]thiazol-2-yl)piperidin-1-yl)ethan-1-one (28); 1-(4-(5-(2,6-dimethylpyridin-4-yl)-6-isopropyl-4H-pyrrolo[3,2-d]thiazol-2-yl)piperidin-1-yl)-2-methylpropan-2-ol (29); 2-(4-(6-isopropyl-5-(1-methyl-1H-pyrrolo[2,3-b]pyridin-3-yl)-4H-pyrrolo[3,2-d]thiazol-2-yl) piperidin-1-yl)-N,N-dimethylacetamide (30); 2-(4-(6-isopropyl-5-(1-methyl-1H-pyrrolo[2,3-b]pyridin-3-yl)-4H-pyrrolo[3,2-d]thiazol-2-yl) piperidin-1-yl) acetamide (31); 2-(dimethylamino)-1-(4-(6-isopropyl-5-(1-methyl-1H-pyrrolo[2,3-b]pyridin-3-yl)-4H-pyrrolo[3,2-d]thiazol-2-yl)piperidin-1-yl)ethan-1-one (32); 6-isopropyl-5-(1-methyl-1H-pyrrolo[2,3-b]pyridin-3-yl)-2-(1-(2-(methylsulfonyl)ethyl)piperidin-4-yl)-4H-pyrrolo[3,2-d]thiazole (33); 6-isopropyl-5-(1-methyl-1H-pyrrolo[2,3-b]pyridin-3-yl)-2-(1-(oxetan-3-yl)piperidin-4-yl)-4H-pyrrolo[3,2-d]thiazole (34); 6-isopropyl-5-(1-methyl-1H-pyrrolo[2,3-b]pyridin-3-yl)-2-(1-(tetrahydro-2H-pyran-4-yl)piperidin-4-yl)-4H-pyrrolo[3,2-d]thiazole (35); 6-isopropyl-2-(1-isopropylpiperidin-4-yl)-5-(1-methyl-1H-pyrrolo[2,3-b]pyridin-3-yl)-4H-pyrrolo[3,2-d]thiazole (36); 5-(6-isopropyl-2-(1-(oxetan-3-yl)piperidin-4-yl)-4H-pyrrolo[3,2-d]thiazol-5-yl)quinoline-8-carbonitrile (37); 5-(6-isopropyl-2-(1-(tetrahydro-2H-pyran-4-yl)piperidin-4-yl)-4H-pyrrolo[3,2-d]thiazol-5-yl) quinoline-8-carbonitrile (38); 5-(2-(1-(dimethylglycyl)piperidin-4-yl)-6-isopropyl-4H-pyrrolo[3,2-d]thiazol-5-yl)quinoline-8-carbonitrile (39); 2-(4-(5-(8-cyanoquinolin-5-yl)-6-isopropyl-4H-pyrrolo[3,2-d]thiazol-2-yl)piperidin-1-yl)-N,N-dimethylacetamide (40); 5-(7,8-dimethyl-[1,2,4]triazolo[1,5-a]pyridin-6-yl)-6-isopropyl-2-(1-(oxetan-3-yl) piperidin-4-yl)-4H-pyrrolo[3,2-d]thiazole (41); 5-(6-isopropyl-2-(piperidin-4-yl)-4H-pyrrolo[3,2-d]thiazol-5-yl)-1,3,4-trimethylpyridin-2 (1H)-one (42); 5-(7,8-dimethyl-[1,2,4]triazolo[1,5-a]pyridin-6-yl)-6-isopropyl-2-(1-(oxetan-3-yl)piperidin-4-yl)-4H-pyrrolo[3,2-d]thiazole (43); 5-(7,8-dimethyl-[1,2,4]triazolo[1,5-a]pyridin-6-yl)-6-isopropyl-2-(1-isopropylpiperidin-4-yl)-4H-pyrrolo[3,2-d]thiazole (44); 5-(7,8-dimethyl-[1,2,4]triazolo[1,5-a]pyridin-6-yl)-6-isopropyl-2-(1-(methylsulfonyl) piperidin-4-yl)-4H-pyrrolo[3,2-d]thiazole (45); 5-(7,8-dimethyl-[1,2,4]triazolo[1,5-a]pyridin-6-yl)-6-isopropyl-2-(1-(tetrahydro-2H-pyran-4-yl)piperidin-4-yl)-4H-pyrrolo[3,2-d]thiazole (46); 5-(7,8-dimethyl-[1,2,4]triazolo[1,5-a]pyridin-6-yl)-6-isopropyl-2-(1-((3-methyloxetan-3-yl) methyl)piperidin-4-yl)-4H-pyrrolo[3,2-d]thiazole (47); 5-(7,8-dimethyl-[1,2,4]triazolo[1,5-a]pyridin-6-yl)-6-isopropyl-2-(1-((tetrahydro-2H-pyran-4-yl)methyl) piperidin-4-yl)-4H-pyrrolo[3,2-d]thiazole (48); 5-(7,8-dimethyl-[1,2,4]triazolo[1,5-a]pyridin-6-yl)-6-isopropyl-2-(1-methylpiperidin-4-yl)-4H-pyrrolo[3,2-d]thiazole (49); 5-(7,8-dimethyl-[1,2,4]triazolo[1,5-a]pyridin-6-yl)-2-(1-ethylpiperidin-4-yl)-6-isopropyl-4H-pyrrolo[3,2-d]thiazole (50); 5-(7,8-dimethyl-[1,2,4]triazolo[1,5-a]pyridin-6-yl)-6-isopropyl-2-(1-propylpiperidin-4-yl)-4H-pyrrolo[3,2-d]thiazole (51); 5-(7,8-dimethyl-[1,2,4]triazolo[1,5-a]pyridin-6-yl)-2-(1-isobutylpiperidin-4-yl)-6-isopropyl-4H-pyrrolo[3,2-d]thiazole (52); 2-(1-(cyclopropylmethyl)piperidin-4-yl)-5-(7,8-dimethyl-[1,2,4]triazolo[1,5-a]pyridin-6-yl)-6-isopropyl-4H-pyrrolo[3,2-d]thiazole (53); 5-(7,8-dimethyl-

[1,2,4]triazolo[1,5-a]pyridin-6-yl)-2-(1-(2-ethylbutyl) piperidin-4-yl)-6-isopropyl-4H-pyrrolo[3,2-d]thiazole (54); 5-(7,8-dimethyl-[1,2,4]triazolo[1,5-a]pyridin-6-yl)-6-isopropyl-2-(1-(2-(methylsulfonyl)ethyl)piperidin-4-yl)-4H-pyrrolo[3,2-d]thiazole (55); 2-(4-(5-(7,8-dimethyl-[1,2,4] triazolo[1,5-a]pyridin-6-yl)-6-isopropyl-4H-pyrrolo[3,2-d] thiazol-2-yl) piperidin-1-yl)-N-methylacetamide (56); 2-(4-(5-(7,8-dimethyl-[1,2,4]triazolo[1,5-a]pyridin-6-yl)-6-isopropyl-4H-pyrrolo[3,2-d]thiazol-2-yl) piperidin-1-yl)-N,N-dimethylacetamide (57); 2-(4-(5-(7,8-dimethyl-[1,2,4] triazolo[1,5-a]pyridin-6-yl)-6-isopropyl-4H-pyrrolo[3,2-d] thiazol-2-yl)piperidin-1-yl)acetamide (58); 1-(4-(5-(7,8-dimethyl-[1,2,4]triazolo[1,5-a]pyridin-6-yl)-6-isopropyl-4H-pyrrolo[3,2-d]thiazol-2-yl)piperidin-1-yl)ethan-1-one (59); 5-(6-isopropyl-2-(1-(oxetan-3-yl)piperidin-4-yl)-4H-pyrrolo[3,2-d]thiazol-5-yl)-1,3,4-trimethylpyridin-2 (1H)-one (60); 5-(6-isopropyl-2-(1-(2-(methylsulfonyl)ethyl)piperidin-4-yl)-4H-pyrrolo[3,2-d]thiazol-5-yl)-1,3,4-trimethylpyridin-2 (1H)-one (61); 2-(4-(6-isopropyl-5-(1,4,5-trimethyl-6-oxo-1,6-dihydropyridin-3-yl)-4H-pyrrolo[3,2-d]thiazol-2-yl)piperidin-1-yl)-N,N-dimethylacetamide (62); 2-(4-(6-isopropyl-5-(1,4,5-trimethyl-6-oxo-1,6-dihydropyridin-3-yl)-4H-pyrrolo[3,2-d]thiazol-2-yl)piperidin-1-yl)-N-methylacetamide (63); or 2-(4-(6-isopropyl-5-(1,4,5-trimethyl-6-oxo-1,6-dihydropyridin-3-yl)-4H-pyrrolo[3,2-d]thiazol-2-yl)piperidin-1-yl)acetamide (64).

One embodiment provides a compound of Formula (I), N-oxide, or a salt thereof wherein said compound is: N-(4-(6-isopropyl-5-(8-methoxy-[1,2,4]triazolo[1,5-a]pyridin-6-yl)-4H-pyrrolo[3,2-d]thiazol-2-yl)cyclohexyl)oxetan-3-amine (65-66); (1-(4-(6-isopropyl-5-(8-methoxy-[1,2,4] triazolo[1,5-a]pyridin-6-yl)-4H-pyrrolo[3,2-d]thiazol-2-yl) cyclohexyl) azetidine-3,3-diyl)dimethanol (67); 6-(4-(6-isopropyl-5-(8-methoxy-[1,2,4]triazolo[1,5-a]pyridin-6-yl)-4H-pyrrolo[3,2-d]thiazol-2-yl)cyclohexyl)-2-oxa-6-azaspiro[3.3]heptane (68-69); N-(4-(6-isopropyl-5-(8-methoxy-[1,2,4]triazolo[1,5-a]pyridin-6-yl)-4H-pyrrolo[3,2-d]thiazol-2-yl)cyclohexyl)-3-methyloxetan-3-amine (70-71); N-ethyl-4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (72-73); 4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (74-75); 2-(4-(azetidin-1-yl)cyclohexyl)-6-isopropyl-5-(8-methoxy-[1,2,4]triazolo[1,5-a]pyridin-6-yl)-4H-pyrrolo[3,2-d]thiazole (76-77); N-isopropyl-4-(6-isopropyl-5-(8-methoxy-[1,2,4]triazolo[1,5-a]pyridin-6-yl)-4H-pyrrolo[3,2-d]thiazol-2-yl)cyclohexan-1-amine (78-79); 4-(4-(6-isopropyl-5-(8-methoxy-[1,2,4]triazolo[1,5-a]pyridin-6-yl)-4H-pyrrolo[3,2-d]thiazol-2-yl) cyclohexyl)thiomorpholine 1,1-dioxide (82-83); 1-((4-(6-isopropyl-5-(8-methoxy-[1,2,4]triazolo[1,5-a]pyridin-6-yl)-4H-pyrrolo[3,2-d]thiazol-2-yl)cyclohexyl)amino)-2-methylpropan-2-ol (84-85); 4-(6-isopropyl-5-(8-methoxy-[1,2,4]triazolo[1,5-a]pyridin-6-yl)-4H-pyrrolo[3,2-d]thiazol-2-yl)-N-(2-methoxy-2-methylpropyl) cyclohexan-1-amine (86-87); N-isopropyl-4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (88-89); (R)-3-fluoro-4-((4-(6-isopropyl-5-(8-methoxy-[1,2,4]triazolo[1,5-a]pyridin-6-yl)-4H-pyrrolo[3,2-d]thiazol-2-yl)cyclohexyl) amino)-2-methylbutan-2-ol (90-91); 4-(6-isopropyl-5-(8-methoxy-[1,2,4]triazolo[1,5-a]pyridin-6-yl)-4H-pyrrolo[3,2-d]thiazol-2-yl)cyclohexan-1-amine (92-93); 3-ethyl-N-(4-(6-isopropyl-5-(8-methoxy-[1,2,4]triazolo[1,5-a]pyridin-6-yl)-4H-pyrrolo[3,2-d]thiazol-2-yl) cyclohexyl)oxetan-3-amine (94-95); 6-(4-(6-isopropyl-5-(8-methoxy-[1,2,4]triazolo[1,5-a]pyridin-6-yl)-4H-pyrrolo[3,2-d]thiazol-2-yl)cyclohexyl)-2-thia-6-azaspiro[3.3]heptane 2,2-dioxide (96-97); 6-isopropyl-5-(8-methoxy-[1,2,4]triazolo[1,5-a]pyridin-6-yl)-2-(4-(pyrrolidin-1-yl)cyclohexyl)-4H-pyrrolo[3,2-d]thiazole (98-99); (R)—N-(1-(4-(6-isopropyl-5-(8-methoxy-[1,2,4]triazolo[1,5-a]pyridin-6-yl)-4H-pyrrolo[3,2-d]thiazol-2-yl)cyclohexyl) pyrrolidin-3-yl) acetamide (100-101); 4-(4-(6-isopropyl-5-(8-methoxy-[1,2,4]triazolo[1,5-a]pyridin-6-yl)-4H-pyrrolo[3,2-d]thiazol-2-yl)cyclohexyl)-1,4-oxazepane (102-103); (1R,5S)-8-(4-(6-isopropyl-5-(8-methoxy-[1,2,4]triazolo[1,5-a]pyridin-6-yl)-4H-pyrrolo[3,2-d]thiazol-2-yl)cyclohexyl)-3-oxa-8-azabicyclo[3.2.1]octane (104-105); 1-((4-(6-isopropyl-5-(8-methoxy-[1,2,4]triazolo[1,5-a]pyridin-6-yl)-4H-pyrrolo[3,2-d]thiazol-2-yl)cyclohexyl) amino)cyclopropane-1-carbonitrile (106-107); 4-(6-isopropyl-5-(8-methoxy-[1,2,4] triazolo[1,5-a]pyridin-6-yl)-4H-pyrrolo[3,2-d]thiazol-2-yl)-N-(1-methylcyclobutyl) cyclohexan-1-amine (108-109); 2-(4-(6-isopropyl-5-(8-methoxy-[1,2,4]triazolo[1,5-a]pyridin-6-yl)-4H-pyrrolo[3,2-d]thiazol-2-yl)cyclohexyl)-7-oxa-2-azaspiro[3.5]nonane (110-111); 7-(4-(6-isopropyl-5-(8-methoxy-[1,2,4]triazolo[1,5-a]pyridin-6-yl)-4H-pyrrolo[3,2-d]thiazol-2-yl)cyclohexyl)-2-oxa-7-azaspiro[3.5]nonane (112-113); 2-(4-(2,7-diazaspiro[4.4]nonan-2-yl)cyclohexyl)-6-isopropyl-5-(8-methoxy-[1,2,4]triazolo[1,5-a] pyridin-6-yl)-4H-pyrrolo[3,2-d]thiazole (114-115); N-(4-(6-isopropyl-5-(8-methoxy-[1,2,4]triazolo[1,5-a]pyridin-6-yl)-4H-pyrrolo[3,2-d]thiazol-2-yl)cyclohexyl)-2-azaspiro[3.3] heptan-6-amine (116-117); 1-(4-(6-isopropyl-5-(8-methoxy-[1,2,4]triazolo[1,5-a]pyridin-6-yl)-4H-pyrrolo[3,2-d] thiazol-2-yl)cyclohexyl)-3-(trifluoromethyl)azetidin-3-ol (118-119); 4-(4-(6-isopropyl-5-(8-methoxy-[1,2,4]triazolo [1,5-a]pyridin-6-yl)-4H-pyrrolo[3,2-d]thiazol-2-yl)cyclohexyl) piperazin-2-one (120-121); 6-isopropyl-5-(8-methoxy-[1,2,4]triazolo[1,5-a]pyridin-6-yl)-2-(4-(3-methoxyazetidin-1-yl)cyclohexyl)-4H-pyrrolo[3,2-d] thiazole (122-123); N-(4-(6-isopropyl-5-(8-methoxy-[1,2,4] triazolo[1,5-a]pyridin-6-yl)-4H-pyrrolo[3,2-d]thiazol-2-yl) cyclohexyl)-N-methyloxetan-3-amine (124-125); 2-(dimethylamino)-N-(4-(6-isopropyl-5-(8-methoxy-[1,2,4] triazolo[1,5-a]pyridin-6-yl)-4H-pyrrolo[3,2-d]thiazol-2-yl) cyclohexyl)acetamide (126); N-(4-(6-isopropyl-5-(8-methoxy-[1,2,4]triazolo[1,5-a]pyridin-6-yl)-4H-pyrrolo[3,2-d]thiazol-2-yl)cyclohexyl) methanesulfonamide (127); trans 2-(ethyl(methyl)amino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (128); 2-(isobutylamino)-N-(4-(6-isopropyl-5-(8-methoxy-[1,2,4]triazolo[1,5-a]pyridin-6-yl)-4H-pyrrolo[3,2-d]thiazol-2-yl) cyclohexyl)acetamide (129); N-(4-(6-isopropyl-5-(8-methyl-[1,2,4]triazolo[1,5-a]pyridin-6-yl)-4H-pyrrolo[3,2-d]thiazol-2-yl)cyclohexyl)oxetan-3-amine (130-131); N-ethyl-4-(6-isopropyl-5-(8-methyl-[1,2,4]triazolo[1,5-a] pyridin-6-yl)-4H-pyrrolo[3,2-d]thiazol-2-yl)-N-methylcyclohexan-1-amine (132); 4-(6-isopropyl-5-(8-methyl-[1,2,4] triazolo[1,5-a]pyridin-6-yl)-4H-pyrrolo[3,2-d]thiazol-2-yl)-N-((3-methyloxetan-3-yl) methyl)cyclohexan-1-amine (134-135); 6-(4-(6-isopropyl-5-(8-methyl-[1,2,4]triazolo[1,5-a]pyridin-6-yl)-4H-pyrrolo[3,2-d]thiazol-2-yl)cyclohexyl)-2-oxa-6-azaspiro[3.3]heptane (136-137); N-(4-(6-isopropyl-5-(8-methyl-[1,2,4]triazolo[1,5-a]pyridin-6-yl)-4H-pyrrolo[3,2-d]thiazol-2-yl)cyclohexyl)bicyclo[1.1.1] pentan-1-amine (138-139); 1-((4-(6-isopropyl-5-(8-methyl-[1,2,4]triazolo[1,5-a]pyridin-6-yl)-4H-pyrrolo[3,2-d] thiazol-2-yl)cyclohexyl)amino)-2-methylpropan-2-ol (140-141); (1-(((4-(6-isopropyl-5-(8-methyl-[1,2,4]triazolo[1,5-a]pyridin-6-yl)-4H-pyrrolo[3,2-d]thiazol-2-yl)cyclohexyl) amino)methyl)cyclopropyl)methanol (142-143); N-(4-(6-isopropyl-5-(7-methyl-[1,2,4]triazolo[1,5-a]pyridin-6-yl)-4H-pyrrolo[3,2-d]thiazol-2-yl)cyclohexyl)-3-methyloxetan-3-amine (144-145); 4-(4-(6-isopropyl-5-(7-methyl-[1,2,4]triazolo[1,5-a]pyridin-6-yl)-4H-pyrrolo[3,2-d]thiazol-2-yl)cyclohexyl)-1,4-oxazepane (146-147); 4-(4-(6-isopropyl-5-(7-methyl-[1,2,4]triazolo[1,5-a]pyridin-6-yl)-4H-pyrrolo[3,2-d]thiazol-2-yl)cyclohexyl)piperazin-2-one (148-149); 6-isopropyl-2-(4-(3-methoxyazetidin-1-yl) cyclohexyl)-5-(7-methyl-[1,2,4]triazolo[1,5-a]pyridin-6-yl)-4H-pyrrolo[3,2-d]thiazole (150-151); N-(4-(6-isopropyl-5-(7-methyl-[1,2,4]triazolo[1,5-a]pyridin-6-yl)-4H-pyrrolo[3,2-d]thiazol-2-yl)cyclohexyl)oxetan-3-amine (152-153); 6-isopropyl-5-(7-methyl-[1,2,4]triazolo[1,5-a]pyridin-6-yl)-2-(4-(pyrrolidin-1-yl)cyclohexyl)-4H-pyrrolo[3,2-d]thiazole (154-155); 1-((4-(6-isopropyl-5-(7-methyl-[1,2,4]triazolo[1,5-a]pyridin-6-yl)-4H-pyrrolo[3,2-d]thiazol-2-yl)cyclohexyl) amino)-2-methylpropan-2-ol (156-157); N-isopropyl-4-(6-isopropyl-5-(7-methyl-[1,2,4]triazolo[1,5-a]pyridin-6-yl)-4H-pyrrolo[3,2-d]thiazol-2-yl)-N-methylcyclohexan-1-amine (158-159); N-(4-(6-isopropyl-5-(7-methyl-[1,2,4]triazolo[1,5-a]pyridin-6-yl)-4H-pyrrolo[3,2-d]thiazol-2-yl)cyclohexyl) tetrahydro-2H-pyran-4-amine (160-161); 2-((4-(6-isopropyl-5-(8-methoxy-[1,2,4]triazolo[1,5-a]pyridin-6-yl)-4H-pyrrolo[3,2-d]thiazol-2-yl)cyclohexyl)(methyl) amino)-N,N-dimethylacetamide (162-163); 4-(6-isopropyl-5-(8-methoxy-[1,2,4]triazolo[1,5-a]pyridin-6-yl)-4H-pyrrolo[3,2-d]thiazol-2-yl)-N-methyl-N-(2-(methylsulfonyl) ethyl) cyclohexan-1-amine (164-165); 1-isopropyl-N-(4-(6-isopropyl-5-(8-methoxy-[1,2,4]triazolo[1,5-a]pyridin-6-yl)-4H-pyrrolo[3,2-d]thiazol-2-yl)cyclohexyl)piperidin-4-amine (166-167); N-(4-(6-isopropyl-5-(8-methoxy-[1,2,4]triazolo[1,5-a]pyridin-6-yl)-4H-pyrrolo[3,2-d]thiazol-2-yl)cyclohexyl)bicyclo[1.1.1]pentan-1-amine (168-169); N1-(4-(6-isopropyl-5-(8-methoxy-[1,2,4]triazolo[1,5-a]pyridin-6-yl)-4H-pyrrolo[3,2-d]thiazol-2-yl) cyclohexyl)-N2-methylethane-1,2-diamine (170-171); 4-(6-isopropyl-5-(1-methyl-1H-pyrrolo[2,3-b]pyridin-3-yl)-4H-pyrrolo[3,2-d]thiazol-2-yl)-N-((3-methyloxetan-3-yl)methyl) cyclohexan-1-amine (172-173); N-ethyl-4-(6-isopropyl-5-(1-methyl-1H-pyrrolo[2,3-b]pyridin-3-yl)-4H-pyrrolo[3,2-d]thiazol-2-yl)-N-methylcyclohexan-1-amine (174-175); N-(4-(6-isopropyl-5-(1-methyl-1H-pyrrolo[2,3-b]pyridin-3-yl)-4H-pyrrolo[3,2-d]thiazol-2-yl) cyclohexyl)bicyclo[1.1.1]pentan-1-amine (176-177); N-(4-(6-isopropyl-5-(1-methyl-1H-pyrrolo[2,3-b]pyridin-3-yl)-4H-pyrrolo[3,2-d]thiazol-2-yl)cyclohexyl)oxetan-3-amine (178-179); 6-(4-(6-isopropyl-5-(1-methyl-1H-pyrrolo[2,3-b]pyridin-3-yl)-4H-pyrrolo[3,2-d]thiazol-2-yl)cyclohexyl)-2-oxa-6-azaspiro[3.3]heptane (180-181); 1-((4-(6-isopropyl-5-(1-methyl-1H-pyrrolo[2,3-b]pyridin-3-yl)-4H-pyrrolo[3,2-d]thiazol-2-yl) cyclohexyl)amino)-2-methylpropan-2-ol (182-183); N-(4-(5-(7,8-dimethyl-[1,2,4]triazolo[1,5-a]pyridin-6-yl)-6-isopropyl-4H-pyrrolo[3,2-d]thiazol-2-yl)cyclohexyl) oxetan-3-amine (184-185); 4-(5-(7,8-dimethyl-[1,2,4]triazolo[1,5-a]pyridin-6-yl)-6-isopropyl-4H-pyrrolo[3,2-d]thiazol-2-yl)-N-(2-methoxy-2-methylpropyl)cyclohexan-1-amine (186-187); 5-(7,8-dimethyl-[1,2,4]triazolo[1,5-a]pyridin-6-yl)-6-isopropyl-2-(4-(3-methoxyazetidin-1-yl) cyclohexyl)-4H-pyrrolo[3,2-d]thiazole (188-189); 4-(5-(7,8-dimethyl-[1,2,4]triazolo[1,5-a]pyridin-6-yl)-6-isopropyl-4H-pyrrolo[3,2-d]thiazol-2-yl)-N-ethyl-N-methylcyclohexan-1-amine (190-191); 6-(4-(5-(7,8-dimethyl-[1,2,4]triazolo[1,5-a]pyridin-6-yl)-6-isopropyl-4H-pyrrolo[3,2-d]thiazol-2-yl)cyclohexyl)-2-oxa-6-azaspiro[3.3]heptane (192-193); 4-(5-(7,8-dimethyl-[1,2,4]triazolo[1,5-a]pyridin-6-yl)-6-isopropyl-4H-pyrrolo[3,2-d]thiazol-2-yl)-N-isopropylcyclohexan-1-amine (194-195); 1-((4-(5-(7,8-dimethyl-[1,2,4]triazolo[1,5-a]pyridin-6-yl)-6-isopropyl-4H-pyrrolo[3,2-d]thiazol-2-yl)cyclohexyl) amino)-2-methylpropan-2-ol (196-197); 4-(5-(7,8-dimethyl-[1,2,4]triazolo[1,5-a]pyridin-6-yl)-6-isopropyl-4H-pyrrolo[3,2-d]thiazol-2-yl)-N-neopentylcyclohexan-1-amine (198-199); N-(4-(5-(7,8-dimethyl-[1,2,4]triazolo[1,5-a]pyridin-6-yl)-6-isopropyl-4H-pyrrolo[3,2-d]thiazol-2-yl)cyclohexyl)tetrahydro-2H-pyran-4-amine (200-201); 4-(5-(7,8-dimethyl-[1,2,4]triazolo[1,5-a]pyridin-6-yl)-6-isopropyl-4H-pyrrolo[3,2-d]thiazol-2-yl)-N-((1-methylcyclobutyl)methyl)cyclohexan-1-amine (202-203); 2-((4-(5-(7,8-dimethyl-[1,2,4]triazolo[1,5-a]pyridin-6-yl)-6-isopropyl-4H-pyrrolo[3,2-d]thiazol-2-yl)cyclohexyl) amino)-N,N-dimethylacetamide (204-205); 2-((4-(5-(7,8-dimethyl-[1,2,4]triazolo[1,5-a]pyridin-6-yl)-6-isopropyl-4H-pyrrolo[3,2-d]thiazol-2-yl) cyclohexyl)amino)-1-morpholinoethan-1-one (206-207); 2-((4-(5-(7,8-dimethyl-[1,2,4]triazolo[1,5-a]pyridin-6-yl)-6-isopropyl-4H-pyrrolo[3,2-d]thiazol-2-yl)cyclohexyl) amino)-N-methylacetamide (208-209); 2-((4-(5-(7,8-dimethyl-[1,2,4]triazolo[1,5-a]pyridin-6-yl)-6-isopropyl-4H-pyrrolo[3,2-d]thiazol-2-yl)cyclohexyl)amino)acetamide (210-211); 4-(4-(5-(7,8-dimethyl-[1,2,4]triazolo[1,5-a]pyridin-6-yl)-6-isopropyl-4H-pyrrolo[3,2-d]thiazol-2-yl)cyclohexyl) morpholine (212-213); 4-(5-(7,8-dimethyl-[1,2,4]triazolo[1,5-a]pyridin-6-yl)-6-isopropyl-4H-pyrrolo[3,2-d]thiazol-2-yl)-N-((1-(methylsulfonyl)cyclopropyl)methyl) cyclohexan-1-amine (214-215); 2-(4-(azetidin-1-yl)cyclohexyl)-5-(7,8-dimethyl-[1,2,4]triazolo[1,5-a]pyridin-6-yl)-6-isopropyl-4H-pyrrolo[3,2-d]thiazole (216-217); 2-(4-(3,3-difluoroazetidin-1-yl)cyclohexyl)-5-(7,8-dimethyl-[1,2,4]triazolo[1,5-a]pyridin-6-yl)-6-isopropyl-4H-pyrrolo[3,2-d]thiazole (218-219); 4-(4-(5-(7,8-dimethyl-[1,2,4]triazolo[1,5-a]pyridin-6-yl)-6-isopropyl-4H-pyrrolo[3,2-d]thiazol-2-yl)cyclohexyl) piperazin-2-one (220-221); 4-(5-(7,8-dimethyl-[1,2,4]triazolo[1,5-a]pyridin-6-yl)-6-isopropyl-4H-pyrrolo[3,2-d]thiazol-2-yl)-N-isopropyl-N-methylcyclohexan-1-amine (222-223); 1-(4-(5-(7,8-dimethyl-[1,2,4]triazolo[1,5-a]pyridin-6-yl)-6-isopropyl-4H-pyrrolo[3,2-d]thiazol-2-yl)cyclohexyl)azetidin-3-ol (224-225); 5-(7,8-dimethyl-[1,2,4]triazolo[1,5-a]pyridin-6-yl)-2-(4-(3-fluoroazetidin-1-yl) cyclohexyl)-6-isopropyl-4H-pyrrolo[3,2-d]thiazole (226-227); 4-(5-(7,8-dimethyl-[1,2,4]triazolo[1,5-a]pyridin-6-yl)-6-isopropyl-4H-pyrrolo[3,2-d]thiazol-2-yl)-N-isobutyl-N-methylcyclohexan-1-amine (228-229); 3-((4-(5-(7,8-dimethyl-[1,2,4]triazolo[1,5-a]pyridin-6-yl)-6-isopropyl-4H-pyrrolo[3,2-d]thiazol-2-yl)cyclohexyl)amino)tetrahydrothiophene 1,1-dioxide (230-232); 6-(4-(5-(7,8-dimethyl-[1,2,4]triazolo[1,5-a]pyridin-6-yl)-6-isopropyl-4H-pyrrolo[3,2-d]thiazol-2-yl)cyclohexyl)-2-thia-6-azaspiro[3.3]heptane 2,2-dioxide (233-234); 1-(4-(5-(7,8-dimethyl-[1,2,4]triazolo[1,5-a]pyridin-6-yl)-6-isopropyl-4H-pyrrolo[3,2-d]thiazol-2-yl)cyclohexyl)-3-(trifluoromethyl)azetidin-3-ol (235-236); 7-(4-(5-(7,8-dimethyl-[1,2,4]triazolo[1,5-a]pyridin-6-yl)-6-isopropyl-4H-pyrrolo[3,2-d]thiazol-2-yl) cyclohexyl)-2-oxa-7-azaspiro[3.5]nonane (237-238); 2-(4-(5-(7,8-dimethyl-[1,2,4]triazolo[1,5-a]pyridin-6-yl)-6-isopropyl-4H-pyrrolo[3,2-d]thiazol-2-yl) cyclohexyl)-7-oxa-2-azaspiro[3.5]nonane (239-240); 5-(6-isopropyl-2-(4-(oxetan-3-ylamino)cyclohexyl)-4H-pyrrolo[3,2-d]thiazol-5-yl)-1,3,4-trimethylpyridin-2 (1H)-one (241-242); 5-(6-isopropyl-2-(4-((2-methoxy-2-methylpropyl)amino)cyclohexyl)-4H-pyrrolo[3,2-d]thiazol-5-yl)-1,3,4-trimethylpyridin-2 (1H)-one (243-244); 5-(2-(4-(2-oxa-6-azaspiro[3.3]heptan-6-yl) cyclohexyl)-6-isopropyl-4H-pyrrolo[3,2-d]thiazol-5-yl)-1,3,4-trimethylpyridin-2 (1H)-one (245-246); 5-(2-(4-(ethyl (methyl)amino)cyclohexyl)-6-isopropyl-4H-pyrrolo[3,2-d]

thiazol-5-yl)-1,3,4-trimethylpyridin-2 (1H)-one (247-248); 5-(6-isopropyl-2-(4-((tetrahydro-2H-pyran-4-yl) amino)cyclohexyl)-4H-pyrrolo[3,2-d]thiazol-5-yl)-1,3,4-trimethylpyridin-2 (1H)-one (249-250); 5-(2-(4-((2-hydroxy-2-methylpropyl)amino)cyclohexyl)-6-isopropyl-4H-pyrrolo [3,2-d]thiazol-5-yl)-1,3,4-trimethylpyridin-2 (1H)-one (251-252); 5-(6-isopropyl-2-(4-(isopropylamino)cyclohexyl)-4H-pyrrolo[3,2-d]thiazol-5-yl)-1,3,4-trimethylpyridin-2 (1H)-one (253-254); 5-(2-(4-(azetidin-1-yl)cyclohexyl)-6-isopropyl-4H-pyrrolo[3,2-d]thiazol-5-yl)-1,3,4-trimethylpyridin-2 (1H)-one (255-256); 5-(6-isopropyl-2-(4-(((1-(methylsulfonyl) cyclopropyl)methyl)amino) cyclohexyl)-4H-pyrrolo[3,2-d]thiazol-5-yl)-1,3,4-trimethylpyridin-2 (1H)-one (257-258); 4-(4-(6-isopropyl-5-(1,4,5-trimethyl-6-oxo-1,6-dihydropyridin-3-yl)-4H-pyrrolo[3,2-d]thiazol-2-yl)cyclohexyl)piperazin-2-one (259-260); 5-(6-isopropyl-2-(4-(isopropyl(methyl)amino) cyclohexyl)-4H-pyrrolo[3,2-d]thiazol-5-yl)-1,3,4-trimethylpyridin-2 (1H)-one (261-262); 5-(2-(4-(3-hydroxyazetidin-1-yl)cyclohexyl)-6-isopropyl-4H-pyrrolo[3,2-d]thiazol-5-yl)-1,3,4-trimethylpyridin-2 (1H)-one (263-264); 5-(2-(4-(3-fluoroazetidin-1-yl)cyclohexyl)-6-isopropyl-4H-pyrrolo [3,2-d]thiazol-5-yl)-1,3,4-trimethylpyridin-2 (1H)-one (265-266); 5-(2-(4-(3-hydroxy-3-(trifluoromethyl)azetidin-1-yl) cyclohexyl)-6-isopropyl-4H-pyrrolo[3,2-d]thiazol-5-yl)-1,3,4-trimethylpyridin-2 (1H)-one (267-268); 6-(4-(6-ethyl-5-(8-methoxy-[1,2,4]triazolo[1,5-a]pyridin-6-yl)-4H-pyrrolo[3,2-d]thiazol-2-yl)cyclohexyl)-2-oxa-6-azaspiro [3.3]heptane (269-270); N-(4-(6-ethyl-5-(8-methoxy-[1,2,4] triazolo[1,5-a]pyridin-6-yl)-4H-pyrrolo[3,2-d]thiazol-2-yl) cyclohexyl) oxetan-3-amine (271-272); N-(4-(5-(8-methoxy-[1,2,4]triazolo[1,5-a]pyridin-6-yl)-6-methyl-4H-pyrrolo[3,2-d]thiazol-2-yl)cyclohexyl)oxetan-3-amine (273); or 4-(4-(5-(8-methoxy-[1,2,4]triazolo[1,5-a]pyridin-6-yl)-6-methyl-4H-pyrrolo[3,2-d]thiazol-2-yl)cyclohexyl) piperazin-2-one (275-276).

One embodiment provides a compound of Formula (I), N-oxide, or a salt thereof wherein said compound is: 5-(7,8-dimethyl-[1,2,4]triazolo[1,5-a]pyridin-6-yl)-6-isopropyl-2-(piperazin-1-yl)-4H-pyrrolo[3,2-d]thiazole (278); 5-(6-isopropyl-2-(piperazin-1-yl)-4H-pyrrolo[3,2-d]thiazol-5-yl)-1,3,4-trimethylpyridin-2 (1H)-one (279); 1-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-2-(dimethylamino)ethan-1-one (280); 1-(4-(5-(7,8-dimethyl-[1,2,4]triazolo[1,5-a]pyridin-6-yl)-6-isopropyl-4H-pyrrolo [3,2-d]thiazol-2-yl)piperazin-1-yl)-2-methylpropan-2-ol (281); 5-(7,8-dimethyl-[1,2,4]triazolo[1,5-a]pyridin-6-yl)-6-isopropyl-2-(4-(2-(methylsulfonyl) ethyl)piperazin-1-yl)-4H-pyrrolo[3,2-d]thiazole (282); 2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-N,N-dimethylacetamide (283); 2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-N-methylacetamide (284); 2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)acetamide (285); 5-(7,8-dimethyl-[1,2,4]triazolo[1,5-a]pyridin-6-yl)-6-isopropyl-2-(4-(oxetan-3-yl)piperazin-1-yl)-4H-pyrrolo[3,2-d]thiazole (286); 5-(7,8-dimethyl-[1,2,4]triazolo[1,5-a]pyridin-6-yl)-6-isopropyl-2-(4-(tetrahydro-2H-pyran-4-yl)piperazin-1-yl)-4H-pyrrolo[3,2-d]thiazole (287); 5-(7,8-dimethyl-[1,2,4] triazolo[1,5-a]pyridin-6-yl)-6-isopropyl-2-(4-isopropylpiperazin-1-yl)-4H-pyrrolo[3,2-d]thiazole (288); 5-(7,8-dimethyl-[1,2,4]triazolo[1,5-a]pyridin-6-yl)-6-isopropyl-2-(4-((3-methyloxetan-3-yl)methyl) piperazin-1-yl)-4H-pyrrolo[3,2-d]thiazole (289); (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole, HCl (308); 5-(7,8-dimethyl-[1,2,4]triazolo[1,5-a]pyridin-6-yl)-2-((2S,5R)-2,5-dimethylpiperazin-1-yl)-6-isopropyl-4H-pyrrolo[3,2-d]thiazole (309); (S)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (310); (R)-6-isopropyl-5-(8-methyl-[1,2,4]triazolo[1,5-a]pyridin-6-yl)-2-(2-methylpiperazin-1-yl)-4H-pyrrolo[3,2-d]thiazole (311); (R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N,N-dimethylacetamide (312); (R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)acetamide (313); (R)-5-(7,8-dimethyl-[1,2,4]triazolo[1,5-a]pyridin-6-yl)-6-isopropyl-2-(2-methyl-4-(2-(methylsulfonyl)ethyl)piperazin-1-yl)-4H-pyrrolo[3,2-d]thiazole (314); (R)-2-(4-(5-(7,8-dimethyl-[1,2,4]triazolo [1,5-a]pyridin-6-yl)-6-isopropyl-4H-pyrrolo[3,2-d]thiazol-2-yl)-3-methylpiperazin-1-yl)-N-methylacetamide (315); (R)-5-(7,8-dimethyl-[1,2,4]triazolo[1,5-a]pyridin-6-yl)-6-isopropyl-2-(2-methyl-4-(oxetan-3-yl) piperazin-1-yl)-4H-pyrrolo[3,2-d]thiazole (316); (R)-5-(7,8-dimethyl-[1,2,4]triazolo[1,5-a]pyridin-6-yl)-6-isopropyl-2-(2-methyl-4-((tetrahydro-2H-pyran-4-yl)methyl)piperazin-1-yl)-4H-pyrrolo[3,2-d]thiazole (317); (R)-5-(7,8-dimethyl-[1,2,4] triazolo[1,5-a]pyridin-6-yl)-6-isopropyl-2-(2-methyl-4-(tetrahydro-2H-pyran-4-yl)piperazin-1-yl)-4H-pyrrolo[3,2-d]thiazole (318); (R)-5-(7,8-dimethyl-[1,2,4]triazolo[1,5-a] pyridin-6-yl)-2-(2,4-dimethylpiperazin-1-yl)-6-isopropyl-4H-pyrrolo[3,2-d]thiazole (319); (R)-5-(7,8-dimethyl-[1,2,4]triazolo[1,5-a]pyridin-6-yl)-2-(4-ethyl-2-methylpiperazin-1-yl)-6-isopropyl-4H-pyrrolo[3,2-d] thiazole (320); (R)-2-(4-(cyclopropylmethyl)-2-methylpiperazin-1-yl)-5-(7,8-dimethyl-[1,2,4]triazolo[1,5-a]pyridin-6-yl)-6-isopropyl-4H-pyrrolo[3,2-d]thiazole (321); (R)-2-(4-cyclobutyl-2-methylpiperazin-1-yl)-5-(7,8-dimethyl-[1,2,4]triazolo[1,5-a]pyridin-6-yl)-6-isopropyl-4H-pyrrolo[3,2-d]thiazole (322); (R)-5-(7,8-dimethyl-[1,2,4]triazolo[1,5-a]pyridin-6-yl)-6-isopropyl-2-(4-(1-isopropylpiperidin-4-yl)-2-methylpiperazin-1-yl)-4H-pyrrolo[3,2-d]thiazole (323); (R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol (325); (R)-1-(4-(5-(7,8-dimethyl-[1,2,4]triazolo[1,5-a] pyridin-6-yl)-6-isopropyl-4H-pyrrolo[3,2-d]thiazol-2-yl)-3-methylpiperazin-1-yl)-2-(methylamino)ethan-1-one (326); (R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(dimethylamino)ethan-1-one (327); 2-((2S,5R)-2,5-dimethyl-4-(oxetan-3-yl)piperazin-1-yl)-5-(7,8-dimethyl-[1,2,4]triazolo[1,5-a]pyridin-6-yl)-6-isopropyl-4H-pyrrolo[3,2-d]thiazole (328); 2-((2S,5R)-2,5-dimethyl-4-(tetrahydro-2H-pyran-4-yl)piperazin-1-yl)-5-(7,8-dimethyl-[1,2,4]triazolo[1,5-a]pyridin-6-yl)-6-isopropyl-4H-pyrrolo[3,2-d]thiazole (329); 5-(7,8-dimethyl-[1,2,4] triazolo[1,5-a]pyridin-6-yl)-6-isopropyl-2-((2S,5R)-4-isopropyl-2,5-dimethylpiperazin-1-yl)-4H-pyrrolo[3,2-d] thiazole (330); 5-(7,8-dimethyl-[1,2,4]triazolo[1,5-a] pyridin-6-yl)-2-((2S,5R)-4-ethyl-2,5-dimethylpiperazin-1-yl)-6-isopropyl-4H-pyrrolo[3,2-d]thiazole (331); 2-((2S,5R)-4-(cyclopropylmethyl)-2,5-dimethylpiperazin-1-yl)-5-(7,8-dimethyl-[1,2,4]triazolo[1,5-a]pyridin-6-yl)-6-isopropyl-4H-pyrrolo[3,2-d]thiazole (332); 2-((2S,5R)-4-cyclobutyl-2,5-dimethylpiperazin-1-yl)-5-(7,8-dimethyl-[1,2,4]triazolo[1,5-a]pyridin-6-yl)-6-isopropyl-4H-pyrrolo[3,2-d]thiazole (333); 5-(7,8-dimethyl-[1,2,4]triazolo[1,5-a]

pyridin-6-yl)-6-isopropyl-2-((2S,5R)-4-isopropyl-2,5-dimethylpiperazin-1-yl)-4H-pyrrolo[3,2-d]thiazole (334); 2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-N,N-dimethylacetamide (335); 2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-N-methylacetamide (336); 2-((2S,5R)-2,5-dimethyl-4-(2-(methylsulfonyl)ethyl)piperazin-1-yl)-5-(7,8-dimethyl-[1,2,4]triazolo[1,5-a]pyridin-6-yl)-6-isopropyl-4H-pyrrolo[3,2-d]thiazole (337); 2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)acetamide (338); 1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-methylpropan-2-ol (339); 1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(methylamino) ethan-1-one (340); 1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(dimethylamino) ethan-1-one (341); (S)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N-methylacetamide (342); (S)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N,N-dimethylacetamide (343); (S)-5-(7,8-dimethyl-[1,2,4]triazolo[1,5-a]pyridin-6-yl)-6-isopropyl-2-(2-methyl-4-(2-(methylsulfonyl)ethyl) piperazin-1-yl)-4H-pyrrolo[3,2-d]thiazole (344); (S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol (345); (S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(dimethylamino)ethan-1-one (346); (S)-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)(1,1-dioxidotetrahydro-2H-thiopyran-4-yl)methanone (347); (S)-5-(7,8-dimethyl-[1,2,4]triazolo[1,5-a]pyridin-6-yl)-6-isopropyl-2-(2-methyl-4-(oxetan-3-yl) piperazin-1-yl)-4H-pyrrolo[3,2-d]thiazole (348); S)-2-(4-cyclobutyl-2-methylpiperazin-1-yl)-5-(7,8-dimethyl-[1,2,4]triazolo[1,5-a]pyridin-6-yl)-6-isopropyl-4H-pyrrolo[3,2-d]thiazole (349); (S)-5-(7,8-dimethyl-[1,2,4]triazolo[1,5-a]pyridin-6-yl)-6-isopropyl-2-(2-methyl-4-(tetrahydro-2H-pyran-4-yl)piperazin-1-yl)-4H-pyrrolo[3,2-d]thiazole (350); (S)-5-(7,8-dimethyl-[1,2,4]triazolo[1,5-a]pyridin-6-yl)-6-isopropyl-2-(4-isopropyl-2-methylpiperazin-1-yl)-4H-pyrrolo[3,2-d]thiazole (351); (S)-2-(4-(cyclopropylmethyl)-2-methylpiperazin-1-yl)-5-(7,8-dimethyl-[1,2,4]triazolo[1,5-a]pyridin-6-yl)-6-isopropyl-4H-pyrrolo[3,2-d]thiazole (352); (R)-2-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-N-methylacetamide (353); (R)-2-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-N,N-dimethylacetamide (354); (R)-2-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)acetamide (355); (R)-6-isopropyl-2-(2-methyl-4-(2-(methylsulfonyl) ethyl) piperazin-1-yl)-5-(8-methyl-[1,2,4]triazolo[1,5-a]pyridin-6-yl)-4H-pyrrolo[3,2-d]thiazole (356); (R)-6-isopropyl-2-(4-(2-methoxyethyl)-2-methylpiperazin-1-yl)-5-(8-methyl-[1,2,4]triazolo[1,5-a]pyridin-6-yl)-4H-pyrrolo[3,2-d]thiazole (357); (R)-2-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)acetonitrile (358); (R)-1-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-2-methylpropan-2-ol (359); (R)-2-(dimethylamino)-1-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl) ethan-1-one (360); (R)-2-(4-isobutyl-2-methylpiperazin-1-yl)-6-isopropyl-5-(8-methyl-[1,2,4]triazolo[1,5-a]pyridin-6-yl)-4H-pyrrolo[3,2-d]thiazole (361); (R)-2-(4-cyclobutyl-2-methylpiperazin-1-yl)-6-isopropyl-5-(8-methyl-[1,2,4]triazolo[1,5-a]pyridin-6-yl)-4H-pyrrolo[3,2-d]thiazole (362); (R)-6-isopropyl-2-(2-methyl-4-(oxetan-3-yl)piperazin-1-yl)-5-(8-methyl-[1,2,4]triazolo[1,5-a]pyridin-6-yl)-4H-pyrrolo[3,2-d]thiazole (363); (R)-6-isopropyl-2-(2-methyl-4-(tetrahydro-2H-pyran-4-yl)piperazin-1-yl)-5-(8-methyl-[1,2,4]triazolo[1,5-a]pyridin-6-yl)-4H-pyrrolo[3,2-d]thiazole (364); (R)-2-(4-(cyclopropylmethyl)-2-methylpiperazin-1-yl)-6-isopropyl-5-(8-methyl-[1,2,4]triazolo[1,5-a]pyridin-6-yl)-4H-pyrrolo[3,2-d]thiazole (365); (R)-6-isopropyl-2-(4-isopropyl-2-methylpiperazin-1-yl)-5-(8-methyl-[1,2,4]triazolo[1,5-a]pyridin-6-yl)-4H-pyrrolo[3,2-d]thiazole (366); or (R)-2-(2,4-dimethylpiperazin-1-yl)-6-isopropyl-5-(8-methyl-[1,2,4]triazolo[1,5-a]pyridin-6-yl)-4H-pyrrolo[3,2-d]thiazole (367).

One embodiment provides a compound of Formula (I), N-oxide, or a salt thereof wherein said compound is: 1-(5-(7,8-dimethyl-[1,2,4]triazolo[1,5-a]pyridin-6-yl)-6-isopropyl-4H-pyrrolo[3,2-d]thiazol-2-yl)-N-(3-methyloxetan-3-yl) piperidin-4-amine (290); 1-((1-(5-(7,8-dimethyl-[1,2,4]triazolo[1,5-a]pyridin-6-yl)-6-isopropyl-4H-pyrrolo[3,2-d]thiazol-2-yl)piperidin-4-yl)amino)-2-methylpropan-2-ol (291); 1-(5-(7,8-dimethyl-[1,2,4]triazolo[1,5-a]pyridin-6-yl)-6-isopropyl-4H-pyrrolo[3,2-d]thiazol-2-yl)-N-isopropyl-N-methylpiperidin-4-amine (292); N-cyclobutyl-1-(5-(7,8-dimethyl-[1,2,4]triazolo[1,5-a]pyridin-6-yl)-6-isopropyl-4H-pyrrolo[3,2-d]thiazol-2-yl) piperidin-4-amine (293); 1-(5-(7,8-dimethyl-[1,2,4]triazolo[1,5-a]pyridin-6-yl)-6-isoropyl-4H-pyrrolo[3,2-d]thiazol-2-yl)-N-(2-methoxy-2-methylpropyl)piperidin-4-amine (294); 1-(5-(7,8-dimethyl-[1,2,4]triazolo[1,5-a]pyridin-6-yl)-6-isopropyl-4H-pyrrolo[3,2-d]thiazol-2-yl)-N-((3-methyloxetan-3-yl) methyl) piperidin-4-amine (295); 1-(5-(7,8-dimethyl-[1,2,4]triazolo[1,5-a]pyridin-6-yl)-6-isopropyl-4H-pyrrolo[3,2-d]thiazol-2-yl)-N-(oxetan-3-yl)piperidin-4-amine (296); 1-(5-(7,8-dimethyl-[1,2,4]triazolo[1,5-a]pyridin-6-yl)-6-isopropyl-4H-pyrrolo[3,2-d]thiazol-2-yl)-N-isopropylpiperidin-4-amine (297); 1-(5-(7,8-dimethyl-[1,2,4]triazolo[1,5-a]pyridin-6-yl)-6-isopropyl-4H-pyrrolo[3,2-d]thiazol-2-yl)-N-ethyl-N-methylpiperidin-4-amine (298); or 1-(5-(7,8-dimethyl-[1,2,4]triazolo[1,5-a]pyridin-6-yl)-6-isopropyl-4H-pyrrolo[3,2-d]thiazol-2-yl)piperidin-4-amine (299).

One embodiment provides a compound of Formula (I), N-oxide, or a salt thereof wherein said compound is: 5-(7,8-dimethyl-[1,2,4]triazolo[1,5-a]pyridin-6-yl)-2-(6-isobutyl-2,6-diazaspiro[3.3]heptan-2-yl)-6-isopropyl-4H-pyrrolo[3,2-d]thiazole (300); 5-(7,8-dimethyl-[1,2,4]triazolo[1,5-a]pyridin-6-yl)-6-isopropyl-2-(6-((tetrahydro-2H-pyran-4-yl) methyl)-2,6-diazaspiro[3.3]heptan-2-yl)-4H-pyrrolo[3,2-d]thiazole (301); 5-(7,8-dimethyl-[1,2,4]triazolo[1,5-a]pyridin-6-yl)-6-isopropyl-2-(6-(oxetan-3-yl)-2,6-diazaspiro[3.3]heptan-2-yl)-4H-pyrrolo[3,2-d]thiazole (302); 1-(6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptan-2-yl)-2-methylpropan-2-ol (303); 5-(7,8-dimethyl-[1,2,4]triazolo[1,5-a]pyridin-6-yl)-6-isopropyl-2-(6-(2-(methylsulfonyl)ethyl)-2,6-diazaspiro[3.3]heptan-2-yl)-4H-pyrrolo[3,2-d]thiazole (304); 5-(6-isopropyl-2-(6-(2-(methylsulfonyl)ethyl)-2,6-diazaspiro[3.3]heptan-2-yl)-4H-pyrrolo[3,2-d]thiazol-5-yl)-1,3,4-trimethylpyridin-2 (1H)-one (305); 5-(6-isopropyl-2-(6-(oxetan-3-yl)-2,6-diazaspiro[3.3]heptan-2-yl)-4H-pyrrolo[3,2-d]thiazol-5-yl)-1,3,4-trimethylpyridin-2 (1H)-one (306); or 5-(6-isopropyl-2-(6-((tetrahydro-2H-pyran-4-yl) methyl)-2,6-diazaspiro[3.3]heptan-2-yl)-4H-pyrrolo[3,2-d]thiazol-5-yl)-1,3,4-trimethylpyridin-2 (1H)-one (307).

One embodiment provides a compound of Formula (I), N-oxide, or a salt thereof wherein said compound is: 5-(7,8-dimethyl-[1,2,4]triazolo[1,5-a]pyridin-6-yl)-N-(4-(dimethylamino) cyclohexyl)-6-isopropyl-4H-pyrrolo[3,2-d]thiazole-2-carboxamide (368-369); 5-(7,8-dimethyl-[1,2,4]triazolo[1,5-a]pyridin-6-yl)-6-isopropyl-N-(2-(pyrrolidin-1-yl) ethyl)-4H-pyrrolo[3,2-d]thiazole-2-carboxamide (370); 5-(7,8-dimethyl-[1,2,4]triazolo[1,5-a]pyridin-6-yl)-6-isopropyl-N-(3-(2-oxopyrrolidin-1-yl)propyl)-4H-pyrrolo[3,2-d]thiazole-2-carboxamide (371); 5-(7,8-dimethyl-[1,2,4]triazolo[1,5-a]pyridin-6-yl)-N-(2-(dimethylamino)ethyl)-6-isopropyl-4H-pyrrolo[3,2-d]thiazole-2-carboxamide (372); 5-(7,8-dimethyl-[1,2,4]triazolo[1,5-a]pyridin-6-yl)-6-isopropyl-N-(2-methyl-2-morpholinopropyl)-4H-pyrrolo[3,2-d]thiazole-2-carboxamide (374); 5-(7,8-dimethyl-[1,2,4]triazolo[1,5-a]pyridin-6-yl)-6-isopropyl-N-(2-(1-methylpiperidin-4-yl)ethyl)-4H-pyrrolo[3,2-d]thiazole-2-carboxamide (381); 5-(7,8-dimethyl-[1,2,4]triazolo[1,5-a]pyridin-6-yl)-N-(2-(dimethylamino)ethyl)-6-isopropyl-N-methyl-4H-pyrrolo[3,2-d]thiazole-2-carboxamide (382); 5-(7,8-dimethyl-[1,2,4]triazolo[1,5-a]pyridin-6-yl)-6-isopropyl-N-(morpholin-2-ylmethyl)-4H-pyrrolo[3,2-d]thiazole-2-carboxamide (386); 6-isopropyl-5-(8-methoxy-[1,2,4]triazolo[1,5-a]pyridin-6-yl)-N-(2-(pyrrolidin-1-yl)ethyl)-4H-pyrrolo[3,2-d]thiazole-2-carboxamide (387); N-(2-(dimethylamino)ethyl)-6-isopropyl-5-(8-methoxy-[1,2,4]triazolo[1,5-a]pyridin-6-yl)-4H-pyrrolo[3,2-d]thiazole-2-carboxamide (388); N-(2,2-difluoroethyl)-6-isopropyl-5-(8-methoxy-[1,2,4]triazolo[1,5-a]pyridin-6-yl)-4H-pyrrolo[3,2-d]thiazole-2-carboxamide (389); 6-isopropyl-5-(8-methoxy-[1,2,4]triazolo[1,5-a]pyridin-6-yl)-N-(2,2,2-trifluoroethyl)-4H-pyrrolo[3,2-d]thiazole-2-carboxamide (390); 6-isopropyl-5-(8-methyl-[1,2,4]triazolo[1,5-a]pyridin-6-yl)-4H-pyrrolo[3,2-d]thiazole-2-carboxamide (391); 6-isopropyl-5-(8-methyl-[1,2,4]triazolo[1,5-a]pyridin-6-yl)-N-((1-(methylsulfonyl) cyclopropyl)methyl)-4H-pyrrolo[3,2-d]thiazole-2-carboxamide (399); or N-(2-(dimethylamino) ethyl)-6-isopropyl-5-(8-methyl-[1,2,4]triazolo[1,5-a]pyridin-6-yl)-4H-pyrrolo[3,2-d]thiazole-2-carboxamide (400).

One embodiment provides a compound of Formula (I), N-oxide, or a salt thereof wherein said compound is: (5-(7,8-dimethyl-[1,2,4]triazolo[1,5-a]pyridin-6-yl)-6-isopropyl-4H-pyrrolo[3,2-d]thiazol-2-yl)(1,1-dioxidothiomorpholino) methanone (373); 1-(4-(5-(7,8-dimethyl-[1,2,4]triazolo[1,5-a]pyridin-6-yl)-6-isopropyl-4H-pyrrolo[3,2-d]thiazole-2-carbonyl)piperazin-1-yl)ethan-1-one (375); (5-(7,8-dimethyl-[1,2,4]triazolo[1,5-a]pyridin-6-yl)-6-isopropyl-4H-pyrrolo[3,2-d]thiazol-2-yl)(4-(dimethylamino) piperidin-1-yl)methanone (376); (5-(7,8-dimethyl-[1,2,4]triazolo[1,5-a]pyridin-6-yl)-6-isopropyl-4H-pyrrolo[3,2-d]thiazol-2-yl)(pyrrolidin-1-yl)methanone (377); 4-(5-(7,8-dimethyl-[1,2,4]triazolo[1,5-a]pyridin-6-yl)-6-isopropyl-4H-pyrrolo[3,2-d]thiazole-2-carbonyl)piperazin-2-one (378); (5-(7,8-dimethyl-[1,2,4]triazolo[1,5-a]pyridin-6-yl)-6-isopropyl-4H-pyrrolo[3,2-d]thiazol-2-yl) (3-fluoroazetidin-1-yl)methanone (379); (5-(7,8-dimethyl-[1,2,4]triazolo[1,5-a]pyridin-6-yl)-6-isopropyl-4H-pyrrolo[3,2-d]thiazol-2-yl)(4-isopropylpiperazin-1-yl)methanone (380); (5-(7,8-dimethyl-[1,2,4]triazolo[1,5-a]pyridin-6-yl)-6-isopropyl-4H-pyrrolo[3,2-d]thiazol-2-yl) (3-(dimethylamino)azetidin-1-yl)methanone (383); (5-(7,8-dimethyl-[1,2,4]triazolo[1,5-a]pyridin-6-yl)-6-isopropyl-4H-pyrrolo[3,2-d]thiazol-2-yl) (4-(methylsulfonyl)piperazin-1-yl) methanone (384); 5-(7,8-dimethyl-[1,2,4]triazolo[1,5-a]pyridin-6-yl)-6-isopropyl-4H-pyrrolo[3,2-d]thiazole-2-carboxamide (385); 4-(6-isopropyl-5-(8-methyl-[1,2,4]triazolo[1,5-a]pyridin-6-yl)-4H-pyrrolo[3,2-d]thiazole-2-carbonyl)piperazin-2-one (392); (6-isopropyl-5-(8-methyl-[1,2,4]triazolo[1,5-a]pyridin-6-yl)-4H-pyrrolo[3,2-d]thiazol-2-yl)(pyrrolidin-1-yl) methanone (393); (6-isopropyl-5-(8-methyl-[1,2,4]triazolo[1,5-a]pyridin-6-yl)-4H-pyrrolo[3,2-d]thiazol-2-yl)(1,4-oxazepan-4-yl)methanone (394); (4-(dimethylamino) piperidin-1-yl)(6-isopropyl-5-(8-methyl-[1,2,4]triazolo[1,5-a]pyridin-6-yl)-4H-pyrrolo[3,2-d]thiazol-2-yl)methanone (395); (6-isopropyl-5-(8-methyl-[1,2,4]triazolo[1,5-a]pyridin-6-yl)-4H-pyrrolo[3,2-d]thiazol-2-yl)(3-methoxyazetidin-1-yl)methanone (396); 6-isopropyl-5-(8-methyl-[1,2,4]triazolo[1,5-a]pyridin-6-yl)-N-(oxetan-3-yl)-4H-pyrrolo[3,2-d]thiazole-2-carboxamide (397); or (6-isopropyl-5-(8-methyl-[1,2,4]triazolo[1,5-a]pyridin-6-yl)-4H-pyrrolo[3,2-d]thiazol-2-yl)(morpholino)methanone (398).

One embodiment provides a compound of Formula (I), N-oxide, or a salt thereof wherein said compound is: N-((5-(7,8-dimethyl-[1,2,4]triazolo[1,5-a]pyridin-6-yl)-6-isopropyl-4H-pyrrolo[3,2-d]thiazol-2-yl)methyl)-1-isopropylpiperidin-4-amine (401); 2-(((5-(7,8-dimethyl-[1,2,4]triazolo[1,5-a]pyridin-6-yl)-6-isopropyl-4H-pyrrolo[3,2-d]thiazol-2-yl) methyl)amino)acetamide (402); 6-((5-(7,8-dimethyl-[1,2,4]triazolo[1,5-a]pyridin-6-yl)-6-isopropyl-4H-pyrrolo[3,2-d]thiazol-2-yl)methyl)-2-thia-6-azaspiro[3.3]heptane 2,2-dioxide (403); 2-((5-(7,8-dimethyl-[1,2,4]triazolo[1,5-a]pyridin-6-yl)-6-isopropyl-4H-pyrrolo[3,2-d]thiazol-2-yl) methyl)-7-oxa-2-azaspiro[3.5]nonane (404); 1-(5-(7,8-dimethyl-[1,2,4]triazolo[1,5-a]pyridin-6-yl)-6-isopropyl-4H-pyrrolo[3,2-d]thiazol-2-yl)-N-((1-(methylsulfonyl) cyclopropyl)methyl)methanamine (405); 4-((5-(7,8-dimethyl-[1,2,4]triazolo[1,5-a]pyridin-6-yl)-6-isopropyl-4H-pyrrolo[3,2-d]thiazol-2-yl)methyl) piperazin-2-one (406); 4-((5-(7,8-dimethyl-[1,2,4]triazolo[1,5-a]pyridin-6-yl)-6-isopropyl-4H-pyrrolo[3,2-d]thiazol-2-yl)methyl)morpholine (407); 6-((5-(7,8-dimethyl-[1,2,4]triazolo[1,5-a]pyridin-6-yl)-6-isopropyl-4H-pyrrolo[3,2-d]thiazol-2-yl) methyl)-2-oxa-6-azaspiro[3.3]heptane (408); or 2-((2,6-diazaspiro[3.3]heptan-2-yl)methyl)-5-(7,8-dimethyl-[1,2,4]triazolo[1,5-a]pyridin-6-yl)-6-isopropyl-4H-pyrrolo[3,2-d]thiazole (409).

One embodiment provides a compound of Formula (I), N-oxide, or a salt thereof wherein said compound is: 6-isopropyl-5-(8-methoxy-[1,2,4]triazolo[1,5-a]pyridin-6-yl)-2-(piperidin-4-yl)-4H-pyrrolo[2,3-d]thiazole (410); 6-isopropyl-5-(8-methyl-[1,2,4]triazolo[1,5-a]pyridin-6-yl)-2-(piperidin-4-yl)-4H-pyrrolo[2,3-d]thiazole (411); or 6-isopropyl-5-(8-methyl-[1,2,4]triazolo[1,5-a]pyridin-6-yl)-2-(1-((3-methyloxetan-3-yl) methyl)piperidin-4-yl)-4H-pyrrolo[2,3-d]thiazole (412).

One embodiment provides a compound of Formula (I), N-oxide, or a salt thereof wherein said compound is 6-isopropyl-5-(8-methoxy-[1,2,4]triazolo[1,5-a]pyridin-6-yl)-2-(piperidin-4-yl)-4H-thieno[3,2-b]pyrrole (413).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

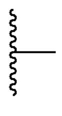

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group $—NH_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, $—CF_3$ and $—CH_2CF_3$.

The term "cyanoalkyl" includes both branched and straight-chain saturated alkyl groups substituted with one or more cyano groups. For example, "cyanoalkyl" includes $—CH_2CN$, $—CH_2CH_2CN$, and $C_{1-4}$ cyanoalkyl.

The term "aminoalkyl" includes both branched and straight-chain saturated alkyl groups substituted with one or more amine groups. For example, "aminoalkyl" includes $—CH_2NH_2$, $—CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes $—CH_2OH$, $—CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes $—CHFCH_2OH$, $—CH_2CHFC(CH_3)_2OH$, and $C_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group ($—OCH_3$). For example, "$C_{1-3}$ alkoxy" denotes alkoxy groups with one to three carbon atoms.

The term "alkoxyalkyl," as used herein, refers to an alkoxy group attached through its oxygen atom to an alkyl group, which is attached to the parent molecular moiety, for example, methoxymethyl group ($—CH_2OCH_3$). For example, "$C_{2-4}$ alkoxyalkyl" denotes alkoxyalkyl groups with two to four carbon atoms, such as $—CH_2OCH_3$, $—CH_2CH_2OCH_3$, $—CH_2OCH_2CH_3$, and $—CH_2CH_2OCH_2CH_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl ($-CH_3$) also includes deuterated methyl groups such as $-CD_3$.

UTILITY

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil;

sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. That recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

ACN acetonitrile
AcOH acetic acid
DIPEA diisopropylethylamine
Boc tert-butoxycarbonyl
DCE dichloroethane
DCM dichloromethane
TEA triethylamine
DMAP dimethylaminopyridine
DMF dimethylformamide
$NaHCO_3$Sodium bicarbonate
BINAP 2,2'-bis(diphenylphosphino)-1,1'-binaphthyl
EtOAc ethyl acetate
H or $H_2$ hydrogen
h, hr or hrs hour(s)
HATU O-(7-azabenzotriazol-1-yl)-N, N, N', N'-tetramethyluronium hexafluorophosphate
HCl hydrochloric acid
NaH Sodium hydride
CO carbon monoxide
HOAc acetic acid
HPLC high pressure liquid chromatography
MTBE methyl tertiary-butyl ether
LC liquid chromatography
M molar
M+1 (M+H)+
NIS n-iodosuccinimide
MeOH methanol
MHz megahertz
min. minute(s)
mM millimolar
MS mass spectrometry
n or N normal
NBS n-bromosuccinimide
nm nanometer
nM nanomolar
NMP N-methylpyrrolidine
$Pd(PPh_3)_4$ tetrakis(triphenylphosphine)palladium
Pd/C palladium on carbon
$PdCl_2$(dppf) [1,1'-bis(diphenylphosphino)ferrocene]dichloropalladium(II)
Pet ether petroleum ether
Ret Time retention time
sat. saturated
SFC supercritical fluid chromatography
TFA trifluoroacetic acid
THE tetrahydrofuran
2nd generation Xphos precatalyst: (chloro(2-dicyclohexylphosphino-2',4',6'-triisopropyl-1,1'-biphenyl)[2-(2'-amino-1,1'-biphenyl)]palladium(II)

Analytical and Preparative HPLC Conditions:

Method A (SCP): Column: XBridge BEH XP C18 (50×2.1) mm, 2.5 μm: Mobile Phase A: 5:95 acetonitrile: water with 10-mM ammonium acetate; Mobile Phase B: 95:5 acetonitrile: water with 10-mM ammonium acetate, Temperature: 50° C., Gradient: 0-100% B over 3 minutes, Flow: 1.11 mL/min; Detection: UV at 220 nm.

Method B (SCP): Column: XBridge BEH XP C18 (50×2.1) mm, 2.5 μm: A: 95% water: 5% acetonitrile; 0.1% TFA; B:5% water: 95% acetonitrile; 0.1% TFA, Temperature: 50° C., Gradient: 0-100% B over 3 minutes, Flow: 1.11 mL/min; Detection: UV at 220 nm.

(C): Kinetex XB-C18 (75×3 mm) 2.6 micron; Solvent A: 10 mM ammonium formate in water: acetonitrile (98:2); Mobile Phase B: 10 mM ammonium formate in water: acetonitrile (2:98); Temperature: 50° C.; Gradient: 0-100% B over 5 minutes; Flow rate: 1.1 mL/min; Detection: UV at 220 nm.

(D): Column: Ascentis Express C18 (50×2.1) mm, 2.7 m; Mobile Phase A: 5:95 acetonitrile: water with 10 mM $NH_4OAc$; Mobile Phase B: 95:5 acetonitrile: water with 10 mM $NH_4OAc$; Temperature: 50° C.; Gradient: 0-100% B over 3 minutes; Flow: 1.1 mL/min.

(E) Waters Acquity SDS Mobile Phase: A: water B: ACN; 5%-95% B in 1 min; Gradient Range: 50%-98% B (0-0.5 min); 98% B (0.5 min-1 min); 98%-2% B (1-1.1 min); Run time: 1.2 min; Flow Rate: 0.7 mL/min; Analysis Time: 1.7 min; Detection: Detector 1: UV at 220 nm; Detector 2: MS ($ES^+$).

(F) Acquity UPLC BEH C18 (3.0×50 mm) 1.7 μm. Buffer: 5 mM ammonium acetate Mobile phase A: Buffer: ACN (95:5); Mobile phase B: Buffer: ACN (5:95) Method: % B: 0 min-20%: 1.1 min −90%:1.7 min-90%. Run time: 2.25 min; Flow Rate: 0.7 mL/min; Detection: Detector 1: UV at 220 nm; Detector 2: MS ($ES^+$).

(G) Column-Luna 3.0 C18 (2) 100 Å LC column (20×4.0 mm) Mercury MS™ M. phase A: 0.1% TFA in Milli-Q Water: M. phase B: 0.1% TFA in ACN, Flow rate: 1.5 mL/min.

(H): Column: Ascentis Express C18 (50×2.1) mm, 2.7 m; Mobile Phase A: 5:95 acetonitrile: water with 0.1% TFA; Mobile Phase B: 95:5 acetonitrile: water with 0.1% TFA; Temperature: 50° C.; Gradient: 0-100% B over 3 minutes; Flow: 1.1 mL/min.

(I) Preparative LCMS: Waters XBridge C18, 19×150 mm, 5-μm particles; Mobile Phase A: 10-mM ammonium acetate; Mobile Phase B: methanol; Gradient: 10-45% B over 20 minutes, then a 5-minute hold at 100% B; Flow: 20 mL/min.

Example 1

6-isopropyl-5-(8-methoxy-[1,2,4]triazolo[1,5-a]pyridin-6-yl)-2-(piperidin-4-yl)-4H-pyrrolo[3,2-d]thiazole (1)

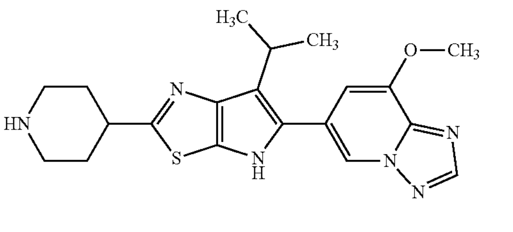

Intermediate 1A: 2-bromothiazole-5-carboxylic acid (1A)

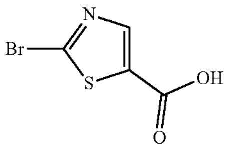

To a solution of methyl 2-bromothiazole-5-carboxylate (100 g, 450 mmol) in methanol (1500 mL) was added 10% NaOH (300 mL, 450 mmol) at 0° C. The reaction mixture was stirred at same temperature for 3 h. The reaction mass was concentrated under vacuum to remove solvent, the solid was dissolved in water (200 mL), acidified with cold 1.5 N HCl to pH ~4-5, the resulting precipitate was filtered and dried to yield 2-bromothiazole-5-carboxylic acid (81 g, 389 mmol, 86% yield) as a white solid product. LCMS retention time 0.35 min [C]. MS ($E^-$) m/z: 208.0 (M+2H).

Intermediate 1B: Tert-butyl (2-bromothiazol-5-yl)carbamate (1B)

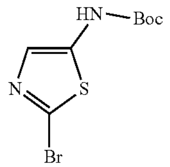

To a solution of 2-bromothiazole-5-carboxylic acid (81 g, 389 mmol) in t-BuOH (1000 mL) was added TEA (65.1 mL, 467 mmol) followed by dropwise addition of diphenylphosphoryl azide (111 mL, 506 mmol) at room temperature, and the resulting solution was heated at 80° C. for 12 h. The reaction mass was concentrated under vacuum, diluted with water (500 mL), brine solution (300 mL), extracted with ethyl acetate (3×500 mL). The separated organic layer was dried over sodium sulphate, filtered and concentrated to afford crude product. The crude was purified by combiflash using 120 g silica column, the compound eluting with 15% EtOAc in Pet ether. The fractions were collected and concentrated to afford tert-butyl (2-bromothiazol-5-yl)carbamate (52 g, 186 mmol, 47.8% yield) as an off-white solid. LCMS retention time 1.57 min [G]. MS ($E^-$) m/z: 281.1 (M+2H).

Intermediate 1C: Tert-butyl 4-(5-((tert-butoxycarbonyl)amino)thiazol-2-yl)-3,6-dihydropyridine-1 (2H)-carboxylate (1C)

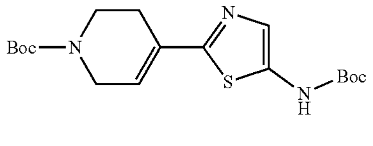

To a solution of tert-butyl (2-bromothiazol-4-yl)carbamate (15 g, 53.7 mmol), tert-butyl 4-(4,4,5,5-tetramethyl-1,3,2-dioxaborolan-2-yl)-3,6-dihydropyridine-1 (2H)-carboxylate (19.94 g, 64.5 mmol) in dioxane (300 mL) and water (34 mL) was added potassium phosphate tribasic (34.2 g, 161 mmol), the resulting solution was degassed with $N_2$ for 10 mins, followed by addition of $PdCl_2(dppf)$-$CH_2Cl_2$ adduct (4.39 g, 5.37 mmol), and additional degassing for 5 min. The resulting mixture was heated at 90° C. for 12 h. The reaction mixture was diluted with ethyl acetate (250 mL), washed with water (2×200 mL), brine (100 mL), dried over sodium sulphate, and concentrated to afford crude product. The crude was purified by combiflash using 120 g silica column, the compound eluting with 45% EtOAc in Pet ether. The fractions were collected and concentrated to afford tert-butyl 4-(4-((tert-butoxycarbonyl)amino)thiazol-2-yl)-3,6-dihydropyridine-1 (2H)-carboxylate (19 g, 49.3 mmol, 92% yield) as a pale yellow solid. LCMS retention time 3.38 min [C]. MS ($E^-$) m/z: 382.1 (M+H).

Intermediate 1D: Tert-butyl4-(5-((tert-butoxycarbonyl)amino)thiazol-2-yl)piperidine-1-carboxylate (1D)

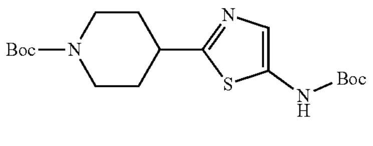

To a solution of tert-butyl 4-(4-((tert-butoxycarbonyl)amino)thiazol-2-yl)-3,6-dihydropyridine-1 (2H)-carboxylate (19 g, 49.8 mmol) and EtOAc (500 mL) was purged with nitrogen ($N_2$), then Pd/C (9.54 g, 8.96 mmol) was added and the reaction was further purged with $N_2$ three times. Hydrogen gas was introduced via a balloon to the mixture; then was stirred at room temperature for 8 h. The suspension was filtered through celite bed, the filtrate was collected and concentrated to afford tert-butyl 4-(4-((tert-butoxycarbonyl) amino)thiazol-2-yl)piperidine-1-carboxylate (18 g, 46.0 mmol, 92% yield) as a pale yellow solid. LCMS retention time 3.24 min [C]. MS ($E^-$) m/z: 384.1 (M+H).

Intermediate 1E: Tert-butyl 4-(5-((tert-butoxycarbonyl)amino)-4-iodothiazol-2-yl)piperidine-1-carboxylate (1E)

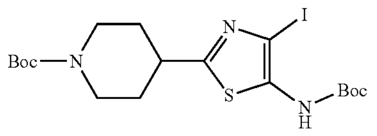

To a solution of tert-butyl 4-(5-((tert-butoxycarbonyl)amino)thiazol-2-yl)piperidine-1-carboxylate (17 g, 44.3 mmol) in acetonitrile (700 mL) was added dropwise NIS (9.97 g, 44.3 mmol) in acetonitrile (250 mL) at 0° C. The resulting solution was stirred at same temperature for 10 min. The reaction mass was quenched with aqueous sodium thiosulphate solution (200 mL) and extracted with EtOAc (3×200 mL). The combined organic layer was dried over sodium sulphate, filtered and concentrated to afford crude product. The crude was purified by combiflash using 120 g silica column, the compound eluting with 16% EtOAc in Pet ether. The fractions were collected and concentrated to afford tert-butyl 4-(5-((tert-butoxycarbonyl) amino)-4-iodothiazol-2-yl) piperidine-1-carboxylate (17 g, 33.0 mmol, 74.5% yield) as a pale yellow solid. LCMS retention time 3.40 min [C]. MS ($E^-$) m/z: 510.1 (M+H).

Intermediate 1F: Tert-butyl 4-(5-((tert-butoxycarbonyl)(3-methylbut-2-en-1-yl)amino)-4-iodothiazol-2-yl)piperidine-1-carboxylate (1F)

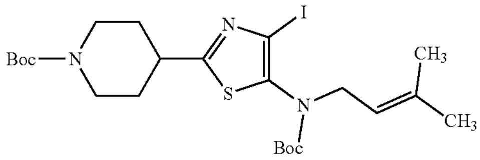

To a solution of tert-butyl 4-(5-((tert-butoxycarbonyl)amino)-4-iodothiazol-2-yl) piperidine-1-carboxylate (17 g, 33.4 mmol) in DMF (250 mL) was added NaH (1.335 g, 33.4 mmol) at 0° C., stirred at same temperature for 10 min. Then 1-bromo-3-methylbut-2-ene (4.27 mL, 36.7 mmol) was added dropwise and allowed to stir at same temperature for 10 min. The reaction mass was quenched with ice water (250 mL) and extracted with EtOAc (3×250 mL). The combined organic layers was dried over sodium sulphate, filtered and concentrated to afford tert-butyl 4-(5-((tert-butoxycarbonyl)(3-methylbut-2-en-1-yl)amino)-4-iodothiazol-2-yl)piperidine-1-carboxylate (17.2 g, 28.3 mmol, 85% yield) as a pale yellow oil. LCMS retention time 4.13 min [C]. MS ($E^-$) m/z: 578.1 (M+H).

Intermediate 1G: Tert-butyl 2-(1-(tert-butoxycarbonyl)piperidin-4-yl)-6-isopropyl-4H-pyrrolo[3,2-d]thiazole-4-carboxylate (1G)

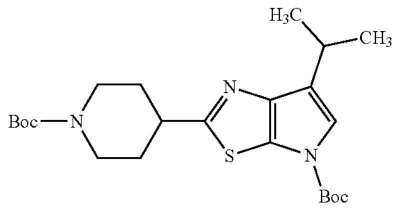

To a solution of tert-butyl 4-(5-((tert-butoxycarbonyl)(3-methylbut-2-en-1-yl)amino)-4-iodothiazol-2-yl)piperidine-1-carboxylate (3.0 g, 5.19 mmol) and potassium carbonate (1.077 g, 7.79 mmol) in DMF (90 mL) was added tetrabutylammonium bromide (1.675 g, 5.19 mmol). The mixture was degassed for 10 min and was added $Pd(OAc)_2$ (0.035 g, 0.156 mmol), further degassed again for 5 min and resulting reaction mixture was heated at 100° C. for 12 h. Reaction mass was filtered through celite washed with EtOAc (100 mL), filtrate was concentrated to afford crude. The crude was purified by combiflash using 40 g silica column, the compound eluting with 18%-45% EtOAc in Pet ether. The fractions were collected and concentrated to afford tert-butyl 2-(1-(tert-butoxycarbonyl)piperidin-4-yl)-6-isopropyl-4H-pyrrolo[3,2-d]thiazole-4-carboxylate (510 mg, 0.245 mmol, 27.71% yield) as a pale yellow solid. LCMS retention time 4.29 min [C]. MS ($E^-$) m/z: 450.1 (M+2).

Intermediate 1H: Tert-butyl 5-bromo-2-(1-(tert-butoxycarbonyl)piperidin-4-yl)-6-isopropyl-4H-pyrrolo[3,2-d]thiazole-4-carboxylate (1H)

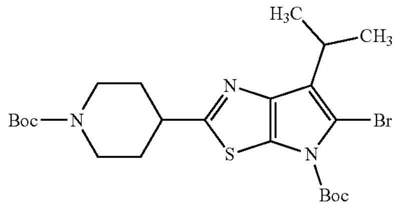

To a solution of tert-butyl 4-(6-isopropyl-4H-pyrrolo[3,2-d]thiazol-2-yl)piperidine-1-carboxylate (480 mg, 1.373 mmol) in DCE (10 ml) was added dropwise NBS (269 mg, 1.511 mmol) dissolved in DCE (10 mL) at 0° C. The resulting solution was stirred at room temperature for 15 min. The reaction mass was quenched with water (50 mL) and extracted with ethyl acetate (3×50 mL). The combined organic layer was dried over sodium sulphate, filtered and concentrated to afford crude product. The crude was purified by combiflash using 24 g silica column, the compound eluting with 8% EtOAc in Pet ether. The fractions were collected and concentrated to afford tert-butyl 4-(5-bromo-6-isopropyl-4H-pyrrolo[3,2-d]thiazol-2-yl)piperidine-1-carboxylate (100 mg, 0.233 mmol, 17.00% yield) as a white solid. LCMS retention time 4.29 min [C]. MS ($E^-$) m/z: 528.1 (M+H).

Intermediate 11: Tert-butyl 2-(1-(tert-butoxycarbonyl)piperidin-4-yl)-6-isopropyl-5-(8-methoxy-[1,2,4]triazolo[1,5-a]pyridin-6-yl)-4H-pyrrolo[3,2-d]thiazole-4-carboxylate (1I)

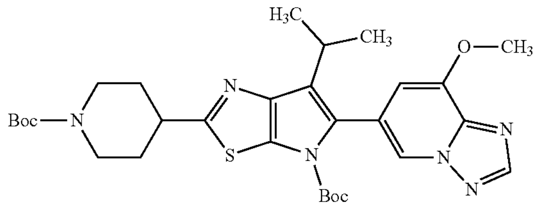

To a solution of tert-butyl 5-bromo-2-(1-(tert-butoxycarbonyl)piperidin-4-yl)-6-isopropyl-4H-pyrrolo[3,2-d]thiazole-4-carboxylate (150 mg, 0.284 mmol), 8-methoxy-6-(4,4,5,5-tetramethyl-1,3,2-dioxaborolan-2-yl)-[1,2,4]triazolo[1,5-a]pyridine (94 mg, 0.341 mmol) in dioxane (5 mL) and water (0.556 mL) was added potassium phosphate tribasic (148 mg, 0.851 mmol), the resulting solution was degassed with $N_2$ for 10 mins and $PdCl_2$(dppf)-$CH_2Cl_2$ adduct (11.59 mg, 0.014 mmol) was added, degassed again for 5 min. The resulting mixture was heated at 85° C. for 3 h. The reaction mixture was diluted with EtOAc (200 mL), washed with water (2×100 mL), brine (50 mL), dried over sodium sulphate, and concentrated to afford crude product. The crude was purified by combiflash using 24 g silica column, the compound eluting with 48% EtOAc in Pet ether. The fractions were collected and concentrated to afford tert-butyl 2-(1-(tert-butoxycarbonyl)piperidin-4-yl)-6-isopropyl-5-(8-methoxy-[1,2,4]triazolo[1,5-a]pyridin-6-yl)-4H-pyrrolo[3,2-d]thiazole-4-carboxylate (130 mg, 0.302 mmol, 76% yield) as a brown solid. LCMS retention time 1.43 min [C]. MS ($E^-$) m/z: 597.1 (M+H).

Example 1: 6-isopropyl-5-(8-methoxy-[1,2,4]triazolo[1,5-a]pyridin-6-yl)-2-(piperidin-4-yl)-4H-pyrrolo[3,2-d]thiazole To a solution of tert-butyl 2-(1-(tert-butoxycarbonyl)piperidin-4-yl)-6-isopropyl-5-(8-methoxy-[1,2,4]triazolo[1,5-a]pyridin-6-yl)-4H-pyrrolo[3,2-d]thiazole-4-carboxylate (95 mg, 0.159 mmol) in DCM (1 mL) was added hydrochloric acid in dioxane (1 ml, 32.9 mmol), the resulting solution was stirred at room temperature for 30 min. The reaction mass was concentrated under vacuum to remove volatiles, washed with diethyl ether (2×5) ml, ether layer was decanted and the solid was dried to afford 6-isopropyl-5-(8-methoxy-[1,2,4]triazolo[1,5-a]pyridin-6-yl)-2-(piperidin-4-yl)-4H-pyrrolo[3,2-d]thiazole (62 mg, 0.156 mmol, 98% yield) as a yellow solid. LCMS retention time 0.93 min [A]. MS ($E^-$) m/z: 397.1 (M+H). $^1$H NMR (400 MHz, DMSO-$d_6$) δ 11.63 (s, 1H), 8.48 (s, 2H), 7.11 (d, J=1.2 Hz, 1H), 4.09-3.98 (m, 3H), 3.23-3.19 (m, 2H), 2.92-2.84 (m, 3H), 2.13 (d, J=10.0 Hz, 2H), 1.90 (s, 1H), 1.88-1.73 (m, 2H), 1.43 (d, J=6.8 Hz, 6H).

The following Examples were prepared according to the general procedure described in Example 1.

TABLE 1

| Ex. No. | Structure | HPLC Method | Ret Time (min) | LCMS $MH^+$ |
|---|---|---|---|---|
| 2 | 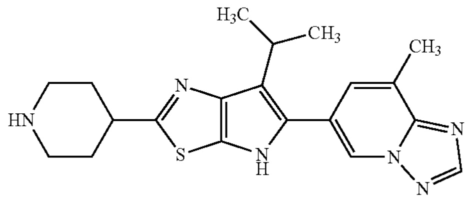 [SMILES: Cc1cc(-c2[nH]c3sc(C4CCNCC4)nc3c2C(C)C)cn2ncnc12] | A | 0.99 | 381.1 |
| 3 | 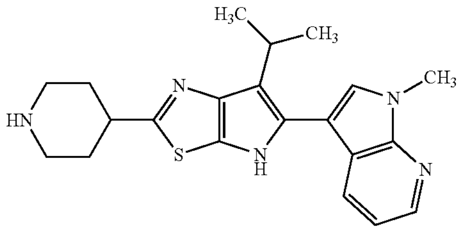 [SMILES: CC(C)c1c(-c2cn(C)c3ncccc23)[nH]c2sc(C3CCNCC3)nc12] | A | 1.26 | 380.0 |
| 4 | 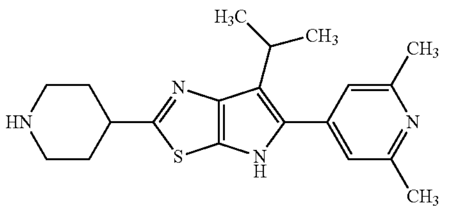 [SMILES: Cc1cc(-c2[nH]c3sc(C4CCNCC4)nc3c2C(C)C)cc(C)n1] | A | 1.17 | 355.2 |

TABLE 1-continued

| Ex. No. | Structure | HPLC Method | Ret Time (min) | LCMS MH+ |
|---|---|---|---|---|
| 5 | 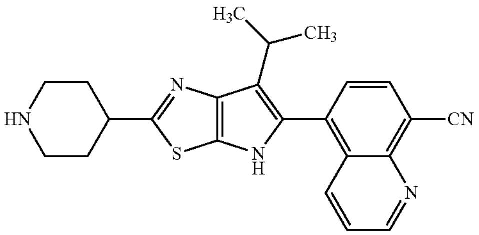 [SMILES: CC(C)c1c(-c2ccc(C#N)c3ncccc23)[nH]c2sc(C3CCNCC3)nc12] | F | 0.89 | 402.2 |

Example 6

2-(dimethylamino)-1-(4-(6-isopropyl-5-(8-methoxy-[1,2,4]triazolo[1,5-a]pyri din-6-yl)-4H-pyrrolo[3,2-d]thiazol-2-yl)piperidin-11-yl)ethan-1-one (6)

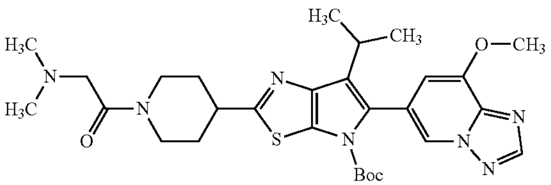

To a solution of 6-isopropyl-5-(8-methoxy-[1,2,4]triazolo[1,5-a]pyridin-6-yl)-2-(piperidin-4-yl)-4H-pyrrolo[3,2-d]thiazole (16 mg, 0.040 mmol) and dimethyl glycine (4.99 mg, 0.048 mmol) in DMF (2 mL) was added TEA (0.011 mL, 0.081 mmol) followed by HATU (16.88 mg, 0.044 mmol). The resulting reaction mixture was stirred at 25° C. for 3 h. The reaction mass was diluted with water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to yield 2-(dimethylamino)-1-(4-(6-isopropyl-5-(8-methoxy-[1,2,4]triazolo[1,5-a]pyridin-6-yl)-4H-pyrrolo[3,2-d]thiazol-2-yl)piperidin-1-yl)ethan-1-one (4.4 mg, 9.14 μmol, 22.64% yield) as a pale yellow solid. LCMS retention time 1.14 min [A]. MS ($E^-$) m/z: 482.2 (M+H). $^1H$ NMR (400 MHz, DMSO-$d_6$) δ 11.62 (s, 1H), 8.55-8.37 (m, 2H), 7.10 (s, 1H), 4.39 (d, J=13.0 Hz, 1H), 4.10-3.98 (m, 3H), 3.36-3.27 (m, 4H), 3.21-3.13 (m, 3H), 2.88-2.78 (m, 1H), 2.31 (s, 4H), 2.07 (d, J=15.4 Hz, 3H), 1.73 (d, J=10.3 Hz, 1H), 1.64-1.50 (m, 1H), 1.42 (d, J=6.8 Hz, 6H).

Example 7

2-(4-(6-isopropyl-5-(8-methoxy-[1,2,4]triazolo[1,5-a]pyridin-6-yl)-4H-pyrrolo[3,2-d]thiazol-2-yl)piperidin-1-yl)-N,N-dimethylacetamide (7)

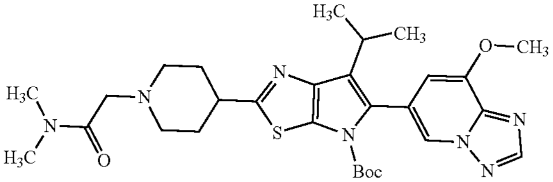

To a solution of 6-isopropyl-5-(8-methoxy-[1,2,4]triazolo[1,5-a]pyridin-6-yl)-2-(piperidin-4-yl)-4H-pyrrolo[3,2-d]thiazole (16 mg, 0.040 mmol) and 2-chloro-N,N-dimethylacetamide (7.07 μL, 0.069 mmol) in DMF (2 mL) was added TEA (0.017 mL, 0.121 mmol). The resulting solution was stirred at room temperature for 12 h. The reaction mass was diluted with water (5 mL) and extracted with EtOAc (3×10 mL). The separated organic layer was dried over sodium sulphate, filtered and dried. The crude sample was purified by prep LCMS using Method I. After Preparative LCMS purification, fractions containing the product was combined and dried using Genevac centrifugal evaporator to afford 2-(4-(6-isopropyl-5-(8-methoxy-[1,2,4]triazolo[1,5-a]pyridin-6-yl)-4H-pyrrolo[3,2-d]thiazol-2-yl)piperidin-1-yl)-N,N-dimethylacetamide (9.5 mg, 0.019 mmol, 46.3% yield) as a pale yellow solid. LCMS retention time 1.29 min [A]. MS ($E^-$) m/z: 482.2 (M+H). $^1H$ NMR (400 MHz, DMSO-$d_6$) δ 11.60 (s, 1H), 8.53-8.39 (m, 2H), 7.10 (s, 1H), 4.11-4.02 (m, 2H), 3.21-3.10 (m, 3H), 3.06-2.97 (m, 3H), 2.92 (d, J=11.0 Hz, 2H), 2.82 (s, 3H), 2.23 (t, J=10.6 Hz, 2H), 2.10-1.99 (m, 2H), 1.90 (s, 2H), 1.83-1.67 (m, 2H), 1.42 (d, J=6.8 Hz, 6H).

The following Examples were prepared according to the general procedure described in Example 7.

TABLE 2

| Ex. No. | Structure | HPLC Method | Ret Time (min) | LCMS MH+ |
|---|---|---|---|---|
| 8 | 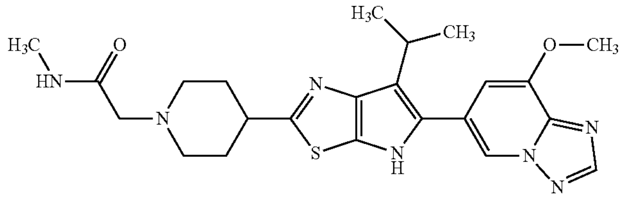 [SMILES: CNC(=O)CN1CCC(c2nc3c(C(C)C)c(-c4cc(OC)c5ncnn5c4)[nH]c3s2)CC1] | A | 1.33 | 468.3 |
| 9 | 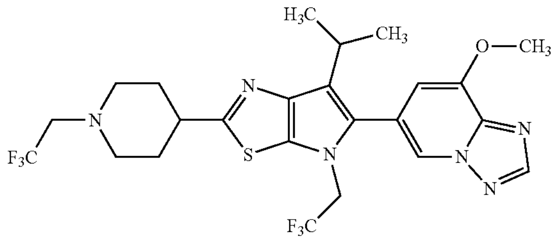 [SMILES: COc1cc(-c2c(C(C)C)c3nc(C4CCN(CC(F)(F)F)CC4)sc3n2CC(F)(F)F)cn2ncnc12] | A | 2.38 | 561.2 |

Example 10

6-isopropyl-2-(1-isopropylpiperidin-4-yl)-5-(8-methoxy-[1,2,4]triazolo[1,5-a]pyridin-6-yl)-4H-pyrrolo[3,2-d]thiazole (10)

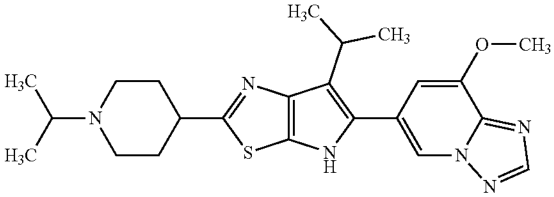

To a solution of 6-isopropyl-5-(8-methoxy-[1,2,4]triazolo[1,5-a]pyridin-6-yl)-2-(piperidin-4-yl)-4H-pyrrolo[3,2-d]thiazole (18 mg, 0.045 mmol) in MeOH (2 mL) was added TEA (0.013 mL, 0.091 mmol), propan-2-one (5.80 mg, 0.050 mmol) followed by acetic acid (0.260 μL, 4.54 μmol) dropwise at 0° C. The resulting solution was stirred at room temperature for 12 h. Then sodium cyanoborohydride (5.71 mg, 0.091 mmol) was added at 0° C. and the reaction mixture was stirred for 2 h at room temperature. The reaction mixture was concentrated, with the residue being dissolved in water (5 mL) and extracted with EtOAc (3×10 mL). The separated organic layer was dried over sodium sulphate, filtered and dried. The crude sample was purified by prep LCMS using Method I. After Preparative LCMS purification, fractions containing the product was combined and dried using Genevac centrifugal evaporator to afford 6-isopropyl-2-(1-isopropylpiperidin-4-yl)-5-(8-methoxy-[1,2,4]triazolo[1,5-a]pyridin-6-yl)-4H-pyrrolo[3,2-d]thiazole (4.14 mg, 0.09 mmol, 20.3% yield) as a pale yellow solid. LCMS retention time 1.15 min [A]. MS ($E^-$) m/z: 439.2 (M+H). $^1$H NMR (400 MHz, DMSO-$d_6$) δ 11.68 (s, 1H), 8.48 (s, 2H), 7.18-7.05 (m, 1H), 4.06 (s, 2H), 3.58-3.46 (m, 3H), 3.25-3.08 (m, 2H), 2.93 (dd, J=12.7, 6.6 Hz, 2H), 2.31 (br. s., 2H), 2.13-2.00 (m, 2H), 1.44 (d, J=6.8 Hz, 2H), 1.28 (d, J=6.6 Hz, 5H), 1.16 (t, J=7.2 Hz, 6H).

The following Examples were prepared according to the general procedure described in Example 10.

TABLE 3

| Ex. No. | Structure | HPLC Method | Ret Time (min) | LCMS MH+ |
|---|---|---|---|---|
| 11 | 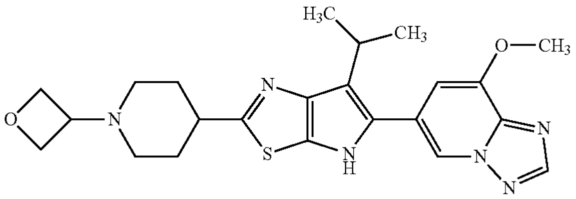 [SMILES: COc1cc(-c2[nH]c3sc(C4CCN(C5COC5)CC4)nc3c2C(C)C)cn2ncnc12] | A | 1.38 | 453.3 |

TABLE 3-continued

| Ex. No. | Structure | HPLC Method | Ret Time (min) | LCMS MH+ |
|---|---|---|---|---|
| 12 | 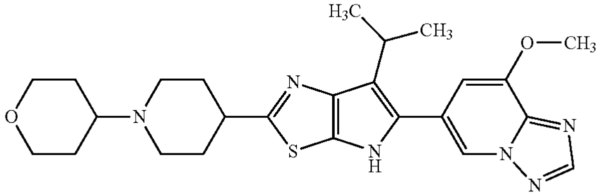 [SMILES: COc1cc(-c2[nH]c3sc(C4CCN(C5CCOCC5)CC4)nc3c2C(C)C)cn2ncnc12] | A | 1.23 | 481.2 |
| 13 | 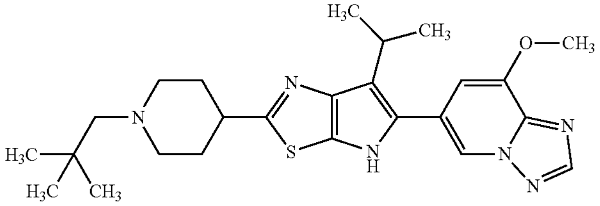 [SMILES: COc1cc(-c2[nH]c3sc(C4CCN(CC(C)(C)C)CC4)nc3c2C(C)C)cn2ncnc12] | A | 2.18 | 467.2 |
| 14 | 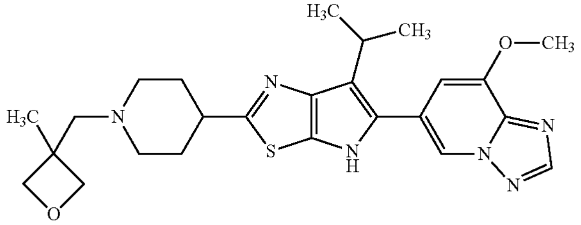 [SMILES: COc1cc(-c2[nH]c3sc(C4CCN(CC5(C)COC5)CC4)nc3c2C(C)C)cn2ncnc12] | A | 1.57 | 481.2 |

Example 15

1-(4-(6-isopropyl-5-(8-methoxy-[1,2,4]triazolo[1,5-a]pyridin-6-yl)-4H-pyrrolo[3,2-d]thiazol-2-yl)piperidin-1-yl)-2-methylpropan-2-ol (15)

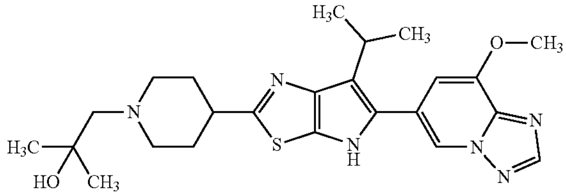

To a solution of 6-isopropyl-5-(8-methoxy-[1,2,4]triazolo[1,5-a]pyridin-6-yl)-2-(piperidin-4-yl)-4H-pyrrolo[3,2-d]thiazole (18 mg, 0.045 mmol) and 1-chloro-2-methylpropan-2-ol (4.93 mg, 0.045 mmol) in DMF (2 mL) was added potassium carbonate (18.82 mg, 0.136 mmol). The resulting solution was heated at 85° C. for 12 h. The reaction mass was diluted with water (5 mL) and extracted with EtOAc (3×10 mL). The separated organic layer was dried over sodium sulphate, filtered and dried. The crude sample was purified by prep LCMS using Method L. After Preparative LCMS purification, fractions containing the product was combined and dried using Genevac centrifugal evaporator to afford 1-(4-(6-isopropyl-5-(8-methoxy-[1,2,4]triazolo[1,5-a]pyridin-6-yl)-4H-pyrrolo[3,2-d]thiazol-2-yl)piperidin-1-yl)-2-methylpropan-2-ol (5.4 mg, 0.012 mmol, 25.4% yield) as a pale yellow solid. LCMS 1.37 min [A]. MS ($E^-$) m/z: 469.2 (M+H). $^1$H NMR (400 MHz, DMSO-$d_6$) δ 11.66 (s, 1H), 8.46 (d, J=1.5 Hz, 2H), 7.09 (s, 1H), 5.30 (br.s., 2H), 4.05 (s, 3H), 3.24-3.14 (m, 4H), 3.11 (br. s., 3H), 2.23 (br. s., 4H), 1.43 (d, J=6.8 Hz, 6H), 1.26 (s, 6H).

Example 16

6-isopropyl-5-(8-methoxy-[1,2,4]triazolo[1,5-a]pyridin-6-yl)-2-(1-(2-(methylsulfonyl)ethyl)piperidin-4-yl)-4H-pyrrolo[3,2-d]thiazole (16)

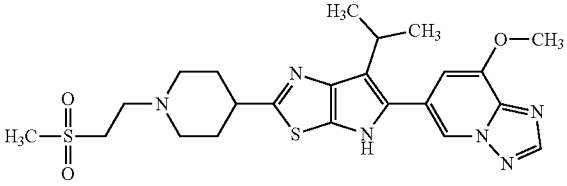

To a solution of 6-isopropyl-5-(8-methoxy-[1,2,4]triazolo[1,5-a]pyridin-6-yl)-2-(piperidin-4-yl)-4H-pyrrolo[3,2-d]thiazole (16 mg, 0.040 mmol) and 1-chloro-2-(methylsulfonyl)ethane (9.78 mg, 0.069 mmol) in DMF (1 mL) was added DIPEA (0.017 mL, 0.121 mmol). The resulting solution was heated at 85° C. for 12 h. The reaction mass was diluted with water (5 mL) and extracted with EtOAc (3×10 mL). The separated organic layer was dried over sodium sulphate, filtered and dried. The crude sample was purified by prep LCMS using Method I. After Preparative LCMS purification, fractions containing the product was combined and dried using Genevac centrifugal evaporator to afford 6-isopropyl-5-(8-methoxy-[1,2,4]triazolo[1,5-a]pyridin-6-yl)-2-(1-(2-(methylsulfonyl)ethyl)piperidin-4-yl)-4H-pyrrolo[3,2-d]thiazole (7.7 mg, 0.015 mmol, 38% yield) as a pale yellow solid. LCMS 1.35 min [A]. MS ($E^-$) m/z: 503.2 (M+H). $^1$H NMR (400 MHz, DMSO-$d_6$) δ 11.60 (s, 1H), 8.46 (s, 2H), 7.11 (s, 1H), 4.05 (s, 3H), 3.31 (d, J=6.1 Hz, 2H), 3.22-3.13 (m, 1H), 3.09-2.91 (m, 6H), 2.75 (br. s., 2H), 2.17 (br. s., 2H), 2.07 (d, J=8.3 Hz, 2H), 1.82-1.65 (m, 2H), 1.43 (d, J=6.8 Hz, 6H).

Example 17

2-(4-(6-isopropyl-5-(8-methyl-[1,2,4]triazolo[1,5-a]pyridin-6-yl)-4H-pyrrolo[3,2-d]thiazol-2-yl)piperidin-1-yl)-N,N-dimethylacetamide (17)

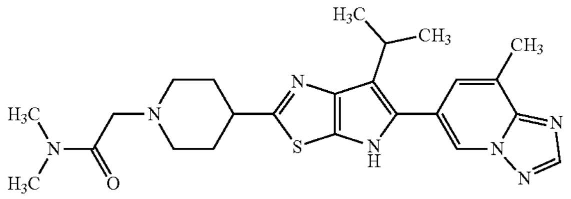

To a solution of 6-isopropyl-5-(8-methyl-[1,2,4]triazolo[1,5-a]pyridin-6-yl)-2-(piperidin-4-yl)-4H-pyrrolo[3,2-d]thiazole (16 mg, 0.042 mmol) in DMF (2 mL) solvent was added TEA (0.018 mL, 0.126 mmol) followed by 2-chloro-N,N-dimethylacetamide (7.36 μl, 0.071 mmol) respectively at room temperature. Then the resulting reaction mixture was stirred at same temperature for 12 h. The reaction mass was diluted with water (5 mL) and extracted with ethyl acetate (3×10 mL). The separated organic layer was dried over sodium sulphate, filtered and dried. The crude sample was purified by prep LCMS using Method I. After Preparative LCMS purification, fractions containing the product was combined and dried using Genevac centrifugal evaporator to afford 2-(4-(6-isopropyl-5-(8-methyl-[1,2,4]triazolo[1,5-a]pyridin-6-yl)-4H-pyrrolo[3,2-d]thiazol-2-yl)piperidin-1-yl)-N,N-dimethylacetamide (4.1 mg, 8.37 μmol, 19.89% yield) as a pale yellow solid. LCMS 1.33 min [A]. MS ($E^-$) m/z: 466.2 (M+H). $^1$H NMR (400 MHz, DMSO-$d_6$) δ 11.62 (s, 1H), 8.71 (s, 1H), 8.50 (s, 1H), 7.55 (s, 1H), 4.26 (s, 3H), 3.18-3.08 (m, 4H), 2.99-2.85 (m, 5H), 2.61 (s, 3H), 2.29 (br. s., 3H), 2.23-2.12 (m, 2H), 1.42 (d, J=6.6 Hz, 6H)

Example 18

1-(4-(6-isopropyl-5-(8-methyl-[1,2,4]triazolo[1,5-a]pyridin-6-yl)-4H-pyrrolo[3,2-d]thiazol-2-yl)piperidin-1-yl)-2-methylpropan-2-ol (18)

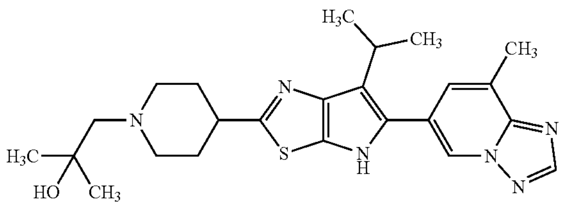

To a solution of 6-isopropyl-5-(8-methyl-[1,2,4]triazolo[1,5-a]pyridin-6-yl)-2-(piperidin-4-yl)-4H-pyrrolo[3,2-d]thiazole (18 mg, 0.047 mmol) in DMF (2 mL) was added potassium carbonate (19.61 mg, 0.142 mmol) followed by 1-chloro-2-methylpropan-2-ol (5.14 mg, 0.047 mmol) dropwise, the resulting light yellow solution was heated at 85° C. for 6 h. The reaction mass was diluted with water (5 mL) and extracted with EtOAc (3×10 mL). The separated organic layer was dried over sodium sulphate, filtered and dried. The crude sample was purified by prep LCMS using Method I. After Preparative LCMS purification, fractions containing the product was combined and dried using Genevac centrifugal evaporator to afford 1-(4-(6-isopropyl-5-(8-methyl-[1,2,4]triazolo[1,5-a]pyridin-6-yl)-4H-pyrrolo[3,2-d]thiazol-2-yl)piperidin-1-yl)-2-methylpropan-2-ol (2.6 mg, 5.51 μmol, 11.66% yield) as a pale yellow solid. LCMS 1.41 min [A]. MS ($E^-$) m/z: 453.2 (M+H). $^1$H NMR (400 MHz, DMSO-$d_6$) δ 11.69-11.54 (m, 1H), 8.73 (s, 1H), 8.51 (s, 1H), 7.55 (s, 1H), 5.24 (br. s., 1H), 3.72 (d, J=10.5 Hz, 2H), 3.22 (br. s., 2H), 3.17 (s, 3H), 3.12 (br. s., 3H), 2.93 (dd, J=12.1, 7.0 Hz, 2H), 2.62 (s, 3H), 2.24 (br. s., 3H), 2.19 (s, 3H), 1.42 (d, J=6.8 Hz, 6H).

Example 19

2-(dimethylamino)-1-(4-(6-isopropyl-5-(8-methyl-[1,2,4]triazolo[1,5-a]pyridin-6-yl)-4H-pyrrolo[3,2-d]thiazol-2-yl)piperidin-1-yl)ethan-1-one (19)

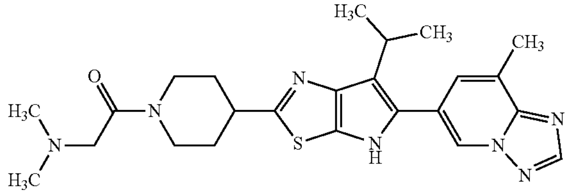

To a solution of 6-isopropyl-5-(8-methyl-[1,2,4]triazolo[1,5-a]pyridin-6-yl)-2-(piperidin-4-yl)-4H-pyrrolo[3,2-d]thiazole (16 mg, 0.042 mmol) and dimethylglycine (5.20 mg, 0.050 mmol) in DMF (2 mL) was added TEA (0.012 mL, 0.084 mmol) followed by HATU (17.59 mg, 0.046 mmol). The resulting reaction mixture was stirred at room temperature for 3 h. The reaction mass was diluted with water (5 mL) and extracted with EtOAc (3×10 mL). The separated organic layer was dried over sodium sulphate, filtered and dried. The crude sample was purified by prep LCMS using Method I. After Preparative LCMS purification, fractions containing the product was combined and dried using Genevac centrifugal evaporator to afford 2-(dimethylamino)-1-(4-(6-isopropyl-5-(8-methyl-[1,2,4]triazolo[1,5-a]pyridin-6-yl)-4H-pyrrolo[3,2-d]thiazol-2-yl)piperidin-1-yl)ethan-1-one (1 mg, 2.083 μmol, 4.95% yield) as a pale yellow solid. LCMS retention time 1.19 min [A]. MS ($E^-$) m/z: 466.2 (M+H). $^1$H NMR (400 MHz, DMSO-$d_6$) δ 11.58 (br. s., 1H), 8.71 (s, 1H), 8.50 (s, 1H), 7.55 (s, 1H), 4.39 (d, J=13.0 Hz, 1H), 4.12 (d, J=13.7 Hz, 1H), 3.14-3.06 (m, 6H), 2.84-2.71 (m, 2H), 2.61 (s, 3H), 2.19 (s, 4H), 2.15-2.02 (m, 2H), 1.80-1.63 (m, 2H), 1.41 (d, J=6.8 Hz, 6H).

Example 20

6-isopropyl-5-(8-methyl-[1,2,4]triazolo[1,5-a]pyridin-6-yl)-2-(1-(oxetan-3-yl)piperidin-4-yl)-4H-pyrrolo[3,2-d]thiazole (20)

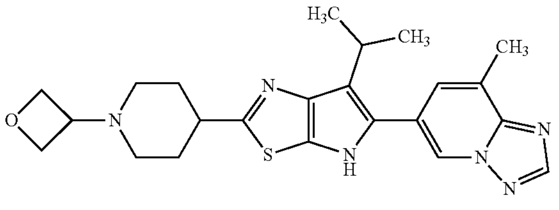

To a solution of 6-isopropyl-5-(8-methyl-[1,2,4]triazolo[1,5-a]pyridin-6-yl)-2-(piperidin-4-yl)-4H-pyrrolo[3,2-d]thiazole (10 mg, 0.026 mmol) in MeOH (2 mL) was added TEA (7.33 μL, 0.053 mmol), oxetan-3-one (2.083 mg, 0.029 mmol) followed by acetic acid (0.150 μL, 2.63 μmol) dropwise at 0° C. The resulting solution was stirred at room temperature for 12 h. Then sodium cyanoborohydride (3.30 mg, 0.053 mmol) was added at 0° C. and stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I to afford 6-isopropyl-5-(8-methyl-[1,2,4]triazolo[1,5-a]pyridin-6-yl)-2-(1-(oxetan-3-yl)piperidin-4-yl)-4H-pyrrolo[3,2-d]thiazole (1 mg, 2.268 μmol, 8.63% yield) as a pale yellow solid. LCMS retention time 1.43 min [A]. MS ($E^-$) m/z: 437.2 (M+H). $^1$H NMR (400 MHz, DMSO-$d_6$) δ 8.71 (s, 1H), 8.50 (s, 2H), 7.55 (s, 1H), 4.55 (t, J=6.5 Hz, 2H), 4.48-4.40 (m, 2H), 3.16-3.10 (m, 2H), 3.04 (d, J=2.9 Hz, 2H), 2.76 (s, 2H), 2.78 (s, 1H), 2.61 (s, 2H), 2.12-2.02 (m, 2H), 1.98-1.86 (m, 1H), 1.84-1.70 (m, 2H), 1.41 (d, J=6.6 Hz, 6H).

The following Examples were prepared according to the general procedure described in Example 20.

TABLE 4

| Ex. No. | Structure | HPLC Method | Ret Time (min) | LCMS MH+ |
|---|---|---|---|---|
| 21 | 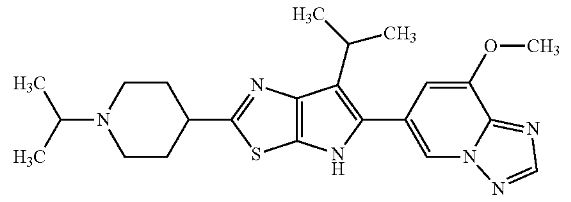 [SMILES: COc1cc(-c2[nH]c3sc(C4CCN(C(C)C)CC4)nc3c2C(C)C)cn2ncnc12] | A | 1.38 | 423.3 |
| 22 | 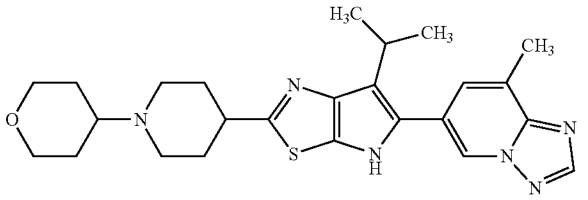 [SMILES: Cc1cc(-c2[nH]c3sc(C4CCN(C5CCOCC5)CC4)nc3c2C(C)C)cn2ncnc12] | A | 1.36 | 465.2 |
| 23 | 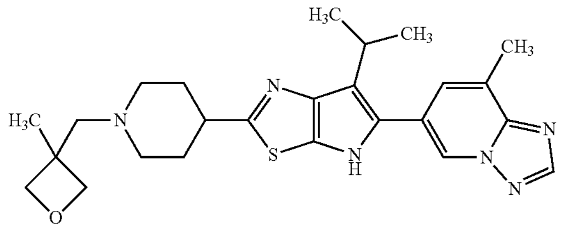 [SMILES: Cc1cc(-c2[nH]c3sc(C4CCN(CC5(C)COC5)CC4)nc3c2C(C)C)cn2ncnc12] | A | 1.63 | 465.2 |

Example 24

2-(4-(5-(2,6-dimethylpyridin-4-yl)-6-isopropyl-4H-pyrrolo[3,2-d]thiazol-2-yl)piperidin-1l-yl)-N,N-dimethylacetamide (24)

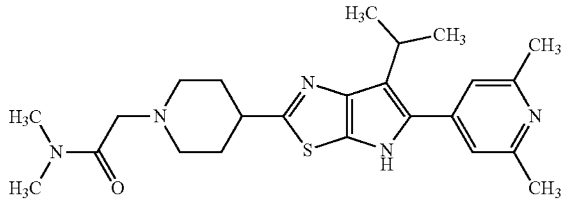

To a solution of 5-(2,6-dimethylpyridin-4-yl)-6-isopropyl-2-(piperidin-4-yl)-4H-pyrrolo[3,2-d]thiazole (20 mg, 0.056 mmol) in DMF (2 mL) solvent was added TEA (0.024 mL, 0.169 mmol) and 2-chloro-N,N-dimethylacetamide (9.88 μL, 0.096 mmol) at room temperature. Then the resulting reaction mixture was stirred at same temperature for 3 h. The reaction mass was diluted with water (5 mL) and extracted with EtOAc (3×10 mL). The separated organic layer was dried over sodium sulphate, filtered and concentrated. The crude sample was purified by prep LCMS using Method L. After Preparative LCMS purification, fractions containing product was combined and dried using Genevac centrifugal evaporator to afford 2-(4-(5-(2,6-dimethylpyridin-4-yl)-6-isopropyl-4H-pyrrolo[3,2-d]thiazol-2-yl)piperidin-1-yl)-N,N-dimethylacetamide (5.4 mg, 0.012 mmol, 21.12% yield) as a pale yellow solid. LCMS retention time 1.50 min [A]. MS ($E^-$) m/z: 440.2 (M+H). $^1H$ NMR (400 MHz, DMSO-$d_6$) δ 11.57 (s, 1H), 7.08 (s, 2H), 3.27 (d, J=6.8 Hz, 2H), 3.18 (br.s, 1H), 2.49-2.36 (m, 7H), 2.12-1.98 (m, 4H), 1.92 (s, 4H), 1.42 (d, J=6.8 Hz, 6H), 1.15 (s, 6H).

Example 25

5-(2,6-dimethylpyridin-4-yl)-6-isopropyl-2-(1-isopropylpiperidin-4-yl)-4H-pyrrolo[3,2-d]thiazole (25)

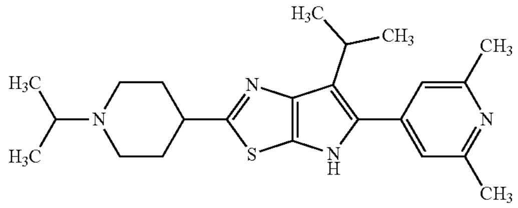

To a solution of 5-(2,6-dimethylpyridin-4-yl)-6-isopropyl-2-(piperidin-4-yl)-4H-pyrrolo[3,2-d]thiazole (20 mg, 0.056 mmol) in MeOH (2 mL) was added TEA (0.016 mL, 0.113 mmol), propan-2-one (3.60 mg, 0.062 mmol) followed by acetic acid (0.323 μL, 5.64 μmol) dropwise at 0° C. The resulting solution was stirred at room temperature for 12 h. Then sodium cyanoborohydride (7.09 mg, 0.113 mmol) was added at 0° C. and stirred for 2 h at room temperature. The reaction mass was concentrated, residue was dissolved in water (5 mL) and extracted with ethyl acetate (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(2,6-dimethylpyridin-4-yl)-6-isopropyl-2-(1-isopropylpiperidin-4-yl)-4H-pyrrolo[3,2-d]thiazole (10.6 mg, 0.027 mmol, 47.4% yield) as a pale yellow solid. LCMS retention time 1.38 min [A]. MS ($E^-$) m/z: 397.2 (M+H). $^1H$ NMR (400 MHz, DMSO-$d_6$) δ 11.57 (s, 1H), 7.72 (d, J=9.8 Hz, 1H), 7.43-7.32 (m, 1H), 4.06 (s, 2H), 3.58-3.46 (m, 3H), 3.25-3.08 (m, 2H), 2.93 (dd, J=12.7, 6.6 Hz, 2H), 2.31 (br. s., 2H), 2.13-2.00 (m, 3H), 1.44 (d, J=6.8 Hz, 4H), 1.28 (d, J=6.6 Hz, 5H), 1.16 (t, J=7.2 Hz, 6H).

The following Examples were prepared according to the general procedure described in Example 25.

TABLE 5

| Ex. No. | Structure | HPLC Method | Ret Time (min) | LCMS MH+ |
|---|---|---|---|---|
| 26 | 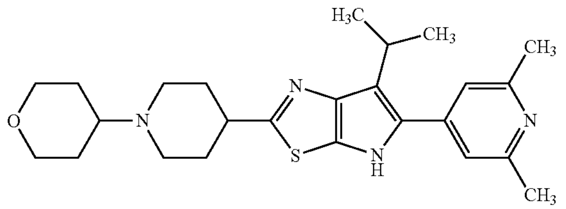 [SMILES: Cc1cc(-c2[nH]c3sc(C4CCN(C5CCOCC5)CC4)nc3c2C(C)C)cc(C)n1] | A | 1.46 | 439.2 |
| 27 | 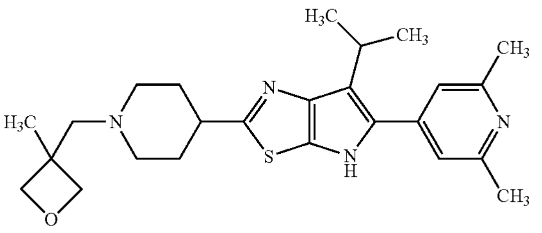 [SMILES: Cc1cc(-c2[nH]c3sc(C4CCN(CC5(C)COC5)CC4)nc3c2C(C)C)cc(C)n1] | A | 1.82 | 439.2 |

Example 28

2-(dimethylamino)-1-(4-(5-(2,6-dimethylpyridin-4-yl)-6-isopropyl-4H-pyrrolo[3,2-d]thiazol-2-yl)piperidin-1-yl)ethan-1-one (28)

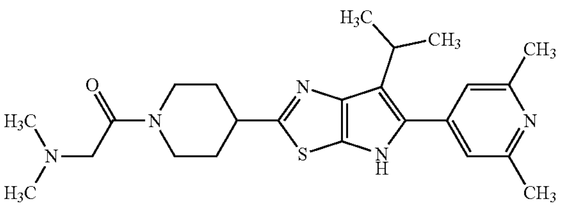

To a solution of 5-(2,6-dimethylpyridin-4-yl)-6-isopropyl-2-(piperidin-4-yl)-4H-pyrrolo[3,2-d]thiazole (20 mg, 0.056 mmol) and dimethylglycine (6.98 mg, 0.068 mmol) in DMF (2 mL) was added TEA (0.016 mL, 0.113 mmol) followed by HATU (23.60 mg, 0.062 mmol). The resulting reaction mixture was stirred at room temperature for 3 h. The reaction mass was diluted with water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 2-(dimethylamino)-1-(4-(5-(2,6-dimethylpyridin-4-yl)-6-isopropyl-4H-pyrrolo[3,2-d]thiazol-2-yl)piperidin-1-yl)ethan-1-one (7.9 mg, 0.018 mmol, 31.9% yield) as a pale yellow solid. LCMS retention time 1.36 min [A]. MS ($E^-$) m/z: 440.2 (M+H). $^1$H NMR (400 MHz, DMSO-$d_6$) δ 11.57 (s, 1H), 7.72 (d, J=9.8 Hz, 1H), 7.43-7.32 (m, 1H), 4.43 (d, J=13.7 Hz, 1H), 4.39-4.24 (m, 2H), 3.72 (br. s., 1H), 3.25 (br. s., 1H), 3.18 (s, 1H), 2.94 (t, J=11.7 Hz, 1H), 2.83 (s, 6H), 2.65 (s, 6H), 2.22-2.09 (m, 2H), 1.83 (d, J=9.5 Hz, 1H), 1.64 (d, J=8.6 Hz, 1H), 1.46 (d, J=6.8 Hz, 6H).

Example 29

1-(4-(5-(2,6-dimethylpyridin-4-yl)-6-isopropyl-4H-pyrrolo[3,2-d]thiazol-2-yl)piperidin-1-yl)-2-methylpropan-2-ol (29)

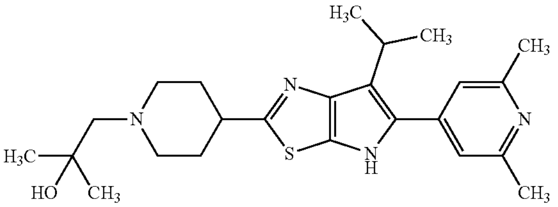

To a solution of 5-(2,6-dimethylpyridin-4-yl)-6-isopropyl-2-(piperidin-4-yl)-4H-pyrrolo[3,2-d]thiazole (20 mg, 0.056 mmol) in DMF (2 mL) was added potassium carbonate (23.39 mg, 0.169 mmol) followed by 1-chloro-2-methylpropan-2-ol (6.12 mg, 0.056 mmol), the resulting light yellow solution was heated at 80° C. for 6 h. The reaction mass was diluted with water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 1-(4-(5-(2,6-dimethylpyridin-4-yl)-6-isopropyl-4H-pyrrolo[3,2-d]thiazol-2-yl)piperidin-1-yl)-2-methylpropan-2-ol (2.8 mg, 6.56 μmol, 11.63% yield) as a pale yellow solid. LCMS 1.61 min [A]. MS ($E^-$) m/z: 427.2 (M+H). $^1$H NMR (400 MHz, DMSO-$d_6$) δ 11.57 (s, 1H), 7.72 (d, J=9.8 Hz, 1H), 7.43-7.32 (m, 1H), 5.24 (br. s., 1H), 3.72 (d, J=10.5 Hz, 2H), 3.22 (br. s., 3H), 3.17 (s, 3H), 3.12 (br. s., 4H), 2.93 (dd, J=12.1, 7.0 Hz, 2H), 2.62 (s, 3H), 2.24 (br. s., 3H), 2.19 (s, 3H), 1.42 (d, J=6.8 Hz, 6H).

Example 30

2-(4-(6-isopropyl-5-(1-methyl-1H-pyrrolo[2,3-b]pyridin-3-yl)-4H-pyrrolo[3,2-d]thiazol-2-yl)piperidin-1-yl)-N,N-dimethylacetamide (30)

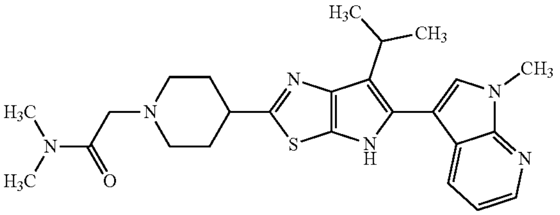

To a solution of 6-isopropyl-5-(1-methyl-1H-pyrrolo[2,3-b]pyridin-3-yl)-2-(piperidin-4-yl)-4H-pyrrolo[3,2-d]thiazole (35 mg, 0.092 mmol) in DMF (2 mL) solvent was added TEA (0.013 mL, 0.092 mmol) and 2-chloro-N,N-dimethylacetamide (45 mg, 0.370 mmol) at room temperature. Then the resulting reaction mixture was stirred at same temperature for 3 h. The reaction mass was diluted with water (5 mL) and extracted with ethyl acetate (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 2-(4-(6-isopropyl-5-(1-methyl-1H-pyrrolo[2,3-b]pyridin-3-yl)-4H-pyrrolo[3,2-d]thiazol-2-yl)piperidin-1-yl)-N,N-dimethylacetamide (7.0 mg, 0.014 mmol, 14.95% yield) as a pale yellow solid. LCMS retention time 1.56 min [A]. MS ($E^-$) m/z: 465.2 (M+H). $^1$H NMR (400 MHz, DMSO-$d_6$) δ 11.16 (s, 1H), 8.34 (dd, J=4.5, 1.6 Hz, 1H), 7.99 (dd, J=7.8, 1.5 Hz, 1H), 7.60 (s, 1H), 7.17 (dd, J=7.9, 4.5 Hz, 1H), 3.91 (d, J=4.6 Hz, 3H), 3.22 (br. s., 2H), 3.11-2.99 (m, 3H), 2.95 (br. s., 2H), 2.90 (s, 1H), 2.87-2.78 (m, 2H), 2.26 (br. s., 2H), 2.07 (d, J=15.2 Hz, 3H), 1.87-1.64 (m, 3H), 1.38 (d, J=6.8 Hz, 6H).

The following Examples were prepared according to the general procedure described in Example 30.

TABLE 6

| Ex. No. | Structure | HPLC Method | Ret Time (min) | LCMS MH+ |
|---|---|---|---|---|
| 31 | 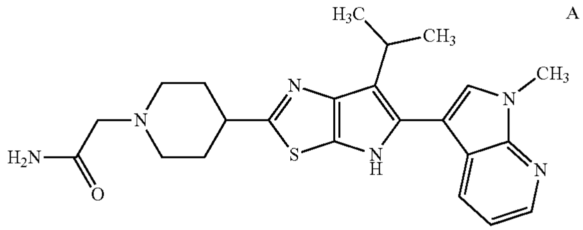 | A | 1.451 | 437.2 |

Example 32

2-(dimethylamino)-1-(4-(6-isopropyl-5-(1-methyl-1H-pyrrolo[2,3-b]pyridin-3-yl)-4H-pyrrolo[3,2-d]thiazol-2-yl)piperidin-1-yl)ethan-1-one (32)

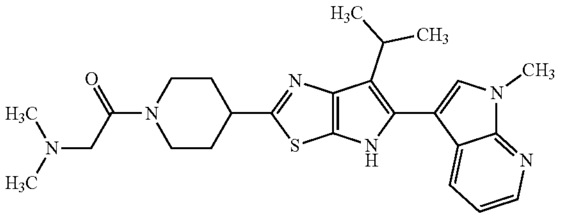

To a solution of 6-isopropyl-5-(1-methyl-1H-pyrrolo[2,3-b]pyridin-3-yl)-2-(piperidin-4-yl)-4H-pyrrolo[3,2-d]thiazole (35 mg, 0.092 mmol) and dimethyl glycine (45 mg, 0.436 mmol) in DMF (2 mL) was added TEA (0.013 mL, 0.092 mmol) followed by HATU (35.1 mg, 0.092 mmol). The resulting reaction mixture was stirred at room temperature for 3 h. The reaction mass was diluted with water (5 mL) and extracted with ethyl acetate (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 2-(dimethylamino)-1-(4-(6-isopropyl-5-(1-methyl-1H-pyrrolo[2,3-b]pyridin-3-yl)-4H-pyrrolo[3,2-d]thiazol-2-yl)piperidin-1-yl)ethan-1-one (12 mg, 0.024 mmol, 26.2% yield) as a pale yellow solid. LCMS retention time 1.44 min [A]. MS ($E^-$) m/z: 465.2 (M+H). $^1$H NMR (400 MHz, DMSO-$d_6$) δ 11.17 (s, 1H), 8.34 (dd, J=4.6, 1.5 Hz, 1H), 7.99 (dd, J=7.8, 1.5 Hz, 1H), 7.60 (s, 1H), 7.18 (dd, J=8.1, 4.6 Hz, 1H), 4.41 (d, J=12.7 Hz, 1H), 4.13 (d, J=13.7 Hz, 1H), 3.93-3.86 (m, 4H), 3.22-3.04 (m, 3H), 2.79 (t, J=11.6 Hz, 1H), 2.26-2.15 (m, 2H), 2.14-1.99 (m, 3H), 1.92 (s, 2H), 1.81-1.66 (m, 2H), 1.66-1.47 (m, 2H), 1.38 (d, J=6.8 Hz, 6H).

Example 33

6-isopropyl-5-(1-methyl-1H-pyrrolo[2,3-b]pyridin-3-yl)-2-(1-(2-(methylsulfonyl)ethyl)piperidin-4-yl)-4H-pyrrolo[3,2-d]thiazole (33)

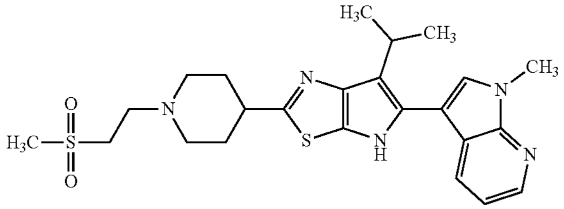

To a solution of 6-isopropyl-5-(1-methyl-1H-pyrrolo[2,3-b]pyridin-3-yl)-2-(piperidin-4-yl)-4H-pyrrolo[3,2-d]thiazole (25 mg, 0.066 mmol) and 1-chloro-2-(methylsulfonyl)ethane (9.39 mg, 0.066 mmol) in DMF (1 mL) was added TEA (0.018 mL, 0.132 mmol). The resulting solution was heated at 90° C. for 12 h. The reaction mass was diluted with water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 6-isopropyl-5-(1-methyl-1H-pyrrolo[2,3-b]pyridin-3-yl)-2-(1-(2-(methylsulfonyl) ethyl)piperidin-4-yl)-4H-pyrrolo[3,2-d]thiazole (4.4 mg, 8.82 μmol, 13.40% yield) as a pale yellow solid. LCMS 1.63 min [A]. MS ($E^-$) m/z: 486.2 (M+H). $^1$H NMR (400 MHz, DMSO-$d_6$) δ 11.16 (s, 1H), 8.33 (dd, J=4.6, 1.5 Hz, 1H), 7.99 (dd, J=7.9, 1.6 Hz, 1H), 7.60 (s, 1H), 7.17 (dd, J=7.9, 4.5 Hz, 1H), 3.91 (d, J=4.9 Hz, 4H), 3.33 (br. s., 2H), 3.12-2.88 (m, 6H), 2.75 (br. s., 2H), 2.16 (br. s., 2H), 2.07 (d, J=7.6 Hz, 2H), 1.75 (d, J=9.5 Hz, 2H), 1.38 (d, J=6.8 Hz, 6H).

Example 34

6-isopropyl-5-(1-methyl-1H-pyrrolo[2,3-b]pyridin-3-yl)-2-(1-(oxetan-3-yl)piperidin-4-yl)-4H-pyrrolo[3,2-d]thiazole (34)

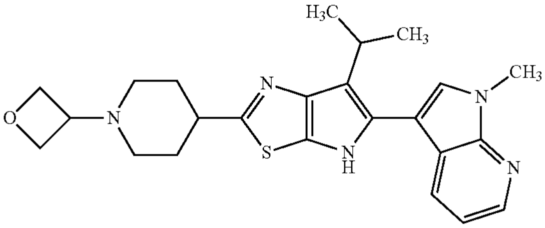

To a solution of 6-isopropyl-5-(1-methyl-1H-pyrrolo[2,3-b]pyridin-3-yl)-2-(piperidin-4-yl)-4H-pyrrolo[3,2-d]thiazole (25 mg, 0.066 mmol) in MeOH (2 mL) were added TEA (0.018 mL, 0.132 mmol) and oxetan-3-one (5.22 mg, 0.072 mmol) followed by acetic acid (0.377 μL, 6.59 μmol) dropwise at 0° C. The resulting solution was stirred at room temperature for 12 h. Then sodium cyanoborohydride (8.28 mg, 0.132 mmol) was added at 0° C. and stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 6-isopropyl-5-(1-methyl-1H-pyrrolo[2,3-b]pyridin-3-yl)-2-(1-(oxetan-3-yl)piperidin-4-yl)-4H-pyrrolo[3,2-d]thiazole as a pale yellow solid. LCMS retention time 1.65 min [A]. MS ($E^-$) m/z: 436.2 (M+H). $^1$H NMR (400 MHz, DMSO-$d_6$) δ 11.15 (s, 1H), 8.34 (dd, J=4.6, 1.5 Hz, 1H), 7.99 (dd, J=7.8, 1.5 Hz, 1H), 7.69-7.46 (m, 2H), 7.18 (dd, J=7.9, 4.5 Hz, 1H), 4.56 (t, J=6.5 Hz, 2H), 4.46 (t, J=6.1 Hz, 2H), 3.99-3.86 (m, 2H), 3.42 (d, J=4.9 Hz, 1H), 3.18 (d, J=5.1 Hz, 1H), 3.12-2.93 (m, 2H), 2.79 (d, J=10.3 Hz, 2H), 2.07 (d, J=8.1 Hz, 2H), 1.94 (t, J=11.0 Hz, 2H), 1.86-1.70 (m, 2H), 1.38 (d, J=7.1 Hz, 6H).

The following Examples were prepared according to the general procedure described in Example 34.

TABLE 7

| Ex. No. | Structure | HPLC Method | Ret Time (min) | LCMS MH$^+$ |
|---|---|---|---|---|
| 35 | 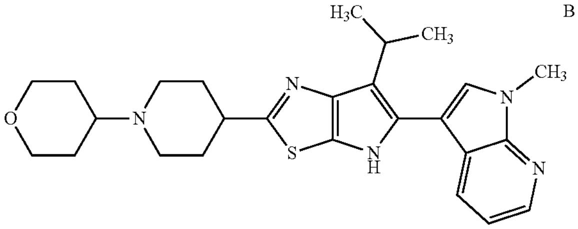 | B | 1.11 | 464.2 |
| 36 | 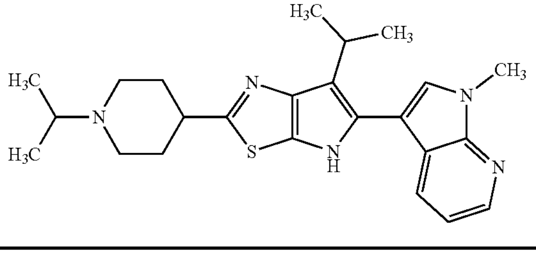 | A | 1.48 | 422.2 |

Example 37

5-(6-isopropyl-2-(1-(oxetan-3-yl)piperidin-4-yl)-4H-pyrrolo[3,2-d]thiazol-5-yl)quinoline-8-carbonitrile (37)

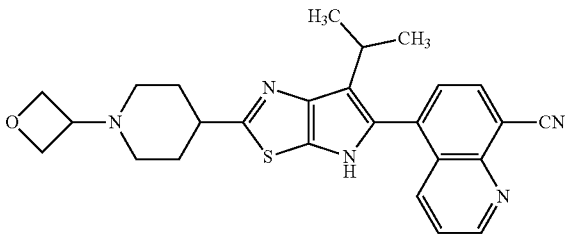

To a solution of 5-(6-isopropyl-2-(piperidin-4-yl)-4H-pyrrolo[3,2-d]thiazol-5-yl)quinoline-8-carbonitrile (25 mg, 0.062 mmol) in MeOH (2 mL) was added oxetan-3-one (4.49 mg, 0.062 mmol), TEA (8.68 μL, 0.062 mmol) followed by acetic acid (0.356 μL, 6.23 μmol) dropwise at 0° C. The resulting solution was stirred at room temperature for 12 h. Then sodium cyanoborohydride (7.83 mg, 0.125 mmol) was added at 0° C. and stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(6-isopropyl-2-(1-(oxetan-3-yl)piperidin-4-yl)-4H-pyrrolo[3,2-d]thiazol-5-yl)quinoline-8-carbonitrile (9.1 mg, 0.020 mmol, 31.4% yield) as a pale yellow solid. LCMS retention time 1.74 min [A]. MS ($E^-$) m/z: 458.2 (M+H). $^1H$ NMR (400 MHz, DMSO-$d_6$) δ 11.70 (s, 1H), 9.13 (dd, J=4.2, 1.7 Hz, 1H), 8.45 (d, J=7.6 Hz, 1H), 8.40 (dd, J=8.6, 1.7 Hz, 1H), 7.75 (dd, J=8.7, 4.3 Hz, 1H), 7.72 (d, J=7.6 Hz, 1H), 4.57 (t, J=6.5 Hz, 2H), 4.47 (t, J=6.1 Hz, 2H), 3.91 (s, 2H), 3.44 (br. s., 1H), 2.90-2.71 (m, 2H), 2.10 (d, J=12.2 Hz, 2H), 1.97 (br. s., 2H), 1.88-1.69 (m, 2H), 1.34 (d, J=6.8 Hz, 6H).

The following Examples were prepared according to the general procedure described in Example 37.

TABLE 8

| Ex. No. | Structure | HPLC Method | Ret Time (min) | LCMS MH⁺ |
|---|---|---|---|---|
| 38 | 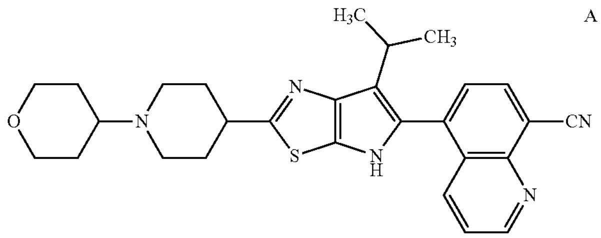 | A | 1.61 | 486.2 |

Example 39

5-(2-(1-(dimethylglycyl)piperidin-4-yl)-6-isopropyl-4H-pyrrolo[3,2-d]thiazol-5-yl)quinoline-8-carbonitrile (39)

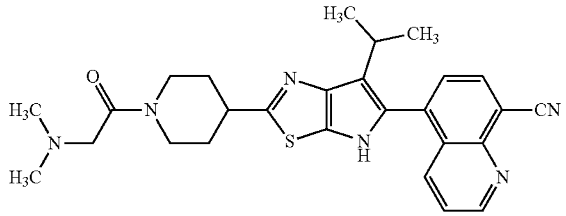

To a solution of 5-(6-isopropyl-2-(piperidin-4-yl)-4H-pyrrolo[3,2-d]thiazol-5-yl)quinoline-8-carbonitrile (20 mg, 0.050 mmol) and dimethylglycine (5.14 mg, 0.050 mmol) in DMF (2 mL) was added TEA (0.014 mL, 0.100 mmol) followed by HATU (18.94 mg, 0.050 mmol). The resulting reaction mixture was stirred at room temperature for 3 h. The reaction mass was diluted with water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(2-(1-(dimethylglycyl)piperidin-4-yl)-6-isopropyl-4H-pyrrolo[3,2-d]thiazol-5-yl)quinoline-8-carbonitrile (10.5 mg, 0.020 mmol, 40.2% yield) as a pale yellow solid. LCMS retention time 1.50 min [A]. MS ($E^-$) m/z: 487.2 (M+H). $^1H$ NMR (400 MHz, DMSO-$d_6$) δ 11.71 (s, 1H), 9.13 (dd, J=4.2, 1.5 Hz, 1H), 8.49-8.42 (m, 1H), 8.39 (dd, J=8.7, 1.6 Hz, 1H), 7.83-7.64 (m, 2H), 4.43 (d, J=12.2 Hz, 1H), 4.15 (d, J=12.2 Hz, 1H), 3.91 (s, 1H), 3.24-3.08 (m, 3H), 2.96-2.86 (m, 1H), 2.84-2.70 (m, 2H), 2.30-2.17 (m, 6H), 2.16-2.04 (m, 2H), 1.92 (s, 1H), 1.34 (d, J=6.8 Hz, 6H).

Example 40

2-(4-(5-(8-cyanoquinolin-5-yl)-6-isopropyl-4H-pyrrolo[3,2-d]thiazol-2-yl)piperidin-1-yl)-N,N-dimethylacetamide (40)

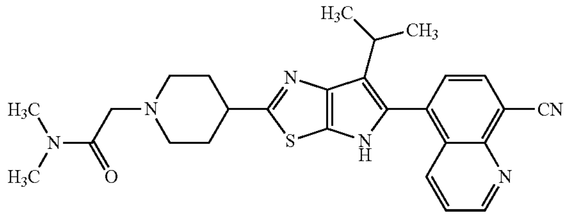

To a solution of 5-(6-isopropyl-2-(piperidin-4-yl)-4H-pyrrolo[3,2-d]thiazol-5-yl)quinoline-8-carbonitrile (20 mg, 0.050 mmol) in DMF (2 mL) was added TEA (0.014 mL, 0.100 mmol) followed by 2-chloro-N,N-dimethylacetamide (6.06 mg, 0.050 mmol) dropwise. The resulting reaction mixture was stirred at room temperature for 3 h. The reaction mass was diluted with water (5 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 2-(4-(5-(8-cyanoquinolin-5-yl)-6-isopropyl-4H-pyrrolo[3,2-d]thiazol-2-yl)piperidin-1-yl)-N,N-dimethylacetamide (7.2 mg, 0.015 mmol, 29.7% yield) as a pale yellow solid. LCMS retention time 1.64 min [A]. MS ($E^-$) m/z: 487.2 (M+H). $^1H$ NMR (400 MHz, DMSO-$d_6$) δ 11.70 (s, 1H), 9.13 (d, J=4.2 Hz, 1H), 8.45 (d, J=7.3 Hz, 1H), 8.40 (d, J=8.6 Hz, 1H), 7.80-7.65 (m, 1H), 3.04 (s, 6H), 2.85 (br. s., 4H), 2.79-2.73 (m, 2H), 2.09 (br. s., 4H), 1.83 (br. s., 2H), 1.34 (d, J=6.8 Hz, 6H).

Example 41

5-(7,8-dimethyl-[1,2,4]triazolo[1,5-a]pyridin-6-yl)-6-isopropyl-2-(1-(oxetan-3-yl)piperidin-4-yl)-4H-pyrrolo[3,2-d]thiazole (41)

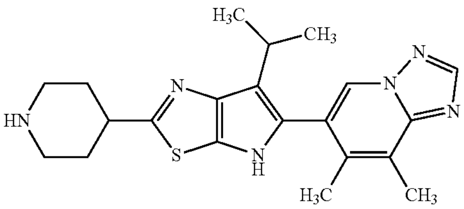

Intermediate 41A: tert-butyl 4-(5-((tert-butoxycarbonyl)amino)-4-((7,8-dimethyl-[1,2,4]triazolo[1,5-a]pyridin-6-yl)ethynyl)thiazol-2-yl)piperidine-1-carboxylate (41A)

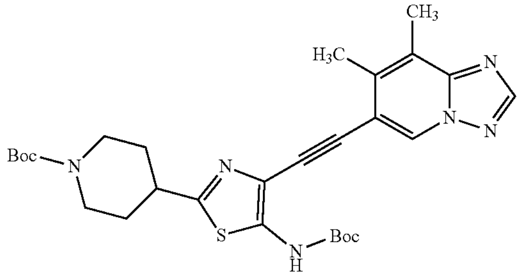

To a solution of tert-butyl 4-(5-((tert-butoxycarbonyl)amino)-4-iodothiazol-2-yl) piperidine-1-carboxylate (2 g, 3.93 mmol) in mixture of toluene (40 mL) and diisopropylamine (10 mL) were added copper(I) iodide (0.075 g, 0.393 mmol) and triphenylphosphine (0.103 g, 0.393 mmol) while purging with argon, bis(triphenylphosphine)palladium (II) dichloride (0.138 g, 0.196 mmol) was added, stirred the reaction mixture for 5 min, 6-ethynyl-7,8-dimethyl-[1,2,4]triazolo[1,5-a]pyridine (1.008 g, 5.89 mmol) was added to the and heated at 45° C. for 3 h in a sealed tube. The reaction mass was diluted with DCM, filtered through celite and washed with water and brine, dried over $Na_2SO_4$, concentrated and purified over silica gel eluting 60% with EtOAc in pet ether to afford tert-butyl 4-(5-((tert-butoxycarbonyl)amino)-4-((7,8-dimethyl-[1,2,4]triazolo[1,5-a]pyridin-6-yl)ethynyl)thiazol-2-yl)piperidine-1-carboxylate as a pale yellow solid. LCMS retention time 2.07 min [F]. MS ($E^-$) m/z: 553.5 (M+H).

Intermediate 41B: tert-butyl 2-(1-(tert-butoxycarbonyl)piperidin-4-yl)-5-(7,8-dimethyl-[1,2,4]triazolo[1,5-a]pyridin-6-yl)-4H-pyrrolo[3,2-d]thiazole-4-carboxylate (41B)

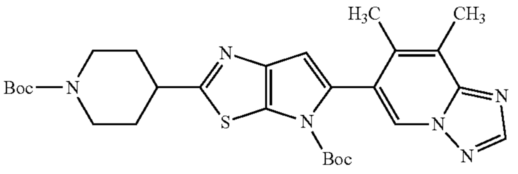

To a stirred solution of tert-butyl 4-(5-((tert-butoxycarbonyl)amino)-4-((7,8-dimethyl-[1,2,4]triazolo[1,5-a]pyridin-6-yl)ethynyl)thiazol-2-yl)piperidine-1-carboxylate (1.9 g, 3.44 mmol) in toluene (40 mL) was added silver acetate (0.574 g, 3.44 mmol), stirred at 100° C. for 30 min in sealed tube. The reaction mixture was filtered through celite, concentrated and purified over 40 g silica column eluting 0 to 70% EtOAc in Pet ether to afford tert-butyl 2-(1-(tert-butoxycarbonyl)piperidin-4-yl)-5-(7,8-dimethyl-[1,2,4]triazolo[1,5-a]pyridin-6-yl)-4H-pyrrolo[3,2-d]thiazole-4-carboxylate (1.8 g, 3.26 mmol, 95% yield) as an off-white solid. LCMS retention time 2.12 min [F]. MS ($E^-$) m/z: 553.6 (M+H).

Intermediate 41C: Tert-butyl 6-bromo-2-(1-(tert-butoxycarbonyl)piperidin-4-yl)-5-(7,8-dimethyl-[1,2,4]triazolo[1,5-]pyridin-6-yl)-4H-pyrrolo[3,2-d]thiazole-4-carboxylate (41C)

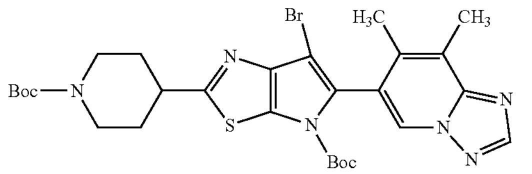

To a solution of tert-butyl 2-(1-(tert-butoxycarbonyl)piperidin-4-yl)-5-(7,8-dimethyl-[1,2,4]triazolo[1,5-a]pyridin-6-yl)-4H-pyrrolo[3,2-d]thiazole-4-carboxylate (1.5 g, 2.71 mmol) in DMF (30 mL) at 0° C. was added a solution of NBS (0.725 g, 4.07 mmol) in DMF (5 mL), then stirred for overnight at room temperature. Next, water (40 mL) was added to the reaction mass, stirred for 20 min at room temperature. The obtained solid was collected by filtration, then dried on vacuum to afford tert-butyl 6-bromo-2-(1-(tert-butoxycarbonyl) piperidin-4-yl)-5-(7,8-dimethyl-[1,2,4]triazolo[1,5-a]pyridin-6-yl)-4H-pyrrolo[3,2-d]thiazole-4-carboxylate (1.4 g, 2.217 mmol, 82% yield) as off-white solid. LCMS retention time 1.16 min [F]. MS ($E^-$) m/z: 633.4 (M+2H).

Intermediate 41D: Tert-butyl 2-(1-(tert-butoxycarbonyl)piperidin-4-yl)-5-(7,8-dimethyl-[1,2,4]triazolo[1,5-a]pyridin-6-yl)-6-(prop-1-en-2-yl)-4H-pyrrolo[3,2-d]thiazole-4-carboxylate (41D)

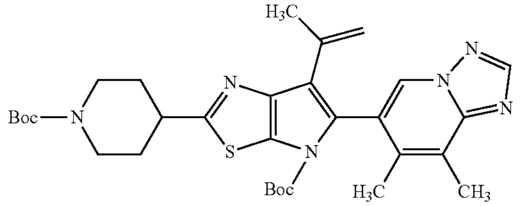

To a solution of tert-butyl 6-bromo-2-(1-(tert-butoxycarbonyl)piperidin-4-yl)-5-(7,8-dimethyl-[1,2,4]triazolo[1,5-a]pyridin-6-yl)-4H-pyrrolo[3,2-d]thiazole-4-carboxylate (1.5 g, 2.375 mmol) and 4,4,5,5-tetramethyl-2-(prop-1-en-2-yl)-1,3,2-dioxaborolane (1.596 g, 9.50 mmol) in 1,4-dioxane (30 mL) and water (3 mL) was added tripotassium phosphate (1.512 g, 7.12 mmol), then purged with nitrogen for 5 mins. $PdCl_2$ (dppf)-$CH_2Cl_2$ adduct (0.194 g, 0.237 mmol) was added and the reaction was again purged for 2 mins. The reaction mixture was heated in a sealed tube at 90° C. for 4 h. The reaction mixture was filtered through celite, concentrated and purified over silica gel eluting 50% EtOAc in Pet ether to afford tert-butyl 2-(1-(tert-butoxycarbonyl)piperidin-4-yl)-5-(7,8-dimethyl-[1,2,4]triazolo[1,5-a]pyridin-6-yl)-6-(prop-1-en-2-yl)-4H-pyrrolo[3,2-d]thiazole-4-carboxylate (1.3 g, 2.193 mmol, 92% yield). LCMS retention time 1.4 min [F]. MS ($E^-$) m/z: 593.4 (M+H).

Intermediate 41E: Tert-butyl 2-(1-(tert-butoxycarbonyl)piperidin-4-yl)-5-(7,8-dimethyl-[1,2,4]triazolo[1,5-a]pyridin-6-yl)-6-isopropyl-4H-pyrrolo[3,2-d]thiazole-4-carboxylate (41E)

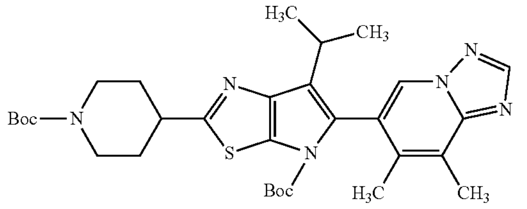

tert-butyl 2-(1-(tert-butoxycarbonyl)piperidin-4-yl)-5-(7,8-dimethyl-[1,2,4]triazolo[1,5-a]pyridin-6-yl)-6-(prop-1-en-2-yl)-4H-pyrrolo[3,2-d]thiazole-4-carboxylate (1.3 g, 2.193 mmol) added to ethyl acetate (30 mL). The flask was purged with $N_2$ and Pd—C(0.233 g, 2.193 mmol) was added. Following purging with nitrogen gas, hydrogen gas was introduced via a balloon. The reaction mixture was stirred at ambient temperature for 4 h. The flask was evacuated and filled with $N_2$. The suspension was filtered and the filtrate was concentrated to get crude product. The crude product was purified over silica gel eluting 50% EtOAc in Pet ether to afford tert-butyl 2-(1-(tert-butoxycarbonyl) piperidin-4-yl)-5-(7,8-dimethyl-[1,2,4]triazolo[1,5-a]pyridin-6-yl)-6-isopropyl-4H-pyrrolo[3,2-d]thiazole-4-carboxylate (0.95 g, 1.597 mmol, 72.8% yield). LCMS retention time 1.57 min [F]. MS ($E^-$) m/z: 595.5 (M+H).

Example 41: 5-(7,8-dimethyl-[1,2,4]triazolo[1,5-a]pyridin-6-yl)-6-isopropyl-2-(piperidin-4-yl)-4H-pyrrolo[3,2-d]thiazole To a stirred solution of tert-butyl 2-(1-(tert-butoxycarbonyl)piperidin-4-yl)-5-(7,8-dimethyl-[1,2,4]triazolo[1,5-a]pyridin-6-yl)-6-isopropyl-4H-pyrrolo[3,2-d]thiazole-4-carboxylate (0.45 g, 0.757 mmol) in DCM (5 mL) was added TFA (2.91 mL, 37.8 mmol) at 0° C., then the reaction mixture was stirred at room temperature for 16 h. The reaction mass was concentrated and 12 mL of MTBE was added to the residue and stirred at room temperature for 5 min, the obtained solid was collected by filtration to afford 5-(7,8-dimethyl-[1,2,4]triazolo[1,5-a]pyridin-6-yl)-6-isopropyl-2-(piperidin-4-yl)-4H-pyrrolo[3,2-d]thiazole (0.28 g, 0.710 mmol, 94% yield) as light brown solid. LCMS retention time 1.127 min [A]. MS ($E^-$) m/z: 395.2 (M+H). $^1H$ NMR (400 MHz, DMSO-$d_6$) δ 11.37-11.30 (m, 1H), 8.72 (s, 1H), 8.45 (s, 1H), 3.20-3.00 (m, 4H), 2.75-2.63 (m, 3H), 2.58 (s, 3H), 2.18 (s, 3H), 2.06-1.98 (m, 2H), 1.74-1.63 (m, 2H), 1.31 (d, J=6.8 Hz, 6H).

The following Intermediate was prepared according to the general procedure described in Intermediate 41.

TABLE 9

| Ex. No. | Structure | HPLC Method | Ret Time (min) | LCMS MH+ |
|---|---|---|---|---|
| 42 | 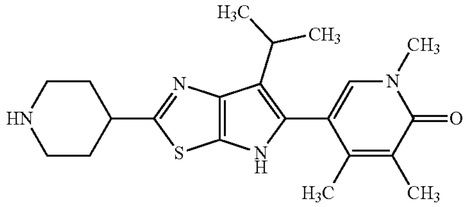 [SMILES: Cc1c(-c2[nH]c3sc(C4CCNCC4)nc3c2C(C)C)cn(C)c(=O)c1C] | C | 1.252 | 385.2 |

Example 43

5-(7,8-dimethyl-[1,2,4]triazolo[1,5-a]pyridin-6-yl)-6-isopropyl-2-(1-(oxetan-3-yl)piperidin-4-yl)-4H-pyrrolo[3,2-d]thiazole (43)

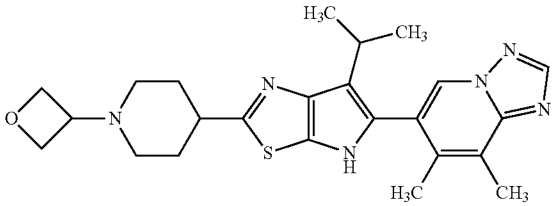

To a solution of 5-(7,8-dimethyl-[1,2,4]triazolo[1,5-a]pyridin-6-yl)-6-isopropyl-2-(piperidin-4-yl)-4H-pyrrolo[3,2-d]thiazole (20 mg, 0.051 mmol) and oxetan-3-one (18.27 mg, 0.253 mmol) in methanol (2 mL) was added AcOH (0.290 μL, 5.07 μmol) and stirred overnight at room temperature, then sodium cyanoborohydride (6.37 mg, 0.101 mmol) was added to the reaction mass at 0° C. and stirred for 2 h at room temperature. The reaction mass was diluted with water (2 ml) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(7,8-dimethyl-[1,2,4]triazolo[1,5-a]pyridin-6-yl)-6-isopropyl-2-(1-(oxetan-3-yl)piperidin-4-yl)-4H-pyrrolo[3,2-d]thiazole (12.1 mg, 0.026 mmol, 52.1% yield). LCMS retention time 1.443 min [A]. MS ($E^-$) m/z: 451.3 (M+H). $^1H$ NMR (400 MHz, DMSO-$d_6$) δ 11.31 (s, 1H), 8.72 (s, 1H), 8.45 (s, 1H), 4.65-4.51 (m, 2H), 4.46 (t, J=6.2 Hz, 2H), 3.91 (s, 2H), 3.44 (br. s., 1H), 3.05 (br. s., 1H), 2.78 (br. s., 2H), 2.74-2.65 (m, 1H), 2.64-2.53 (m, 3H), 2.19 (s, 3H), 2.14-2.04 (m, 2H), 1.94. (d, J=17.9 Hz, 2H), 1.85-1.71 (m, 2H), 1.31 (d, J=6.8 Hz, 6H).

The following Examples were prepared according to the general procedure described in Example 43.

TABLE 10

| Ex. No. | Structure | HPLC Method | Ret Time (min) | LCMS MH+ |
|---|---|---|---|---|
| 44 | 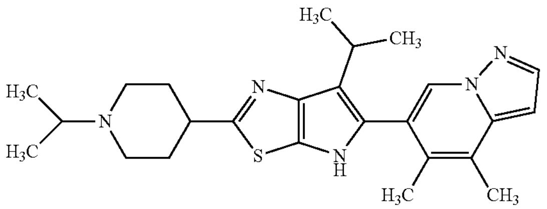 [SMILES: Cc1c(-c2[nH]c3sc(C4CCN(C(C)C)CC4)nc3c2C(C)C)cn2nccc2c1C] | A | 1.205 | 437.3 |
| 45 | 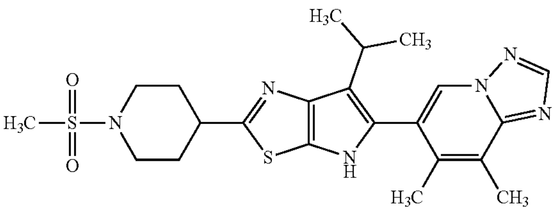 [SMILES: Cc1c(-c2[nH]c3sc(C4CCN(S(C)(=O)=O)CC4)nc3c2C(C)C)cn2ncnc2c1C] | A | 1.512 | 473.2 |

TABLE 10-continued
| Ex. No. | Structure | HPLC Method | Ret Time (min) | LCMS MH+ |
|---|---|---|---|---|
| 46 | 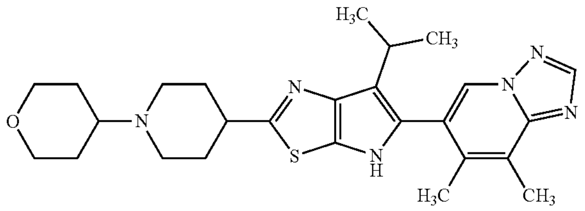 | A | 1.397 | 479.3 |
| 47 | 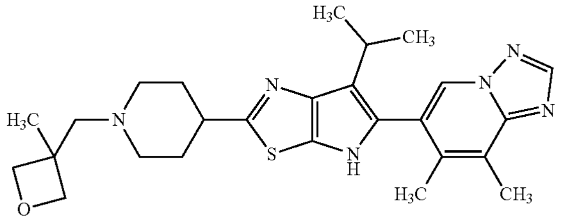 [SMILES: Cc1c(-c2[nH]c3sc(C4CCN(CC5(C)COC5)CC4)nc3c2C(C)C)cn2ncnc2c1C] | A | 1.638 | 479.3 |
| 48 | 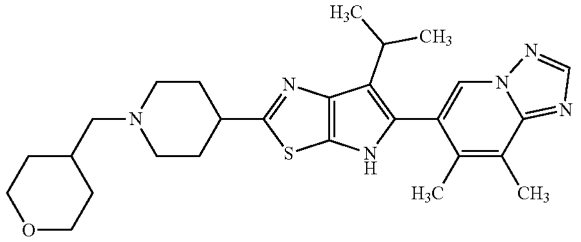 [SMILES: Cc1c(-c2[nH]c3sc(C4CCN(CC5CCOCC5)CC4)nc3c2C(C)C)cn2ncnc2c1C] | A | 1.973 | 493.3 |
| 49 | 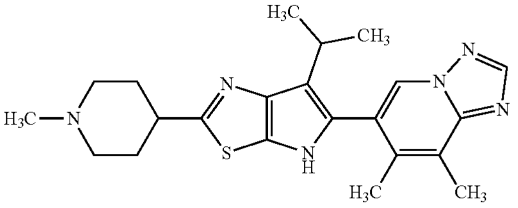 [SMILES: Cc1c(-c2[nH]c3sc(C4CCN(C)CC4)nc3c2C(C)C)cn2ncnc2c1C] | A | 1.385 | 409.2 |
| 50 | 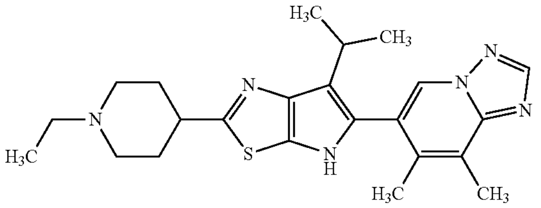 [SMILES: CCN1CCC(c2nc3c(C(C)C)c(-c4cn5ncnc5c(C)c4C)[nH]c3s2)CC1] | A | 1.502 | 423.2 |
| 51 | 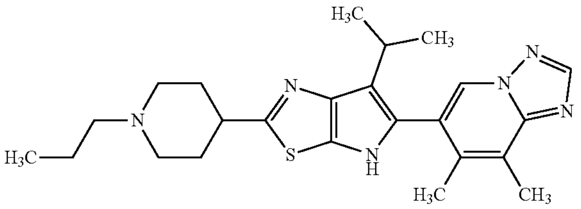 | A | 1.743 | 437.3 |
| 52 | 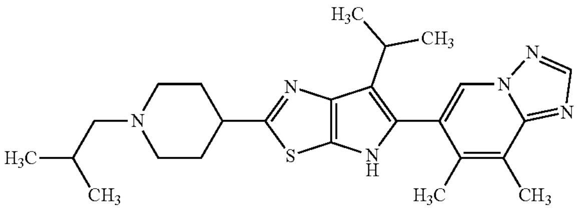 | A | 2.084 | 451.3 |

TABLE 10-continued

| Ex. No. | Structure | HPLC Method | Ret Time (min) | LCMS MH+ |
|---|---|---|---|---|
| 53 | 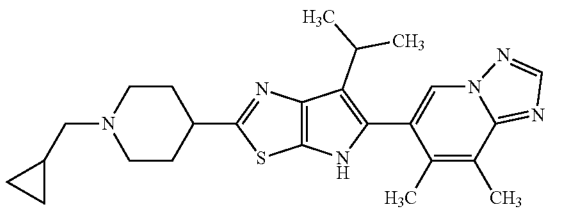 [SMILES: Cc1c(-c2[nH]c3sc(C4CCN(CC5CC5)CC4)nc3c2C(C)C)cn2ncnc2c1C] | A | 1.732 | 449.3 |
| 54 | 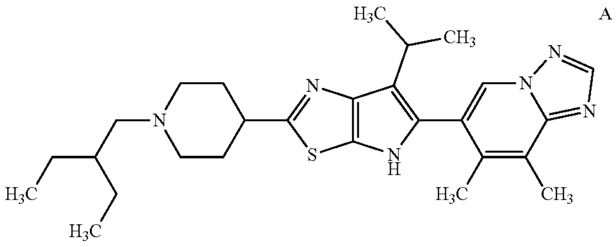 | A | 2.240 | 479.3 |

Example 55

5-(7,8-dimethyl-[1,2,4]triazolo[1,5-a]pyridin-6-yl)-6-isopropyl-2-(1-(2-(methylsulfonyl)ethyl)piperidin-4-yl)-4H-pyrrolo[3,2-d]thiazole (55)

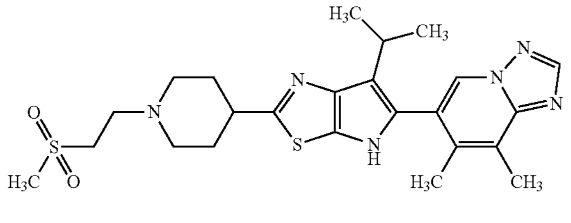

To a solution of 5-(7,8-dimethyl-[1,2,4]triazolo[1,5-a]pyridin-6-yl)-6-isopropyl-2-(piperidin-4-yl)-4H-pyrrolo[3,2-d]thiazole (20 mg, 0.051 mmol) and 1-chloro-2-(methylsulfonyl)ethane (7.23 mg, 0.051 mmol) in mixture of THF (1.5 mL) and DMF (0.5 mL) was added TEA (7.07 μL, 0.051 mmol) and stirred for overnight at room temperature. The reaction mass was diluted with water (2 ml) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(7,8-dimethyl-[1,2,4]triazolo[1,5-a]pyridin-6-yl)-6-isopropyl-2-(1-(2-(methylsulfonyl)ethyl)piperidin-4-yl)-4H-pyrrolo[3,2-d]thiazole (7.4 mg, 0.015 mmol, 29.2% yield) LCMS retention time 0.974 min [B]. MS ($E^-$) m/z: 501.3 (M+H). $^1H$ NMR (400 MHz, DMSO-$d_6$) δ 11.31 (s, 1H), 8.72 (s, 1H), 8.45 (s, 1H), 3.06 (s, 4H), 3.01 (br. s., 2H), 2.82-2.63 (m, 4H), 2.58 (s, 3H), 2.18 (s, 6H), 2.11-1.99 (m, 2H), 1.76 (d, J=11.5 Hz, 2H), 1.31 (d, J=6.8 Hz, 6H).

The following Examples were prepared according to the general procedure described in Example 55.

TABLE 11

| Ex. No. | Structure | HPLC Method | Ret Time (min) | LCMS MH+ |
|---|---|---|---|---|
| 56 | 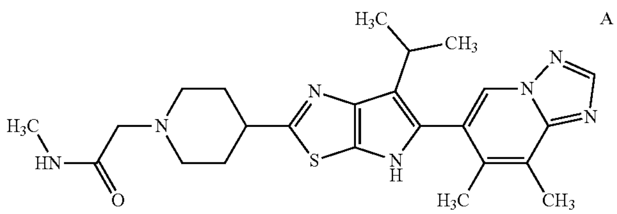 | A | 1.401 | 466.3 |

TABLE 11-continued

| Ex. No. | Structure | HPLC Method | Ret Time (min) | LCMS MH+ |
|---|---|---|---|---|
| 57 | 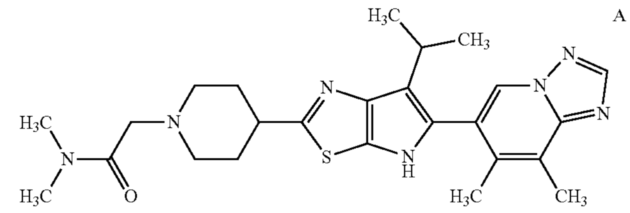 | A | 1.325 | 480.3 |
| 58 | 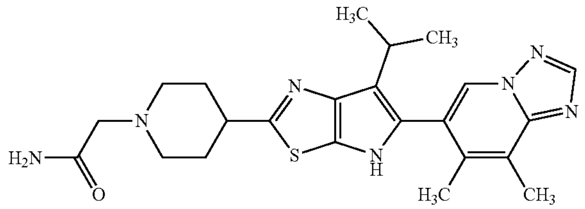 [SMILES: Cc1c(-c2[nH]c3sc(C4CCN(CC(N)=O)CC4)nc3c2C(C)C)cn2ncnc2c1C] | A | 1.299 | 452.2 |

Example 59

1-(4-(5-(7,8-dimethyl-[1,2,4]triazolo[1,5-a]pyridin-6-yl)-6-isopropyl-4H-pyrrolo[3,2-d]thiazol-2-yl)piperidin-1l-yl)ethan-1-one (59)

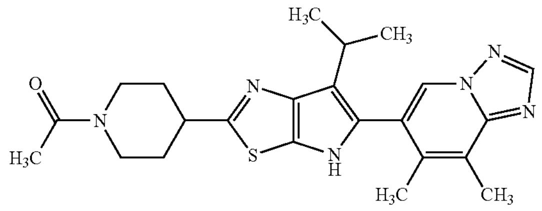

To a solution of 5-(7,8-dimethyl-[1,2,4]triazolo[1,5-a]pyridin-6-yl)-6-isopropyl-2-(piperidin-4-yl)-4H-pyrrolo[3,2-d]thiazole (25 mg, 0.063 mmol) in DCM were added TEA (26.5 µL, 0.190 mmol) and acetyl chloride (24.87 mg, 0.317 mmol) at 0° C., then stirred for 2 h at room temperature. The reaction mass was diluted with water (10 mL) and extracted with DCM (3×10 mL). The separated organic layer was dried over sodium sulphate, filtered and concentrated. The crude sample was purified by prep LCMS using Method L. After Preparative LCMS purification, fractions containing the product was combined and dried using Genevac centrifugal evaporator to afford 1-(4-(5-(7,8-dimethyl-[1,2,4]triazolo[1,5-a]pyridin-6-yl)-6-isopropyl-4H-pyrrolo[3,2-d]thiazol-2-yl)piperidin-1-yl)ethan-1-one (15.5 mg, 0.035 mmol, 54.5% yield). LCMS retention time 1.387 min [A]. MS ($E^-$) m/z: 437.2 (M+H). $^1$H NMR (400 MHz, DMSO-$d_6$) δ 11.32 (s, 1H), 8.72 (s, 1H), 8.45 (s, 1H), 4.44 (d, J=12.7 Hz, 1H), 3.99-3.89 (m, 1H), 3.27-3.17 (m, 1H), 2.90 (s, 1H), 2.80-2.62 (m, 5H), 2.58 (s, 3H), 2.19 (s, 3H), 2.15-1.95 (m, 2H), 1.74 (dd, J=12.3, 3.5 Hz, 1H), 1.57 (dd, J=12.3, 3.8 Hz, 1H), 1.31 (d, J=6.8 Hz, 6H).

Example 60

5-(6-isopropyl-2-(1-(oxetan-3-yl)piperidin-4-yl)-4H-pyrrolo[3,2-d]thiazol-5-yl)-1,3,4-trimethylpyridin-2(1H)-one (60)

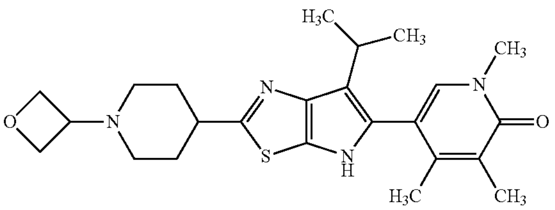

To a solution of 5-(6-isopropyl-2-(piperidin-4-yl)-4H-pyrrolo[3,2-d]thiazol-5-yl)-1,3,4-trimethylpyridin-2 (1H)-one (40 mg, 0.104 mmol) and oxetan-3-one (37.5 mg, 0.520 mmol) in methanol (2 mL) was added AcOH (0.595 µL, 10.40 µmol) and stirred for overnight at room temperature. Sodium cyanoborohydride (13.07 mg, 0.208 mmol) was added to the reaction mass at 0° C. and stirred for 2 h at room temperature. The reaction mass was diluted with water (2 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(6-isopropyl-2-(1-(oxetan-3-yl)piperidin-4-yl)-4H-pyrrolo[3,2-d]thiazol-5-yl)-1,3,4-trimethylpyridin-2 (1H)-one (17 mg, 0.037 mmol, 35.9% yield) as white solid. LCMS retention time 1.925 min [C]. MS ($E^-$) m/z: 441.2 (M+H). $^1$H NMR (400 MHz, DMSO-$d_6$) δ 11.05 (s, 1H) 7.53 (s, 1H) 4.52-4.58 (m, 2H) 4.45 (t, J=6.02 Hz, 2H) 3.46 (s, 3H) 3.40-3.44 (m, 1H) 3.37 (s, 1H) 2.95-3.05 (m, 2H) 2.66-2.81 (m, 3H) 2.54-2.63 (m, 1H) 2.31-2.36 (m, 2H) 2.04 (s, 3H) 1.88-1.98 (m, 2H) 1.70-1.83 (m, 2H) 1.29 (d, J=7.03 Hz, 6H).

Example 61

5-(6-isopropyl-2-(1-(2-(methylsulfonyl)ethyl)piperidin-4-yl)-4H-pyrrolo[3,2-d]thiazol-5-yl)-1,3,4-trimethylpyridin-2 (1H)-one (61)

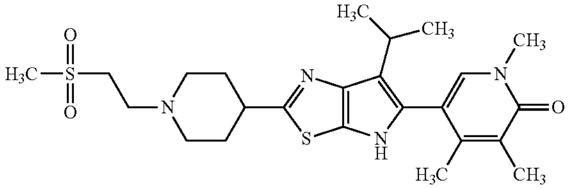

To a solution of and 5-(6-isopropyl-2-(piperidin-4-yl)-4H-pyrrolo[3,2-d]thiazol-5-yl)-1,3,4-trimethylpyridin-2 (1H)-one (40 mg, 0.104 mmol) and 1-chloro-2-(methylsulfonyl)ethane (14.83 mg, 0.104 mmol) in mixture of THF (1.5 mL) and DMF (0.5 mL) was added TEA (0.014 mL, 0.104 mmol) and stirred for overnight at room temperature. The reaction mass was diluted with water (2 mL) and extracted with EtOAc (3×10 mL). The separated organic layer was dried over sodium sulphate, filtered and concentrated. The crude sample was purified by prep LCMS using Method I. After Preparative LCMS purification, fractions containing the product was combined and dried using Genevac centrifugal evaporator to afford 5-(6-isopropyl-2-(1-(2-(methylsulfonyl)ethyl)piperidin-4-yl)-4H-pyrrolo[3,2-d]thiazol-5-yl)-1,3,4-trimethylpyridin-2 (1H)-one (16 mg, 0.032 mmol, 30.5% yield). LCMS retention time 1.949 min [C]. MS ($E^-$) m/z: 491.2 (M+H). $^1$H NMR (400 MHz, DMSO-$d_6$) δ ppm 11.06 (s, 1H) 7.53 (s, 1H) 3.46 (s, 3H) 3.05 (s, 3H) 2.98 (d, J=11.55 Hz, 3H) 2.63-2.79 (m, 5H) 2.10-2.34 (m, 3H) 2.04 (s, 5H) 1.65-1.82 (m, 4H) 1.29 (d, J=7.03 Hz, 6H).

The following Examples were prepared according to the general procedure described in Example 61.

TABLE 12

| Ex. No. | Structure | HPLC Method | Ret Time (min) | LCMS MH$^+$ |
|---|---|---|---|---|
| 62 | 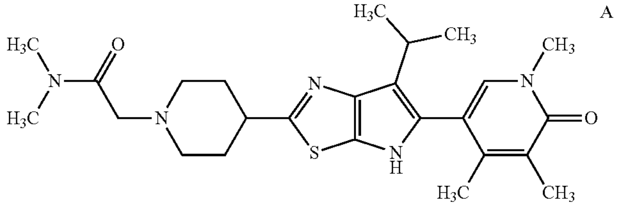 | A | 1.323 | 470.3 |
| 63 | 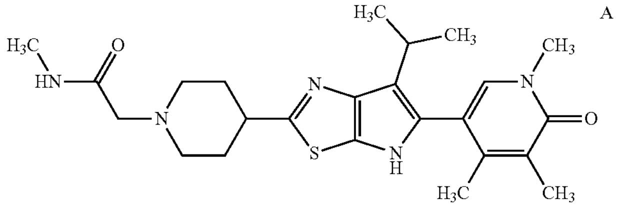 | A | 1.373 | 456.3 |
| 64 | 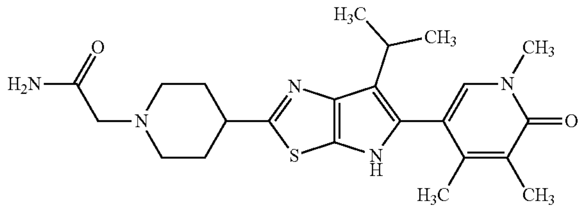 | A | 1.28 | 442.2 |

Examples 65 and 66

N-(4-(6-isopropyl-5-(8-methoxy-[1,2,4]triazolo[1,5-a]pyridin-6-yl)-4H-pyrrolo[3,2-d]thiazol-2-yl)cyclohexyl)oxetan-3-amine (65 and 66)

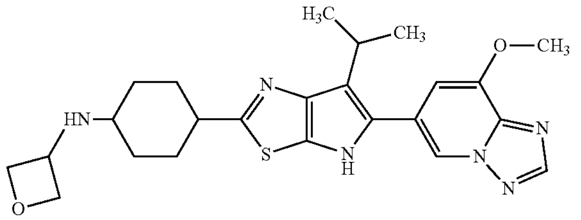

Intermediate 65A: Tert-butyl (2-(1,4-dioxaspiro[4.5]dec-7-en-8-yl)thiazol-5-yl)carbamate (65A)

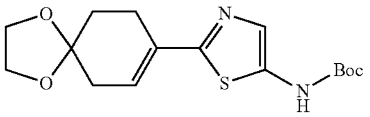

To a solution of tert-butyl (2-bromothiazol-5-yl)carbamate (70 g, 251 mmol) and 4,4,5,5-tetramethyl-2-(1,4-dioxaspiro[4.5]dec-7-en-8-yl)-1,3,2-dioxaborolane (100 g, 376 mmol) in dioxane (1500 mL) was added potassium phosphate tribasic (160 g, 752 mmol) dissolved in 375 mL water. The reaction mixture was degassed with argon for 20 min prior, then $PdCl_2$ (dppf)-$CH_2Cl_2$ adduct (20.48 g, 25.08 mmol) was added. The reaction mixture was degassed again for 5 min. and the mixture was stirred at 80° C. for 12 h. The reaction mixture was diluted with EtOAc (3000 mL), poured into a separatory funnel and was washed with water (2×1500 mL), brine (1500 mL), dried over sodium sulphate, and concentrated to afford crude product. The crude was purified using silica gel chromatography, eluting with 30% ethyl acetate in hexane, the fractions was collected and concentrated to afford tert-butyl (2-(1,4-dioxaspiro[4.5]dec-7-en-8-yl)thiazol-5-yl)carbamate (75 g, 84% yield) as a yellow solid. LCMS retention time 2.44 min [C]. MS ($E^-$) m/z: 339.2 (M+H).

Intermediate 65B: Tert-butyl (2-(1,4-dioxaspiro[4.5]decan-8-yl)thiazol-5-yl)carbamate (65B)

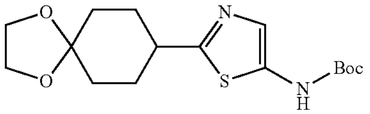

To a solution of tert-butyl (2-(1,4-dioxaspiro[4.5]dec-7-en-8-yl)thiazol-5-yl)carbamate (75 g, 222 mmol) in MeOH (1000 mL) and ethyl acetate (1000 mL). The flask was purged with $N_2$ and Pd/C (23.58 g, 222 mmol) was added. Following pump/purging with $N_2$ 3×, $H_2$ gas was introduced via a balloon. The reaction mixture was stirred at ambient temperature for 12 h. The flask was evacuated and filled with $N_2$. The suspension was filtered and the filtrate was concentrated to afford crude product. The crude sample was purified by silica gel chromatography, eluting with 30% EtOAc in pet ether, the fractions were collected and concentrated to afford tert-butyl (2-(1,4-dioxaspiro[4.5]decan-8-yl)thiazol-5-yl)carbamate (70 g, 88% yield) as a pale white solid. LCMS retention time 2.36 min [C], MS ($E^-$) m/z: 341 (M+H).

Intermediate 65C: Tert-butyl (4-iodo-2-(1,4-dioxaspiro[4.5]decan-8-yl)thiazol-5-yl) carbamate (65C)

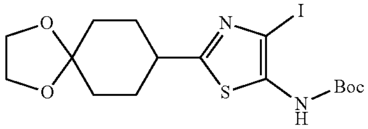

To a solution of tert-butyl (2-(1,4-dioxaspiro[4.5]decan-8-yl)thiazol-5-yl)carbamate (50 g, 147 mmol) in acetonitrile (2000 mL), was added NIS (36.3 g, 162 mmol) dissolved in acetonitrile (2000 mL) dropwise and stirred the reaction mass at 0° C. for 30 min. The reaction mass was diluted with ethyl acetate (2000 mL), washed with water (1500 mL), saturated NaCl (1500 mL), finally dried over sodium sulphate and concentrated at 45° C. to afford crude product. The crude was purified using silica gel chromatography, eluting with 30% EtOAc in pet ether, the fractions was collected and concentrated to afford tert-butyl (4-iodo-2-(1,4-dioxaspiro[4.5]decan-8-yl)thiazol-5-yl)carbamate (45 g, 66% yield) as yellow solid. LCMS retention time 3.05 min [C]. MS ($E^-$) m/z: 467.2 (M+H).

Intermediate 65D: tert-butyl (4-iodo-2-(1,4-dioxaspiro [4.5]decan-8-yl) thiazol-5-yl)(3-methylbut-2-en-1-yl)carbamate (65D)

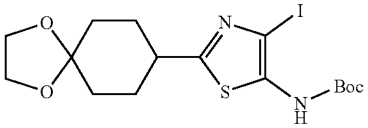

To a solution of tert-butyl (4-iodo-2-(1,4-dioxaspiro[4.5]decan-8-yl)thiazol-5-yl)carbamate (30 g, 64.3 mmol) in DMF (100 mL), was added NaH (5.15 g, 129 mmol), slowly in portions. Next, 1-bromo-3-methylbut-2-ene (18.44 mL, 96 mmol) at 0° C. was added dropwise and stirred the reaction mass at same temperature for 20 min. The reaction mass was quenched with ice cold water and diluted with EtOAc (1000 mL), poured into a separatory funnel and was brine (1000 mL), dried over sodium sulphate, and concentrated to afford crude product. The crude was purified using silica gel chromatography, eluting with 30% EtOAc in pet ether, the fractions was collected and concentrated to afford tert-butyl (4-iodo-2-(1,4-dioxaspiro[4.5]decan-8-yl)thiazol- 5-yl)carbamate (28 g, 81% yield) as white solid. LCMS retention time 2.5 min [C]. MS ($E^-$) m/z: 535.2 (M+H).

Intermediate 65E: tert-butyl 6-isopropyl-2-(1,4-dioxaspiro [4.5]decan-8-yl)-4H-pyrrolo[3,2-d]thiazole-4-carboxylate (65E)

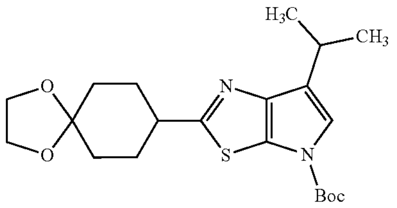

To a solution of tert-butyl (4-iodo-2-(1,4-dioxaspiro[4.5] decan-8-yl)thiazol-5-yl)(3-methylbut-2-en-1-yl)carbamate (28 g, 52.4 mmol) in DMF (600 mL), was added potassium carbonate (14.48 g, 105 mmol), tetrabutylammonium bromide (50.7 g, 157 mmol) was degassed for 10 min with argon and $PdOAc_2$ (1.176 g, 5.24 mmol) was added. The reaction mixture was heated to 90° C. for 12 h. The reaction mass was diluted with EtOAc and passed through pad of celite. Combined organic extracts was concentrated to give crude product. The crude was purified using silica gel chromatography, eluting with 10% EtOAc in Pet ether, the fractions was collected and concentrated to afford tert-butyl 6-isopropyl-2-(1,4-dioxaspiro [4.5]decan-8-yl)-4H-pyrrolo [3,2-d]thiazole-4-carboxylate (9.5 g, 40% yield) as pale yellow solid. LCMS retention time 2.5 min [C]. MS ($E^-$) m/z: 535.2 (M+H).

Intermediate 65F: tert-butyl 5-bromo-6-isopropyl-2-(1,4-dioxaspiro[4.5]decan-8-yl)-4H-pyrrolo[3,2-d] thiazole-4-carboxylate (65F)

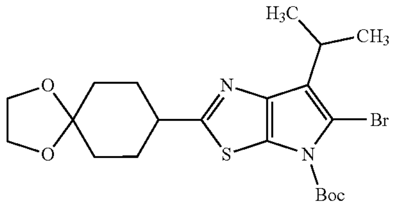

To a tert-butyl 6-isopropyl-2-(1,4-dioxaspiro[4.5]decan-8-yl)-4H-pyrrolo[3,2-d]thiazole-4-carboxylate (9.5 g, 23.37 mmol) in DCE (100 mL), was added NBS (3.74 g, 21.03 mmol) in DCE (100 mL) dropwise at 0° C. and the reaction mass was stirred at same temperature for 20 min. The reaction mass was quenched with saturated sodium sulphite (50 mL) and diluted with DCM (500 mL), poured into a separatory funnel and was brine (500 mL), dried over sodium sulphate, and concentrated to afford crude product. The crude was purified using silica gel chromatography, eluting with 30% EtOAc in Pet ether, the fractions was collected and concentrated to afford tert-butyl 5-bromo-6-isopropyl-2-(1,4-dioxaspiro[4.5]decan-8-yl)-4H-pyrrolo[3,2-d]thiazole-4-carboxylate (6.2 g, 54% yield) as pale yellow solid. LCMS retention time 2.3 min [C]. MS ($E^-$) m/z: 485.2 (M+H).

Intermediate 65G: tert-butyl 6-isopropyl-5-(8-methoxy-[1,2,4]triazolo[1,5-a]pyridin-6-yl)-2-(1,4-dioxaspiro[4.5]decan-8-yl)-4H-pyrrolo[3,2-d]thiazole-4-carboxylate (65G)

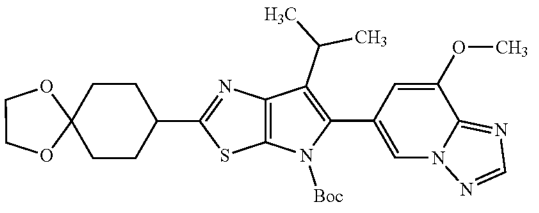

To a solution of tert-butyl 5-bromo-6-isopropyl-2-(1,4-dioxaspiro[4.5]decan-8-yl)-4H-pyrrolo[3,2-d]thiazole-4-carboxylate (5.5 g, 11.33 mmol) in dioxane (150 mL) and water (20 mL) was added potassium phosphate tribasic (7.21 g, 34.0 mmol) and 8-methoxy-6-(4,4,5,5-tetramethyl-1,3,2-dioxaborolan-2-yl)-[1,2,4]triazolo[1,5-a]pyridine (6.23 g, 22.66 mmol). The reaction was degassed for 10 min with argon and $PdCl_2(dppf)\text{-}CH_2Cl_2$ adduct (0.925 g, 1.133 mmol) was added. The reaction mixture was heated to 75° C. for 4 h. The reaction mixture was diluted with EtOAc (3000 mL), poured into a separatory funnel and was washed with water (2×500 mL), brine (500 mL), dried over sodium sulphate, and concentrated to afford crude product. The crude was purified using silica gel chromatography, eluting with 40% EtOAc in Pet ether, the fractions was collected and concentrated to afford tert-butyl (2-(1,4-dioxaspiro[4.5]dec-7-en-8-yl)thiazol-5-yl)carbamate (3.7 g, 60% yield) as yellow solid. LCMS retention time 3.58 min [C]. MS ($E^-$) m/z: 554.2 (M+H).

Intermediate 65H: 4-(6-isopropyl-5-(8-methoxy-[1,2,4]triazolo[1,5-a]pyridin-6-yl)-4H-pyrrolo[3,2-d] thiazol-2-yl)cyclohexan-1-one (65H)

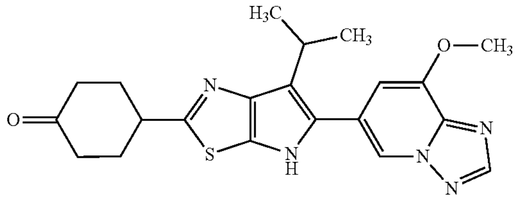

To a solution of tert-butyl 6-isopropyl-5-(8-methoxy-[1,2,4] triazolo[1,5-a]pyridin-6-yl)-2-(1,4-dioxaspiro[4.5]decan-8-yl)-4H-pyrrolo[3,2-d]thiazole-4-carboxylate (3.5 g, 6.32 mmol) in DCM (55.0 mL) was added TFA (55 mL) and stirred at ambient temperature for 12 h. The reaction mass was concentrated under reduced pressure and the residue obtained was triturated with n-hexane to afford 4-(6-isopropyl-5-(8-methoxy-[1,2,4]triazolo[1,5-a]pyridin-6-yl)-4H-pyrrolo[3,2-d]thiazol-2-yl)cyclohexan-1-one (2.5 g, 92%) as a buff color solid. LCMS retention time 2.82 min [C]. MS ($E^-$) m/z: 410.2 (M+H). $^1H$ NMR (400 MHz, DMSO-$d_6$) δ 11.63 (s, 1H), 8.57-8.38 (m, 2H), 7.13 (d, J=1.0 Hz, 1H), 4.07 (s, 3H), 3.64-3.51 (m, 1H), 3.25-3.14 (m, 1H), 2.65-2.53 (m, 2H), 2.44-2.28 (m, 4H), 2.12-1.93 (m, 2H), 1.45 (d, J=6.8 Hz, 6H).

The following intermediate was prepared according to the general procedure described in Intermediate 65H.

TABLE 13

| Ex. No. | Structure | HPLC Method | Ret Time (min) | LCMS MH+ |
|---|---|---|---|---|
| 65I | 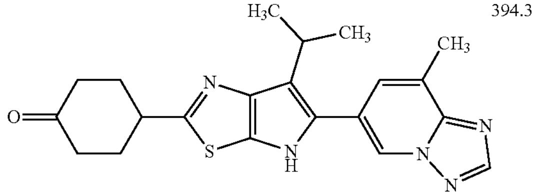 | 394.3 | 2.24 | C |

Examples 65 and 66: N-(4-(6-isopropyl-5-(8-methoxy-[1,2,4]triazolo[1,5-a]pyridin-6-yl)-4H-pyrrolo[3,2-d]thiazol-2-yl)cyclohexyl)oxetan-3-amine To a solution of 4-(6-isopropyl-5-(8-methoxy-[1,2,4]triazolo[1,5-a]pyridin-6-yl)-4H-pyrrolo[3,2-d]thiazol-2-yl)cyclohexan-1-one (2.6 g, 6.35 mmol) in THE (20 mL), DMF (20.00 mL) was added acetic acid (0.363 mL, 6.35 mmol), oxetan-3-amine (9.28 g, 127 mmol) and was stirred at ambient temperature for 12 h. The reaction mixture was concentrated to remove DMF and THE and the residue obtained was taken in 30 mL of Aldrich grade dry methanol and cooled to −78° C. under nitrogen atmosphere. Added $NaCNBH_4$ (1.995 g, 31.7 mmol), in one pot. The reaction was continued at the same temperature (−78° C.) for 3 h and brought to 0° C. in 1 h. The reaction was quenched with 10 mL of ice cold water and the reaction mixture was concentrated. The residue was extracted with 10% of methanol in DCM (100 mL×2). Organic layer was concentrated and the crude product obtained was purified by prep LCMS using Method I. The fractions corresponding to Peak 1 (Isomer 1) and Peak 2 (Isomer 2) were collected and concentrated. This was further triturated with absolute ethanol (100 mL×2) and the white solid obtained was taken in deionized water (150 mL) and lyophilized for 2 days. NMR showed presence of ethanol. Lyophilized compound was further taken in deionized water (150 mL) and repeated the lyophilization for another 2 days.

Example 65 (Isomer 1): LCMS retention time 1.62 min [C]. MS ($E^-$) m/z: 467.3 (M+H). $^1H$ NMR (400 MHz, DMSO-$d_6$) δ 11.58 (s, 1H), 8.56-8.37 (m, 2H), 7.10 (s, 1H), 4.64 (t, J=6.6 Hz, 2H), 4.33 (t, J=6.4 Hz, 2H), 4.05 (s, 3H), 3.98 (t, J=6.7 Hz, 1H), 3.23-3.12 (m, 1H), 2.99-2.89 (m, 1H), 2.43 (t, J=11.0 Hz, 1H), 2.17-2.04 (m, 2H), 1.85 (d, J=10.5 Hz, 2H), 1.59-1.46 (m, 2H), 1.42 (d, J=6.6 Hz, 6H), 1.28-1.10 (m, 2H).

Example 66 (Isomer 2): LCMS retention time 2.82 min [C]. MS ($E^-$) m/z: 467.3 (M+H). $^1H$ NMR (400 MHz, DMSO-$d_6$) δ 11.60 (s, 1H), 8.56-8.38 (m, 2H), 7.12 (s, 1H), 4.63 (t, J=6.6 Hz, 2H), 4.35 (t, J=6.4 Hz, 2H), 4.17 (d, J=4.9 Hz, 1H), 4.06 (s, 3H), 3.98-3.85 (m, 1H), 3.26-3.06 (m, 1H), 2.09-1.95 (m, 2H), 1.80 (br. s., 2H), 1.65-1.54 (m, 3H), 1.49 (d, J=7.8 Hz, 1H), 1.44 (d, J=6.8 Hz, 6H), 1.24 (s, 2H).

The following Examples were prepared according to the general procedure described in Examples 65 and 66.

TABLE 14

| Ex. No. | Structure | HPLC Method | Ret Time (min) | LCMS MH+ |
|---|---|---|---|---|
| 67 | 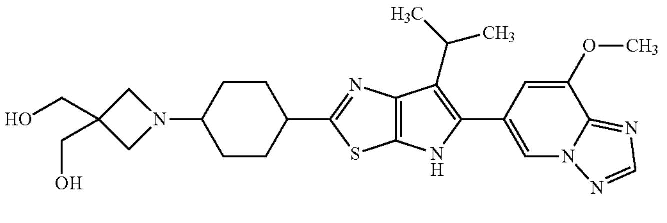 [SMILES: COc1cc(-c2[nH]c3sc(C4CCC(N5CC(CO)(CO)C5)CC4)nc3c2C(C)C)cn2ncnc12] Isomer 1 | 511.3 | 3.43 | D |
| 68 | 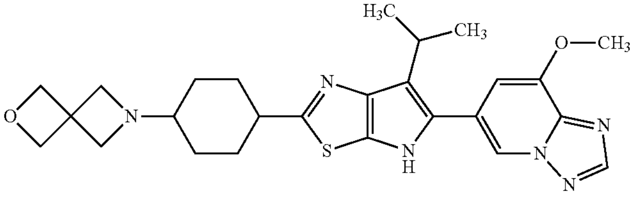 [SMILES: COc1cc(-c2[nH]c3sc(C4CCC(N5CC6(COC6)C5)CC4)nc3c2C(C)C)cn2ncnc12] Isomer 1 | 493.4 | 1.30 | D |

TABLE 14-continued
| Ex. No. | Structure | HPLC Method | Ret Time (min) | LCMS MH+ |
|---|---|---|---|---|
| 69 | 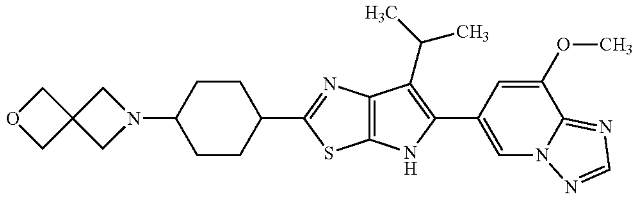 [SMILES: COc1cc(-c2[nH]c3sc(C4CCC(N5CC6(COC6)C5)CC4)nc3c2C(C)C)cn2ncnc12] Isomer 1 | 493.4 | 1.45 | D |
| 70 | 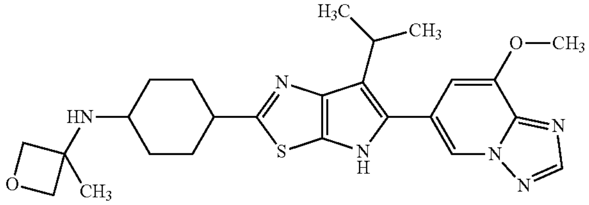 [SMILES: COc1cc(-c2[nH]c3sc(C4CCC(NC5(C)COC5)CC4)nc3c2C(C)C)cn2ncnc12] Isomer 1 | 481.3 | 1.45 | D |
| 71 | 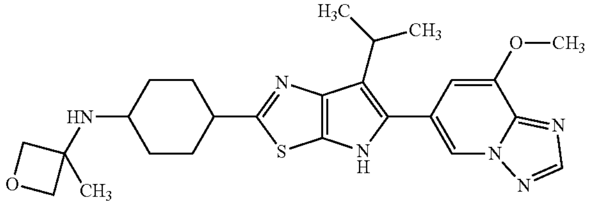 [SMILES: COc1cc(-c2[nH]c3sc(C4CCC(NC5(C)COC5)CC4)nc3c2C(C)C)cn2ncnc12] Isomer 2 | 481.3 | 1.63 | D |
| 72 | 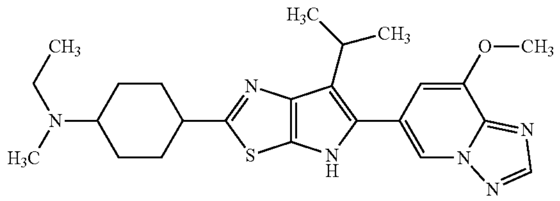 [SMILES: CCN(C)C1CCC(c2nc3c(C(C)C)c(-c4cc(OC)c5ncnn5c4)[nH]c3s2)CC1] Isomer 1 | 453.3 | 1.23 | D |
| 73 | 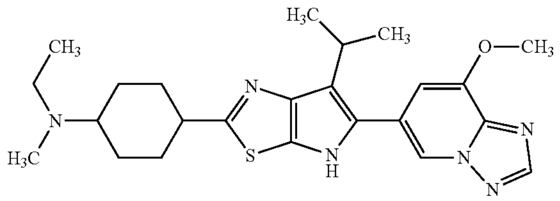 [SMILES: CCN(C)C1CCC(c2nc3c(C(C)C)c(-c4cc(OC)c5ncnn5c4)[nH]c3s2)CC1] Isomer 2 | 453.3 | 1.33 | D |
| 74 | 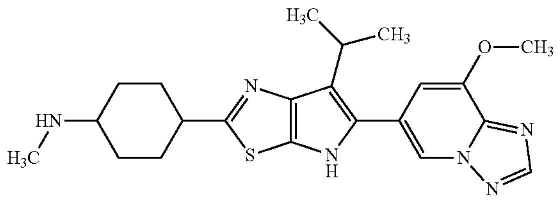 [SMILES: CNC1CCC(c2nc3c(C(C)C)c(-c4cc(OC)c5ncnn5c4)[nH]c3s2)CC1] Isomer 1 | 425.3 | 1.13 | D |

TABLE 14-continued
| Ex. No. | Structure | HPLC Method | Ret Time (min) | LCMS MH+ |
|---|---|---|---|---|
| 75 | 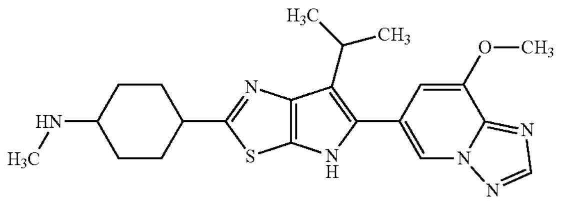 [SMILES: CNC1CCC(c2nc3c(C(C)C)c(-c4cc(OC)c5ncnn5c4)[nH]c3s2)CC1] Isomer 2 | 425.3 | 1.22 | D |
| 76 | 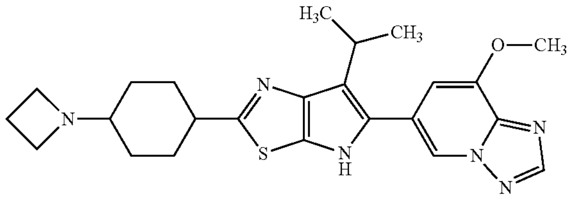 [SMILES: COc1cc(-c2[nH]c3sc(C4CCC(N5CCC5)CC4)nc3c2C(C)C)cn2ncnc12] Isomer 1 | 451.3 | 1.21 | D |
| 77 | 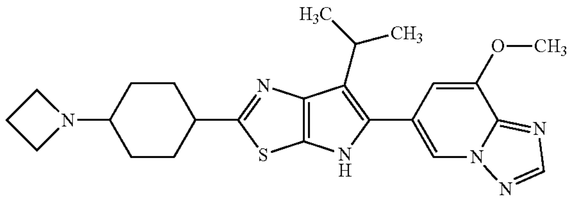 [SMILES: COc1cc(-c2[nH]c3sc(C4CCC(N5CCC5)CC4)nc3c2C(C)C)cn2ncnc12] Isomer 2 | 451.3 | 1.30 | D |
| 78 | 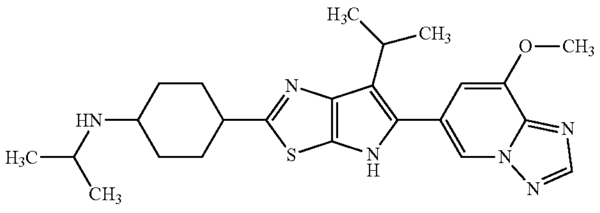 Isomer 1 | 453.3 | 1.25 | D |
| 79 | 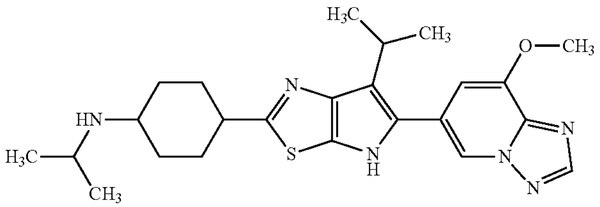 [SMILES: COc1cc(-c2[nH]c3sc(C4CCC(NC(C)C)CC4)nc3c2C(C)C)cn2ncnc12] Isomer 2 | 453.3 | 1.31 | D |
| 82 | 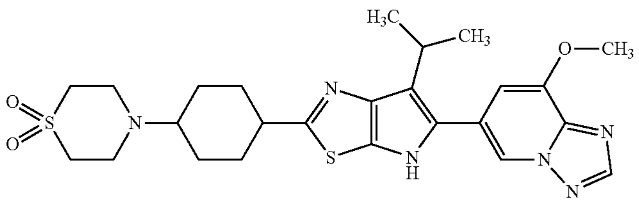 [SMILES: COc1cc(-c2[nH]c3sc(C4CCC(N5CCS(=O)(=O)CC5)CC4)nc3c2C(C)C)cn2ncnc12] Isomer 1 | 529.3 | 1.56 | C |

TABLE 14-continued
| Ex. No. | Structure | HPLC Method | Ret Time (min) | LCMS MH+ |
|---|---|---|---|---|
| 83 | 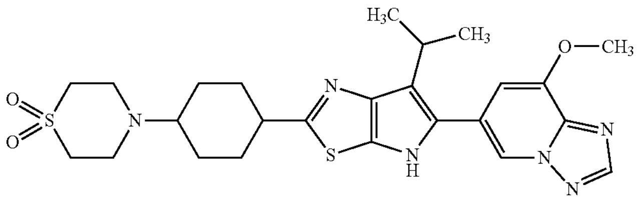 [SMILES: COc1cc(-c2[nH]c3sc(C4CCC(N5CCS(=O)(=O)CC5)CC4)nc3c2C(C)C)cn2ncnc12] Isomer 2 | 529.3 | 1.72 | D |
| 84 | 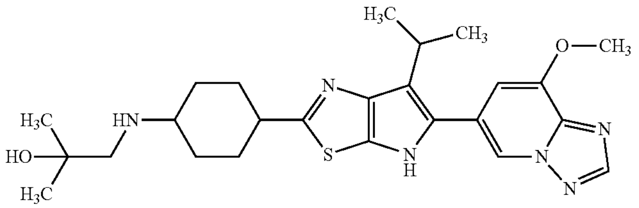 [SMILES: COc1cc(-c2[nH]c3sc(C4CCC(NCC(C)(C)O)CC4)nc3c2C(C)C)cn2ncnc12] Isomer 1 | 483.3 | 1.21 | D |
| 85 | 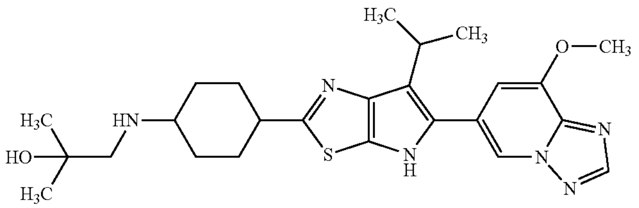 [SMILES: COc1cc(-c2[nH]c3sc(C4CCC(NCC(C)(C)O)CC4)nc3c2C(C)C)cn2ncnc12] Isomer 2 | 483.3 | 1.36 | D |
| 86 | 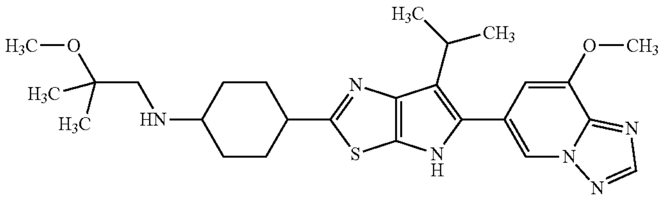 [SMILES: COc1cc(-c2[nH]c3sc(C4CCC(NCC(C)(C)OC)CC4)nc3c2C(C)C)cn2ncnc12] Isomer 2 | 497.3 | 1.37 | D |
| 87 | 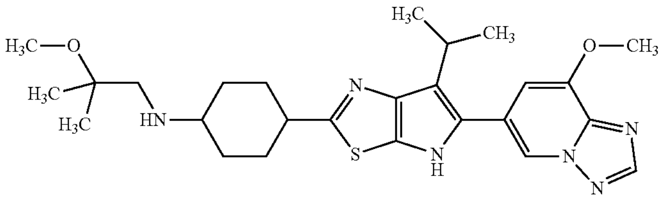 [SMILES: COc1cc(-c2[nH]c3sc(C4CCC(NCC(C)(C)OC)CC4)nc3c2C(C)C)cn2ncnc12] Isomer 2 | 497.3 | 1.57 | D |
| 88 | 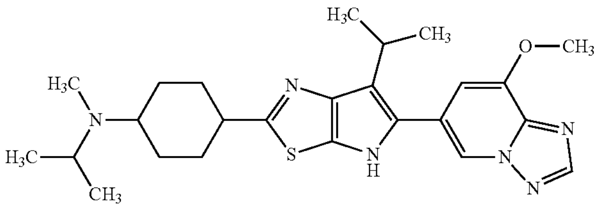 [SMILES: COc1cc(-c2[nH]c3sc(C4CCC(N(C)C(C)C)CC4)nc3c2C(C)C)cn2ncnc12] Isomer 1 | 467.3 | 1.27 | D |

TABLE 14-continued
| Ex. No. | Structure | HPLC Method | Ret Time (min) | LCMS MH+ |
|---|---|---|---|---|
| 89 | 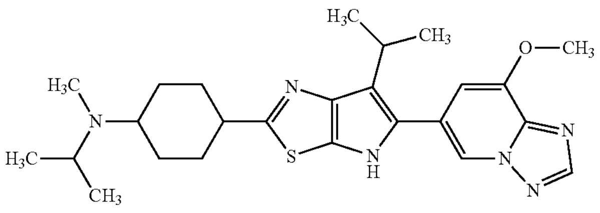 [SMILES: COc1cc(-c2[nH]c3sc(C4CCC(N(C)C(C)C)CC4)nc3c2C(C)C)cn2ncnc12] Isomer 2 | 467.3 | 1.39 | A |
| 90 | 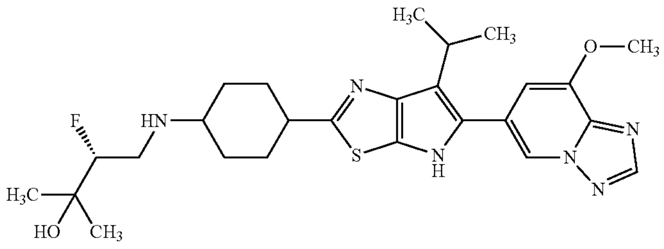 Isomer 1 | 515.3 | 1.31 | A |
| 91 | 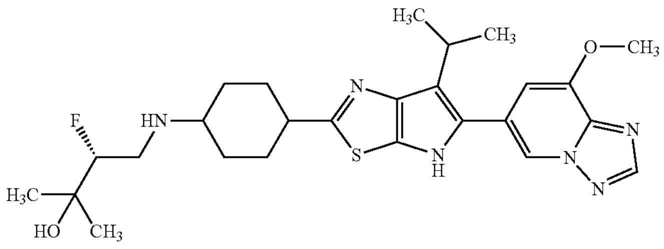 [SMILES: COc1cc(-c2[nH]c3sc(C4CCC(NC[C@@H](F)C(C)(C)O)CC4)nc3c2C(C)C)cn2ncnc12] Isomer 2 | 515.3 | 1.52 | A |
| 92 | 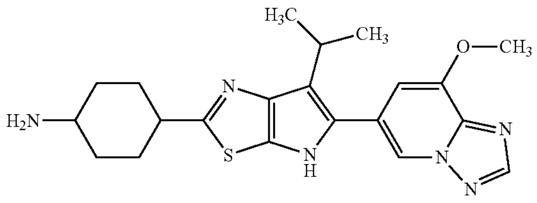 [SMILES: COc1cc(-c2[nH]c3sc(C4CCC(N)CC4)nc3c2C(C)C)cn2ncnc12] Isomer 1 | 1.01 | 411.2 | A |
| 93 | 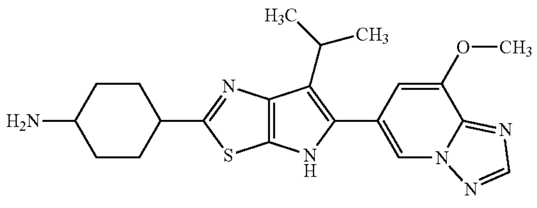 [SMILES: COc1cc(-c2[nH]c3sc(C4CCC(N)CC4)nc3c2C(C)C)cn2ncnc12] Isomer 2 | 1.1 | 411.2 | A |

TABLE 14-continued
| Ex. No. | Structure | HPLC Method | Ret Time (min) | LCMS MH+ |
| --- | --- | --- | --- | --- |
| 94 | 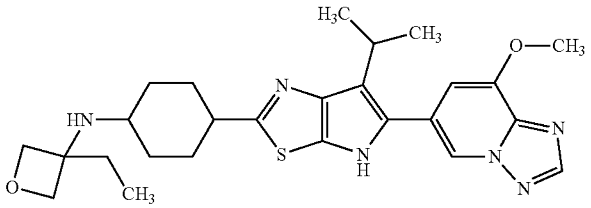 [SMILES: CCC1(NC2CCC(c3nc4c(C(C)C)c(-c5cc(OC)c6ncnn6c5)[nH]c4s3)CC2)COC1] Isomer 1 | 495.3 | 1.66 | A |
| 95 | 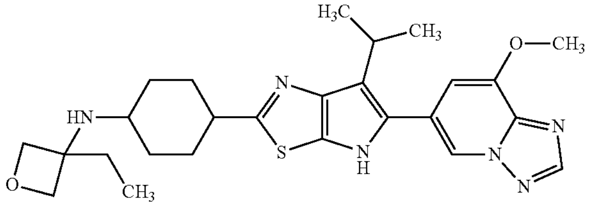 [SMILES: CCC1(NC2CCC(c3nc4c(C(C)C)c(-c5cc(OC)c6ncnn6c5)[nH]c4s3)CC2)COC1] Isomer 2 | 495.3 | 1.89 | A |
| 96 | 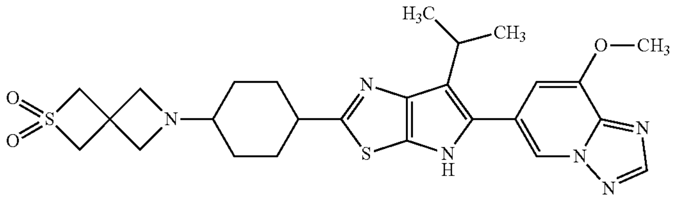 [SMILES: COc1cc(-c2[nH]c3sc(C4CCC(N5CC6(C5)CS(=O)(=O)C6)CC4)nc3c2C(C)C)cn2ncnc12] | 541.2 | 1.49 | A |
| 97 | 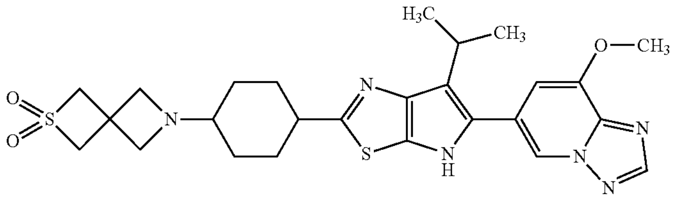 [SMILES: COc1cc(-c2[nH]c3sc(C4CCC(N5CC6(C5)CS(=O)(=O)C6)CC4)nc3c2C(C)C)cn2ncnc12] | 541.2 | 1.73 | A |
| 98 | 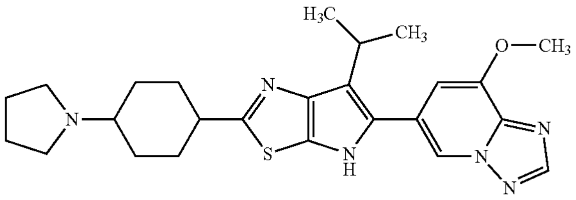 [SMILES: COc1cc(-c2[nH]c3sc(C4CCC(N5CCCC5)CC4)nc3c2C(C)C)cn2ncnc12] | 465.3 | 1.28 | A |
| 99 | 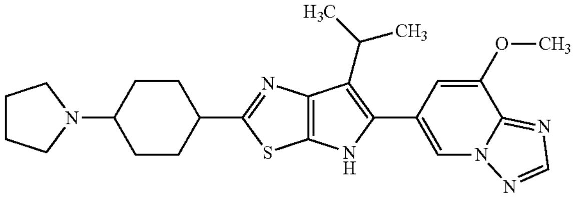 [SMILES: COc1cc(-c2[nH]c3sc(C4CCC(N5CCCC5)CC4)nc3c2C(C)C)cn2ncnc12] | 465.3 | 1.56 | A |
| 100 | 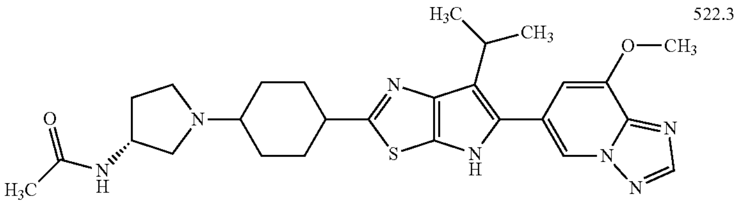 | 522.3 | 1.24 | A |

TABLE 14-continued
| Ex. No. | Structure | HPLC Method | Ret Time (min) | LCMS MH+ |
|---|---|---|---|---|
| 101 | 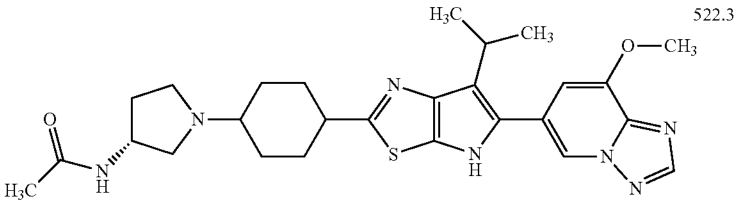 | 522.3 | 1.25 | A |
| 102 | 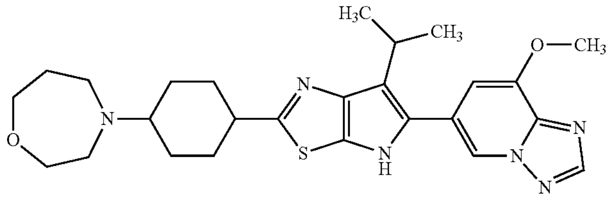 [SMILES: COc1cc(-c2[nH]c3sc(C4CCC(N5CCCOCC5)CC4)nc3c2C(C)C)cn2ncnc12] | 495.3 | 1.55 | A |
| 103 | 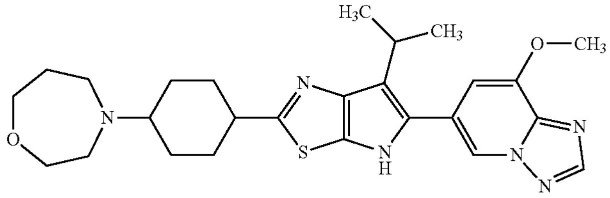 [SMILES: COc1cc(-c2[nH]c3sc(C4CCC(N5CCCOCC5)CC4)nc3c2C(C)C)cn2ncnc12] | 495.3 | | A |
| 104 | 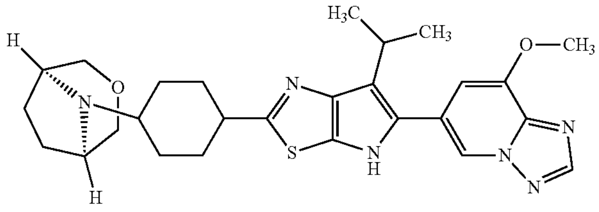 [SMILES: COc1cc(-c2[nH]c3sc(C4CCC(N5[C@@H]6CC[C@H]5COC6)CC4)nc3c2C(C)C)cn2ncnc12] | 507.3 | 1.43 | A |
| 105 | 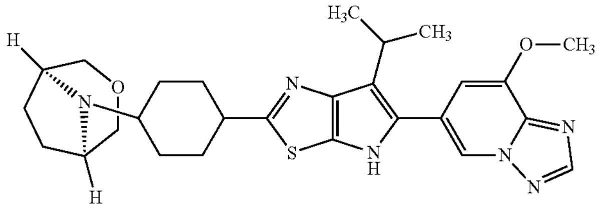 [SMILES: COc1cc(-c2[nH]c3sc(C4CCC(N5[C@@H]6CC[C@H]5COC6)CC4)nc3c2C(C)C)cn2ncnc12] | 507.3 | 1.75 | A |
| 106 | 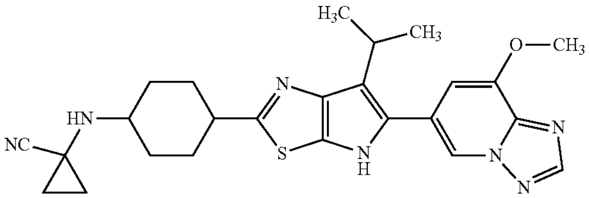 [SMILES: COc1cc(-c2[nH]c3sc(C4CCC(NC5(C#N)CC5)CC4)nc3c2C(C)C)cn2ncnc12] | 476.2 | 1.82 | A |
| 107 | 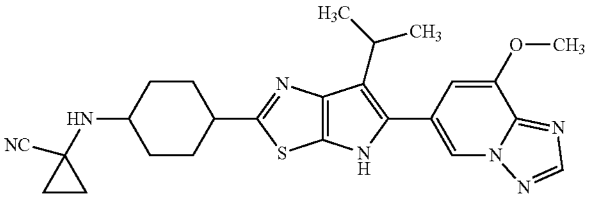 [SMILES: COc1cc(-c2[nH]c3sc(C4CCC(NC5(C#N)CC5)CC4)nc3c2C(C)C)cn2ncnc12] | 476.2 | 1.98 | A |

TABLE 14-continued
| Ex. No. | Structure | HPLC Method | Ret Time (min) | LCMS MH+ |
|---|---|---|---|---|
| 108 | 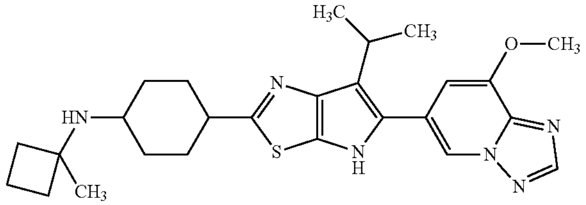 [SMILES: COc1cc(-c2[nH]c3sc(C4CCC(NC5(C)CCC5)CC4)nc3c2C(C)C)cn2ncnc12] | 479.3 | 1.42 | A |
| 109 | 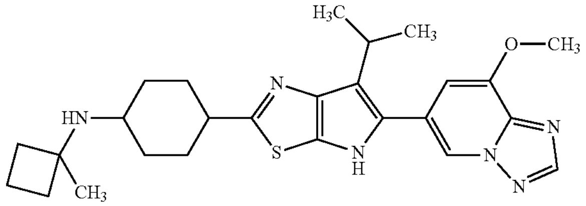 [SMILES: COc1cc(-c2[nH]c3sc(C4CCC(NC5(C)CCC5)CC4)nc3c2C(C)C)cn2ncnc12] | 479.3 | 1.54 | A |
| 110 | 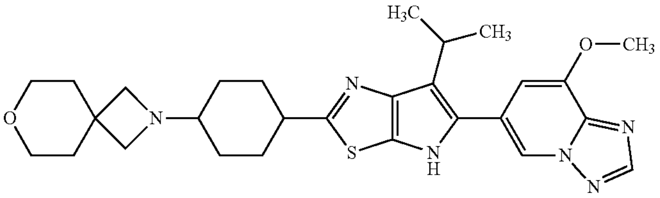 [SMILES: COc1cc(-c2[nH]c3sc(C4CCC(N5CC6(CCOCC6)C5)CC4)nc3c2C(C)C)cn2ncnc12] | 521.3 | 1.32 | A |
| 111 | 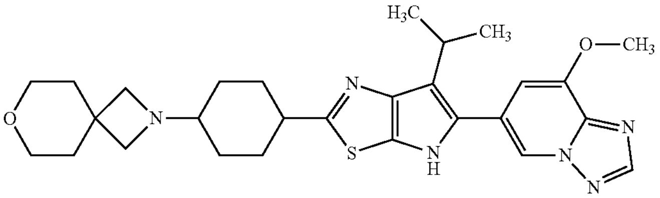 [SMILES: COc1cc(-c2[nH]c3sc(C4CCC(N5CC6(CCOCC6)C5)CC4)nc3c2C(C)C)cn2ncnc12] | 521.3 | 1.70 | A |
| 112 | 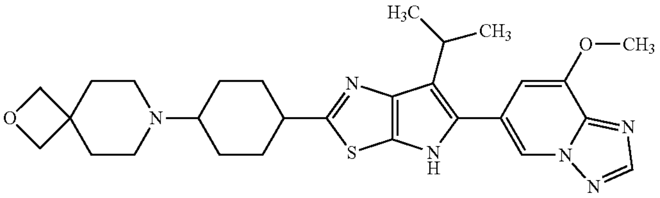 [SMILES: COc1cc(-c2[nH]c3sc(C4CCC(N5CCC6(CC5)COC6)CC4)nc3c2C(C)C)cn2ncnc12] | 521.3 | 1.13 | B |
| 113 | 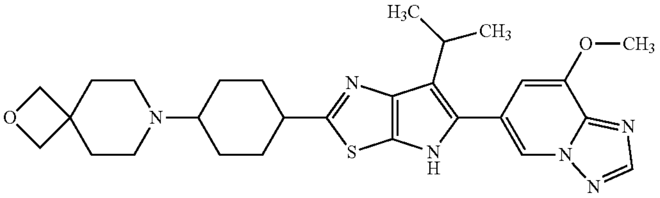 [SMILES: COc1cc(-c2[nH]c3sc(C4CCC(N5CCC6(CC5)COC6)CC4)nc3c2C(C)C)cn2ncnc12] | 521.3 | 1.63 | B |
| 114 | 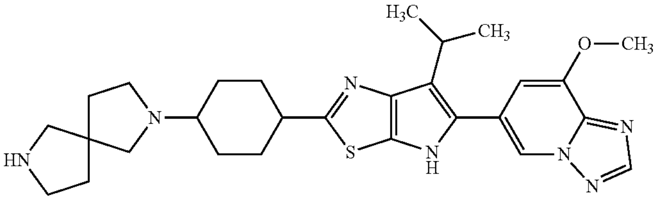 [SMILES: COc1cc(-c2[nH]c3sc(C4CCC(N5CCC6(CCNC6)C5)CC4)nc3c2C(C)C)cn2ncnc12] | 520.3 | 1.34 | A |

TABLE 14-continued
| Ex. No. | Structure | HPLC Method | Ret Time (min) | LCMS MH+ |
|---|---|---|---|---|
| 115 | 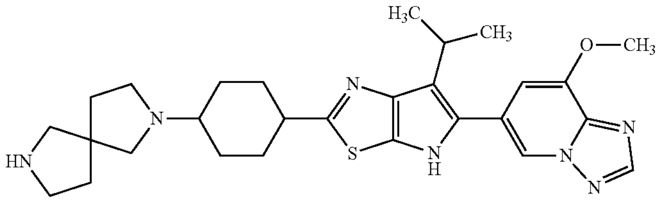 [SMILES: COc1cc(-c2[nH]c3sc(C4CCC(N5CCC6(CCNC6)C5)CC4)nc3c2C(C)C)cn2ncnc12] | 520.3 | 1.49 | A |
| 116 | 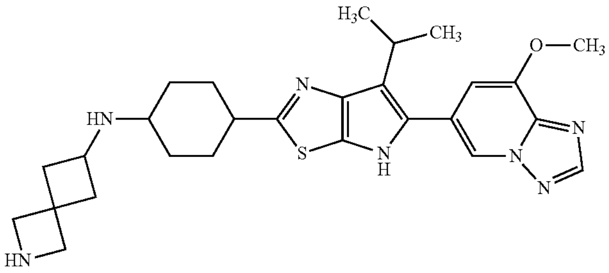 [SMILES: COc1cc(-c2[nH]c3sc(C4CCC(NC5CC6(CNC6)C5)CC4)nc3c2C(C)C)cn2ncnc12] | 506.3 | 1.33 | A |
| 117 | 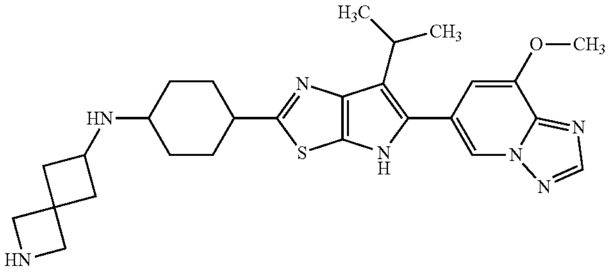 [SMILES: COc1cc(-c2[nH]c3sc(C4CCC(NC5CC6(CNC6)C5)CC4)nc3c2C(C)C)cn2ncnc12] | 506.3 | 1.22 | A |
| 118 | 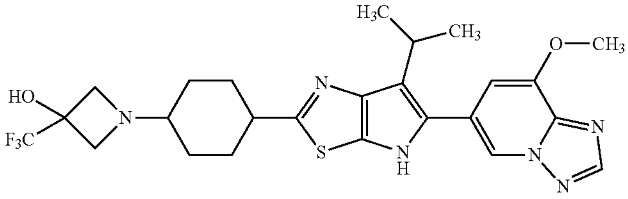 [SMILES: COc1cc(-c2[nH]c3sc(C4CCC(N5CC(O)(C(F)(F)F)C5)CC4)nc3c2C(C)C)cn2ncnc12] | 535.3 | 1.69 | A |
| 119 | 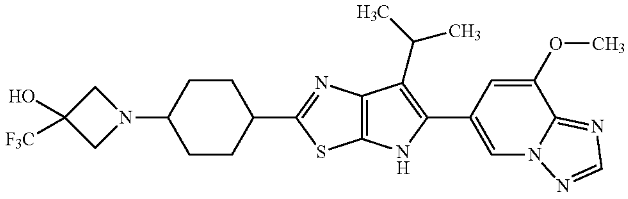 [SMILES: COc1cc(-c2[nH]c3sc(C4CCC(N5CC(O)(C(F)(F)F)C5)CC4)nc3c2C(C)C)cn2ncnc12] | 535.3 | 1.98 | A |
| 120 | 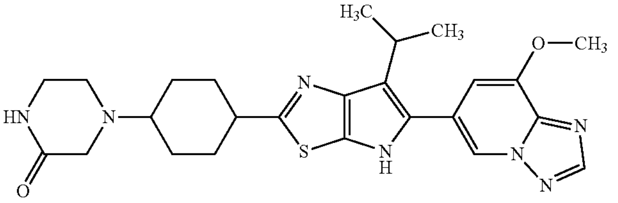 [SMILES: COc1cc(-c2[nH]c3sc(C4CCC(N5CCNC(=O)C5)CC4)nc3c2C(C)C)cn2ncnc12] | 494.2 | 1.73 | A |

TABLE 14-continued

| Ex. No. | Structure | HPLC Method | Ret Time (min) | LCMS MH+ |
|---|---|---|---|---|
| 121 | 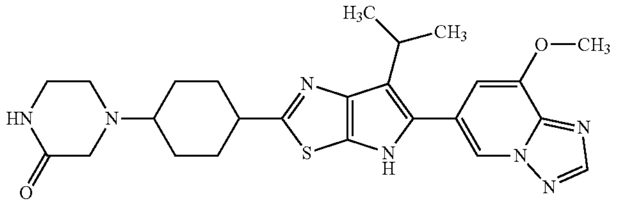 [SMILES: COc1cc(-c2[nH]c3sc(C4CCC(N5CCNC(=O)C5)CC4)nc3c2C(C)C)cn2ncnc12] | 494.2 | 2.01 | A |
| 122 | 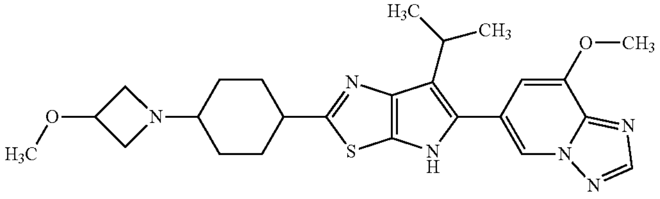 [SMILES: COc1cc(-c2[nH]c3sc(C4CCC(N5CC(OC)C5)CC4)nc3c2C(C)C)cn2ncnc12] | 481.3 | 1.38 | D |
| 123 | 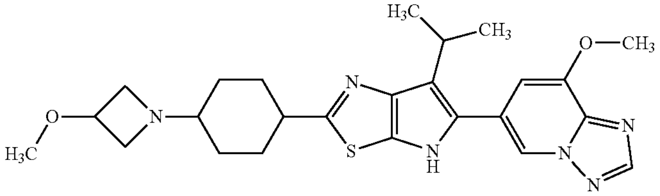 [SMILES: COc1cc(-c2[nH]c3sc(C4CCC(N5CC(OC)C5)CC4)nc3c2C(C)C)cn2ncnc12] | 481.3 | 1.60 | D |
| 124 | 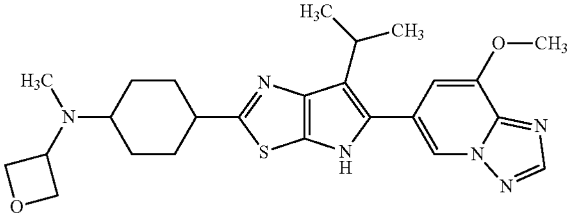 [SMILES: COc1cc(-c2[nH]c3sc(C4CCC(N(C)C5COC5)CC4)nc3c2C(C)C)cn2ncnc12] | 481.3 | 1.66 | D |
| 125 | 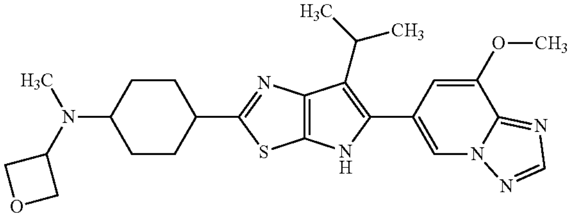 [SMILES: COc1cc(-c2[nH]c3sc(C4CCC(N(C)C5COC5)CC4)nc3c2C(C)C)cn2ncnc12] | 523.3 | 1.56 | D |

Example 126

2-(dimethylamino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (126)

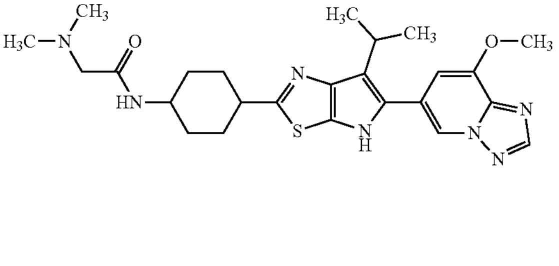

To 4-(6-isopropyl-5-(8-methoxy-[1,2,4]triazolo[1,5-a]pyridin-6-yl)-4H-pyrrolo[3,2-d]thiazol-2-yl)cyclohexan-1-amine (20 mg, 0.049 mmol) in DMF (5 mL) was added dimethylglycine (5.02 mg, 0.049 mmol), TEA (6.79 µL, 0.049 mmol) and HATU (18.52 mg, 0.049 mmol). The reaction mixture was stirred at ambient temperature for 12 h, then was quenched with 1 mL of ice cold water and concentrated under vacuum. The residue was extracted with 10% of methanol in DCM (5 mL×2). Organic layer was concentrated and the crude product obtained was purified by prep LCMS using Method I. After Preparative LCMS purification, fractions containing the product was combined and dried using Genevac centrifugal evaporator to afford 2-(dimethylamino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (4.6 mg, 18% yield) as a pale white solid. LCMS retention time 1.42 min [C]. MS ($E^-$) m/z: 496.2 (M+H). $^1$H NMR (400 MHz, DMSO-$d_6$) δ 11.62 (s, 1H), 8.55-8.38 (m, 2H), 7.75-7.63 (m, 1H), 7.12 (d, J=1.2 Hz, 1H), 4.06 (s, 3H), 3.75-3.62 (m, 1H), 3.24-3.13 (m, 1H), 3.06-2.89 (m, 3H), 2.33-2.23 (m, 6H), 2.20-2.12 (m, 2H), 1.97-1.83 (m, 2H), 1.71-1.54 (m, 2H), 1.44 (d, J=6.8 Hz, 6H).

Example 127

N-(4-(6-isopropyl-5-(8-methoxy-[1,2,4]triazolo[1,5-a]pyridin-6-yl)-4H-pyrrolo[3,2-d]thiazol-2-yl)cyclohexyl)methanesulfonamide (127)

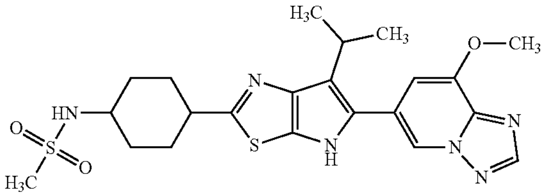

To 4-(6-isopropyl-5-(8-methoxy-[1,2,4]triazolo[1,5-a]pyridin-6-yl)-4H-pyrrolo[3,2-d]thiazol-2-yl)cyclohexan-1-amine (20 mg, 0.049 mmol) in DCM (5 mL) were added TEA (6.79 μL, 0.049 mmol) and methanesulfonyl chloride (5.58 mg, 0.049 mmol). The reaction mixture was stirred at ambient temperature for 12 h. The reaction was quenched with 1 mL of ice cold water and the reaction mass was concentrated. The residue was extracted with 10% of methanol in DCM (5 mL×2). Organic layer was concentrated and the crude product obtained was purified by prep LCMS using Method I. After Preparative LCMS purification, fractions containing the product was combined and dried using Genevac centrifugal evaporator to afford N-(4-(6-isopropyl-5-(8-methoxy-[1,2,4]triazolo[1,5-a]pyridin-6-yl)-4H-pyrrolo[3,2-d]thiazol-2-yl)cyclohexyl)methanesulfonamide (3.6 mg, 15% yield) as a pale white solid. LCMS retention time 1.42 min [C]. MS ($E^-$) m/z: 489.2 (M+H). $^1H$ NMR (400 MHz, DMSO-$d_6$) δ 11.61 (s, 1H), 8.52-8.44 (m, 2H), 7.12 (d, J=1.2 Hz, 1H), 7.08 (d, J=7.3 Hz, 1H), 4.06 (s, 3H), 3.27-3.13 (m, 2H), 2.94 (s, 4H), 2.20-2.10 (m, 2H), 2.07-1.96 (m, 2H), 1.71-1.57 (m, 2H), 1.43 (d, J=6.8 Hz, 7H).

Example 128

Trans 2-(ethyl(methyl)amino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (128)

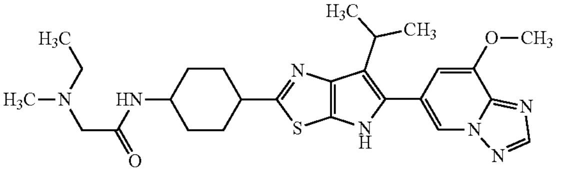

Intermediate 128A: Chloro-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (128A)

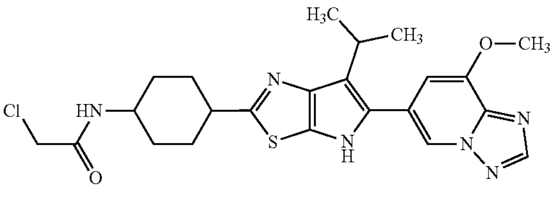

To a mixture of trans 4-(6-isopropyl-5-(8-methoxy-[1,2,4]triazolo[1,5-a]pyridin-6-yl)-4H-pyrrolo[3,2-d]thiazol-2-yl)cyclohexan-1-amine (100 mg, 0.244 mmol) in DCM (5 mL) were added TEA (0.068 mL, 0.487 mmol) and 2-chloroacetyl chloride (27.5 mg, 0.244 mmol). The reaction mixture was stirred at ambient temperature for 12 h. The reaction mass was diluted with DCM, washed with water, concentrated to afford 2-chloro-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (80 mg, 0.164 mmol, 68%) as colorless liquid. LCMS retention time 1.26 min [C]. MS ($E^-$) m/z: 488.1 (M+H).

Example 128

To 2-chloro-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (10 mg, 0.021 mmol) in DCM (5 mL) were added TEA (5.72 μL, 0.041 mmol), N-methylethanamine (3.64 mg, 0.062 mmol) and was stirred at ambient temperature for 12 h. The reaction was quenched with 1 mL of ice cold water and the reaction mass was concentrated. The residue was extracted with 10% of methanol in DCM (5 mL×2). The organic layer was concentrated and the crude product obtained was purified by prep LCMS using Method I. After Preparative LCMS purification, fractions containing the product was combined and dried using Genevac centrifugal to afford 2-(ethyl(methyl)amino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (6.3 mg, 60% yield) as a pale white solid. LCMS retention time 1.58 min [C]. MS ($E^-$) m/z: 510.1 (M+H). $^1H$ NMR (400 MHz, DMSO-$d_6$) δ 11.62 (s, 1H), 8.55-8.41 (m, 2H), 7.75-7.54 (m, 1H), 7.12 (d, J=1.2 Hz, 1H), 4.06 (s, 3H), 3.75-3.62 (m, 1H), 3.18 (td, J=6.9, 13.6 Hz, 1H), 3.09-2.92 (m, 3H), 2.29 (s, 3H), 2.19-2.10 (m, 2H), 1.97-1.81 (m, 3H), 1.69-1.54 (m, 2H), 1.44 (d, J=6.8 Hz, 6H), 1.04 (t, J=7.1 Hz, 3H).

The following Examples were prepared according to the general procedure described in Examples 128.

TABLE 15

| Ex. No. | Structure | HPLC Method | Ret Time (min) | LCMS MH+ |
|---|---|---|---|---|
| 129 | 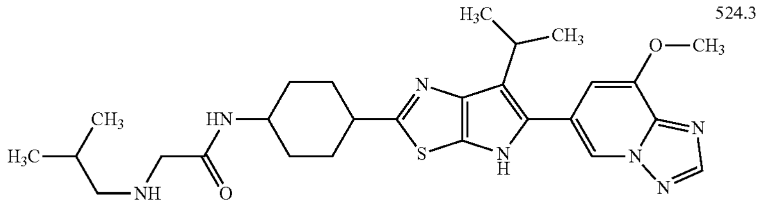 | 524.3 | 1.72 | A |

Examples 130 and 131

N-(4-(6-isopropyl-5-(8-methyl-[1,2,4]triazolo[1,5-a]pyridin-6-yl)-4H-pyrrolo[3,2-d]thiazol-2-yl)cyclohexyl)oxetan-3-amine (130-131)

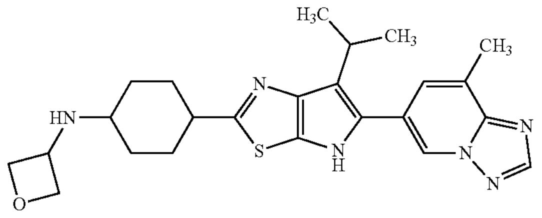

N-(4-(6-isopropyl-5-(8-methyl-[1,2,4]triazolo[1,5-a]pyridin-6-yl)-4H-pyrrolo[3,2-d]thiazol-2-yl)cyclohexyl)oxetan-3-amine was prepared as described in Examples 65 and 66 using 4-(6-isopropyl-5-(8-methyl-[1,2,4]triazolo[1,5-a]pyridin-6-yl)-4H-pyrrolo[3,2-d]thiazol-2-yl)cyclohexan-1-one (0.1 g, 0.254 mmol) as a starting intermediate.

Example 130 (Isomer 1): After Preparative LCMS purification, fractions containing Isomer 1 was collected and evaporated to dryness to yield a pale white solid (0.0016, 1.4% yield). LCMS retention time 1.42 min [C]. MS ($E^-$) m/z: 451.3 (M+H). $^1$H NMR (400 MHz, DMSO-$d_6$) δ 11.56 (s, 1H), 8.69 (s, 1H), 8.49 (s, 1H), 7.54 (s, 1H), 4.75 (t, J=7.2 Hz, 2H), 4.56 (t, J=6.6 Hz, 2H), 3.19-3.07 (m, 4H), 2.61 (s, 3H), 2.17 (d, J=12.2 Hz, 2H), 1.98 (br. s., 2H), 1.59 (d, J=12.5 Hz, 2H), 1.40 (d, J=6.8 Hz, 8H).

Example 131 (Isomer 2): After Preparative LCMS purification, fractions containing Isomer 2 was collected and evaporated to dryness to yield a pale white solid (0.0074 6.4% yield). LCMS retention time 1.58 min [C]. MS ($E^-$) m/z: 451.3 (M+H). $^1$H NMR (400 MHz, DMSO-$d_6$) δ 11.55 (s, 1H), 8.70 (s, 1H), 8.49 (s, 1H), 7.56 (s, 1H), 4.63 (t, J=6.6 Hz, 2H), 4.35 (t, J=6.2 Hz, 2H), 3.99-3.92 (m, 1H), 3.22-3.06 (m, 3H), 2.68 (d, J=2.2 Hz, 1H), 2.61 (s, 3H), 2.07-1.97 (m, 2H), 1.77 (d, J=13.4 Hz, 2H), 1.65-1.48 (m, 4H), 1.42 (d, J=6.8 Hz, 6H).

The following Examples were prepared according to the general procedure described in Examples 130 and 131.

TABLE 16

| Ex. No. | Structure | HPLC Method | Ret Time (min) | LCMS MH+ |
|---|---|---|---|---|
| 132 | 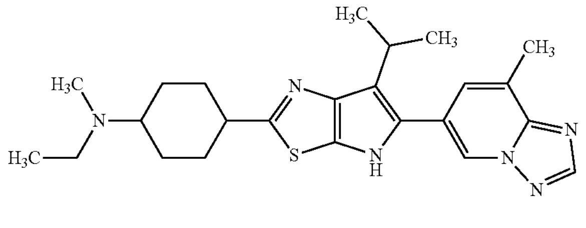 [SMILES: CCN(C)C1CCC(c2nc3c(C(C)C)c(-c4cc(C)c5ncnn5c4)[nH]c3s2)CC1] Isomer 2 | 437.2 | 3.43 | D |
| 134 | 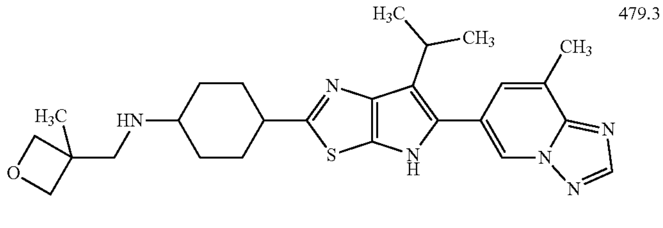 Isomer 1 | 479.3 | 1.36 | D |

TABLE 16-continued
| Ex. No. | Structure | HPLC Method | Ret Time (min) | LCMS MH+ |
|---|---|---|---|---|
| 135 | 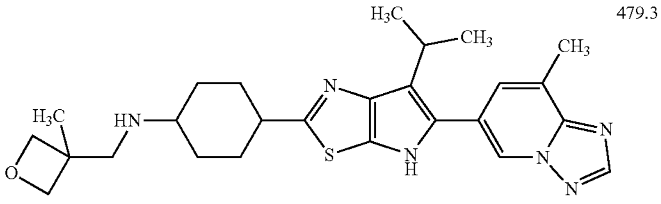 Isomer 2 | 479.3 | 1.57 | D |
| 136 | 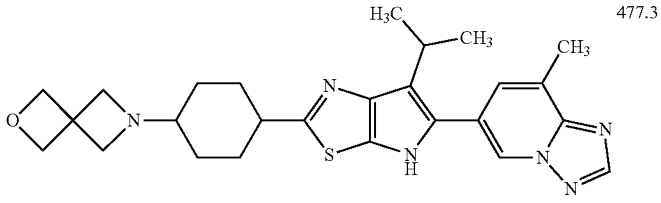 Isomer 1 | 477.3 | 1.21 | D |
| 137 | 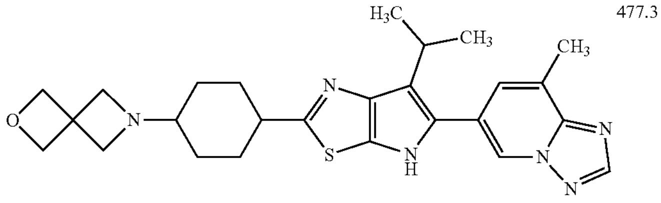 Isomer 2 | 477.3 | 1.21 | D |
| 138 | 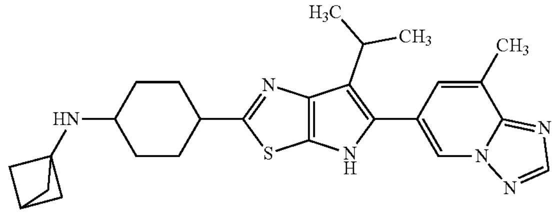 [SMILES: Cc1cc(-c2[nH]c3sc(C4CCC(NC56CC(C5)C6)CC4)nc3c2C(C)C)cn2ncnc12] Isomer 1 | 461.2 | 1.89 | D |
| 139 | 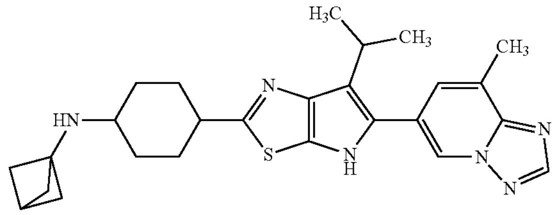 [SMILES: Cc1cc(-c2[nH]c3sc(C4CCC(NC56CC(C5)C6)CC4)nc3c2C(C)C)cn2ncnc12] Isomer 2 | 461.2 | 2.12 | D |
| 140 | 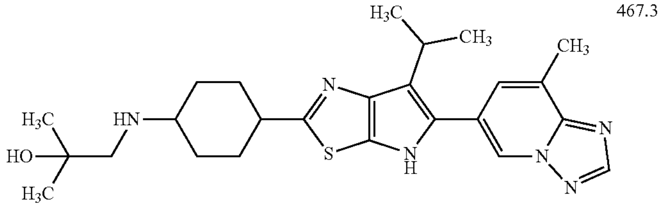 Isomer 1 | 467.3 | 1.17 | H |

TABLE 16-continued
| Ex. No. | Structure | HPLC Method | Ret Time (min) | LCMS MH+ |
|---|---|---|---|---|
| 141 | 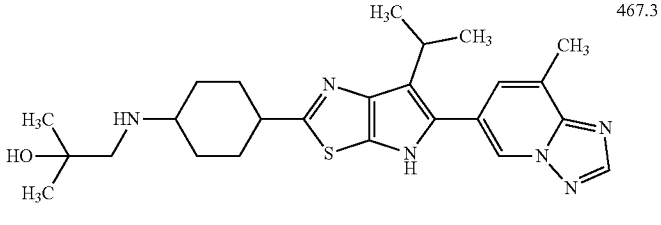 Isomer 2 | 467.3 | 1.42 | D |
| 142 | 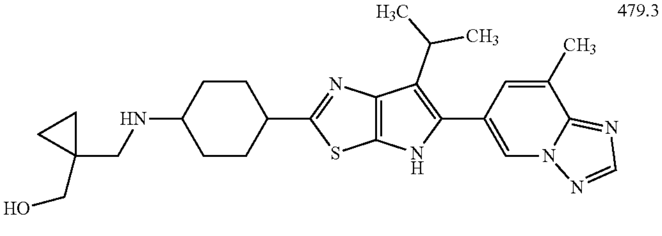 Isomer 1 | 479.3 | 1.29 | D |
| 143 | 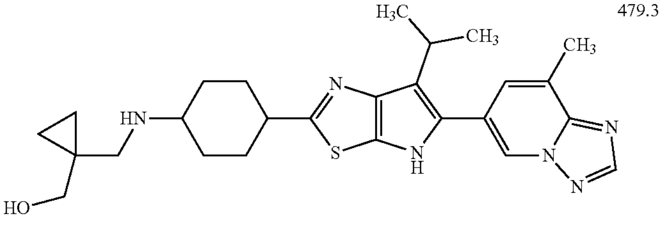 Isomer 2 | 479.3 | 1.41 | D |
Examples 144 and 145
N-(4-(6-isopropyl-5-(7-methyl-[1,2,4]triazolo[1,5-a]pyridin-6-yl)-4H-pyrrolo[3,2-d]thiazol-2-yl)cyclohexyl)-3-methyloxetan-3-amine
(144-145)
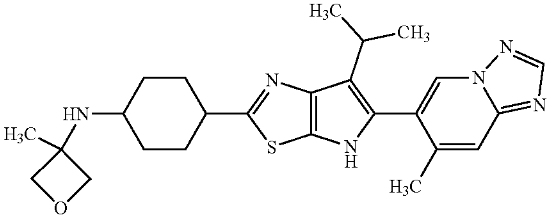
Intermediate 144A: Tert-butyl (4-((7-methyl-[1,2,4]triazolo[1,5-a]pyridin-6-yl)ethynyl)-2-(1,4-dioxaspiro[4.5]decan-8-yl)thiazol-5-yl)carbamate
(144A)
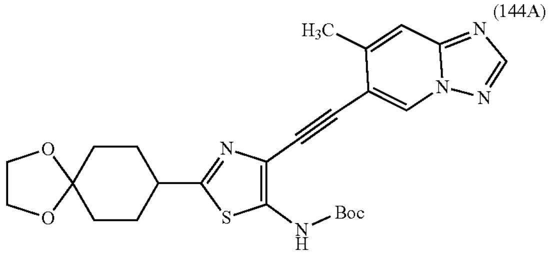 [SMILES: Cc1cc2ncnn2cc1C#Cc1nc(C2CCC3(CC2)OCCO3)sc1NC(=O)OC(C)(C)C]

To a solution of tert-butyl (4-iodo-2-(1,4-dioxaspiro[4.5]decan-8-yl)thiazol-5-yl) carbamate (4.0 g, 8.58 mmol) in toluene (50 mL) and DIPEA (10.00 mL) was added triphenylphosphine (0.225 g, 0.858 mmol) and copper(I) iodide (0.163 g, 0.858 mmol), degassed for 10 min with argon. Next, 6-ethynyl-7-methyl-[1,2,4]triazolo[1,5-a]pyridine (1.753 g, 11.15 mmol) was added, followed by bis(triphenylphosphine)palladium(II) dichloride (0.33 g, 0.429 mmol) degassed again for 5 min. The resulting reaction mixture was heated at 45° C. for 3 h. The reaction was mass was filtered, washed with ethyl acetate (100 ml), the filtrate was concentrated to afford crude product. The crude was purified by combiflash using 40 g silica column by eluting with 60% EtOAc/Pet ether. Following concentration of fractions, collected tert-butyl (4-((7-methyl-[1,2,4]triazolo[1,5-a]pyridin-6-yl)ethynyl)-2-(1,4-dioxaspiro[4.5]decan-8-yl)thiazol-5-yl)carbamate (2.0 g, 4.04 mmol, 47.0% yield) as a pale yellow solid. LCMS retention time 3.01 min [E]. MS ($E^-$) m/z: 496.2 (M+H).

Intermediate 144B: Tert-butyl 5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (144B)

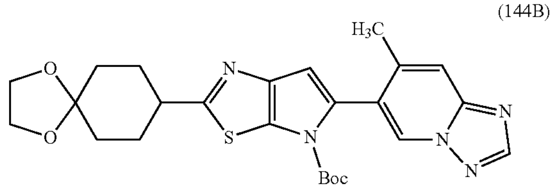 [SMILES: Cc1cc2ncnn2cc1-c1cc2nc(C3CCC4(CC3)OCCO4)sc2n1C(=O)OC(C)(C)C]

To a solution of tert-butyl (4-((7-methyl-[1,2,4]triazolo[1,5-a]pyridin-6-yl)ethynyl)-2-(1,4-dioxaspiro[4.5]decan-8-yl)thiazol-5-yl)carbamate (3.5 g, 7.06 mmol) in toluene (50 mL) was added silver acetate (1.179 g, 7.06 mmol). The resulting solution was heated at 100° C. for 45 min. The reaction mass was filtered through celite, washed with EtOAc (10 mL) and the filtrate was concentrated to afford tert-butyl 5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (2.0 g, 4.04 mmol, 57.1% yield) as a pale yellow solid. LCMS retention time 2.91 min [E]. MS ($E^-$) m/z: 496.2.1 (M+H).

Intermediate 144C: Tert-butyl 6-bromo-5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (144C)

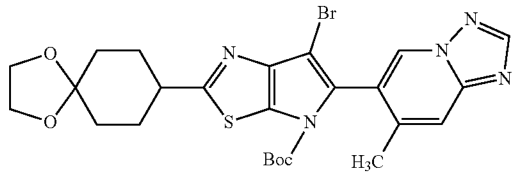

To a solution of tert-butyl 5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (2.0 g, 4.04 mmol) in DMF (50 mL) was added NBS (0.790 g, 4.44 mmol) in DMF (20 mL) dropwise at 0° C. The reaction mixture was stirred at room temperature for 12 h. The reaction was quenched with ice water (70 ml), stirred for 10 min, the resulting precipitate was filtered and dried to afford tert-butyl 6-bromo-5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (1.6 g, 2.79 mmol, 69.0% yield) as a pale yellow solid. LCMS retention time 3.24 min [E]. MS ($E^-$) m/z: 576.2 (M+2H).

Intermediate 144D: Tert-butyl 5-(7-methyl-[1,2,4]triazolo[1,5-a]pyridin-6-yl)-6-(prop-1-en-2-yl)-2-(1,4-dioxaspiro[4.5]decan-8-yl)-4H-pyrrolo[3,2-d]thiazole-4-carboxylate (144D)

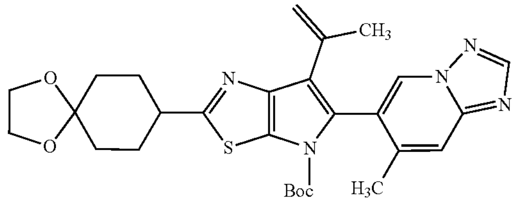

To a solution of tert-butyl 6-bromo-5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (1.6 g, 2.79 mmol) in dioxane (15 mL) and water (1.667 mL) was added potassium phosphate, tribasic (0.970 g, 5.57 mmol). The solution was degassed for 10 min., $PdCl_2(dppf)-CH_2Cl_2$ adduct (0.227 g, 0.279 mmol) was added, and the reaction mixture was degassed again for 5 min, followed by addition of 4,4,5,5-tetramethyl-2-(prop-1-en-2-yl)-1,3,2-dioxaborolane (2.63 mL, 13.93 mmol). The resulting reaction mixture was heated at 70° C. for 4 h. The reaction mass was concentrated, diluted with water (100 mL) and extracted with DCM (3×100 ml). The separated organic layer was dried over sodium sulphate, filtered and concentrated. The crude was purified by combiflash using 40 g silica column by eluting with 80% EtOAc/Pet ether. Following concentration of fractions, collected tert-butyl 5-(7-methyl-[1,2,4]triazolo[1,5-a]pyridin-6-yl)-6-(prop-1-en-2-yl)-2-(1,4-dioxaspiro[4.5]decan-8-yl)-4H-pyrrolo[3,2-d]thiazole-4-carboxylate (1.1 g, 2.054 mmol, 73.7% yield) as a pale yellow solid. LCMS retention time 3.59 min [E]. MS ($E^-$) m/z: 536.2 (M+H).

Intermediate 144E: Tert-butyl 6-isopropyl-5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (144E)

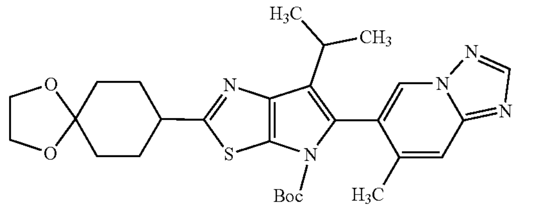

A solution of tert-butyl 5-(7-methyl-[1,2,4]triazolo[1,5-a]pyridin-6-yl)-6-(prop-1-en-2-yl)-2-(1,4-dioxaspiro[4.5]decan-8-yl)-4H-pyrrolo[3,2-d]thiazole-4-carboxylate (1.1 g, 2.054 mmol) in methanol (75 mL) and DCM (25 mL) was purged with nitrogen gas and Pd/C (0.874 g, 4.11 mmol) was added. The system was evacuated under vacuum and purged with hydrogen gas and left to stir under hydrogen atmosphere for 24 h. The reaction mass was filtered through a plug of celite pad. The celite pad was rinsed with additional methanol and the filtrate was concentrated to dryness to afford tert-butyl 6-isopropyl-5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate as white solid (0.85 g, 92%). LCMS retention time 2.22 min [F]. MS ($E^-$) m/z: 538.2 (M+H).

Intermediate 144F: 4-(6-isopropyl-5-(7-methyl-[1,2,4]triazolo[1,5-a]pyridin-6-yl)-4H-pyrrolo[3,2-d]thiazol-2-yl)cyclohexan-1-one (144F)

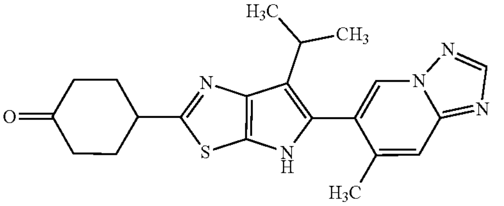

To a solution of tert-butyl 6-isopropyl-5-(7-methyl-[1,2,4]triazolo[1,5-a]pyridin-6-yl)-2-(1,4-dioxaspiro[4.5]decan-8-yl)-4H-pyrrolo[3,2-d]thiazole-4-carboxylate (1.1 g, 2.046 mmol) in DCM (20 mL) was added TFA (10 mL, 130 mmol) dropwise and stirred at room temperature for 12 h. The reaction mass was diluted with DCM (20 mL) and washed with 10% $NaHCO_3$ (20 mL). The reaction mass was concentrated and co-distilled with DCM and pet ether (3×20 mL) and dried under vacuum to afford 4-(6-isopropyl-5-(7-methyl-[1,2,4]triazolo[1,5-a]pyridin-6-yl)-4H-pyrrolo[3,2-d]thiazol-2-yl)cyclohexan-1-one (0.8 g, 2.033 mmol, 99% yield) as a yellow solid. LCMS retention time 1.34 min [F]. MS ($E^-$) m/z: 394.2 (M+H).

The following Intermediates were prepared in a similar manner to Intermediate 144 & 145:

TABLE 17

| Ex. No. | Structure | HPLC Method | Ret Time (min) | LCMS $MH^+$ |
|---|---|---|---|---|
| 144G | 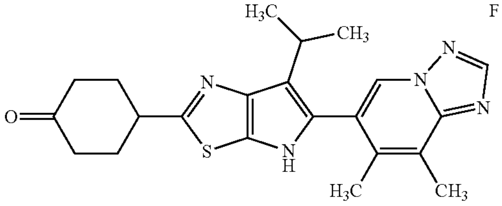 | F | 1.42 | 408.5 |
| 144H | 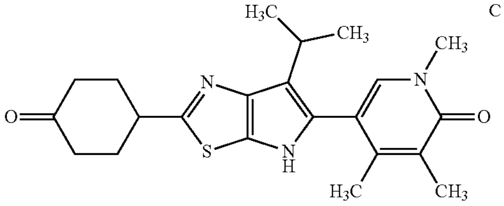 | C | 2.237 | 398.2 |
| 144I | 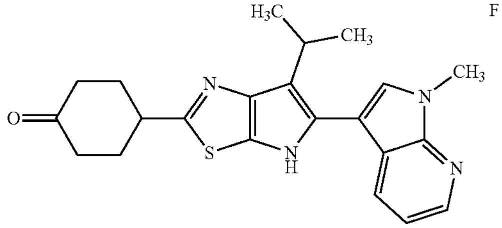 | F | 1.26 | 393.3 |

Examples 144 and 145: N-(4-(6-isopropyl-5-(7-methyl-[1,2,4]triazolo[1,5-a]pyridin-6-yl)-4H-pyrrolo[3,2-d]thiazol-2-yl)cyclohexyl)-3-methyloxetan-3-amine To a solution of 4-(6-isopropyl-5-(7-methyl-[1,2,4]triazolo[1,5-a]pyridin-6-yl)-4H-pyrrolo[3,2-d]thiazol-2-yl)cyclohexan-1-one (75 mg, 0.191 mmol) in THF (5 mL) and DMF (5 mL) was added 3-methyloxetan-3-amine (16.60 mg, 0.191 mmol) followed by TEA (0.027 mL, 0.191 mmol) dropwise, the resulting light yellow solution was stirred under nitrogen at room temperature for 12 h. Then sodium cyanoborohydride (23.95 mg, 0.381 mmol) was added at 0° C. and continued stirring at room temperature for 2 h. The reaction mass was concentrated to remove volatiles, crude was diluted with DCM (30 mL) and washed with water (25 mL). The separated organic layer was dried over sodium sulphate, filtered and concentrated. The crude product obtained was purified by prep LCMS using Method I. After Preparative LCMS purification, fractions containing Isomers 1 and 2 were collected and dried separately using Genevac centrifugal evaporator to afford Isomer 1 and Isomer 2.

Example 144 (Isomer 1) was obtained as a pale yellow solid (23 mg, 0.048 mmol, 24.93% yield). LCMS retention time 1.38 min [A]. MS ($E^-$) m/z: 465.3. $^1$H NMR (400 MHz, DMSO-$d_6$) δ 11.32 (s, 1H) 8.84 (s, 1H) 8.49 (s, 1H) 7.80 (s, 1H) 4.41 (d, J=5.38 Hz, 2H) 4.21 (d, J=5.62 Hz, 2H) 2.91-2.98 (m, 1H) 2.68-2.77 (m, 2H) 2.57-2.65 (m, 2H) 2.28 (s, 3H) 2.06-2.15 (m, 2H) 1.73-1.81 (m, 2H) 1.58 (qd, J=12.76, 2.81 Hz, 2H) 1.44 (s, 3H) 1.31 (d, J=6.85 Hz, 6H).

Example 145 (Isomer 2) was obtained as a pale yellow solid. LCMS retention time 1.58 min [A]. MS ($E^-$) m/z: 465.3. $^1$H NMR (400 MHz, DMSO-$d_6$) δ 11.31-11.38 (m, 1H) 8.86 (s, 1H) 8.49 (s, 1H) 7.81 (s, 1H) 4.42 (d, J=5.62 Hz, 2H) 4.18 (d, J=5.62 Hz, 2H) 3.13-3.18 (m, 1H) 2.79-2.86 (m, 1H) 2.71-2.78 (m, 1H) 2.29 (s, 3H) 2.03-2.14 (m, 2H) 1.78-1.88 (m, 2H) 1.54-1.64 (m, 2H) 1.49 (br d, J=3.18 Hz, 2H) 1.42 (s, 3H) 1.33 (d, J=6.85 Hz, 6H).

The following Examples were prepared according to the general procedure described in Examples 144 and 145.

TABLE 18

| Ex. No. | Structure | HPLC Method | Ret Time (min) | LCMS MH+ |
|---|---|---|---|---|
| 146 | 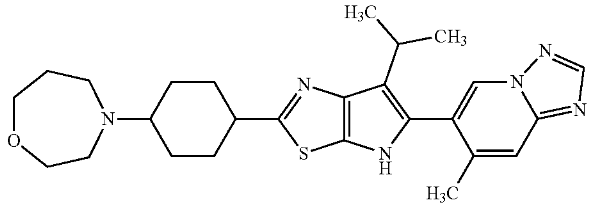 [SMILES: Cc1cc2ncnn2cc1-c1[nH]c2sc(C3CCC(N4CCCOCC4)CC3)nc2c1C(C)C] Isomer 1 | A | 1.31 | 479.3 |
| 147 | 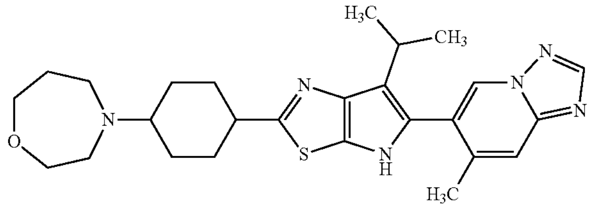 [SMILES: Cc1cc2ncnn2cc1-c1[nH]c2sc(C3CCC(N4CCCOCC4)CC3)nc2c1C(C)C] Isomer 2 | A | 1.43 | 479.3 |
| 148 | 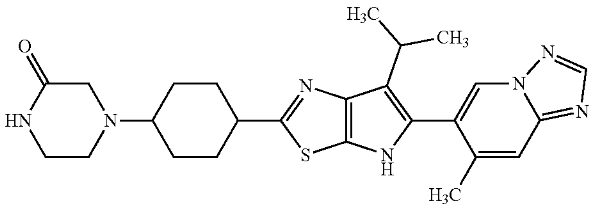 [SMILES: Cc1cc2ncnn2cc1-c1[nH]c2sc(C3CCC(N4CCNC(=O)C4)CC3)nc2c1C(C)C] Isomer 1 | A | 1.29 | 478.3 |
| 149 | 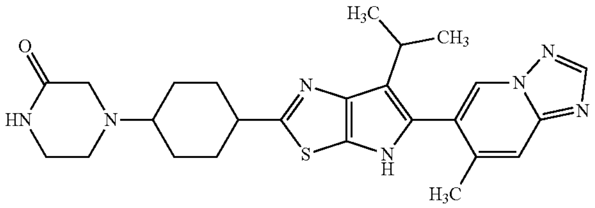 | A | 1.47 | 478.3 |

TABLE 18-continued
| Ex. No. | Structure | HPLC Method | Ret Time (min) | LCMS MH+ |
|---|---|---|---|---|
| | Isomer 2 | | | |
| 150 | 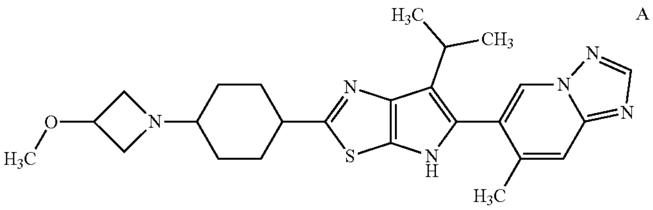 Isomer 1 | A | 1.33 | 465.3 |
| 151 | 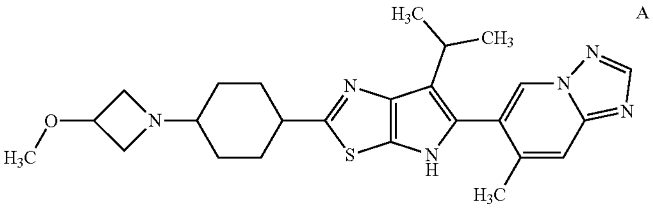 Isomer 2 | A | 1.52 | 465.2 |
| 152 | 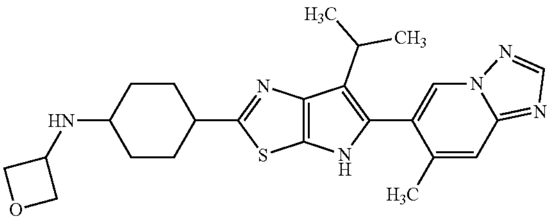 [SMILES: Cc1cc2ncnn2cc1-c1[nH]c2sc(C3CCC(NC4COC4)CC3)nc2c1C(C)C] Isomer 1 | A | 1.34 | 451.3 |
| 153 | 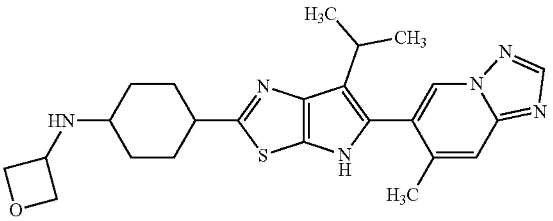 [SMILES: Cc1cc2ncnn2cc1-c1[nH]c2sc(C3CCC(NC4COC4)CC3)nc2c1C(C)C] Isomer 2 | A | 1.49 | 451.2 |
| 154 | 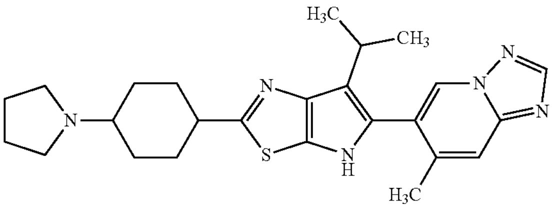 Isomer 1 | A | 1.17 | 449.2 |
| 155 | 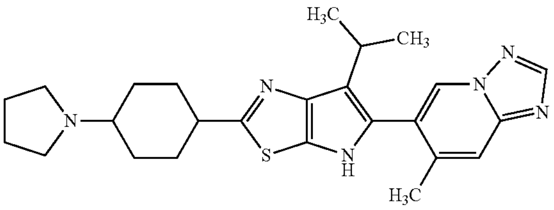 [SMILES: Cc1cc2ncnn2cc1-c1[nH]c2sc(C3CCC(N4CCCC4)CC3)nc2c1C(C)C] | A | 1.27 | 449.3 |

TABLE 18-continued
| Ex. No. | Structure | HPLC Method | Ret Time (min) | LCMS MH+ |
|---|---|---|---|---|
| | Isomer 2 | | | |
| 156 | 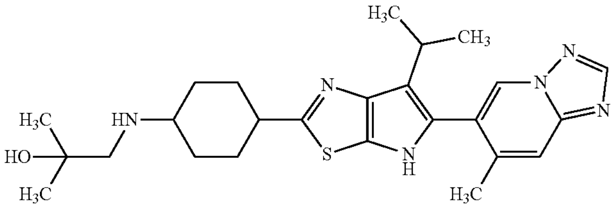 Isomer 1 | A | 1.14 | 467.2 |
| 157 | 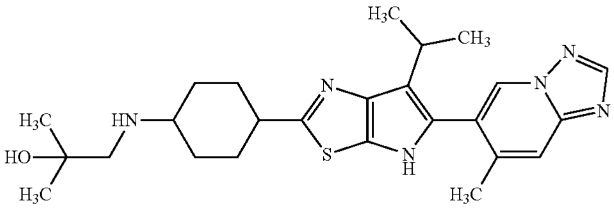 Isomer 2 | A | 1.29 | 467.3 |
| 158 | 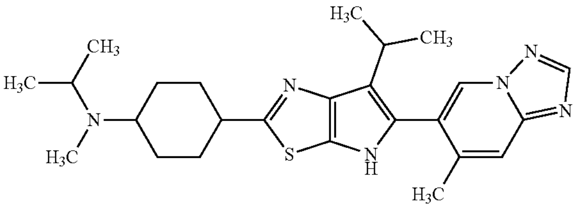 [SMILES: Cc1cc2ncnn2cc1-c1[nH]c2sc(C3CCC(N(C)C(C)C)CC3)nc2c1C(C)C] Isomer 1 | A | 1.20 | 451.2 |
| 159 | 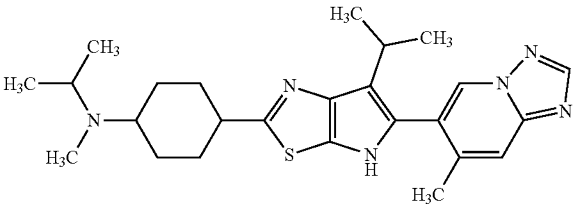 Isomer 2 | A | 1.24 | 451.3 |
| 160 | 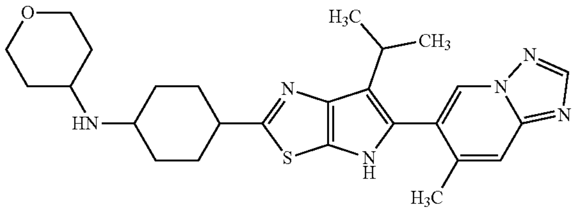 [SMILES: Cc1cc2ncnn2cc1-c1[nH]c2sc(C3CCC(NC4CCOCC4)CC3)nc2c1C(C)C] Isomer 1 | A | 1.15 | 479.3 |

TABLE 18-continued

| Ex. No. | Structure | HPLC Method | Ret Time (min) | LCMS MH+ |
|---|---|---|---|---|
| 161 | 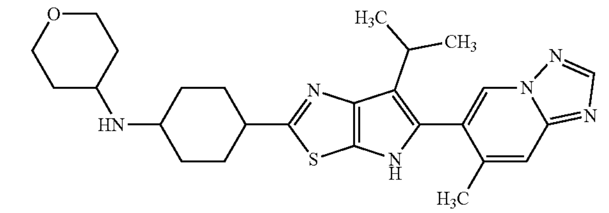 [SMILES: Cc1cc2ncnn2cc1-c1[nH]c2sc(C3CCC(NC4CCOCC4)CC3)nc2c1C(C)C] Isomer 2 | A | 1.29 | 479.2 |

Examples 162 and 163

2-((4-(6-isopropyl-5-(8-methoxy-[1,2,4]triazolo[1,5-a]pyridin-6-yl)-4H-pyrrolo[3,2-d]thiazol-2-yl)cyclohexyl)(methyl)amino)-N,N-dimethylacetamide (162-163)

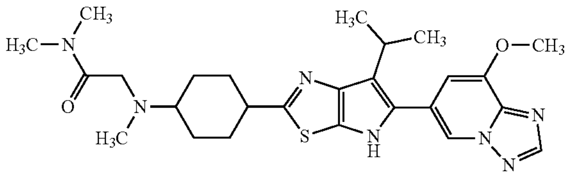

Intermediate 162A: 4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (162A)

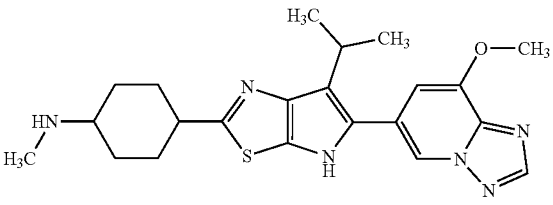

To a solution of 4-(6-isopropyl-5-(8-methoxy-[1,2,4]triazolo[1,5-a]pyridin-6-yl)-4H-pyrrolo[3,2-d]thiazol-2-yl)cyclohexan-1-one (200 mg, 0.488 mmol) in THF (5 mL) and DMF (5 mL) was added methanamine in THE (4.88 mL, 9.77 mmol) followed by acetic acid (2.80 μl, 0.049 mmol) dropwise, the resulting light yellow solution was stirred under nitrogen at room temperature for 12 h. Then sodium cyanoborohydride (61.4 mg, 0.977 mmol) was added at 0° C. and continued stirring at room temperature for 2 h. The reaction mass was concentrated to remove volatiles, crude was diluted with DCM (30 mL) and washed with water (25 mL), the separated organic layer was dried over sodium sulphate, filtered and concentrated to afford 4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (250 mg, 0.353 mmol, 72.3% yield) as a yellow solid. LCMS retention time 1.6 min [C]. MS ($E^-$) m/z: 425.3.

Examples 162 and 163: 2-((4-(6-isopropyl-5-(8-methoxy-[1,2,4]triazolo[1,5-a]pyridin-6-yl)-4H-pyrrolo[3,2-d]thiazol-2-yl)cyclohexyl)(methyl)amino)-N,N-dimethylacetamide To a solution of 4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (70 mg, 0.165 mmol) in THF (2 mL) and DMF (1 mL) was added TEA (0.046 mL, 0.330 mmol) followed by 2-chloro-N,N-dimethylacetamide (20.04 mg, 0.165 mmol). The resulting solution was stirred at room temperature for 12 h. The reaction mass was diluted with water (5 mL) and extracted with EtOAc (3×10 mL). The separated organic layer was dried over sodium sulphate, filtered and concentrated. The crude product obtained was purified by prep LCMS using Method I. After Preparative LCMS purification, fractions containing Isomers 1 and 2 were collected and dried separately using Genevac centrifugal evaporator to afford Isomer 1 and Isomer 2.

Example 162 (Isomer 1) was obtained as a pale yellow solid (19.8 mg, 0.036 mmol, 22.01% yield). LCMS retention time 1.30 min [A]. MS ($E^-$) m/z: 510.2 (M+H). $^1$H NMR (400 MHz, DMSO-$d_6$) δ 11.62 (s, 1H), 8.57-8.43 (m, 2H), 7.12 (s, 1H), 4.12-3.99 (m, 3H), 3.24-3.14 (m, 2H), 3.01 (s, 5H), 2.92-2.77 (m, 5H), 2.74 (s, 2H), 2.22 (br. s., 3H), 1.92 (s, 1H), 1.60 (br. s., 3H), 1.44 (d, J=6.8 Hz, 6H).

Example 163 (Isomer 2) was obtained as a pale yellow solid (4.1 mg, 7.32 μmol, 4.44% yield). LCMS retention time 1.44 min [A]. MS ($E^-$) m/z: 510.2 (M+H). $^1$H NMR (400 MHz, DMSO-$d_6$) δ 11.61 (s, 1H), 8.55-8.42 (m, 2H), 7.14 (d, J=1.2 Hz, 1H), 4.07 (s, 3H), 3.28 (br. s., 1H), 3.25-3.15 (m, 2H), 3.09-2.93 (m, 3H), 2.82 (s, 3H), 2.55 (s, 2H), 2.30-2.16 (m, 3H), 2.16-2.03 (m, 2H), 1.81 (d, J=9.0 Hz, 3H), 1.64 (br. s., 2H), 1.52-1.37 (m, 6H).

The following Examples were prepared according to the general procedure described in Examples 162 and 163.

TABLE 19
| Ex. No. | Structure | HPLC Method | Ret Time (min) | LCMS MH+ |
|---|---|---|---|---|
| 164 | 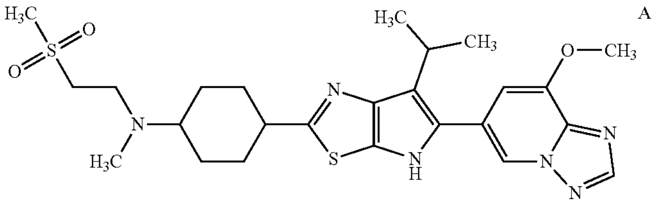 Isomer 1 | A | 1.56 | 531.3 |
| 165 | 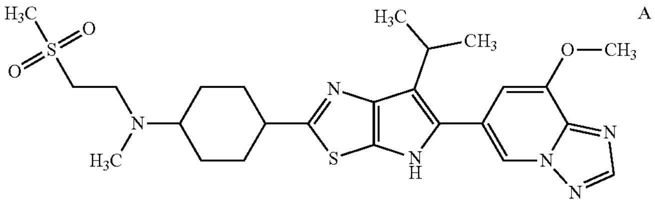 Isomer 2 | A | 1.71 | 531.2 |
The following Examples were prepared according to the general procedure described in Intermediates 144 and 145.
TABLE 20
| Ex. No. | Structure | HPLC Method | Ret Time (min) | LCMS MH+ |
|---|---|---|---|---|
| 166 | 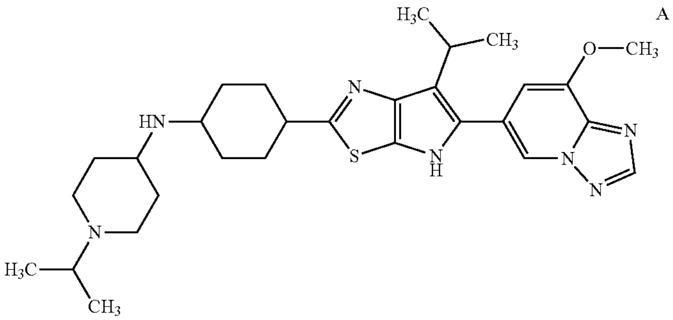 Isomer 1 | A | 1.34 | 536.1 |
| 167 | 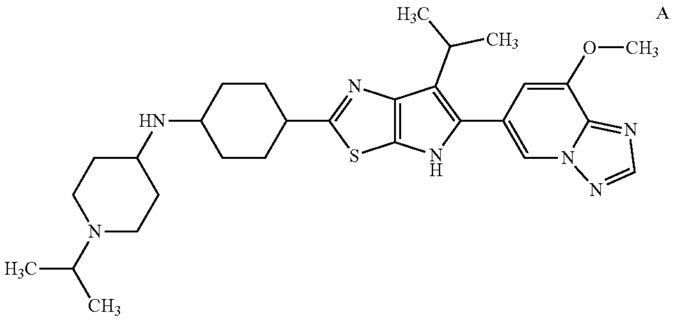 Isomer 2 | A | 1.47 | 536.2 |

TABLE 20-continued

| Ex. No. | Structure | HPLC Method | Ret Time (min) | LCMS $MH^+$ |
|---|---|---|---|---|
| 168 | 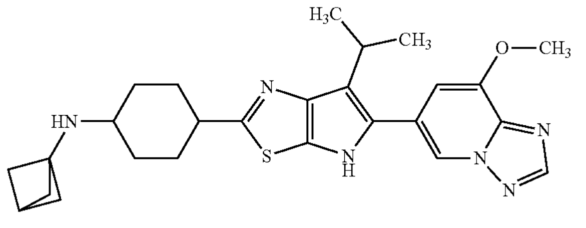 [SMILES: COc1cc(-c2[nH]c3sc(C4CCC(NC56CC(C5)C6)CC4)nc3c2C(C)C)cn2ncnc12] Isomer 1 | A | 1.83 | 477.2 |
| 169 | 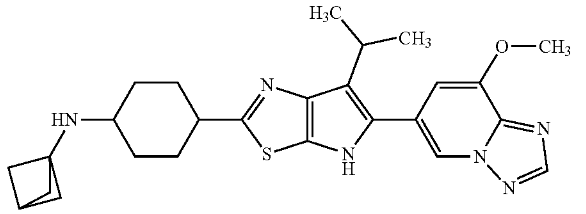 [SMILES: COc1cc(-c2[nH]c3sc(C4CCC(NC56CC(C5)C6)CC4)nc3c2C(C)C)cn2ncnc12] Isomer 2 | A | 2.06 | 477.3 |
| 170 | 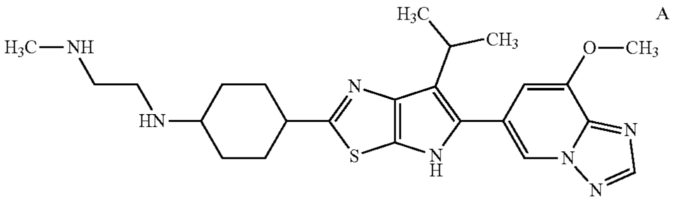 Isomer 1 | A | 1.34 | 482.3 |
| 171 | 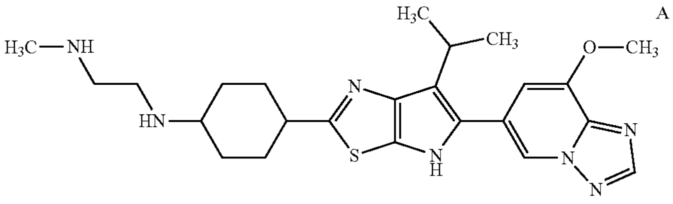 Isomer 2 | A | 1.33 | 482.2 |

Examples 172 and 173

4-(6-isopropyl-5-(1-methyl-1H-pyrrolo[2,3-b]pyridin-3-yl)-4H-pyrrolo[3,2-d]thiazol-2-yl)-N-((3-methyloxetan-3-yl)methyl)cyclohexan-1-amine (172-173)

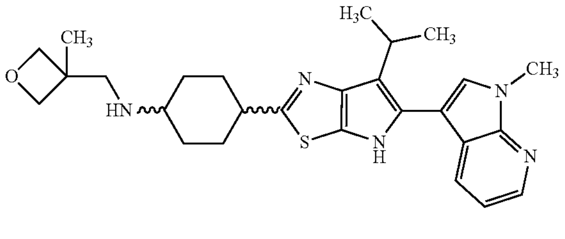

To a solution of 4-(6-isopropyl-5-(1-methyl-1H-pyrrolo[2,3-b]pyridin-3-yl)-4H-pyrrolo[3,2-d]thiazol-2-yl)cyclohexan-1-one (75 mg, 0.191 mmol) in THE (3 mL) and DMF (2 mL) was added (3-methyloxetan-3-yl)methanamine (19.33 mg, 0.191 mmol) followed by acetic acid (1.094 µL, 0.019 mmol) dropwise at 0° C., the resulting light yellow solution was stirred under nitrogen at room temperature for 12 h. Then sodium cyanoborohydride (24.01 mg, 0.382 mmol) was added at 0° C. and continued stirring at the room temperature for 2 h. The reaction mass was diluted with water (5 mL) and extracted with EtOAc (3×10 mL). The separated organic layer was dried over sodium sulphate, filtered and concentrated. The crude product obtained was purified by prep LCMS using Method I. After Preparative LCMS purification, fractions containing Isomers 1 and 2 were collected and dried separately using Genevac centrifugal evaporator.

Example 172 (Isomer 1) was obtained as a pale yellow solid (2.7 mg, 5.42 µmol, 2.84% yield). LCMS retention time 1.48 min [A]. MS ($E^-$) m/z: 478.3 (M+H). $^1$H NMR (400 MHz, DMSO-$d_6$) δ 11.16 (s, 1H), 8.39-8.28 (m, 1H), 8.00-7.97 (m, 1H), 7.60 (s, 1H), 7.18 (dd, J=8.1, 4.6 Hz, 1H), 4.43 (d, J=6.4 Hz, 2H), 4.28 (d, J=6.4 Hz, 2H), 3.91 (d, J=3.4 Hz, 4H), 3.23 (br. s., 3H), 3.13-3.00 (m, 3H), 2.23 (br. s., 3H), 1.69-1.46 (m, 4H), 1.43-1.32 (m, 6H).

Example 173 (Isomer 2) was obtained as a pale yellow solid (3.0 mg, 5.69 μmol, 2.98% yield) as a pale yellow solid. LCMS retention time 1.53 min [A]. MS ($E^-$) m/z: 478.3 (M+H). $^1H$ NMR (400 MHz, DMSO-$d_6$) δ 11.17 (s, 1H), 8.34 (d, J=4.4 Hz, 1H), 7.98 (d, J=7.8 Hz, 1H), 7.60 (s, 2H), 7.18 (dd, J=7.7, 4.5 Hz, 1H), 4.38 (d, J=6.1 Hz, 2H), 4.28-4.13 (m, 2H), 3.96-3.86 (m, 3H), 3.18-3.02 (m, 2H), 2.90 (s, 1H), 2.74 (s, 1H), 2.28 (br. s., 2H), 2.08 (br. s., 1H), 2.02 (s, 1H), 1.92 (s, 2H), 1.89-1.79 (m, 2H), 1.74 (d, J=12.0 Hz, 2H), 1.40 (d, J=6.8 Hz, 6H).

The following Examples were prepared according to the general procedure described in Examples 172 and 173.

TABLE 21

| Ex. No. | Structure | HPLC Method | Ret Time (min) | LCMS $MH^+$ |
|---|---|---|---|---|
| 174 | 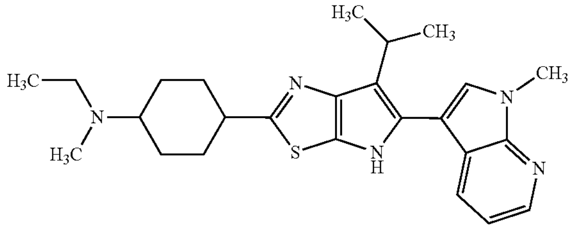 [SMILES: CCN(C)C1CCC(c2nc3c(C(C)C)c(-c4cn(C)c5ncccc45)[nH]c3s2)CC1] Isomer 1 | A | 1.47 | 436.2 |
| 175 | 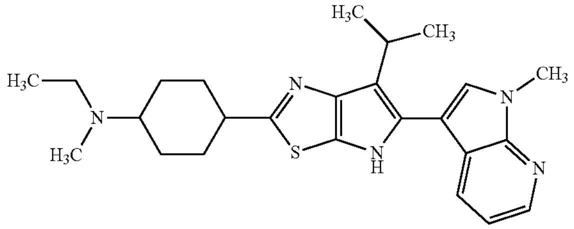 [SMILES: CCN(C)C1CCC(c2nc3c(C(C)C)c(-c4cn(C)c5ncccc45)[nH]c3s2)CC1] Isomer 2 | A | 1.56 | 436.1 |
| 176 | 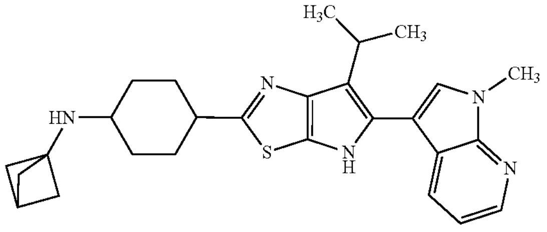 [SMILES: CC(C)c1c(-c2cn(C)c3ncccc23)[nH]c2sc(C3CCC(NC45CC(C4)C5)CC3)nc12] Isomer 1 | A | 2.26 | 460.2 |
| 177 | 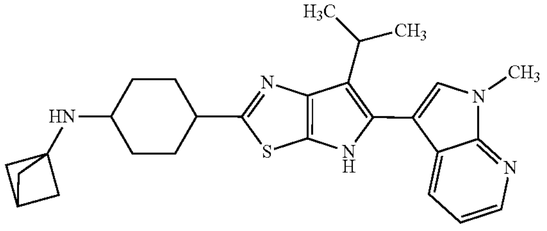 [SMILES: CC(C)c1c(-c2cn(C)c3ncccc23)[nH]c2sc(C3CCC(NC45CC(C4)C5)CC3)nc12] Isomer 2 | A | 2.04 | 460.1 |

TABLE 21-continued
| Ex. No. | Structure | HPLC Method | Ret Time (min) | LCMS MH+ |
|---|---|---|---|---|
| 178 | 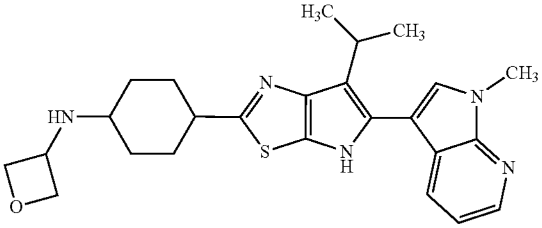 [SMILES: CC(C)c1c(-c2cn(C)c3ncccc23)[nH]c2sc(C3CCC(NC4COC4)CC3)nc12] Isomer 1 | A | 1.59 | 450.2 |
| 179 | 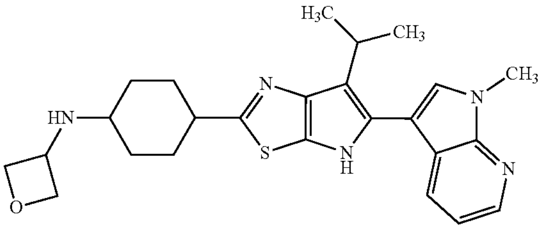 [SMILES: CC(C)c1c(-c2cn(C)c3ncccc23)[nH]c2sc(C3CCC(NC4COC4)CC3)nc12] Isomer 2 | A | 1.73 | 450.1 |
| 180 | 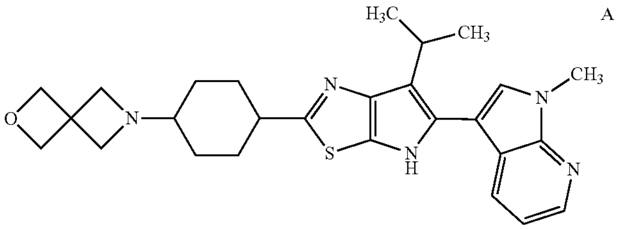 Isomer 1 | A | 1.52 | 476.2 |
| 181 | 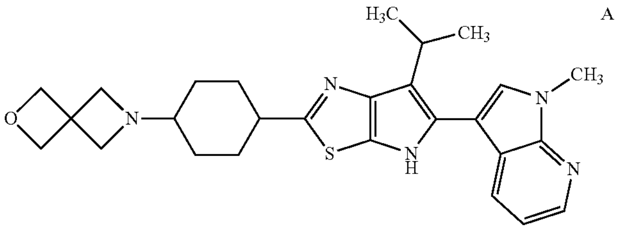 Isomer 2 | A | 1.65 | 476.1 |
| 182 | 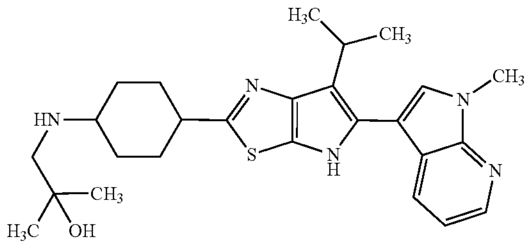 [SMILES: CC(C)c1c(-c2cn(C)c3ncccc23)[nH]c2sc(C3CCC(NCC(C)(C)O)CC3)nc12] Isomer 1 | A | 1.57 | 466.3 |

TABLE 21-continued

| Ex. No. | Structure | HPLC Method | Ret Time (min) | LCMS MH+ |
|---|---|---|---|---|
| 183 | 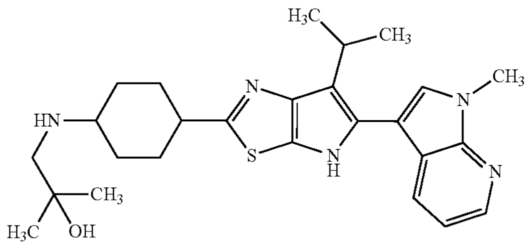 [SMILES: CC(C)c1c(-c2cn(C)c3ncccc23)[nH]c2sc(C3CCC(NCC(C)(C)O)CC3)nc12] Isomer 2 | A | 1.44 | 466.2 |

Examples 184 and 185

N-(4-(5-(7,8-dimethyl-[1,2,4]triazolo[1,5-a]pyridin-6-yl)-6-isopropyl-4H-pyrrolo[3,2-d]thiazol-2-yl)cyclohexyl)oxetan-3-amine (184-185)

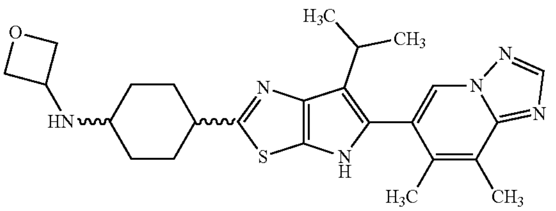

To a solution of 4-(5-(7,8-dimethyl-[1,2,4]triazolo[1,5-a]pyridin-6-yl)-6-isopropyl-4H-pyrrolo[3,2-d]thiazol-2-yl)cyclohexan-1-one (50 mg, 0.123 mmol) and oxetan-3-amine (90 mg, 1.227 mmol) in mixture of DMF (1 mL) and THE (1 mL) at 0° C., was added AcOH (7.02 μL, 0.123 mmol) and stirred for overnight at room temperature. Sodium cyanoborohydride (15.42 mg, 0.245 mmol) was added to the reaction mixture at 0° C. and continued stirring at the room temperature for 2 h. The reaction mass was diluted with water (5 mL) and extracted with ethyl acetate (3×10 mL). The separated organic layer was dried over sodium sulphate, filtered and concentrated. The crude product obtained was purified by prep LCMS using Method I. After Preparative LCMS purification, fractions containing Isomers 1 and 2 were collected and dried separately using Genevac centrifugal evaporator.

Example 184 (Isomer 1): (9.9 mg, 0.021 mmol, 17.19% yield). LCMS retention time 1.348 min [A]. MS ($E^-$) m/z: 465.3 (M+H). $^1H$ NMR (400 MHz, DMSO-$d_6$) δ 11.30 (s, 1H), 8.72 (s, 1H), 8.46 (s, 1H), 4.65 (t, J=6.7 Hz, 2H), 4.35 (t, J=6.1 Hz, 2H), 4.07-3.96 (m, 1H), 2.95 (tt, J=11.9, 3.6 Hz, 2H), 2.76-2.66 (m, 2H), 2.57 (s, 3H), 2.18 (s, 3H), 2.15-2.04 (m, 2H), 1.86 (d, J=11.0 Hz, 2H), 1.63-1.42 (m, 2H), 1.41-1.12 (m, 7H), 1.12-0.97 (m, 1H).

Example 185 (Isomer 2): (9.1 mg, 0.018 mmol, 14.6400 yield). LCMS retention time 1.514 min [A]. MS ($E^-$) m/z: 465.3 (M+H). $^1H$ NMR (400 MHz, DMSO-$d_6$) δ 11.37 (s, 1H), 8.72 (d, J=8.8 Hz, 1H), 8.47 (d, J=0.7 Hz, 1H), 4.68-4.59 (m, 2H), 4.55 (d, J=4.9 Hz, 2H), 3.63 (qd, J=11.5, 5.4 Hz, 1H), 3.25-3.18 (m, 1H), 2.97-2.86 (m, 1H), 2.79-2.68 (m, 1H), 2.65-2.55 (m, 3H), 2.40-2.32 (m, 1H), 2.19 (s, 3H), 1.9 (d, J=9.3 Hz, 1H), 1.93-1.82 (m, 3H), 1.82-1.59 (m, 2H), 1.34 (d, J=6.8 Hz, 6H), 1.17 (t, J=7.2 Hz, 2H).

The following Examples were prepared according to the general procedure described in Examples 184 and 185.

TABLE 22A

| Ex. No. | Structure | HPLC Method | Ret Time (min) | LCMS MH+ |
|---|---|---|---|---|
| 186 | 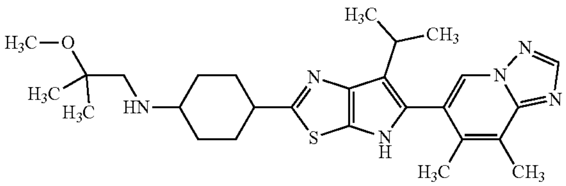 [SMILES: COC(C)(C)CNC1CCC(c2nc3c(C(C)C)c(-c4cn5ncnc5c(C)c4C)[nH]c3s2)CC1] Isomer 1 | A | 1.351 | 495.3 |

TABLE 22A-continued
| Ex. No. | Structure | HPLC Method | Ret Time (min) | LCMS MH+ |
|---|---|---|---|---|
| 187 | 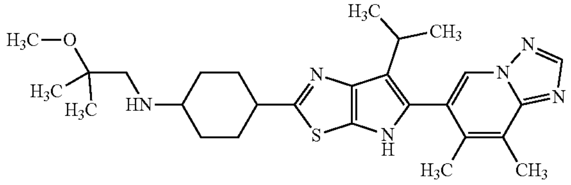 Isomer 2 | A | 1.518 | 495.3 |
| 188 | 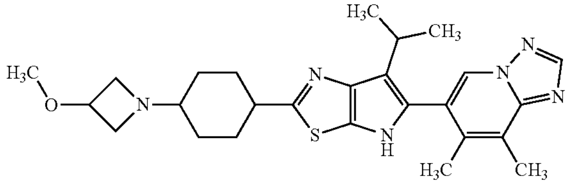 [SMILES: COC1CN(C2CCC(c3nc4c(C(C)C)c(-c5cn6ncnc6c(C)c5C)[nH]c4s3)CC2)C1] Isomer 1 | A | 1.337 | 479.3 |
| 189 | 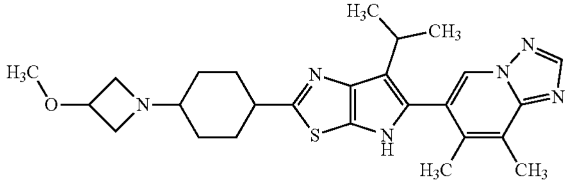 Isomer 2 | A | 1.542 | 479.3 |
| 190 | 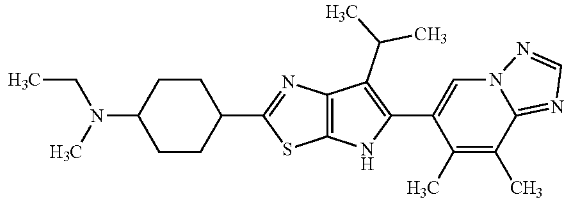 [SMILES: CCN(C)C1CCC(c2nc3c(C(C)C)c(-c4cn5ncnc5c(C)c4C)[nH]c3s2)CC1] Isomer 1 | A | 1.168 | 451.3 |
| 191 | 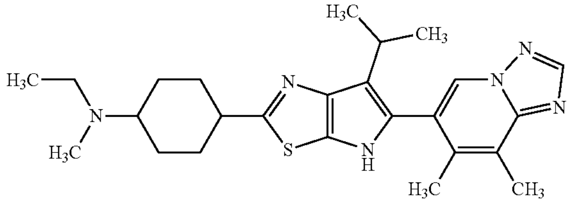 [SMILES: CCN(C)C1CCC(c2nc3c(C(C)C)c(-c4cn5ncnc5c(C)c4C)[nH]c3s2)CC1] Isomer 2 | A | 1.267 | 451.3 |
| 192 | 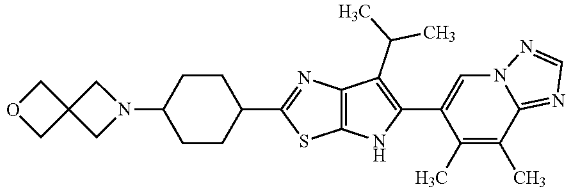 [SMILES: Cc1c(-c2[nH]c3sc(C4CCC(N5CC6(COC6)C5)CC4)nc3c2C(C)C)cn2ncnc2c1C] Isomer 1 | A | 1.258 | 491.3 |

TABLE 22A-continued
| Ex. No. | Structure | HPLC Method | Ret Time (min) | LCMS MH+ |
|---|---|---|---|---|
| 193 | 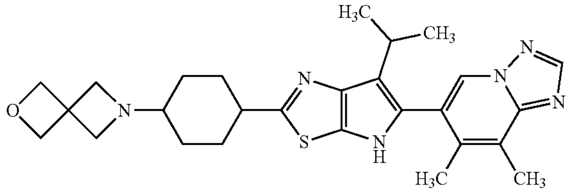 [SMILES: Cc1c(-c2[nH]c3sc(C4CCC(N5CC6(COC6)C5)CC4)nc3c2C(C)C)cn2ncnc2c1C] Isomer 2 | A | 1.428 | 491.3 |
| 194 | 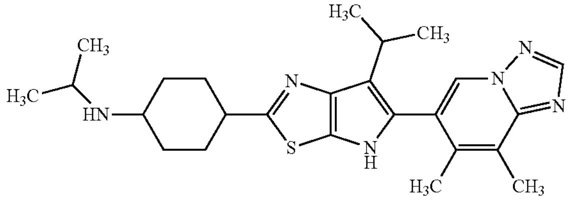 [SMILES: Cc1c(-c2[nH]c3sc(C4CCC(NC(C)C)CC4)nc3c2C(C)C)cn2ncnc2c1C] Isomer 1 | A | 1.181 | 451.3 |
| 195 | 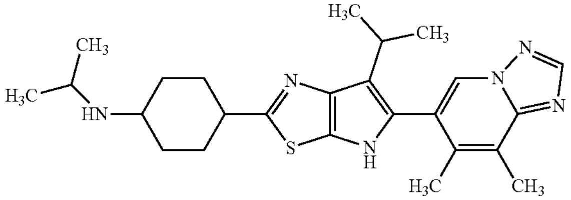 [SMILES: Cc1c(-c2[nH]c3sc(C4CCC(NC(C)C)CC4)nc3c2C(C)C)cn2ncnc2c1C] Isomer 2 | A | 1.288 | 451.3 |
| 196 | 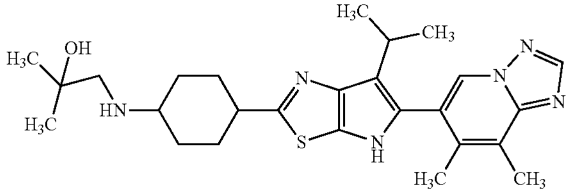 Isomer 1 | A | 1.156 | 481.3 |
| 197 | 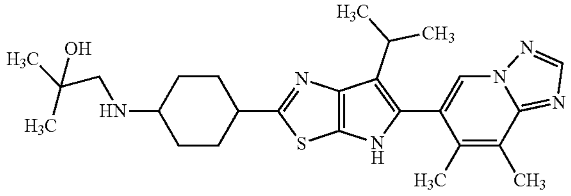 Isomer 2 | A | 1.228 | 481.3 |
| 198 | 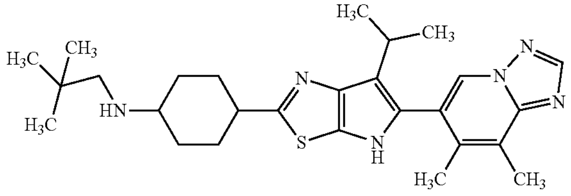 [SMILES: Cc1c(-c2[nH]c3sc(C4CCC(NCC(C)(C)C)CC4)nc3c2C(C)C)cn2ncnc2c1C] Isomer 1 | A | 1.439 | 479.3 |

TABLE 22A-continued
| Ex. No. | Structure | HPLC Method | Ret Time (min) | LCMS $MH^+$ |
|---|---|---|---|---|
| 199 | 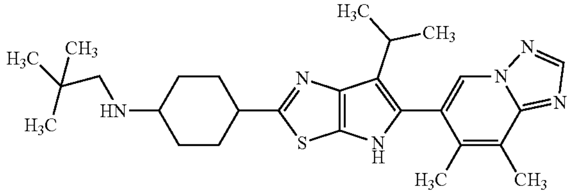 Isomer 2 | A | 1.668 | 479.3 |
| 200 | 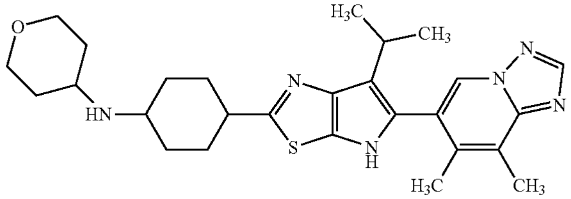 Isomer 1 | A | 1.173 | 493.3 |
| 201 | 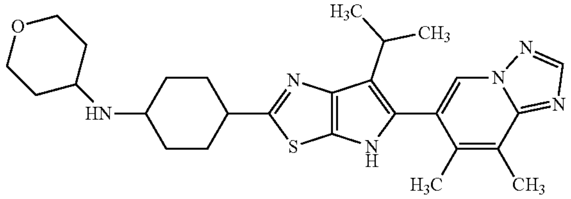 [SMILES: Cc1c(-c2[nH]c3sc(C4CCC(NC5CCOCC5)CC4)nc3c2C(C)C)cn2ncnc2c1C] Isomer 2 | A | 1.3 | 493.3 |
| 202 | 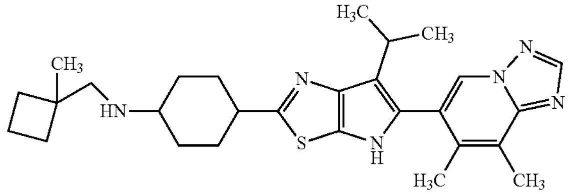 [SMILES: Cc1c(-c2[nH]c3sc(C4CCC(NCC5(C)CCC5)CC4)nc3c2C(C)C)cn2ncnc2c1C] Isomer 1 | A | 1.276 | 493.3 |
| 203 | 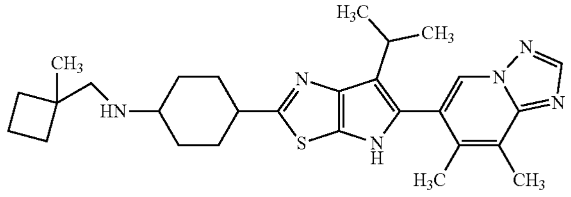 [SMILES: Cc1c(-c2[nH]c3sc(C4CCC(NCC5(C)CCC5)CC4)nc3c2C(C)C)cn2ncnc2c1C] Isomer 2 | A | 1.505 | 493.3 |
| 212 | 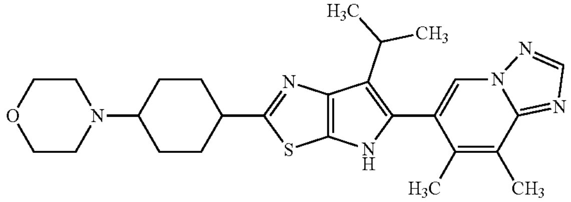 [SMILES: Cc1c(-c2[nH]c3sc(C4CCC(N5CCOCC5)CC4)nc3c2C(C)C)cn2ncnc2c1C] Isomer 1 | A | 1.579 | 479.3 |

TABLE 22A-continued
| Ex. No. | Structure | HPLC Method | Ret Time (min) | LCMS MH+ |
|---|---|---|---|---|
| 213 | 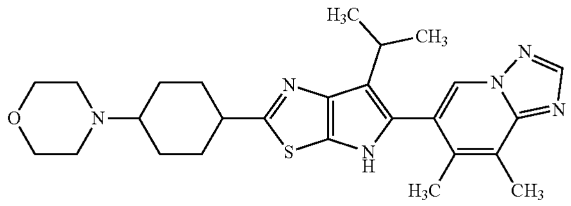 [SMILES: Cc1c(-c2[nH]c3sc(C4CCC(N5CCOCC5)CC4)nc3c2C(C)C)cn2ncnc2c1C] Isomer 2 | A | 1.838 | 479.3 |
| 214 | 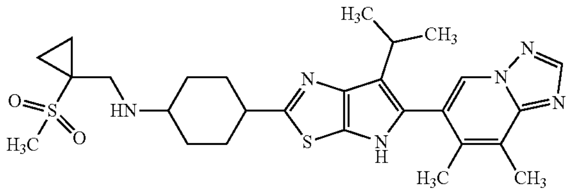 [SMILES: Cc1c(-c2[nH]c3sc(C4CCC(NCC5(S(C)(=O)=O)CC5)CC4)nc3c2C(C)C)cn2ncnc2c1C] Isomer 1 | A | 1.623 | 541.3 |
| 215 | 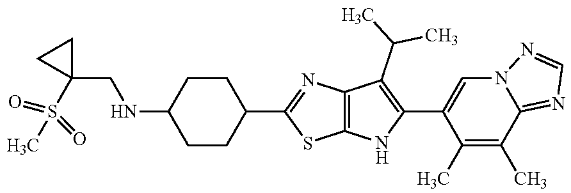 [SMILES: Cc1c(-c2[nH]c3sc(C4CCC(NCC5(S(C)(=O)=O)CC5)CC4)nc3c2C(C)C)cn2ncnc2c1C] Isomer 2 | A | 1.849 | 541.3 |
| 216 | 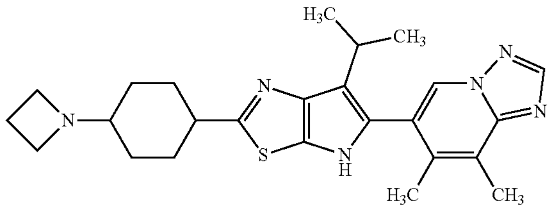 [SMILES: Cc1c(-c2[nH]c3sc(C4CCC(N5CCC5)CC4)nc3c2C(C)C)cn2ncnc2c1C] Isomer 1 | A | 1.353 | 449.3 |
| 217 | 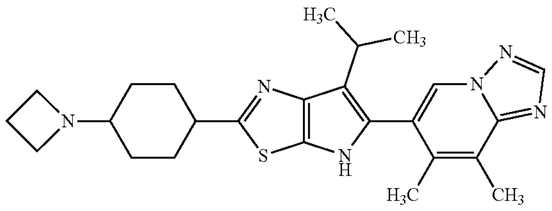 Isomer 2 | A | 1.272 | 449.3 |
| 218 | 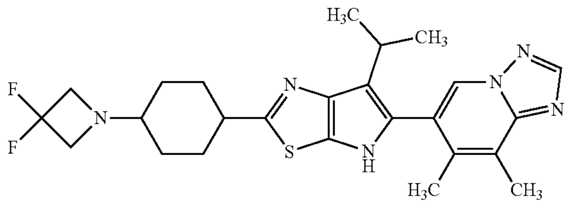 [SMILES: Cc1c(-c2[nH]c3sc(C4CCC(N5CC(F)(F)C5)CC4)nc3c2C(C)C)cn2ncnc2c1C] Isomer 1 | A | 1.969 | 485.3 |

TABLE 22A-continued
| Ex. No. | Structure | HPLC Method | Ret Time (min) | LCMS MH+ |
|---|---|---|---|---|
| 219 | 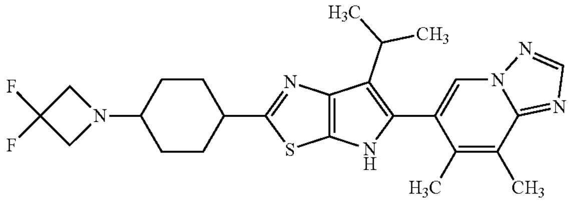 [SMILES: Cc1c(-c2[nH]c3sc(C4CCC(N5CC(F)(F)C5)CC4)nc3c2C(C)C)cn2ncnc2c1C] Isomer 2 | A | 2.215 | 485.3 |
| 220 | 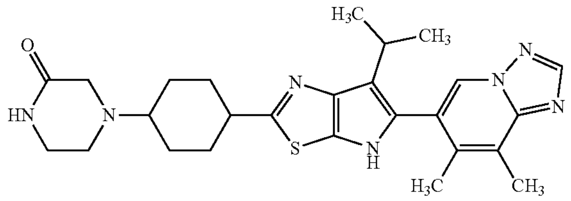 [SMILES: Cc1c(-c2[nH]c3sc(C4CCC(N5CCNC(=O)C5)CC4)nc3c2C(C)C)cn2ncnc2c1C] Isomer 1 | A | 1.409 | 492.3 |
| 221 | 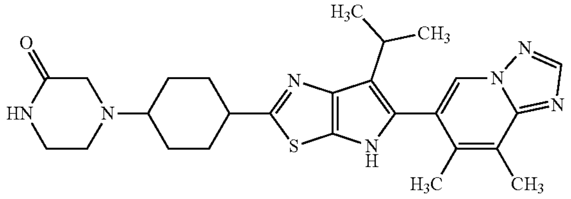 Isomer 2 | A | 1.583 | 492.3 |
| 222 | 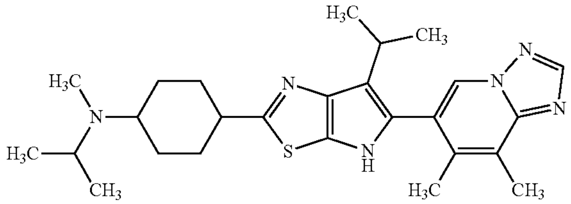 [SMILES: Cc1c(-c2[nH]c3sc(C4CCC(N(C)C(C)C)CC4)nc3c2C(C)C)cn2ncnc2c1C] Isomer 1 | A | 1.398 | 465.3 |
| 223 | 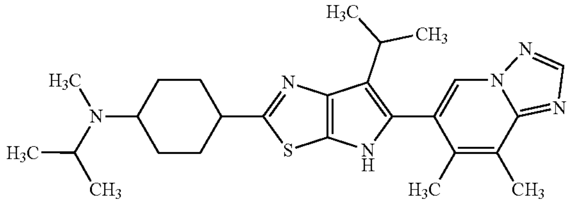 Isomer 2 | A | 1.436 | 465.3 |
| 224 | 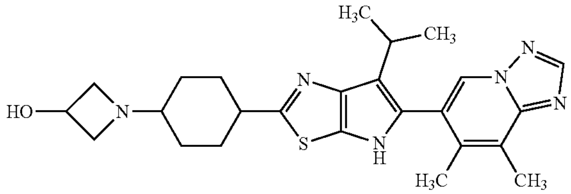 [SMILES: Cc1c(-c2[nH]c3sc(C4CCC(N5CC(O)C5)CC4)nc3c2C(C)C)cn2ncnc2c1C] Isomer 1 | A | 1.231 | 465.3 |

TABLE 22A-continued
| Ex. No. | Structure | HPLC Method | Ret Time (min) | LCMS MH+ |
|---|---|---|---|---|
| 225 | 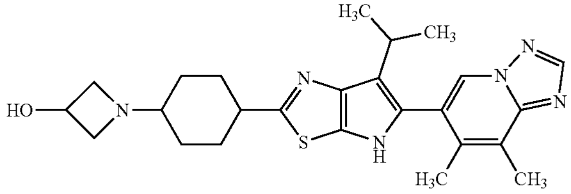 [SMILES: Cc1c(-c2[nH]c3sc(C4CCC(N5CC(O)C5)CC4)nc3c2C(C)C)cn2ncnc2c1C] Isomer 2 | A | 1.334 | 465.3 |
| 226 | 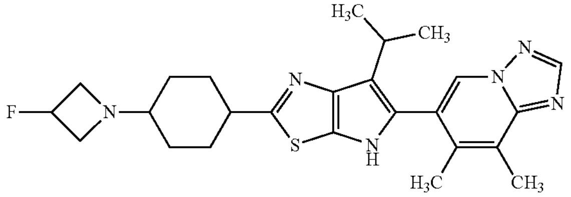 [SMILES: Cc1c(-c2[nH]c3sc(C4CCC(N5CC(F)C5)CC4)nc3c2C(C)C)cn2ncnc2c1C] Isomer 1 | A | 1.720 | 467.3 |
| 227 | 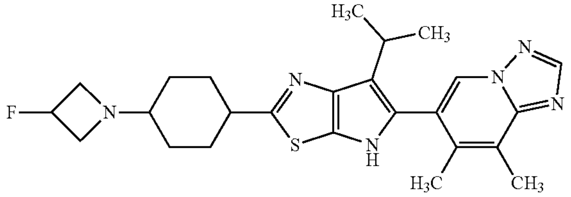 [SMILES: Cc1c(-c2[nH]c3sc(C4CCC(N5CC(F)C5)CC4)nc3c2C(C)C)cn2ncnc2c1C] Isomer 2 | A | 2.015 | 467.3 |
| 228 | 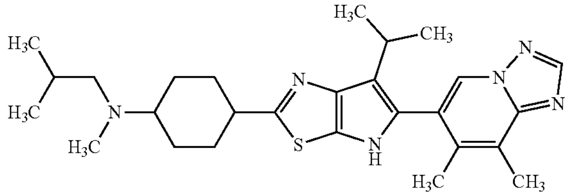 [SMILES: Cc1c(-c2[nH]c3sc(C4CCC(N(C)CC(C)C)CC4)nc3c2C(C)C)cn2ncnc2c1C] Isomer 1 | A | 1.921 | 479.3 |
| 229 | 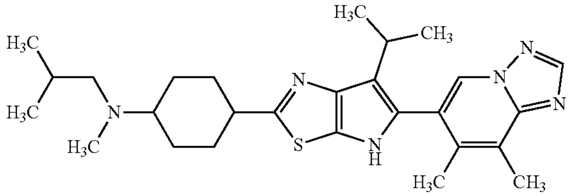 [SMILES: Cc1c(-c2[nH]c3sc(C4CCC(N(C)CC(C)C)CC4)nc3c2C(C)C)cn2ncnc2c1C] Isomer 2 | A | 1.917 | 479.3 |
| 230 | 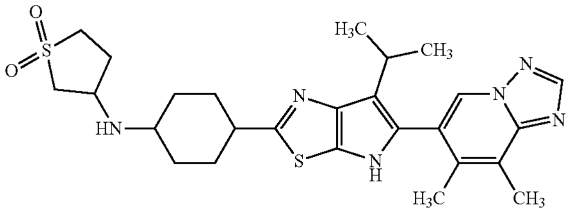 [SMILES: Cc1c(-c2[nH]c3sc(C4CCC(NC5CCS(=O)(=O)C5)CC4)nc3c2C(C)C)cn2ncnc2c1C] racemate | C | 2.462 | 527.2 |

TABLE 22A-continued
| Ex. No. | Structure | HPLC Method | Ret Time (min) | LCMS MH+ |
|---|---|---|---|---|
| 231 | 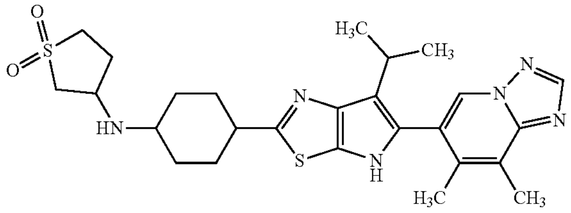 [SMILES: Cc1c(-c2[nH]c3sc(C4CCC(NC5CCS(=O)(=O)C5)CC4)nc3c2C(C)C)cn2ncnc2c1C] Isomer 1 | C | 2.059 | 527.2 |
| 232 | 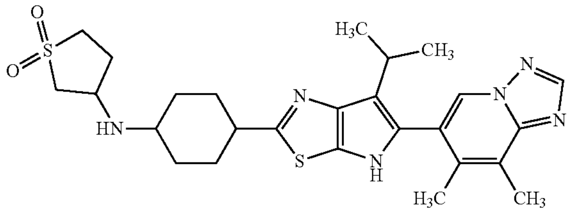 [SMILES: Cc1c(-c2[nH]c3sc(C4CCC(NC5CCS(=O)(=O)C5)CC4)nc3c2C(C)C)cn2ncnc2c1C] Isomer 2 | C | 2.024 | 527.2 |
| 233 | 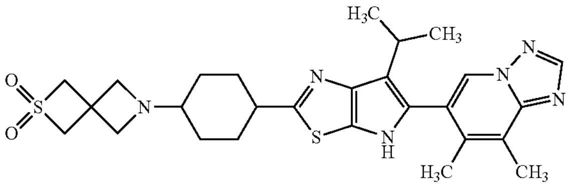 [SMILES: Cc1c(-c2[nH]c3sc(C4CCC(N5CC6(C5)CS(=O)(=O)C6)CC4)nc3c2C(C)C)cn2ncnc2c1C] Isomer 1 | C | 2.097 | 539.2 |
| 234 | 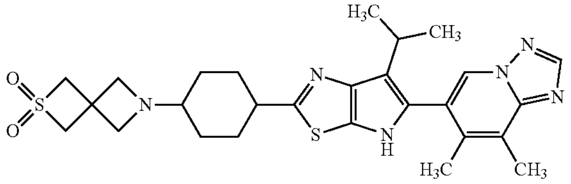 Isomer 2 | C | 2.056 | 539.2 |
| 235 | 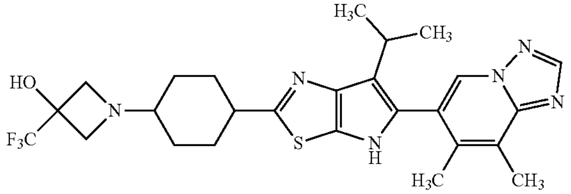 [SMILES: Cc1c(-c2[nH]c3sc(C4CCC(N5CC(O)(C(F)(F)F)C5)CC4)nc3c2C(C)C)cn2ncnc2c1C] Isomer 1 | A | 1.768 | 533.3 |
| 236 | 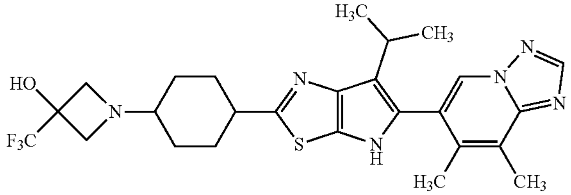 [SMILES: Cc1c(-c2[nH]c3sc(C4CCC(N5CC(O)(C(F)(F)F)C5)CC4)nc3c2C(C)C)cn2ncnc2c1C] Isomer 2 | A | 2.032 | 533.2 |

TABLE 22A-continued
| Ex. No. | Structure | HPLC Method | Ret Time (min) | LCMS MH+ |
|---|---|---|---|---|
| 237 | 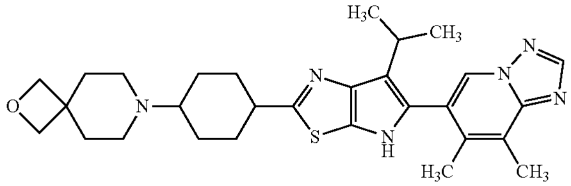 [SMILES: Cc1c(-c2[nH]c3sc(C4CCC(N5CCC6(CC5)COC6)CC4)nc3c2C(C)C)cn2ncnc2c1C] Isomer 1 | C | 1.916 | 519.2 |
| 238 | 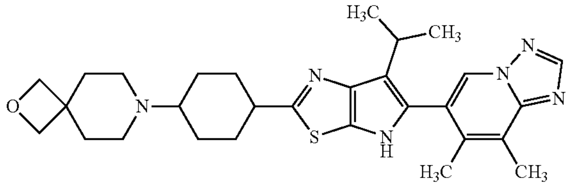 [SMILES: Cc1c(-c2[nH]c3sc(C4CCC(N5CCC6(CC5)COC6)CC4)nc3c2C(C)C)cn2ncnc2c1C] Isomer 2 | C | 2.080 | 519.2 |
| 239 | 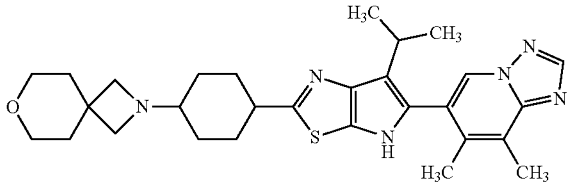 [SMILES: Cc1c(-c2[nH]c3sc(C4CCC(N5CC6(CCOCC6)C5)CC4)nc3c2C(C)C)cn2ncnc2c1C] Isomer 1 | C | 1.818 | 519.2 |
| 240 | 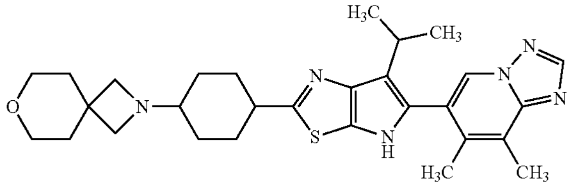 [SMILES: Cc1c(-c2[nH]c3sc(C4CCC(N5CC6(CCOCC6)C5)CC4)nc3c2C(C)C)cn2ncnc2c1C] Isomer 2 | C | 2.012 | 519.2 |
TABLE 22B
The following Examples were prepared according to the general procedure described in Intermediate 162.
| Ex. No. | Structure | HPLC Method | Ret Time (min) | LCMS MH+ |
|---|---|---|---|---|
| 204 | 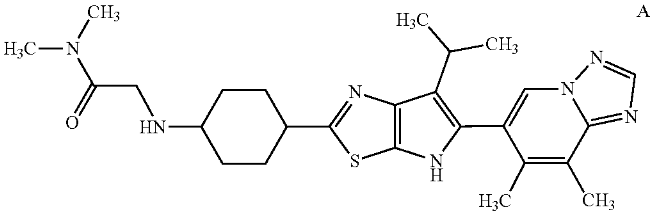 Isomer 1 | A | 1.2 | 494.3 |

TABLE 22B-continued
| The following Examples were prepared according to the general procedure described in Intermediate 162. | | | | |
|---|---|---|---|---|
| Ex. No. | Structure | HPLC Method | Ret Time (min) | LCMS MH+ |
| 205 | 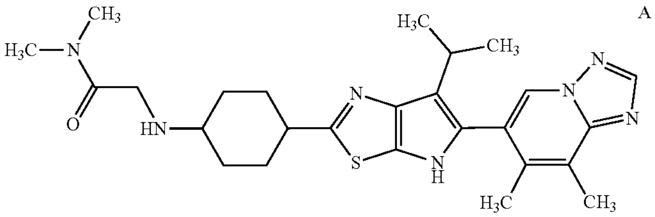 Isomer 2 | A | 1.35 | 494.3 |
| 206 | 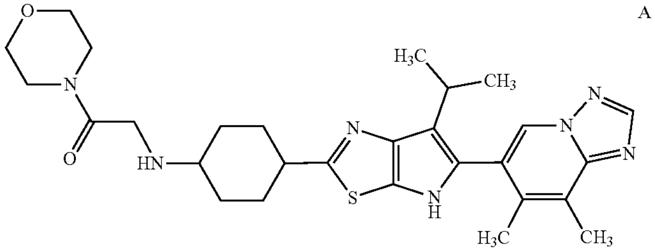 Isomer 1 | A | 1.224 | 536.3 |
| 207 | 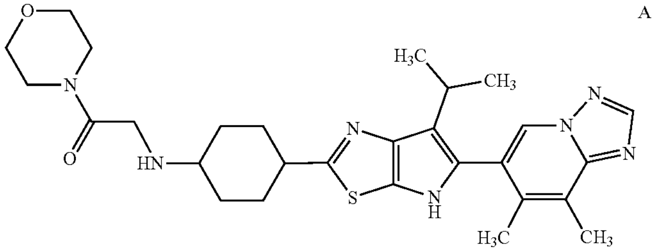 Isomer 2 | A | 1.381 | 536.3 |
| 208 | 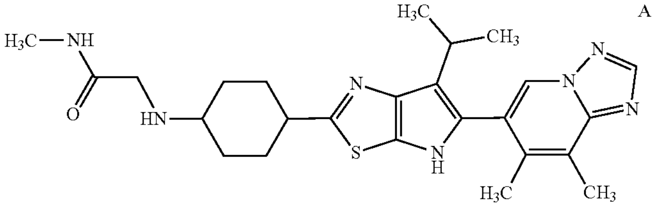 Isomer 1 | A | 1.244 | 480.3 |

TABLE 22B-continued

The following Examples were prepared according to the general procedure described in Intermediate 162.

| Ex. No. | Structure | HPLC Method | Ret Time (min) | LCMS MH+ |
|---|---|---|---|---|
| 209 | 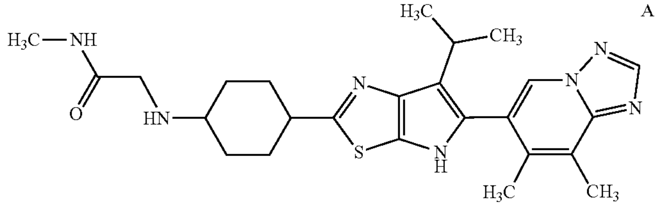 Isomer 2 | A | 1.152 | 480.3 |
| 210 | 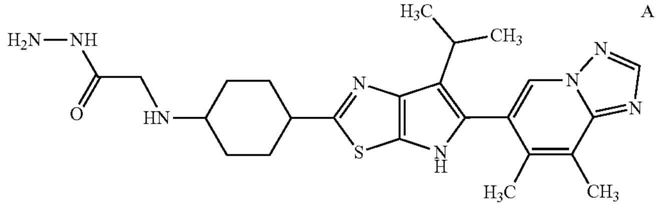 Isomer 1 | A | 1.417 | 466.2 |
| 211 | 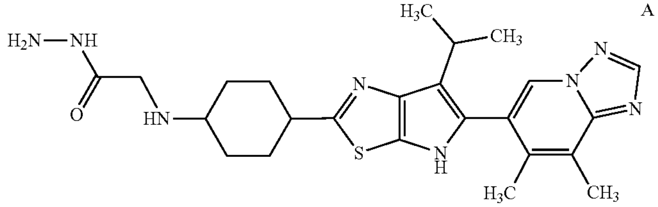 Isomer 2 | A | 1.267 | 466.2 |

Examples 241 and 242

5-(6-isopropyl-2-(4-(oxetan-3-ylamino)cyclohexyl)-4H-pyrrolo[3,2-d]thiazol-5-yl)-1,3,4-trimethylpyridin-2 (1H)-one (241-242)

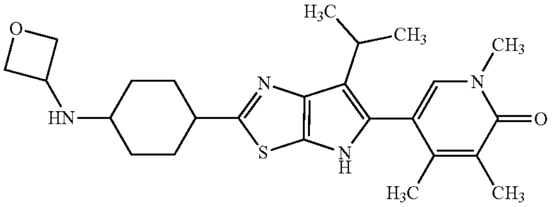

To a solution of 5-(6-isopropyl-2-(4-oxocyclohexyl)-4H-pyrrolo[3,2-d]thiazol-5-yl)-1,3,4-trimethylpyridin-2 (1H)-one (50 mg, 0.126 mmol) and oxetan-3-amine (92 mg, 1.258 mmol) in mixture of DMF (1 mL) and THE (1 mL) at 0° C., was added AcOH (7.20 μL, 0.126 mmol) and stirred for overnight at room temperature. Sodium cyanoborohydride (15.42 mg, 0.245 mmol) was added to the reaction mixture at 0° C. and continued stirring at the room temperature for 2 h. The reaction mass was diluted with water (5 mL) and extracted with EtOAc (3×10 mL). The separated organic layer was dried over sodium sulphate, filtered and concentrated. The crude product obtained was purified by prep LCMS using Method I. After Preparative LCMS purification, fractions containing Isomers 1 and 2 were collected and dried separately using Genevac centrifugal evaporator.

Example 241 (Isomer 1): (13.6 mg, 0.028 mmol, 22.29% yield). LCMS retention time 1.523 min [A]. MS ($E^-$) m/z: 455.3 (M+H). $^1$H NMR (400 MHz, DMSO-$d_6$) δ 11.02 (s, 1H), 7.52 (s, 1H), 4.64 (t, J=6.6 Hz, 2H), 4.34 (t, J=6.4 Hz, 2H), 4.06-3.94 (m, 1H), 3.94-3.86 (m, 1H), 3.46 (s, 3H), 2.98-2.87 (m, 2H), 2.74-2.68 (m, 1H), 2.18-1.97 (m, 6H), 1.93 (s, 2H), 1.85 (d, J=10.3 Hz, 2H), 1.61-1.45 (m, 2H), 1.36-1.08 (m, 8H).

Example 242 (Isomer 2): (7.8 mg, 0.016 mmol, 12.89% yield). LCMS retention time 1.702 min [A]. MS ($E^-$) m/z: 455.3 (M+H). $^1$H NMR (400 MHz, DMSO-$d_6$) δ 11.03 (s, 1H), 7.53 (s, 1H), 4.64 (t, J=6.6 Hz, 2H), 4.35 (t, J=6.2 Hz, 2H), 3.97 (br. s., 1H), 3.46 (s, 3H), 3.12-3.05 (m, 2H), 2.79-2.64 (m, 2H), 2.13-1.86 (m, 8H), 1.85-1.69 (m, 2H), 1.57 (d, J=4.6 Hz, 4H), 1.37-1.24 (m, 6H).

The following Examples were prepared according to the general procedure described in Examples 241 and 242.

TABLE 23
| Ex. No. | Structure | HPLC Method | Ret Time (min) | LCMS MH+ |
|---|---|---|---|---|
| 243 | 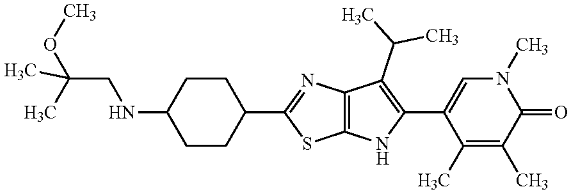 Isomer 1 | A | 1.434 | 485.3 |
| 244 | 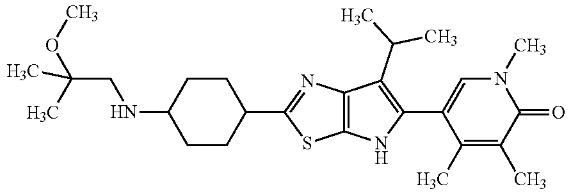 [SMILES: COC(C)(C)CNC1CCC(c2nc3c(C(C)C)c(-c4cn(C)c(=O)c(C)c4C)[nH]c3s2)CC1] Isomer 2 | A | 1.606 | 485.3 |
| 245 | 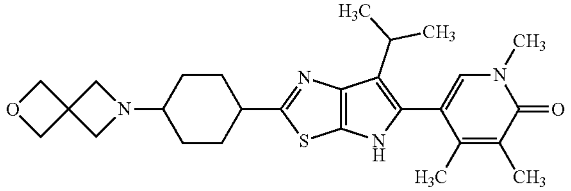 [SMILES: Cc1c(-c2[nH]c3sc(C4CCC(N5CC6(COC6)C5)CC4)nc3c2C(C)C)cn(C)c(=O)c1C] Isomer 1 | A | 1.421 | 481.3 |
| 246 | 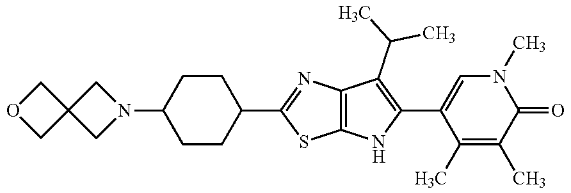 [SMILES: Cc1c(-c2[nH]c3sc(C4CCC(N5CC6(COC6)C5)CC4)nc3c2C(C)C)cn(C)c(=O)c1C] Isomer 2 | A | 1.61 | 481.3 |
| 247 | 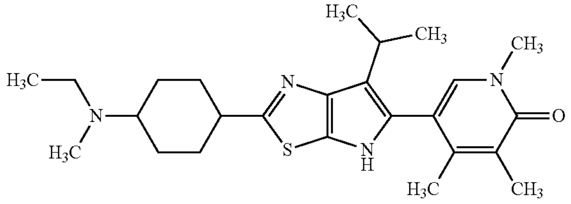 Isomer 1 | A | 1.26 | 441.3 |
| 248 | 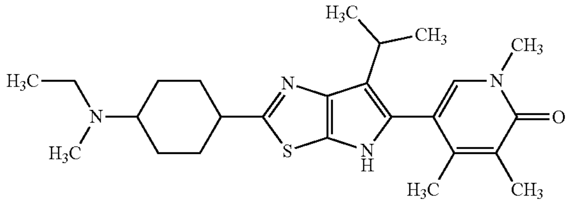 Isomer 2 | A | 1.372 | 441.3 |

TABLE 23-continued
| Ex. No. | Structure | HPLC Method | Ret Time (min) | LCMS MH+ |
|---|---|---|---|---|
| 249 | 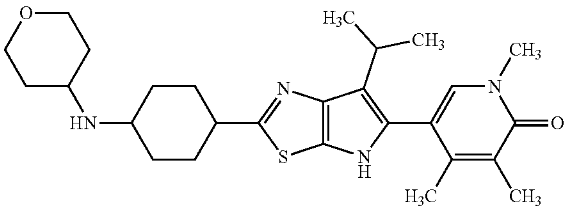 [SMILES: Cc1c(-c2[nH]c3sc(C4CCC(NC5CCOCC5)CC4)nc3c2C(C)C)cn(C)c(=O)c1C] Isomer 1 | A | 1.268 | 483.3 |
| 250 | 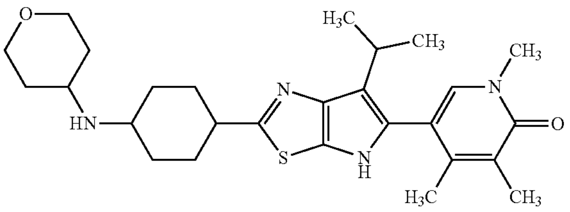 [SMILES: Cc1c(-c2[nH]c3sc(C4CCC(NC5CCOCC5)CC4)nc3c2C(C)C)cn(C)c(=O)c1C] Isomer 2 | A | 1.756 | 483.3 |
| 251 | 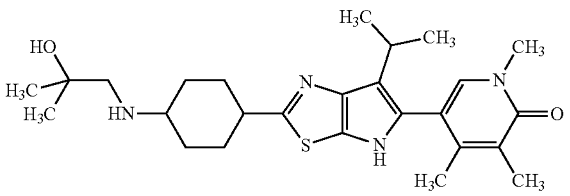 [SMILES: Cc1c(-c2[nH]c3sc(C4CCC(NCC(C)(C)O)CC4)nc3c2C(C)C)cn(C)c(=O)c1C] Isomer 1 | A | 1.232 | 471.3 |
| 252 | 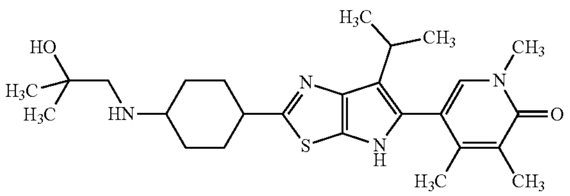 [SMILES: Cc1c(-c2[nH]c3sc(C4CCC(NCC(C)(C)O)CC4)nc3c2C(C)C)cn(C)c(=O)c1C] Isomer 2 | A | 1.382 | 471.3 |
| 253 | 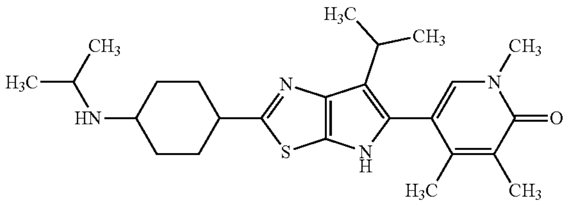 Isomer 1 | A | 1.269 | 441.3 |
| 254 | 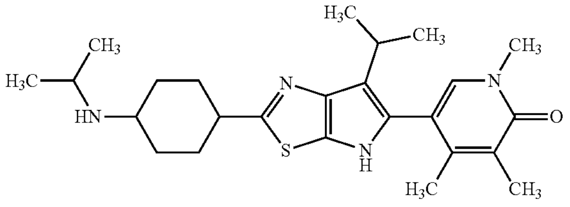 [SMILES: Cc1c(-c2[nH]c3sc(C4CCC(NC(C)C)CC4)nc3c2C(C)C)cn(C)c(=O)c1C] Isomer 2 | A | 1.404 | 441.3 |

TABLE 23-continued
| Ex. No. | Structure | HPLC Method | Ret Time (min) | LCMS MH+ |
|---|---|---|---|---|
| 255 | 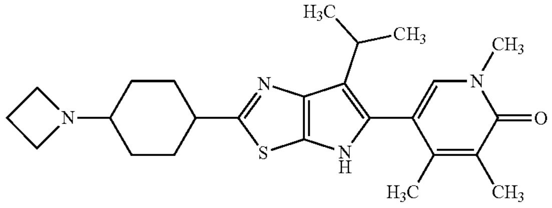 [SMILES: Cc1c(-c2[nH]c3sc(C4CCC(N5CCC5)CC4)nc3c2C(C)C)cn(C)c(=O)c1C] Isomer 1 | A | 1.200 | 439.3 |
| 256 | 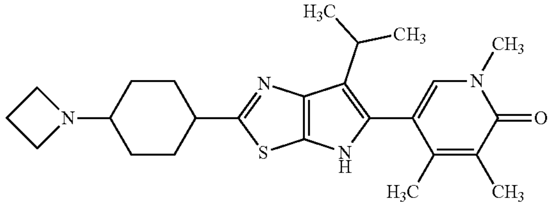 [SMILES: Cc1c(-c2[nH]c3sc(C4CCC(N5CCC5)CC4)nc3c2C(C)C)cn(C)c(=O)c1C] Isomer 2 | A | 1.296 | 439.2 |
| 257 | 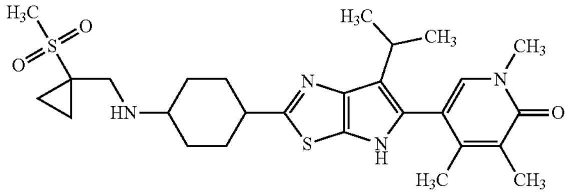 [SMILES: Cc1c(-c2[nH]c3sc(C4CCC(NCC5(S(C)(=O)=O)CC5)CC4)nc3c2C(C)C)cn(C)c(=O)c1C] Isomer 1 | A | 1.521 | 531.2 |
| 258 | 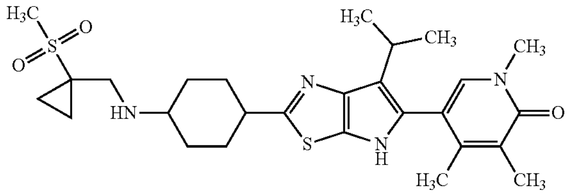 [SMILES: Cc1c(-c2[nH]c3sc(C4CCC(NCC5(S(C)(=O)=O)CC5)CC4)nc3c2C(C)C)cn(C)c(=O)c1C] Isomer 2 | A | 1.743 | 531.2 |
| 259 | 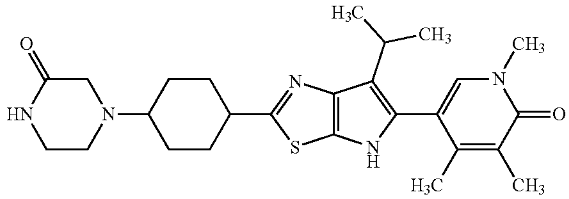 [SMILES: Cc1c(-c2[nH]c3sc(C4CCC(N5CCNC(=O)C5)CC4)nc3c2C(C)C)cn(C)c(=O)c1C] Isomer 1 | A | 1.317 | 482.2 |
| 260 | 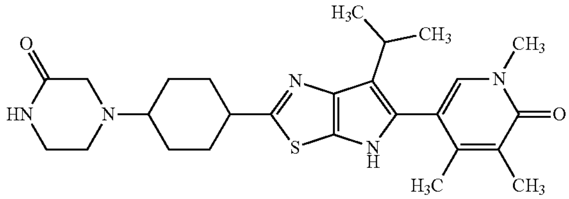 [SMILES: Cc1c(-c2[nH]c3sc(C4CCC(N5CCNC(=O)C5)CC4)nc3c2C(C)C)cn(C)c(=O)c1C] Isomer 2 | A | 1.490 | 482.2 |

TABLE 23-continued
| Ex. No. | Structure | HPLC Method | Ret Time (min) | LCMS MH+ |
|---|---|---|---|---|
| 261 | 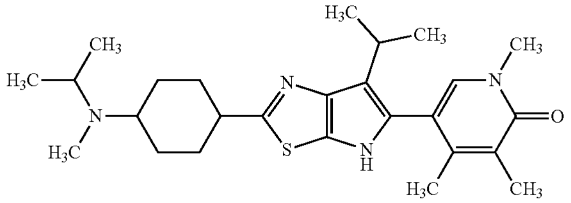 [SMILES: Cc1c(-c2[nH]c3sc(C4CCC(N(C)C(C)C)CC4)nc3c2C(C)C)cn(C)c(=O)c1C] Isomer 1 | A | 1.285 | 455.3 |
| 262 | 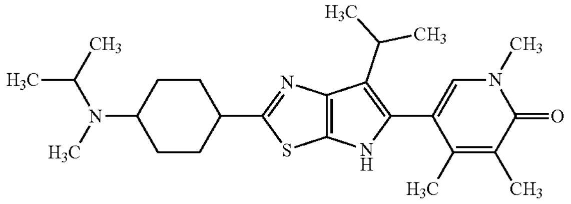 [SMILES: Cc1c(-c2[nH]c3sc(C4CCC(N(C)C(C)C)CC4)nc3c2C(C)C)cn(C)c(=O)c1C] Isomer 2 | A | 1.409 | 455.3 |
| 263 | 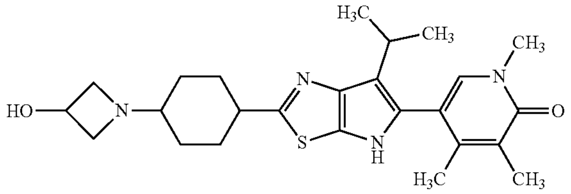 [SMILES: Cc1c(-c2[nH]c3sc(C4CCC(N5CC(O)C5)CC4)nc3c2C(C)C)cn(C)c(=O)c1C] Isomer 1 | A | 1.153 | 455.3 |
| 264 | 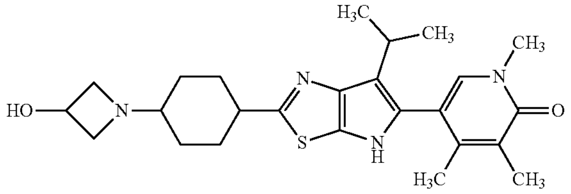 Isomer 2 | A | 1.278 | 455.2 |
| 265 | 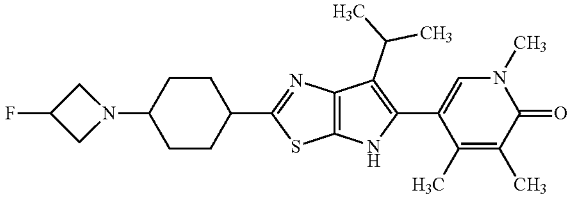 [SMILES: Cc1c(-c2[nH]c3sc(C4CCC(N5CC(F)C5)CC4)nc3c2C(C)C)cn(C)c(=O)c1C] Isomer 1 | A | 1.598 | 457.3 |
| 266 | 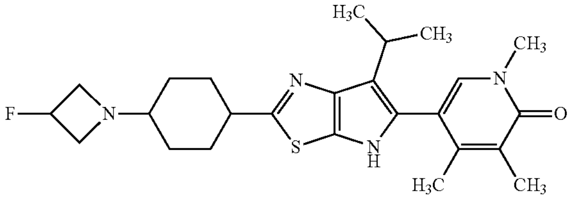 [SMILES: Cc1c(-c2[nH]c3sc(C4CCC(N5CC(F)C5)CC4)nc3c2C(C)C)cn(C)c(=O)c1C] Isomer 2 | A | 1.878 | 457.2 |

TABLE 23-continued

| Ex. No. | Structure | HPLC Method | Ret Time (min) | LCMS MH+ |
|---|---|---|---|---|
| 267 | 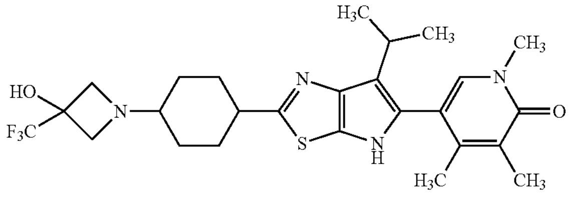 [SMILES: Cc1c(-c2[nH]c3sc(C4CCC(N5CC(O)(C(F)(F)F)C5)CC4)nc3c2C(C)C)cn(C)c(=O)c1C] Isomer 1 | A | 1.698 | 523.3 |
| 268 | 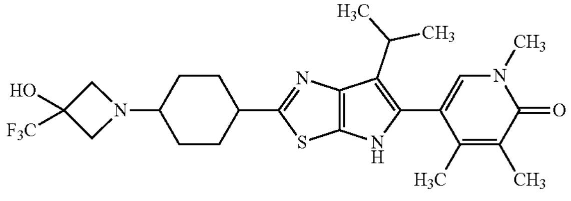 [SMILES: Cc1c(-c2[nH]c3sc(C4CCC(N5CC(O)(C(F)(F)F)C5)CC4)nc3c2C(C)C)cn(C)c(=O)c1C] Isomer 2 | A | 1.977 | 523.2 |

Examples 269 and 270

6-(4-(6-ethyl-5-(8-methoxy-[1,2,4]triazolo[1,5-a]pyridin-6-yl)-4H-pyrrolo[3,2-d]thiazol-2-yl)cyclohexyl)-2-oxa-6-azaspiro[3.3]heptane (269-270)

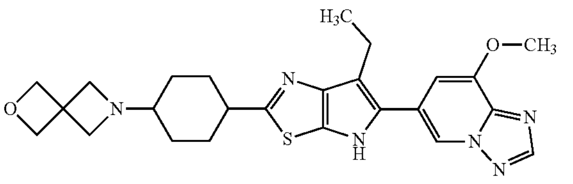

Intermediate 269A: tert-butyl 5-(8-methoxy-[1,2,4]triazolo[1,5-a]pyridin-6-yl)-2-(1,4-dioxaspiro[4.5]decan-8-yl)-6-vinyl-4H-pyrrolo[3,2-d]thiazole-4-carboxylate (269A)

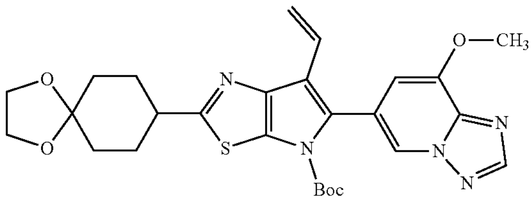

To a solution of tert-butyl 6-bromo-5-(8-methoxy-[1,2,4]triazolo[1,5-a]pyridin-6-yl)-2-(1,4-dioxaspiro[4.5]decan-8-yl)-4H-pyrrolo[3,2-d]thiazole-4-carboxylate (220 mg, 0.373 mmol) in dioxane (10 mL) and water (2.500 mL) were added vinylboronic acid (34.8 mg, 0.484 mmol) and potassium phosphate tribasic (237 mg, 1.118 mmol). The solution was degassed for 10 min with argon and $PdCl_2(dppf)$-$CH_2Cl_2$ adduct (30.4 mg, 0.037 mmol) was added. The resulting reaction mixture was heated at 90° C. for 12 h. The reaction mass was concentrated, diluted with water (100 mL) and extracted with DCM (3×100 mL). The separated organic layer was dried over sodium sulphate, filtered and concentrated. The crude was purified by Combiflash using 40 g silica column by eluting with 40% EtOAc/Pet ether. Following concentration of fractions, collected tert-butyl 5-(8-methoxy-[1,2,4]triazolo[1,5-a]pyridin-6-yl)-2-(1,4-dioxaspiro[4.5]decan-8-yl)-6-vinyl-4H-pyrrolo[3,2-d]thiazole-4-carboxylate (0.18 g, 90% yield) as a pale yellow solid. LCMS retention time 3.35 min [C]. MS ($E^-$) m/z: 538.2 (M+H).

Intermediate 269B: tert-butyl 6-ethyl-5-(8-methoxy-[1,2,4]triazolo[1,5-a]pyridin-6-yl)-2-(1,4-dioxaspiro[4.5]decan-8-yl)-4H-pyrrolo[3,2-d]thiazole-4-carboxylate (269B)

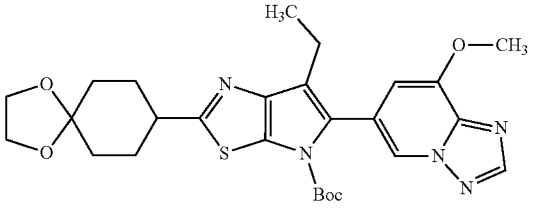

To a solution of tert-butyl 5-(8-methoxy-[1,2,4]triazolo[1,5-a]pyridin-6-yl)-2-(1,4-dioxaspiro[4.5]decan-8-yl)-6-vinyl-4H-pyrrolo[3,2-d]thiazole-4-carboxylate (0.18 g, 0.335 mmol) in THE (10 mL), methanol (2.5 mL) was purged with nitrogen gas and Pd—C (0.036 g, 0.335 mmol) was added. The system was evacuated under vacuum and purged with hydrogen gas and allowed to stir under hydrogen atmosphere for 24 h. The reaction mass was filtered through a plug of celite pad to afford tert-butyl 6-ethyl-5-(8-methoxy-[1,2,4]triazolo[1,5-a]pyridin-6-yl)-2-(1,4-dioxaspiro[4.5]decan-8-yl)-4H-pyrrolo[3,2-d]thiazole-4-carboxylate (0.15 g, 83%) as a yellow solid. LCMS retention time 1.48 min [C]. MS ($E^-$) m/z: 540.2 (M+H).

Intermediate 269C: 4-(6-ethyl-5-(8-methoxy-[1,2,4]triazolo[1,5-a]pyridin-6-yl)-4H-pyrrolo[3,2-d]thiazol-2-yl)cyclohexan-1-one (269C)

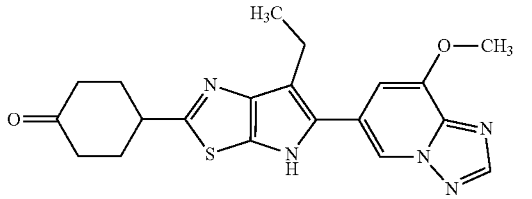

To a solution of tert-butyl 6-ethyl-5-(8-methoxy-[1,2,4]triazolo[1,5-a]pyridin-6-yl)-2-(1,4-dioxaspiro[4.5]decan-8-yl)-4H-pyrrolo[3,2-d]thiazole-4-carboxylate (120 mg, 0.222 mmol) in DCM (5.00 mL) was added TFA (5 mL) and stirred at room temperature for 12 h. Reaction mass was concentrated to afford 4-(6-ethyl-5-(8-methoxy-[1,2,4]triazolo[1,5-a]pyridin-6-yl)-4H-pyrrolo[3,2-d]thiazol-2-yl)cyclohexan-1-one (80 mg, 91%) as a yellow solid. LCMS retention time 2.31 min [C]. MS ($E^-$) m/z: 396.2 (M+H).

Examples 269 and 270: 6-(4-(6-ethyl-5-(8-methoxy-[1,2,4]triazolo[1,5-a]pyridin-6-yl)-4H-pyrrolo[3,2-d]thiazol-2-yl)cyclohexyl)-2-oxa-6-azaspiro[3.3]heptane To a solution of 4-(6-ethyl-5-(8-methoxy-[1,2,4]triazolo[1,5-a]pyridin-6-yl)-4H-pyrrolo[3,2-d]thiazol-2-yl)cyclohexan-1-one (100 mg, 0.253 mmol) in THE (5 mL), DMF (5.00 mL) was added acetic acid (0.014 mL, 0.253 mmol) followed by 2-oxa-6-azaspiro[3.3]heptane (376 mg, 3.79 mmol) and was stirred at ambient temperature for 12 h. The reaction mixture was concentrated to remove DMF and THE and the residue obtained was taken in 3 mL of dry methanol and cooled to −78° C. under nitrogen atmosphere. $NaCNBH_4$ (79 mg, 1.264 mmol) was added in one portion. The reaction was continued at the same temperature (−78° C.) for 3 h and then brought to 0° C. over 1 h. The reaction was quenched with 10 mL of ice cold water and concentrated. The residue was extracted with 10% of methanol in DCM (10 mL×2). Organic layer was concentrated and the crude product obtained was purified by prep LCMS using Method I. After Preparative LCMS purification, fractions containing Isomers 1 and 2 were collected and dried separately using Genevac centrifugal evaporator.

Example 269 (Isomer 1) was obtained as a pale yellow solid (3 mg, 2.3%). LCMS retention time 1.12 min [A]. MS ($E^-$) m/z: 479.2 (M+H). $^1H$ NMR (400 MHz, DMSO-$d_6$) δ 11.68 (s, 1H), 8.53 (d, J=1.5 Hz, 1H), 8.50-8.44 (m, 1H), 7.17 (d, J=1.2 Hz, 1H), 4.61 (s, 4H), 4.06 (s, 3H), 2.95-2.80 (m, 4H), 2.15-2.07 (m, 2H), 1.91 (s, 1H), 1.85-1.77 (m, 2H), 1.57-1.41 (m, 2H), 1.36-1.28 (m, 3H), 1.15-0.97 (m, 3H).

Example 270 (Isomer 2) was obtained as a pale yellow solid (2.5 mg, 1.9%). LCMS retention time 1.02 min [A]. MS ($E^-$) m/z: 479.2 (M+H). $^1H$ NMR (400 MHz, DMSO-$d_6$) δ 11.69 (s, 1H), 8.53 (d, J=1.5 Hz, 1H), 8.47 (s, 1H), 7.18 (d, J=1.2 Hz, 1H), 4.62 (s, 4H), 4.10-4.01 (m, 4H), 3.30-3.21 (m, 4H), 3.08-3.00 (m, 1H), 2.90-2.79 (m, 4H), 2.74 (s, 1H), 2.29-2.14 (m, 1H), 1.97-1.84 (m, 3H), 1.81-1.63 (m, 3H), 1.61-1.41 (m, 4H), 1.37-1.29 (m, 3H), 1.17-1.06 (m, 3H).

The following Examples were prepared according to the general procedure described in Examples 269 and 270.

TABLE 24

| Ex. No. | Structure | HPLC Method | Ret Time (min) | LCMS $MH^+$ |
|---|---|---|---|---|
| 271 | 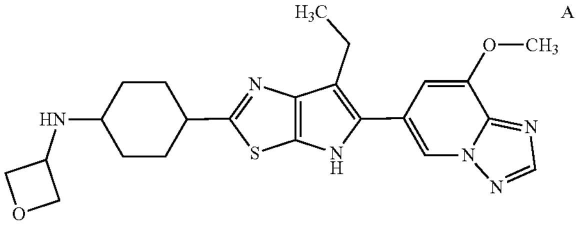 Isomer 1 | A | 1.19 | 453.3 |
| 272 | 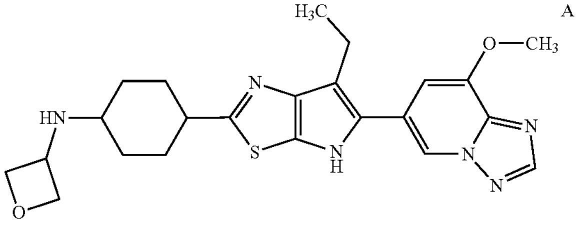 Isomer 2 | A | 1.02 | 453.2 |

Example 273

N-(4-(5-(8-methoxy-[1,2,4]triazolo[1,5-a]pyridin-6-yl)-6-methyl-4H-pyrrolo[3,2-d]thiazol-2-yl)cyclohexyl)oxetan-3-amine (273)

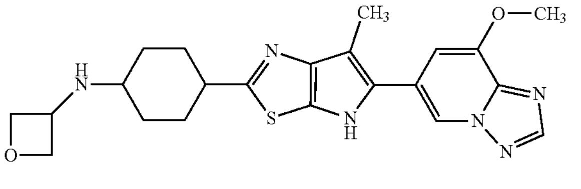

Intermediate 273A: tert-butyl 5-(8-methoxy-[1,2,4]triazolo[1,5-a]pyridin-6-yl)-6-methyl-2-(1,4-dioxaspiro[4.5]decan-8-yl)-4H-pyrrolo[3,2-d]thiazole-4-carboxylate (273A)

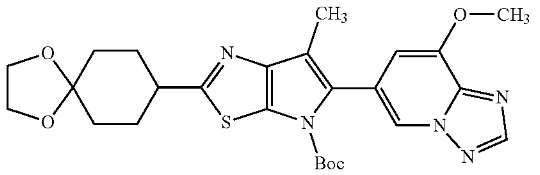

To a solution of tert-butyl 6-bromo-5-(8-methoxy-[1,2,4]triazolo[1,5-a]pyridin-6-yl)-2-(1,4-dioxaspiro[4.5]decan-8-yl)-4H-pyrrolo[3,2-d]thiazole-4-carboxylate (600 mg, 1.016 mmol) in THF (30 mL) and water (7.5 mL) was added methylboronic acid (304 mg, 5.08 mmol), potassium phosphate tribasic (702 mg, 3.05 mmol). The solution was degassed for 10 min with argon and chloro(2-dicyclohexylphosphino-2',4',6'-triisopropyl-1,1'-biphenyl)[2-(2'-amino-1,1'-biphenyl)]palladium(II) (80 mg, 0.102 mmol) was added. The resulting reaction mixture was heated at 70° C. for 12 h. The reaction mass was concentrated, diluted with water (100 mL) and extracted with DCM (3×100 mL). The separated organic layer was dried over sodium sulphate, filtered and concentrated. The crude was purified by combiflash using 40 g silica column by eluting with 40% EtOAc/Pet ether. Following concentration of fractions, collected tert-butyl 5-(8-methoxy-[1,2,4]triazolo[1,5-a]pyridin-6-yl)-6-methyl-2-(1,4-dioxaspiro[4.5]decan-8-yl)-4H-pyrrolo[3,2-d]thiazole-4-carboxylate (0.35 g, 65% yield) as a pale yellow solid. LCMS retention time 2.78 min [C]. MS ($E^-$) m/z: 526.2 (M+H).

Intermediate 273B: 4-(5-(8-methoxy-[1,2,4]triazolo[1,5-a]pyridin-6-yl)-6-methyl-4H-pyrrolo[3,2-d]thiazol-2-yl)cyclohexan-1-one (273B)

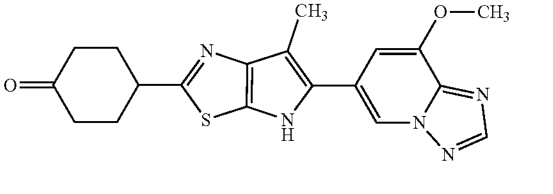

To a solution of tert-butyl 5-(8-methoxy-[1,2,4]triazolo[1,5-a]pyridin-6-yl)-6-methyl-2-(1,4-dioxaspiro[4.5]decan-8-yl)-4H-pyrrolo[3,2-d]thiazole-4-carboxylate (350 mg, 1.142 mmol) in DCM (10.00 mL) was added TFA (10 mL) and stirred at room temperature for 12 h. Reaction mass was concentrated to afford 4-(5-(8-methoxy-[1,2,4]triazolo[1,5-a]pyridin-6-yl)-6-methyl-4H-pyrrolo[3,2-d]thiazol-2-yl)cyclohexan-1-one (250 mg, 58%) as yellow solid. LCMS retention time 1.64 min [C]. MS ($E^-$) m/z: 382.2 (M+H).

Example 273: N-(4-(5-(8-methoxy-[1,2,4]triazolo[1,5-a]pyridin-6-yl)-6-methyl-4H-pyrrolo[3,2-d]thiazol-2-yl)cyclohexyl)oxetan-3-amine To a solution of 4-(5-(8-methoxy-[1,2,4]triazolo[1,5-a]pyridin-6-yl)-6-methyl-4H-pyrrolo[3,2-d]thiazol-2-yl)cyclohexan-1-one (80 mg, 0.210 mmol) in THF (2 mL) and DMF (2.00 mL) was added acetic acid (0.012 mL, 0.210 mmol) followed by oxetan-3-amine (0.012 mL, 0.210 mmol) and the solution was stirred at ambient temperature for 12 h. $NaCNBH_3$ (13.18 mg, 0.210 mmol) was added and the reaction was continued at room temperature for 1 h. The reaction was quenched with 10 mL water and extracted with 10% of methanol in DCM (10 mL×2). Organic layer was concentrated. The crude product obtained was purified by prep LCMS using Method I. After Preparative LCMS purification, fractions containing Isomers 1 and 2 were collected and dried separately using Genevac centrifugal evaporator to afford Example 273 (Isomer 1: 3.5 mg, 3.7%) as a pale yellow solid and Example 273 (Isomer 2: 3.5 mg, 3.7%) as a pale yellow solid.

Example 273 (Isomer 1): LCMS retention time 1.20 min [A]. MS ($E^-$) m/z: 439.2 (M+H). $^1H$ NMR (400 MHz, DMSO-$d_6$) δ 11.72 (s, 1H), 8.59 (d, J=1.2 Hz, 1H), 8.46 (s, 1H), 7.23 (d, J=1.2 Hz, 1H), 4.64 (t, J=6.5 Hz, 2H), 4.32 (t, J=6.2 Hz, 2H), 4.07 (s, 3H), 3.98 (quin, J=6.8 Hz, 1H), 2.97-2.90 (m, 1H), 2.47-2.36 (m, 4H), 2.16-2.04 (m, 2H), 1.91 (s, 2H), 1.88-1.78 (m, 2H), 1.61-1.45 (m, 2H), 1.27-1.11 (m, 2H).

The following Examples were prepared according to the general procedure described in Example 273.

TABLE 25

| Ex. No. | Structure | HPLC Method | Ret Time (min) | LCMS MH+ |
|---|---|---|---|---|
| 275 | 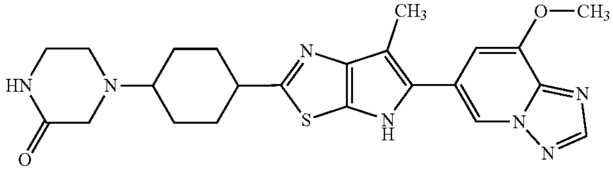 [SMILES: COc1cc(-c2[nH]c3sc(C4CCC(N5CCNC(=O)C5)CC4)nc3c2C)cn2ncnc12] Isomer 1 | A | 1.19 | 466.1 |
| 276 | 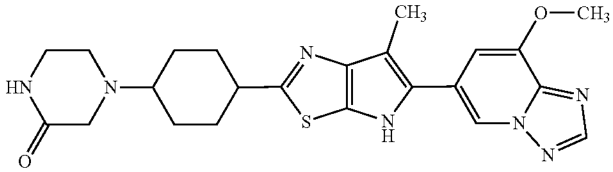 [SMILES: COc1cc(-c2[nH]c3sc(C4CCC(N5CCNC(=O)C5)CC4)nc3c2C)cn2ncnc12] Isomer 2 | A | 1.02 | 466.2 |

Intermediate 277B 6-ethynyl-7,8-dimethyl-[1,2,4]triazolo[1,5-a]pyridine (277B)

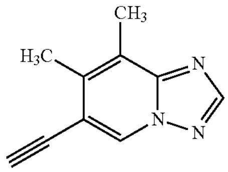

Intermediate 277A: 7,8-dimethyl-6-((trimethylsilyl)ethynyl)-[1,2,4]triazolo[1,5-a]pyridine (277A)

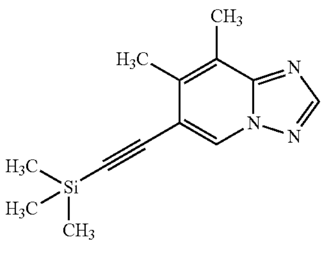

To a solution of 6-bromo-7,8-dimethyl-[1,2,4]triazolo[1,5-a]pyridine (15 g, 66.3 mmol) in TEA (100 mL) was added copper(I) iodide (1.264 g, 6.63 mmol), degassed for 10 min with argon. Then bis(triphenylphosphine)palladium (II) dichloride (3.26 g, 4.64 mmol) was added followed by trimethylsilylacetylene (13.03 g, 133 mmol). The resulting reaction mixture was heated at 80° C. for 12 h. The reaction mass was filtered through celite bed, washed with ethyl acetate (200 mL). The filtrate was diluted with water (250 mL) and extracted with ethyl acetate (2×200 mL). The separated organic layer was dried over sodium sulphate, filtered and concentrated to afford 7,8-dimethyl-6-((trimethylsilyl)ethynyl)-[1,2,4]triazolo[1,5-a]pyridine (16 g, 55.9 mmol, 84% yield) as a brown oil. LCMS 1.90 min [F]. MS ($E^-$) m/z: 244.2 (M+H).

Intermediate 277B: 6-ethynyl-7,8-dimethyl-[1,2,4]triazolo[1,5-a]pyridine

To a solution of 7,8-dimethyl-6-((trimethylsilyl)ethynyl)-[1,2,4]triazolo[1,5-a]pyridine (16 g, 65.7 mmol) in methanol (150 mL) was added potassium carbonate (18.17 g, 131 mmol), stirred at room temperature for 2 h. The reaction mass was concentrated, diluted with water (150 mL) and extracted with DCM (3×250 mL). The separated organic layer was dried over sodium sulphate, filtered and concentrated. The crude was purified by Combiflash using 120 g silica column by eluting with 75% EtOAc/Pet ether. Following concentration of fractions, collected 6-ethynyl-7,8-dimethyl-[1,2,4]triazolo[1,5-a]pyridine (7.2 g, 42.1 mmol, 64.0% yield) as a white solid. LCMS 1.81 min [C]. MS ($E^-$) m/z: 172.2 (M+H).

The following Intermediates were prepared according to the general procedure described in Intermediate 277B.

TABLE 26

| INT | Structure | HPLC Method | Ret Time (min) | LCMS MH+ |
|---|---|---|---|---|
| 277 C | 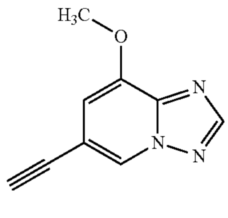 | F | 0.46 | 174.2 |

TABLE 26-continued

| INT | Structure | HPLC Method | Ret Time (min) | LCMS MH+ |
|---|---|---|---|---|
| 277 D | 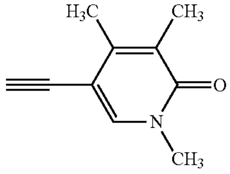 | F | 0.95 | 162.3 |
| 277 E | 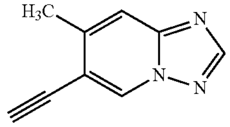 | F | 0.99 | 158.2 |

Example 278

5-(7,8-dimethyl-[1,2,4]triazolo[1,5-a]pyridin-6-yl)-6-isopropyl-2-(piperazin-1-yl)-4H-pyrrolo[3,2-d]thiazole (278)

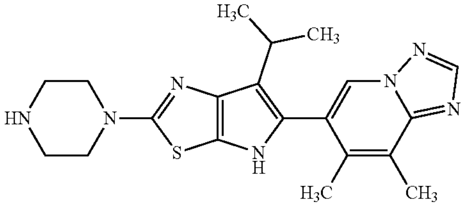

Intermediate 278A: Methyl 5-((tert-butoxycarbonyl)amino)thiazole-2-carboxylate (278A)

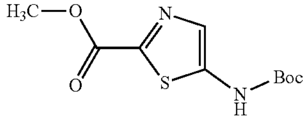

To a solution of tert-butyl (2-bromothiazol-5-yl)carbamate (10 g, 35.8 mmol) in methanol (75 mL) and DMF (75 mL) were added DPPF (3.97 g, 7.16 mmol) and $PdOAc_2$ (0.804 g, 3.58 mmol). The solution was degassed for 10 min with argon. The reaction mass was saturated with CO gas, followed by the addition of TEA (19.97 mL, 143 mmol), then the mixture was stirred at 80° C. in presence of CO with 10 kg/cm$^2$ pressure for 7 h. Concentrated the reaction mass, the residue was dissolved in DCM (100 mL), washed with water (2×100 mL), dried over sodium sulphate, filtered and concentrated to afford crude compound. The crude was purified by ISCO using 120 g silica column, the compound eluting with 35% ethyl acetate in pet ether, the fractions was collected and concentrated to afford methyl 5-((tert-butoxycarbonyl)amino)thiazole-2-carboxylate (7.5 g, 29.0 mmol, 81% yield) as an off-white solid. LCMS retention time 2.10 min [C]. MS ($E^-$) m/z: 259.1 (M+H).

Intermediate 278B: Methyl 5-((tert-butoxycarbonyl)amino)-4-iodothiazole-2-carboxylate (278B)

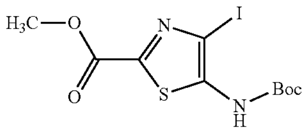

To a solution of methyl 5-((tert-butoxycarbonyl)amino)thiazole-2-carboxylate (7.5 g, 29.0 mmol) in acetonitrile (150 mL) was added NIS (6.53 g, 29.0 mmol) in acetonitrile (50 mL) dropwise at 0° C., stirred at same temperature for 10 min. The reaction was quenched with water (250 mL) and extracted with ethyl acetate (3×200 mL). The separated organic layer was dried over sodium sulphate, filtered and concentrated to afford crude product. The crude was purified by Combiflash using 80 g silica column by eluting with 31% EtOAc/Pet ether. Following concentration of fractions, collected methyl 5-((tert-butoxycarbonyl) amino)-4-iodothiazole-2-carboxylate (8.2 g, 21.34 mmol, 73.5% yield) as a pale yellow solid. LCMS retention time 1.64 min [F]. MS ($E^-$) m/z: 384.1 (M+H).

Intermediate 278C: Methyl 5-((tert-butoxycarbonyl)amino)-4-((7,8-dimethyl-[1,2,4]triazolo[1,5-a]pyridin-6-yl)ethynyl)thiazole-2-carboxylate (278C)

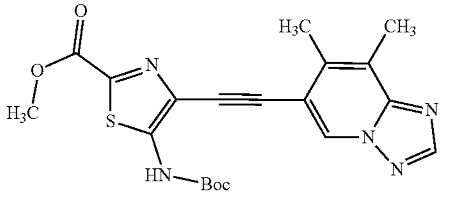

To a solution of methyl 5-((tert-butoxycarbonyl)amino)-4-iodothiazole-2-carboxylate (2.0 g, 5.21 mmol) in toluene (50 mL) and DIPEA (10.00 mL) was added triphenylphosphine (0.137 g, 0.521 mmol) and copper (I) iodide (0.099 g, 0.521 mmol), degassed for 10 min with argon. Then 6-ethynyl-7,8-dimethyl-[1,2,4]triazolo[1,5-a]pyridine (1.159 g, 6.77 mmol) was added followed by bis(triphenylphosphine) palladium(II)dichloride (0.183 g, 0.260 mmol) degassed again for 5 min. The resulting reaction mixture was heated at 45° C. for 3 h. The reaction was mass was filtered, washed with ethyl acetate (100 mL), filtrate was concentrated to afford crude product. The crude was purified by combiflash using 40 g silica column by eluting with 4% $MeOH/CHCl_3$. Following concentration of fractions, collected methyl 5-((tert-butoxycarbonyl)amino)-4-((7,8-dimethyl-[1,2,4]triazolo[1,5-a]pyridin-6-yl) ethynyl)thiazole-2-carboxylate (1.4 g, 3.28 mmol, 62.9% yield)) as a pale yellow solid. LCMS retention time 2.71 min [C]. MS ($E^-$) m/z: 428.2.1 (M+H).

Intermediate 278D: 4-(tert-butyl) 2-methyl 5-(7,8-dimethyl-[1,2,4]triazolo[1,5-a]pyridin-6-yl)-4H-pyrrolo[3,2-d]thiazole-2,4-dicarboxylate (278D)

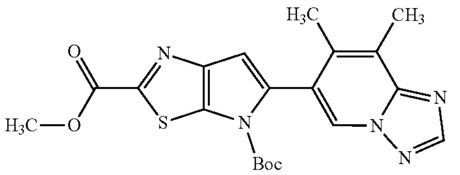

To a solution of methyl 5-((tert-butoxycarbonyl)amino)-4-((7,8-dimethyl-[1,2,4]triazolo[1,5-a]pyridin-6-yl)ethynyl) thiazole-2-carboxylate (1.3 g, 3.04 mmol) in toluene (15 mL) was added silver acetate (0.508 g, 3.04 mmol), resulting solution was heated at 100° C. for 45 min. The reaction mass was filtered through celite, washed with ethyl acetate (10 mL), filtrate was concentrated to afford 4-(tert-butyl) 2-methyl 5-(7,8-dimethyl-[1,2,4]triazolo[1,5-a]pyridin-6-yl)-4H-pyrrolo[3,2-d]thiazole-2,4-dicarboxylate (1.3 g, 2.80 mmol, 92% yield) as a pale yellow solid. LCMS retention time 2.71 min [C]. MS ($E^-$) m/z: 428.2.1 (M+H).

Intermediate 278E: 4-(tert-butyl) 2-methyl 6-bromo-5-(7,8-dimethyl-[1,2,4]triazolo[1,5-a]pyridin-6-yl)-4H-pyrrolo[3,2-d]thiazole-2,4-dicarboxylate (278E)

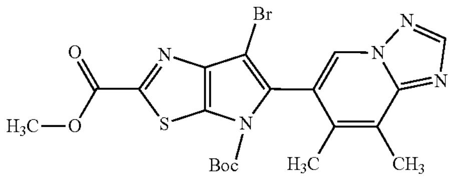

To a solution of 4-(tert-butyl) 2-methyl 5-(7,8-dimethyl-[1,2,4]triazolo[1,5-a]pyridin-6-yl)-4H-pyrrolo[3,2-d]thiazole-2,4-dicarboxylate (1.3 g, 3.04 mmol) in DMF (15 mL) was added NBS (0.541 g, 3.04 mmol) in DMF (5 mL) dropwise at 0° C., allowed to stir at room temperature for 12 h. The reaction mass was quenched with ice water (70 mL), stirred for 10 min, the resulting precipitate was filtered and dried to afford 4-(tert-butyl) 2-methyl 6-bromo-5-(7,8-dimethyl-[1,2,4]triazolo[1,5-a]pyridin-6-yl)-4H-pyrrolo[3,2-d] thiazole-2,4-dicarboxylate (0.9 g, 1.777 mmol, 58.4% yield) as a pale yellow solid. LCMS retention time 3.01 min [C]. MS ($E^-$) m/z: 508.2 (M+2H).

Intermediate 278F: 4-(tert-butyl) 2-methyl 5-(7,8-dimethyl-[1,2,4]triazolo[1,5-a]pyridin-6-yl)-6-(prop-1-en-2-yl)-4H-pyrrolo[3,2-d]thiazole-2,4-dicarboxylate (278F)

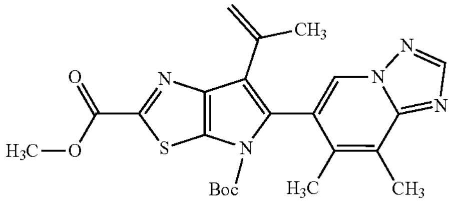

To a solution of 4-(tert-butyl) 2-methyl 6-bromo-5-(7,8-dimethyl-[1,2,4]triazolo[1,5-a]pyridin-6-yl)-4H-pyrrolo[3,2-d]thiazole-2,4-dicarboxylate (2.1 g, 4.15 mmol) in THF (15 mL) and water (1.667 mL) was added potassium phosphate, tribasic (1.445 g, 8.29 mmol), degassed for 10 min and then chloro(2-dicyclohexylphosphino-2',4',6'-triisopropyl-1,1'-biphenyl)[2-(2'-amino-1,1'-biphenyl)]palladium(II) (0.326 g, 0.415 mmol) was added and the reaction mixture was degassed again for 5 min, followed by addition of 4,4,5,5-tetramethyl-2-(prop-1-en-2-yl)-1,3,2-dioxaborolane (3.48 g, 20.74 mmol). The reaction mixture was heated at 70° C. for 4 h. The reaction mass was concentrated, diluted with water (100 mL) and extracted with DCM (3×100 mL). The separated organic layer was dried over sodium sulphate, filtered and concentrated. The crude was purified by Combiflash using 24 g silica column by eluting with 41% EtOAc/Pet ether. Following concentration of fractions, collected 4-(tert-butyl) 2-methyl 5-(7,8-dimethyl-[1,2,4]triazolo[1,5-a]pyridin-6-yl)-6-(prop-1-en-2-yl)-4H-pyrrolo[3,2-d]thiazole-2,4-dicarboxylate (1.3 g, 2.78 mmol, 67.0% yield) as a pale yellow solid. LCMS retention time 1.86 min [F]. MS ($E^-$) m/z: 468.2 (M+H).

Intermediate 278G: 4-(tert-butyl) 2-methyl 5-(7,8-dimethyl-[1,2,4]triazolo[1,5-a]pyridin-6-yl)-6-isopropyl-4H-pyrrolo[3,2-d]thiazole-2,4-dicarboxylate (278G)

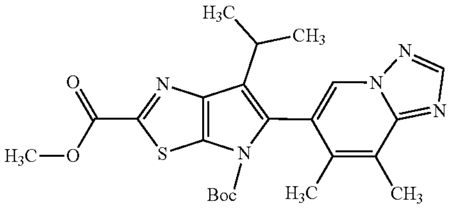

A solution of 4-(tert-butyl) 2-methyl 5-(7,8-dimethyl-[1,2,4]triazolo[1,5-a]pyridin-6-yl)-6-(prop-1-en-2-yl)-4H-pyrrolo[3,2-d]thiazole-2,4-dicarboxylate (1.3 g, 2.78 mmol) in methanol (75 mL), was purged with nitrogen gas and Pd/C (0.444 g, 0.417 mmol) was added. The system was evacuated under vacuum and purged with hydrogen gas and allowed to stir under hydrogen atmosphere for 24 h. The reaction mass was filtered through a plug of celite pad. The celite pad was rinsed with additional methanol and the filtrate was concentrated to dryness to give 4-(tert-butyl) 2-methyl 5-(7,8-dimethyl-[1,2,4]triazolo[1,5-a]pyridin-6-yl)-6-isopropyl-4H-pyrrolo[3,2-d]thiazole-2,4-dicarboxylate (1.15 g, 2.449 mmol, 88% yield) as white solid. LCMS retention time 1.92 min [F]. MS ($E^-$) m/z: 470.2 (M+H).

Intermediate 278H: Methyl 5-(7,8-dimethyl-[1,2,4]triazolo[1,5-a]pyridin-6-yl)-6-isopropyl-4H-pyrrolo[3,2-d]thiazole-2-carboxylate (278H)

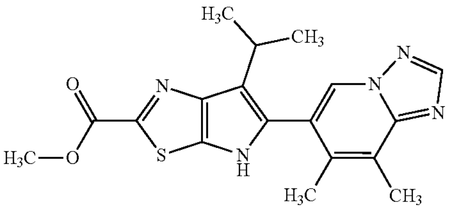

To a solution of 4-(tert-butyl) 2-methyl 5-(7,8-dimethyl-[1,2,4]triazolo[1,5-a]pyridin-6-yl)-6-isopropyl-4H-pyrrolo[3,2-d]thiazole-2,4-dicarboxylate (1.1 g, 2.343 mmol) in DCM (10 mL) was added TFA (1.805 mL, 23.43 mmol) dropwise and stirred at room temperature for 12 h. The reaction mass was diluted with DCM (20 mL) and washed with 10% $NaHCO_3$ (20 mL). The separated organic layer was dried over sodium sulphate, filtered and concentrated to afford methyl 5-(7,8-dimethyl-[1,2,4]triazolo[1,5-a]pyridin-6-yl)-6-isopropyl-4H-pyrrolo[3,2-d]thiazole-2-carboxylate (0.86 g, 2.328 mmol, 99% yield) as a pale yellow solid. LCMS retention time 2.39 min [C]. MS ($E^-$) m/z: 370.2 (M+H).

Intermediate 2781: 5-(7,8-dimethyl-[1,2,4]triazolo[1,5-a]pyridin-6-yl)-6-isopropyl-4H-pyrrolo[3,2-d]thiazole-2-carboxylic acid

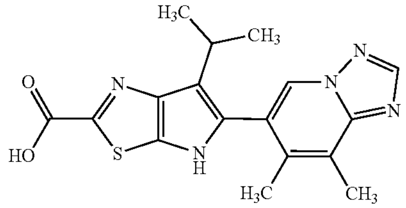 [SMILES: Cc1c(-c2[nH]c3sc(C(=O)O)nc3c2C(C)C)cn2ncnc2c1C]

To a solution of methyl 5-(7,8-dimethyl-[1,2,4]triazolo[1,5-a]pyridin-6-yl)-6-isopropyl-4H-pyrrolo[3,2-d]thiazole-2-carboxylate (0.86 g, 2.328 mmol) in methanol (10 mL) was added 10% sodium hydroxide (5 mL, 2.328 mmol) dropwise and stirred at room temperature for 3 h. The reaction mass was concentrated, aqueous layer was acidified to pH ~4-5, the resulting precipitate was filtered and dried to afford 5-(7,8-dimethyl-[1,2,4]triazolo[1,5-a]pyridin-6-yl)-6-isopropyl-4H-pyrrolo[3,2-d]thiazole-2-carboxylic acid (0.7 g, 1.970 mmol, 85% yield) as an off-white solid. LCMS retention time 0.94 min [C]. MS ($E^-$) m/z: 355.2 (M+H).

The following Intermediate was prepared according to the general procedure described in Intermediate 2781.

TABLE 27

| Int. | Structure | HPLC Method | Ret Time (min) | LCMS $MH^+$ |
|---|---|---|---|---|
| 278J | 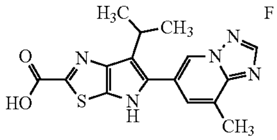 | F | 0.58 | 342.2 |

Intermediate 278K: 5-(7,8-dimethyl-[1,2,4]triazolo[1,5-a]pyridin-6-yl)-6-isopropyl-4H-pyrrolo[3,2-d]thiazole (278K)

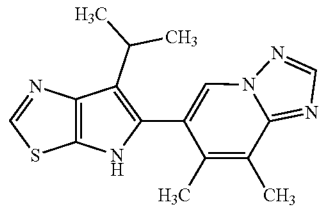

A solution of 5-(7,8-dimethyl-[1,2,4]triazolo[1,5-a]pyridin-6-yl)-6-isopropyl-4H-pyrrolo[3,2-d]thiazole-2-carboxylic acid (400 mg, 1.125 mmol) in THE (10 mL) was heated at 70° C. for 1 h. The reaction mass was concentrated to afford 5-(7,8-dimethyl-[1,2,4]triazolo[1,5-a]pyridin-6-yl)-6-isopropyl-4H-pyrrolo[3,2-d]thiazole (340 mg, 1.092 mmol, 97% yield) as a pale yellow solid. LCMS retention time 1.26 min [F]. MS ($E^-$) m/z: 3122 (M+H).

Intermediate 278L: 2-bromo-5-(7,8-dimethyl-[1,2,4]triazolo[1,5-a]pyridin-6-yl)-6-isopropyl-4H-pyrrolo[3,2-d]thiazole (278L)

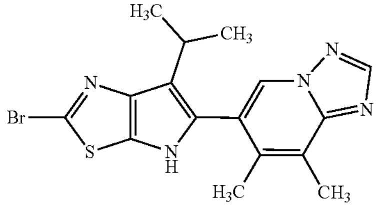

To a solution of 5-(7,8-dimethyl-[1,2,4]triazolo[1,5-a]pyridin-6-yl)-6-isopropyl-4H-pyrrolo[3,2-d]thiazole (340 mg, 1.092 mmol) in DMF (10 mL) was added NBS (194 mg, 1.092 mmol) in DMF (3 mL) dropwise at 0° C. and the reaction mixture was stirred at room temperature for 2 h. The reaction was quenched with water (50 mL), stirred for 10 min, and the resulting precipitate was filtered and dried to afford 2-bromo-5-(7,8-dimethyl-[1,2,4]triazolo[1,5-a]pyridin-6-yl)-6-isopropyl-4H-pyrrolo[3,2-d]thiazole (275 mg, 0.705 mmol, 64.5% yield) as an off-white solid. LCMS retention time 1.52 min [G]. MS ($E^-$) m/z: 390.2 (M+H).

The following Intermediate was prepared according to the general procedure described in Intermediate 278L.

TABLE 28

| Int. | Structure | HPLC Method | Ret Time (min) | LCMS $MH^+$ |
|---|---|---|---|---|
| 278M | 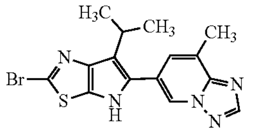 [SMILES: Cc1cc(-c2[nH]c3sc(Br)nc3c2C(C)C)cn2ncnc12] | F | 1.56 | 376.2 |

Intermediate 278N: Tert-butyl 4-(5-(7,8-dimethyl-[1,2,4]triazolo[1,5-a]pyridin-6-yl)-6-isopropyl-4H-pyrrolo[3,2-d]thiazol-2-yl)piperazine-1-carboxylate (278N)

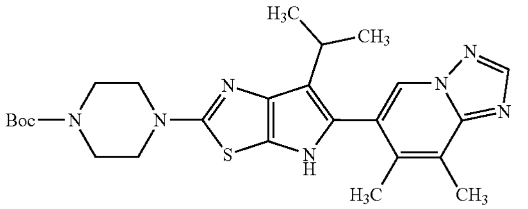

To a solution of 2-bromo-5-(7,8-dimethyl-[1,2,4]triazolo[1,5-a]pyridin-6-yl)-6-isopropyl-4H-pyrrolo[3,2-d]thiazole (250 mg, 0.641 mmol) and tert-butyl piperazine-1-carboxylate (179 mg, 0.961 mmol) in toluene (7 mL) was added cesium carbonate (417 mg, 1.281 mmol). The resulting solution was degassed with $N_2$ for 10 mins and $Pd_2(dba)_3$ (58.7 mg, 0.064 mmol) was added, followed by BINAP (399 mg, 0.641 mmol) at which point the solution was degassed again for 5 min. The resulting mixture was heated at 90° C. for 12 h. The cooled reaction mixture was diluted with ethyl acetate (500 mL), washed with water (2×50 mL), brine (50 mL), dried over sodium sulphate, and concentrated to afford crude product. The crude was purified by combiflash using 24 g silica column, the compound eluting with 75% ethyl acetate in Pet ether. The fractions were collected and concentrated to afford tert-butyl 4-(5-(7,8-dimethyl-[1,2,4]triazolo[1,5-a]pyridin-6-yl)-6-isopropyl-4H-pyrrolo[3,2-d]thiazol-2-yl)piperazine-1-carboxylate (210 mg, 0.424 mmol, 66.1% yield) as a pale yellow solid. LCMS retention time 3.48 min [C]. MS ($E^-$) m/z: 496.2 (M+H).

Example 278: 5-(7,8-dimethyl-[1,2,4]triazolo[1,5-a]pyridin-6-yl)-6-isopropyl-2-(piperazin-1-yl)-4H-pyrrolo[3,2-d]thiazole To a solution of tert-butyl 4-(5-(7,8-dimethyl-[1,2,4]triazolo[1,5-a]pyridin-6-yl)-6-isopropyl-4H-pyrrolo[3,2-d]thiazol-2-yl)piperazine-1-carboxylate (210 mg, 0.424 mmol) in DCM (10 mL) was added HCl in dioxane (2 mL, 8.00 mmol) dropwise and stirred at room temperature for 1 h. The reaction mass was diluted with DCM (20 mL) and washed with 10% $NaHCO_3$ (20 mL). The separated organic layer was dried over sodium sulphate, filtered and concentrated to afford 5-(7,8-dimethyl-[1,2,4]triazolo[1,5-a]pyridin-6-yl)-6-isopropyl-2-(piperazin-1-yl)-4H-pyrrolo[3,2-d]thiazole (170 mg, 100% yield) as a pale yellow solid. LCMS retention time 1.62 min [C]. MS ($E^-$) m/z: 396.2 (M+H).

The following Example was prepared according to the general procedure described in Example 278.

TABLE 29

| Ex. No. | Structure | HPLC Method | Ret Time (min) | LCMS $MH^+$ |
|---|---|---|---|---|
| 279 | 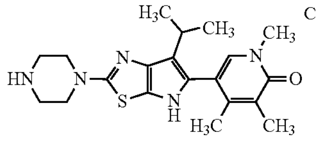 | C | 1.34 | 386.2 |

Example 280

1-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-2-(dimethylamino)ethan-1-one (280)

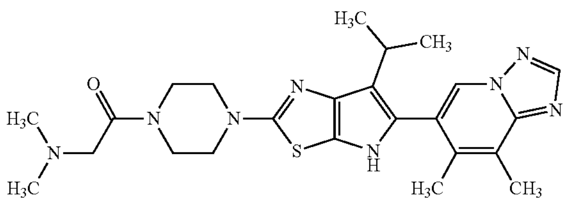

To a solution of 5-(7,8-dimethyl-[1,2,4]triazolo[1,5-a]pyridin-6-yl)-6-isopropyl-2-(piperazin-1-yl)-4H-pyrrolo[3,2-d]thiazole (68 mg, 0.172 mmol) and dimethylglycine (17.73 mg, 0.172 mmol)) in DMF (1 mL) was added HATU (65.4 mg, 0.172 mmol), followed by TEA (0.024 mL, 0.172 mmol). The resulting solution was stirred at room temperature for 12 h. The reaction mass was diluted with water (5 mL) and extracted with EtOAc (3×10 mL). The separated organic layer was dried over sodium sulphate, filtered and concentrated. LCMS retention time 1.76 min [C]. MS ($E^-$) m/z: 481.2 (M+H). $^1H$ NMR (400 MHz, DMSO-$d_6$) δ 10.97 (s, 1H), 8.68 (s, 1H), 8.44 (s, 1H), 4.17 (s, 4H), 3.91 (s, 4H), 3.37 (br. s., 2H), 2.77-2.58 (m, 4H), 2.27 (s, 6H), 2.18 (s, 3H), 1.98 (s, 2H), 1.26 (d, J=6.8 Hz, 6H).

Example 281

1-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-2-methylpropan-2-ol (281)

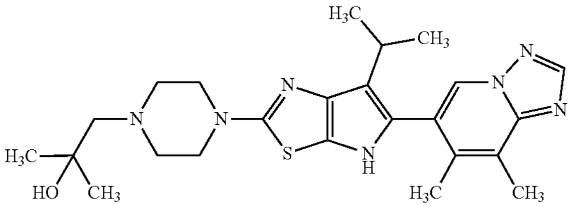

To a solution of 5-(7,8-dimethyl-[1,2,4]triazolo[1,5-a]pyridin-6-yl)-6-isopropyl-2-(piperazin-1-yl)-4H-pyrrolo[3,2-d]thiazole (25 mg, 0.063 mmol) and 1-chloro-2-methyl-propan-2-ol (6.86 mg, 0.063 mmol) in DMF (1 mL) was added potassium carbonate (17.47 mg, 0.126 mmol). The resulting solution was heated at 80° C. for 12 h. The reaction mass was diluted with water (5 mL) and extracted with EtOAc (3×10 mL). The separated organic layer was dried over sodium sulphate, filtered and concentrated. The reaction mass was purified by prep LCMS using Method I, the fractions containing the product were combined and dried using Genevac centrifugal evaporator to afford 1-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-2-methylpropan-2-ol (16.7 mg, 0.035 mmol, 55.9% yield) as a pale yellow solid. LCMS retention time 2.01 min [A]. MS ($E^-$) m/z: 468.2 (M+H). $^1$H NMR (400 MHz, DMSO-$d_6$) δ 10.97 (s, 1H), 8.68 (s, 1H), 8.44 (s, 1H), 4.17 (s, 1H), 3.91 (s, 1H), 3.37 (br. s., 3H), 2.77-2.58 (m, 5H), 2.58-2.53 (m, 3H), 2.27 (s, 2H), 2.18 (s, 3H), 1.26 (d, J=6.8 Hz, 6H), 1.13 (s, 6H).

Example 282

5-(7,8-dimethyl-[1,2,4]triazolo[1,5-a]pyridin-6-yl)-6-isopropyl-2-(4-(2-(methylsulfonyl)ethyl)piperazin-1-yl)-4H-pyrrolo[3,2-d]thiazole (282)

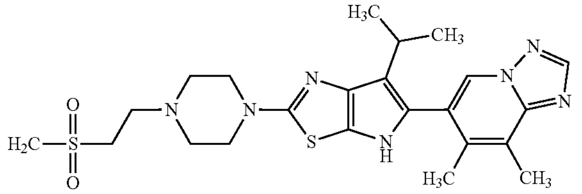

To a solution of 5-(7,8-dimethyl-[1,2,4]triazolo[1,5-a]pyridin-6-yl)-6-isopropyl-2-(piperazin-1-yl)-4H-pyrrolo[3,2-d]thiazole (25 mg, 0.063 mmol) and 1-chloro-2-(methylsulfonyl)ethane (9.01 mg, 0.063 mmol) in DMF (1 mL) was added TEA (8.81 μL, 0.063 mmol). The resulting solution was heated at 90° C. for 12 h. The reaction mass was diluted with water (5 mL) and extracted with EtOAc (3×10 mL). The separated organic layer was dried over sodium sulphate, filtered and concentrated. The reaction mass was purified by prep LCMS using Method I, the fractions containing the product was combined and dried using Genevac centrifugal evaporator to afford 5-(7,8-dimethyl-[1,2,4]triazolo[1,5-a]pyridin-6-yl)-6-isopropyl-2-(4-(2-(methylsulfonyl)ethyl)piperazin-1-yl)-4H-pyrrolo[3,2-d]thiazole as a pale yellow solid. LCMS retention time 1.70 min [A]. MS ($E^-$) m/z: 502.3 (M+H). $^1$H NMR (400 MHz, DMSO-$d_6$) δ 11.06 (s, 1H), 8.69 (s, 1H), 8.46 (s, 1H), 3.36 (br. s., 8H), 3.13 (s, 3H), 2.68-2.61 (m, 2H), 2.60-2.53 (m, 6H), 2.17 (s, 3H), 1.34-1.18 (m, 6H).

Example 283

2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-N,N-dimethylacetamide (283)

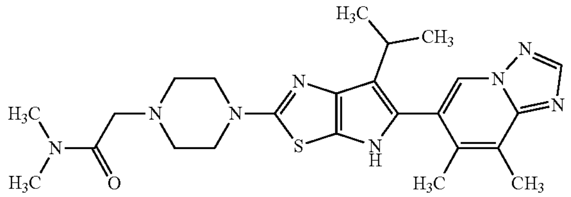

To a solution of 5-(7,8-dimethyl-[1,2,4]triazolo[1,5-a]pyridin-6-yl)-6-isopropyl-2-(piperazin-1-yl)-4H-pyrrolo[3,2-d]thiazole (25 mg, 0.063 mmol) and 2-chloro-N,N-dimethylacetamide (7.68 mg, 0.063 mmol) in DMF (1 mL) was added TEA (8.81 μL, 0.063 mmol). The resulting solution was stirred at room temperature for 12 h. The reaction mass was diluted with water (5 mL) and extracted with EtOAc (3×10 mL). The separated organic layer was dried over sodium sulphate, filtered and concentrated. The reaction mass was purified by prep LCMS using Method I, the fractions containing the product was combined and dried using Genevac centrifugal evaporator to afford 2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-N,N-dimethylacetamide (19.5 mg, 0.039 mmol, 62.3% yield) as a pale yellow solid. LCMS retention time 1.72 min [A]. MS ($E^-$) m/z: 481.2 (M+H). $^1$H NMR (400 MHz, DMSO-$d_6$) δ 10.98 (s, 1H), 8.68 (s, 1H), 8.44 (s, 1H), 3.39 (br. s., 4H), 3.23 (s, 2H), 3.03 (s, 3H), 2.83 (s, 3H), 2.66-2.58 (m, 5H), 2.56 (s, 3H), 2.18 (s, 3H), 1.26 (d, J=6.8 Hz, 6H).

The following Examples were prepared according to the general procedure described in Example 283.

| Ex. No. | Structure | HPLC Method | Ret Time (min) | LCMS $MH^+$ |
|---|---|---|---|---|
| 284 | 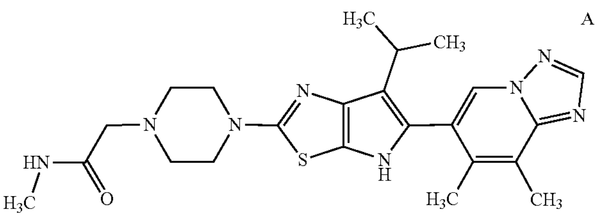 | A | 1.66 | 467.3 |

-continued

| Ex. No. | Structure | HPLC Method | Ret Time (min) | LCMS MH+ |
|---|---|---|---|---|
| 285 | 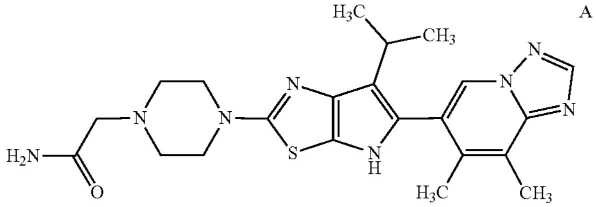 | A | 1.56 | 453.2 |

Example 286

5-(7,8-dimethyl-[1,2,4]triazolo[1,5-a]pyridin-6-yl)-6-isopropyl-2-(4-(oxetan-3-yl)piperazin-1-yl)-4H-pyrrolo[3,2-d]thiazole (286)

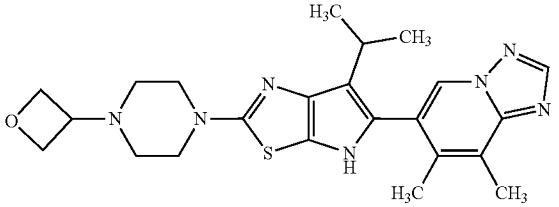

To a solution of 5-(7,8-dimethyl-[1,2,4]triazolo[1,5-a]pyridin-6-yl)-6-isopropyl-2-(piperazin-1-yl)-4H-pyrrolo[3,2-d]thiazole (65 mg, 0.164 mmol) and oxetan-3-one (11.84 mg, 0.164 mmol) in methanol (2 mL) was added TEA (0.023 mL, 0.164 mmol) followed by acetic acid (9.41 μL, 0.164 mmol) at 0° C. The resulting solution was stirred at room temperature for 12 h. Then sodium cyanoborohydride (10.33 mg, 0.164 mmol) was added at 0° C. and stirred for 2 h at room temperature. The reaction mass was concentrated, residue was dissolved in water (5 mL) and extracted with EtOAc (3×10 mL). The separated organic layer was dried over sodium sulphate, filtered and dried. LCMS retention time 2.16 min [C]. MS ($E^-$) m/z: 452.2 (M+H). 1H NMR (400 MHz, DMSO-$d_6$) δ 10.97 (s, 1H), 8.68 (s, 1H), 8.44 (s, 1H), 4.59 (s, 2H), 4.48 (s, 2H), 3.37 (m, 5H), 2.81 (s, 1H), 2.52 (s, 3H), 2.27 (m, 4H), 2.18 (s, 3H), 1.26 (d, J=6.8 Hz, 6H).

The following Examples were prepared according to the general procedure described in Example 286.

| Ex. No. | Structure | HPLC Method | Ret Time (min) | LCMS MH+ |
|---|---|---|---|---|
| 287 | 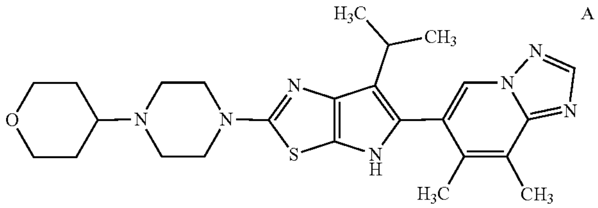 | A | 1.86 | 480.3 |
| 288 | 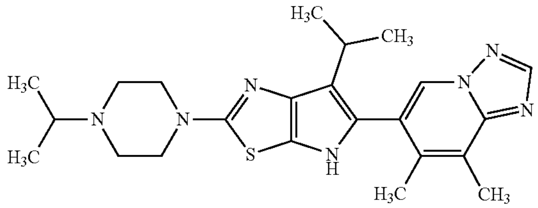 | A | 1.99 | 438.2 |
| 289 | 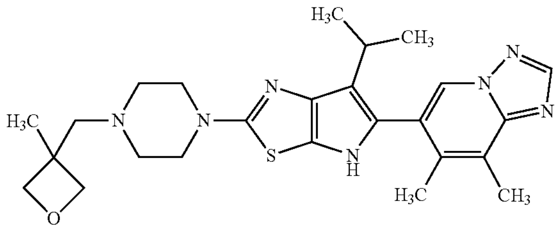 [SMILES: Cc1c(-c2[nH]c3sc(N4CCN(CC5(C)COC5)CC4)nc3c2C(C)C)cn2ncnc2c1C] | A | 2.03 | 480.2 |

Example 290

1-(5-(7,8-dimethyl-[1,2,4]triazolo[1,5-a]pyridin-6-yl)-6-isopropyl-4H-pyrrolo[3,2-d]thiazol-2-yl)-N-(3-methyloxetan-3-yl)piperidin-4-amine (290)

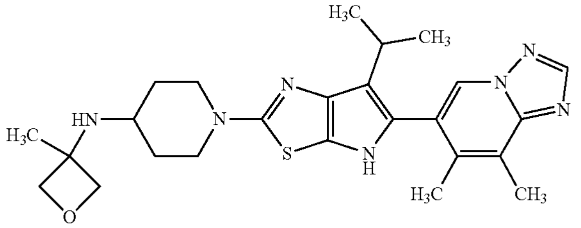

Intermediate 290A: 8-(5-(7,8-dimethyl-[1,2,4]triazolo[1,5-a]pyridin-6-yl)-6-isopropyl-4H-pyrrolo[3,2-d]thiazol-2-yl)-1,4-dioxa-8-azaspiro[4.5]decane (290A)

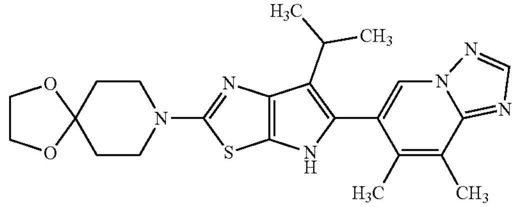

To a solution of 2-bromo-5-(7,8-dimethyl-[1,2,4]triazolo[1,5-a]pyridin-6-yl)-6-isopropyl-4H-pyrrolo[3,2-d]thiazole (500 mg, 1.281 mmol) and 1,4-dioxa-8-azaspiro[4.5]decane (275 mg, 1.922 mmol in toluene (15 mL) was added cesium carbonate (835 mg, 2.56 mmol). The solution was degassed for 10 min and then $Pd_2(dba)_3$ (117 mg, 0.128 mmol) was added, followed by BINAP (80 mg, 0.128 mmol). The reaction mixture was degassed again for 5 min. and was heated at 90° C. for 16 h. The reaction mixture was diluted with water (100 mL) and extracted with ethyl acetate (2×100 mL). The separated organic layer was dried over sodium sulphate, filtered and concentrated to afford crude product. The crude was purified by Combiflash using 24 g silica column by eluting with 45% ethyl acetate\DCM. Following concentration of fractions, collected 8-(5-(7,8-dimethyl-[1,2,4]triazolo[1,5-a]pyridin-6-yl)-6-isopropyl-4H-pyrrolo[3,2-d]thiazol-2-yl)-1,4-dioxa-8-azaspiro[4.5]decane (490 mg, 1.083 mmol, 85% yield) as a pale yellow solid. LCMS retention time 1.54 min [F]. MS ($E^-$) m/z: 453.2 (M+H).

Intermediate 290B: 1-(5-(7,8-dimethyl-[1,2,4]triazolo[1,5-a]pyridin-6-yl)-6-isopropyl-4H-pyrrolo[3,2-d]thiazol-2-yl)piperidin-4-one (290B)

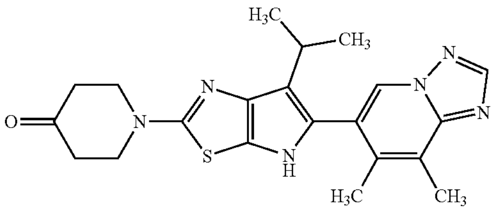

To a solution of 8-(5-(7,8-dimethyl-[1,2,4]triazolo[1,5-a]pyridin-6-yl)-6-isopropyl-4H-pyrrolo[3,2-d]thiazol-2-yl)-1,4-dioxa-8-azaspiro[4.5]decane (450 mg, 0.994 mmol) in DCM (10 mL) was added TFA (3 mL, 38.9 mmol) dropwise and stirred at room temperature for 12 h. The reaction mass was concentrated to afford 1-(5-(7,8-dimethyl-[1,2,4]triazolo[1,5-a]pyridin-6-yl)-6-isopropyl-4H-pyrrolo[3,2-d]thiazol-2-yl)piperidin-4-one (400 mg, 0.979 mmol, 98% yield) as a yellow oil. LCMS retention time 1.36 min [F]. MS ($E^-$) m/z: 409.2 (M+H).

Example 290: 1-(5-(7,8-dimethyl-[1,2,4]triazolo[1,5-a]pyridin-6-yl)-6-isopropyl-4H-pyrrolo[3,2-d]thiazol-2-yl)-N-(3-methyloxetan-3-yl)piperidin-4-amine To a solution of 1-(5-(7,8-dimethyl-[1,2,4]triazolo[1,5-a]pyridin-6-yl)-6-isopropyl-4H-pyrrolo[3,2-d]thiazol-2-yl)piperidin-4-one (25 mg, 0.061 mmol) and 3-methyloxetan-3-amine (5.33 mg, 0.061 mmol) in methanol (1 mL) was added acetic acid (3.50 µL, 0.061 mmol) at 0° C. The resulting solution was stirred at room temperature for 12 h, then sodium cyanoborohydride (7.69 mg, 0.122 mmol) was added at 0° C. and the reaction mixture was stirred for 2 h at room temperature. The reaction mass was concentrated, residue was dissolved in water (5 mL) and extracted with EtOAc (3×10 mL). The separated organic layer was dried over sodium sulphate, filtered and concentrated. The reaction mass was purified by prep LCMS using Method I, the fractions containing the product was combined and dried using Genevac centrifugal evaporator to afford 1-(5-(7,8-dimethyl-[1,2,4]triazolo[1,5-a]pyridin-6-yl)-6-isopropyl-4H-pyrrolo[3,2-d]thiazol-2-yl)-N-(3-methyloxetan-3-yl)piperidin-4-amine (14.1 mg, 48%) as a pale yellow solid. LCMS retention time 1.75 min [A]. MS ($E^-$) m/z: 480.2 (M+H). $^1H$ NMR (400 MHz, DMSO-$d_6$) δ 10.95 (s, 1H), 8.67 (s, 1H), 8.44 (s, 1H), 4.42 (d, J=5.1 Hz, 2H), 4.21 (d, J=5.4 Hz, 2H), 3.91 (s, 1H), 3.82 (d, J=12.2 Hz, 2H), 3.01 (t, J=11.6 Hz, 2H), 2.81 (br. s., 1H), 2.63 (dt, J=13.6, 6.8 Hz, 1H), 2.59-2.53 (m, 2H), 2.18 (s, 3H), 1.70 (d, J=12.5 Hz, 2H), 1.46 (s, 2H), 1.37 (d, J=11.2 Hz, 2H), 1.26 (d, J=6.8 Hz, 6H).

The following Examples were prepared according to the general procedure described in Example 290.

TABLE 30
| Ex. No. | Structure | HPLC Method | Ret Time (min) | LCMS MH+ |
|---|---|---|---|---|
| 291 | 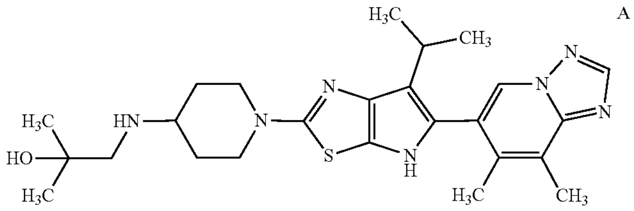 | A | 1.52 | 482.3 |
| 292 | 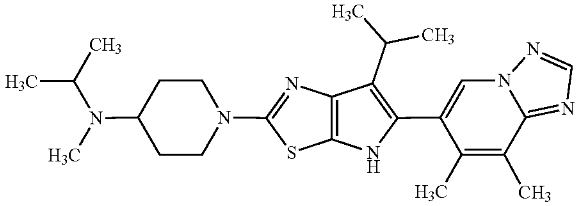 | A | 1.55 | 466.3 |
| 293 | 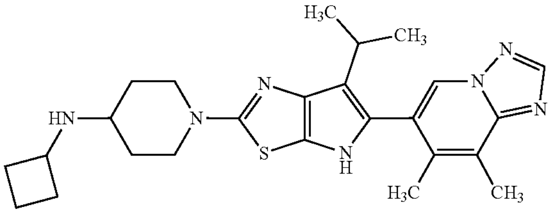 [SMILES: Cc1c(-c2[nH]c3sc(N4CCC(NC5CCC5)CC4)nc3c2C(C)C)cn2ncnc2c1C] | A | 1.65 | 464.2 |
| 294 | 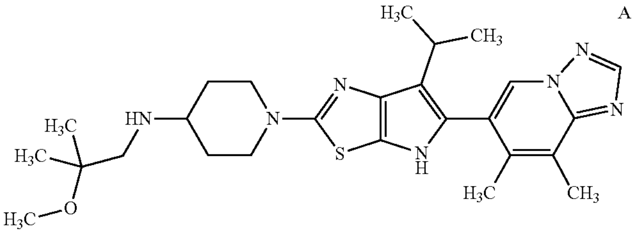 | A | 1.78 | 496.2 |
| 295 | 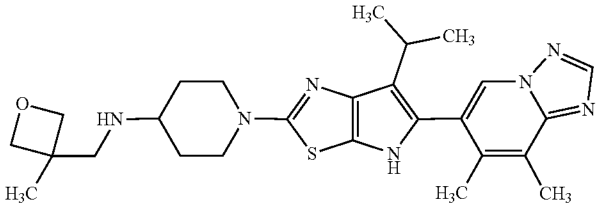 [SMILES: Cc1c(-c2[nH]c3sc(N4CCC(NCC5(C)COC5)CC4)nc3c2C(C)C)cn2ncnc2c1C] | A | 1.73 | 494.2 |
| 296 | 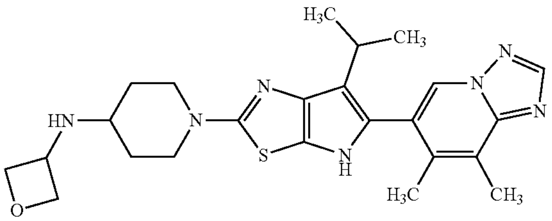 [SMILES: Cc1c(-c2[nH]c3sc(N4CCC(NC5COC5)CC4)nc3c2C(C)C)cn2ncnc2c1C] | A | 1.66 | 466.3 |
| 297 | 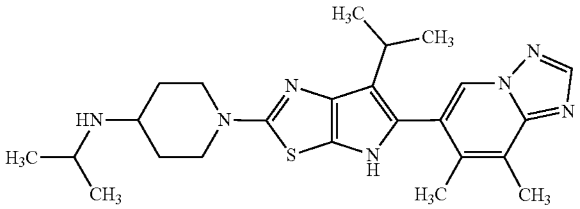 [SMILES: Cc1c(-c2[nH]c3sc(N4CCC(NC(C)C)CC4)nc3c2C(C)C)cn2ncnc2c1C] | A | 1.50 | 452.3 |

TABLE 30-continued

| Ex. No. | Structure | HPLC Method | Ret Time (min) | LCMS MH+ |
|---|---|---|---|---|
| 298 | 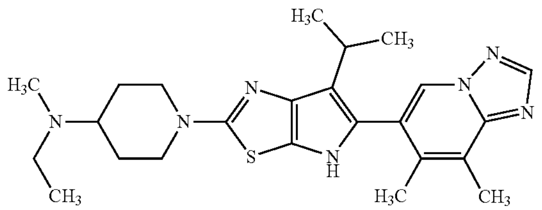 [SMILES: CCN(C)C1CCN(c2nc3c(C(C)C)c(-c4cn5ncnc5c(C)c4C)[nH]c3s2)CC1] | B | 1.38 | 452.3 |
| 299 | 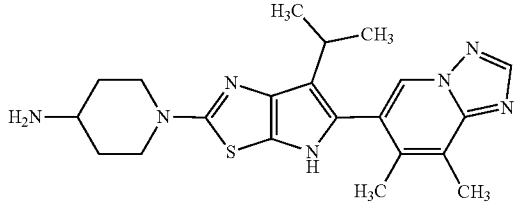 | A | 1.34 | 410.2 |

Example 300

5-(7,8-dimethyl-[1,2,4]triazolo[1,5-a]pyridin-6-yl)-2-(6-isobutyl-2,6-diazaspiro[3.3]heptan-2-yl)-6-isopropyl-4H-pyrrolo[3,2-d]thiazole (300)

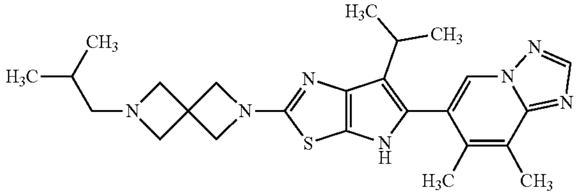

Intermediate 300A: Tert-butyl 6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptane-2-carboxylate (300A)

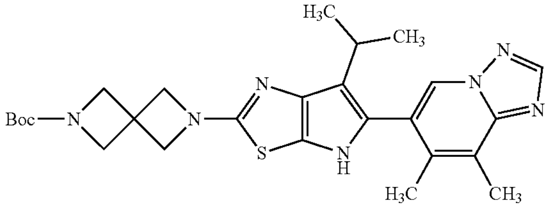

To a solution of 2-bromo-5-(7,8-dimethyl-[1,2,4]triazolo[1,5-a]pyridin-6-yl)-6-isopropyl-4H-pyrrolo[3,2-d]thiazole (0.85 g, 2.178 mmol) and tert-butyl 2,6-diazaspiro[3.3]heptane-2-carboxylate (0.518 g, 2.61 mmol) in toluene (15 mL) was added cesium carbonate (1.419 g, 4.36 mmol). The mixture was degassed for 10 min and then $Pd_2(dba)_3$ (0.199 g, 0.218 mmol) was added, followed by BINAP (0.136 g, 0.218 mmol) after which the solution was degassed again for 5 min. The resulting reaction mixture was heated at 90° C. for 16 h. The reaction mixture was diluted with water (100 mL) and extracted with EtOAc (2×100 mL). The separated organic layer was dried over sodium sulphate, filtered and concentrated to afford crude product. The crude was purified by Combiflash using 24 g silica column by eluting with 45% ethyl acetate\DCM. Following concentration of fractions, collected tert-butyl 6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptane-2-carboxylate (550 mg, 1.083 mmol, 49.7% yield) as a yellow solid. LCMS retention time 1.80 min [F]. MS ($E^-$) m/z: 508.2 (M+H).

Intermediate 300B: 5-(7,8-dimethyl-[1,2,4]triazolo[1,5-a]pyridin-6-yl)-6-isopropyl-2-(2,6-diazaspiro[3.3]heptan-2-yl)-4H-pyrrolo[3,2-d]thiazole (300B)

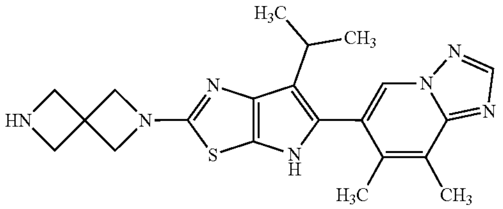

To a solution of tert-butyl 6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptane-2-carboxylate (400 mg, 0.788 mmol) in DCM (10 mL) was added TFA (3 mL, 38.9 mmol) dropwise and the solution was stirred at room temperature for 12 h. The reaction mass was concentrated to afford 5-(7,8-dimethyl-[1,2,4]triazolo[1,5-a]pyridin-6-yl)-6-isopropyl-2-(2,6-diazaspiro[3.3]heptan-2-yl)-4H-pyrrolo[3,2-d]thiazole (400 mg, 0.979 mmol, 98% yield) as a yellow solid. LCMS retention time 1.32 min [A]. MS ($E^-$) m/z: 408.2 (M+H). $^1$H NMR (400 MHz, DMSO-$d_6$) δ 11.00 (d, J=4.2 Hz, 1H), 8.67 (s, 1H), 8.44 (d, J=2.0 Hz, 1H), 4.32 (s, 1H), 4.18 (s, 2H), 4.15 (s, 3H), 4.05 (s, 1H), 2.65-2.59 (m, 1H), 2.58-2.54 (m, 2H), 2.16 (d, J=2.4 Hz, 3H), 1.91 (s, 1H), 1.76 (s, 1H), 1.25 (d, J=7.1 Hz, 6H).

Example 300: 5-(7,8-dimethyl-[1,2,4]triazolo[1,5-a]pyridin-6-yl)-2-(6-isobutyl-2,6-diazaspiro[3.3]heptan-2-yl)-6-isopropyl-4H-pyrrolo[3,2-d]thiazole To a solution of 5-(7,8-dimethyl-[1,2,4]triazolo[1,5-a]pyridin-6-yl)-6-isopropyl-2-(2,6-diazaspiro[3.3]heptan-2-yl)-4H-pyrrolo[3,2-d]thiazole (50 mg, 0.123 mmol) and isobutyraldehyde (8.85 mg, 0.123 mmol) in methanol (1 mL) was added acetic acid (7.02 μL, 0.123 mmol) at 0° C. The resulting solution was stirred at room temperature for 12 h, then sodium cyanoborohydride (15.42 mg, 0.245 mmol) was added at 0° C. and the reaction mixture was stirred for 2 h at room temperature. The reaction mass was concentrated, residue was dissolved in water (5 mL) and extracted with EtOAc (3×10 mL). The separated organic layer was dried over sodium sulphate, filtered and concentrated. The reaction mass was purified by prep LCMS using Method I, the fractions containing the product was combined and dried using Genevac centrifugal evaporator to afford 5-(7,8-dimethyl-[1,2,4]triazolo[1,5-a]pyridin-6-yl)-2-(6-isobutyl-2,6-diazaspiro[3.3]heptan-2-yl)-6-isopropyl-4H-pyrrolo[3,2-d]thiazole (18.9 mg, 0.039 mmol, 31.9% yield) as a pale yellow solid. LCMS retention time 1.52 min [A]. MS ($E^-$) m/z: 464.2 (M+H).

The following Examples were prepared according to the general procedure described in Example 300.

TABLE 31

| Ex. No. | Structure | HPLC Method | Ret Time (min) | LCMS MH+ |
|---|---|---|---|---|
| 301 | 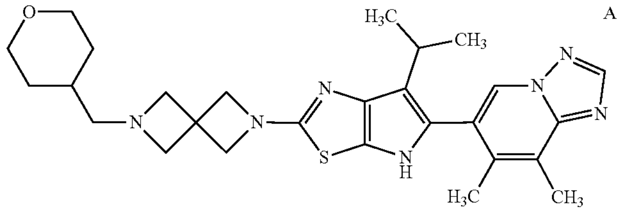 | A | 1.40 | 506.2 |
| 302 | 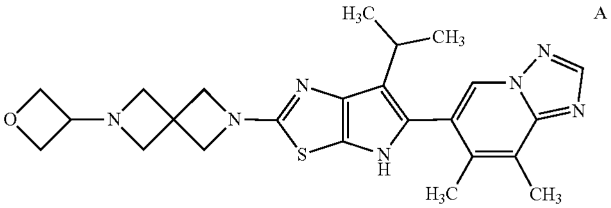 | A | 1.35 | 464.2 |

Example 303

1-(6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptan-2-yl)-2-methylpropan-2-ol (303)

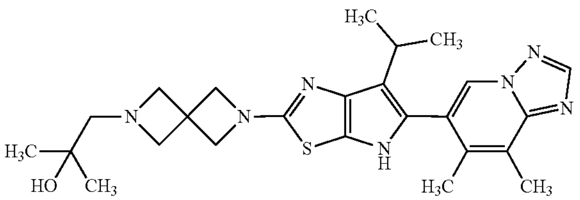

To a solution of 5-(7,8-dimethyl-[1,2,4]triazolo[1,5-a]pyridin-6-yl)-6-isopropyl-2-(2,6-diazaspiro[3.3]heptan-2-yl)-4H-pyrrolo[3,2-d]thiazole (50 mg, 0.123 mmol) and 1-chloro-2-methylpropan-2-ol (13.32 mg, 0.123 mmol) in DMF (1 mL) was added potassium carbonate (16.96 mg, 0.123 mmol). The resulting solution was heated at 80° C. for 12 h. The reaction mass was diluted with water (5 mL) and extracted with ethyl acetate (3×10 mL). The separated organic layer was dried over sodium sulphate, filtered and concentrated. The crude product was purified by prep LCMS using Method I, the fractions containing the product was combined and dried using Genevac centrifugal evaporator to afford 1-(6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptan-2-yl)-2-methylpropan-2-ol (5.6 mg, 0.011 mmol, 9.04% yield) as a pale yellow solid. LCMS retention time 1.28 min [A]. MS ($E^-$) m/z: 480.2 (M+H). $^1$H NMR (400 MHz, DMSO-$d_6$) δ 11.00-10.95 (m, 1H), 8.66 (s, 1H), 8.44 (s, 1H), 4.14-4.05 (m, 2H), 3.91 (s, 2H), 2.65-2.59 (m, 2H), 2.56 (s, 3H), 2.19-2.13 (m, 2H), 1.92 (s, 2H), 1.25 (d, J=6.8 Hz, 5H), 1.15-1.00 (m, 6H).

Example 304

5-(7,8-dimethyl-[1,2,4]triazolo[1,5-a]pyridin-6-yl)-6-isopropyl-2-(6-(2-(methylsulfonyl)ethyl)-2,6-diazaspiro[3.3]heptan-2-yl)-4H-pyrrolo[3,2-d]thiazole (304)

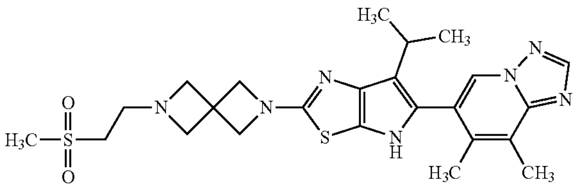

To a solution of 5-(7,8-dimethyl-[1,2,4]triazolo[1,5-a]pyridin-6-yl)-6-isopropyl-2-(2,6-diazaspiro[3.3]heptan-2-yl)-4H-pyrrolo[3,2-d]thiazole (100 mg, 0.245 mmol) and 1-chloro-2-(methylsulfonyl)ethane (35.0 mg, 0.245 mmol) in THF (1 mL) and DMF (1 mL) was added TEA (0.034 mL, 0.245 mmol). The resulting solution was stirred at room temperature for 12 h. The reaction mass was diluted with water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford 5-(7,8-dimethyl-[1,2,4]triazolo[1,5-a]pyridin-6-yl)-6-isopropyl-2-(6-(2-(methylsulfonyl)ethyl)-2,6-diazaspiro[3.3]heptan-2-yl)-4H-pyrrolo[3,2-d]thiazole (23 mg, 0.044 mmol, 18.02% yield) as a pale yellow solid. LCMS retention time 1.81 min [C]. MS ($E^-$) m/z: 514.2 (M+H).

Example 305

5-(6-isopropyl-2-(6-(2-(methylsulfonyl)ethyl)-2,6-diazaspiro[3.3]heptan-2-yl)-4H-pyrrolo[3,2-d]thiazol-5-yl)-1,3,4-trimethylpyridin-2 (1H)-one (305)

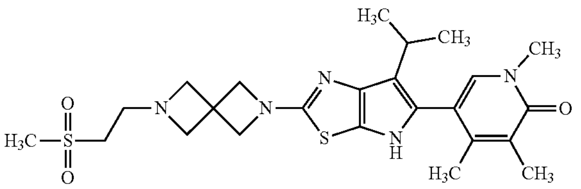

To a solution of 5-(6-isopropyl-2-(2,6-diazaspiro[3.3]heptan-2-yl)-4H-pyrrolo[3,2-d]thiazol-5-yl)-1,3,4-trimethylpyridin-2 (1H)-one (25 mg, 0.063 mmol) and 1-chloro-2-(methylsulfonyl)ethane (8.97 mg, 0.063 mmol) in THF (1 mL) and DMF (1 mL) was added TEA (8.77 μL, 0.063 mmol). The resulting solution was stirred at room temperature for 12 h. The reaction mass was diluted with water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford 5-(6-isopropyl-2-(6-(2-(methylsulfonyl)ethyl)-2,6-diazaspiro[3.3]heptan-2-yl)-4H-pyrrolo[3,2-d]thiazol-5-yl)-1,3,4-trimethylpyridin-2 (1H)-one (13.3 mg, 0.026 mmol, 41.6% yield) as a pale yellow solid. LCMS retention time 1.24 min [A]. MS ($E^-$) m/z: 504.2 (M+H).

Example 306

5-(6-isopropyl-2-(6-(oxetan-3-yl)-2,6-diazaspiro[3.3]heptan-2-yl)-4H-pyrrolo[3,2-d]thiazol-5-yl)-1,3,4-trimethylpyridin-2 (1H)-one (306)

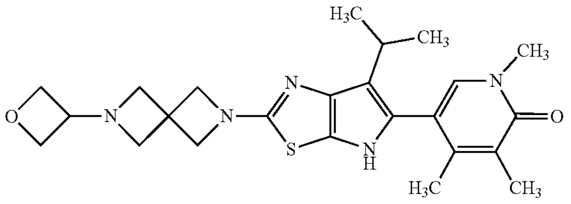

To a solution of 5-(6-isopropyl-2-(2,6-diazaspiro[3.3]heptan-2-yl)-4H-pyrrolo[3,2-d]thiazol-5-yl)-1,3,4-trimethylpyridin-2 (1H)-one (30 mg, 0.075 mmol) and oxetan-3-one (5.44 mg, 0.075 mmol) in methanol (1 mL) was added TEA (10.52 μL, 0.075 mmol) followed by acetic acid (4.32 μL, 0.075 mmol) at 0° C. The resulting solution was stirred at room temperature for 12 h, then sodium cyanoborohydride (9.48 mg, 0.151 mmol) was added at 0° C. and the reaction mixture was stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford 5-(6-isopropyl-2-(6-(oxetan-3-yl)-2,6-diazaspiro[3.3]heptan-2-yl)-4H-pyrrolo[3,2-d]thiazol-5-yl)-1,3,4-trimethylpyridin-2 (1H)-one (1.0 mg, 2.205 μmol, 2.92% yield) as a pale yellow solid. LCMS retention time 1.27 min [A]. MS ($E^-$) m/z: 454.2 (M+H).

The following Example was prepared according to the general procedure described in Example 306.

TABLE 32

| Ex. No. | Structure | HPLC Method | Ret Time (min) | LCMS MH+ |
|---|---|---|---|---|
| 307 | 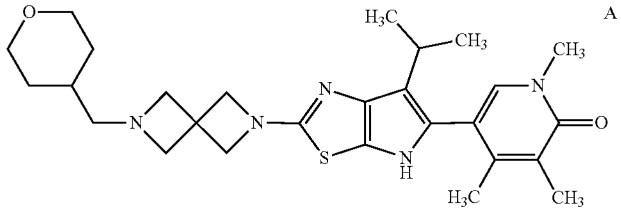 | A | 1.31 | 496.2 |

Example 308

(R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole, HCl (308)

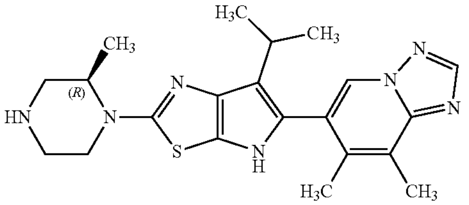

Intermediate 308A: Tert-butyl (R)-4-(5-(7,8-dimethyl-[1,2,4]triazolo[1,5-a]pyridin-6-yl)-6-isopropyl-4H-pyrrolo[3,2-d]thiazol-2-yl)-3-methylpiperazine-1-carboxylate (308A)

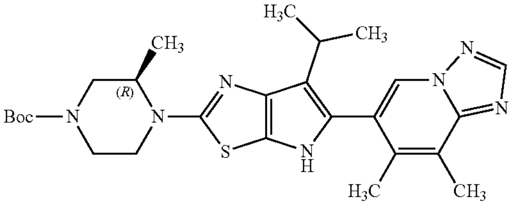

To a solution of 2-bromo-5-(7,8-dimethyl-[1,2,4]triazolo[1,5-a]pyridin-6-yl)-6-isopropyl-4H-pyrrolo[3,2-d]thiazole (2.0 g, 5.12 mmol) and tert-butyl (R)-3-methylpiperazine-1-carboxylate (1.539 g, 7.69 mmol) in dioxane (60 mL) was potassium carbonate (2.125 g, 15.37 mmol). The solution was degassed for 10 min and then XPhos Pd G2 (0.403 g, 0.512 mmol) was added and the reaction mixture was degassed again for 5 min. The resulting reaction mixture was heated at 110° C. for 16 h. The reaction mixture was diluted with water (100 mL) and extracted with EtOAc (2×100 mL). The separated organic layer was dried over sodium sulphate, filtered and concentrated to afford crude product. The crude was purified by combiflash using 40 g silica column by eluting with 65% ethyl acetate\DCM. Following concentration of fractions, collected tert-butyl (R)-4-(5-(7,8-dimethyl-[1,2,4]triazolo[1,5-a]pyridin-6-yl)-6-isopropyl-4H-pyrrolo[3,2-d]thiazol-2-yl)-3-methylpiperazine-1-carboxylate (2.2 g, 4.32 mmol, 84% yield) as a yellow solid. LCMS retention time 3.62 min [C]. MS ($E^-$) m/z: 508.2 (M−H).

The following Intermediates were prepared according to the general procedure described in Intermediate 308A.

TABLE 33

| Int. | Structure | HPLC Method | Ret Time (min) | LCMS MH+ |
|---|---|---|---|---|
| 308B | 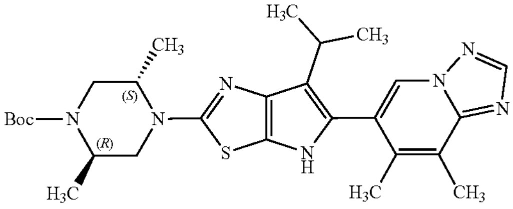 | F | 2.33 | 524.2 |

TABLE 33-continued

| Int. | Structure | HPLC Method | Ret Time (min) | LCMS $MH^+$ |
|---|---|---|---|---|
| 308C | 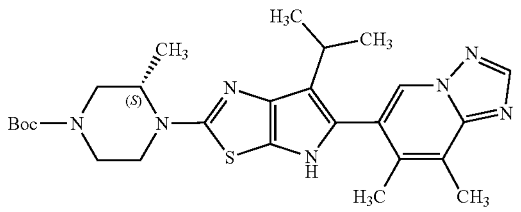 | F | 2.13 | 510.3 |
| 308D | 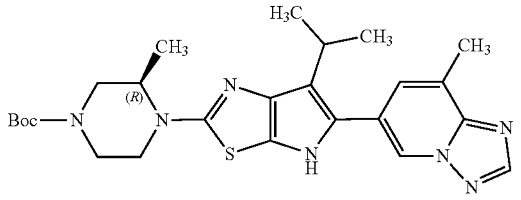 | F | 1.87 | 496.2 |

Example 308: (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole, HCl To a solution tert-butyl (R)-4-(5-(7,8-dimethyl-[1,2,4]triazolo[1,5-a]pyridin-6-yl)-6-isopropyl-4H-pyrrolo[3,2-d]thiazol-2-yl)-3-methylpiperazine-1-carboxylate (2.2 g, 4.32 mmol) in DCM (10 mL) was added 4 M hydrochloric acid in dioxane (10 mL, 329 mmol) dropwise and stirred at room temperature for 12 h. The reaction mass was diluted with water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole, HCl (1.9 g, 4.18 mmol, 97% yield) as a pale yellow solid. LCMS retention time 1.31 min [A]. MS ($E^-$) m/z: 410.2 (M+H). $^1$H NMR (400 MHz, DMSO-$d_6$) δ 10.91 (s, 1H) 8.65 (s, 1H) 8.43 (s, 1H) 3.92 (br dd, J=5.14, 2.69 Hz, 1H) 3.45-3.49 (m, 1H) 2.93-2.98 (m, 1H) 2.85-2.91 (m, 1H) 2.74-2.80 (m, 1H) 2.60-2.71 (m, 1H) 2.56 (s, 3H) 2.19 (s, 3H) 1.26 (d, J=6.85 Hz, 9H).

The following Examples were prepared according to the general procedure described in Example 308.

TABLE 34

| Ex. No. | Structure | HPLC Method | Ret Time (min) | LCMS $MH^+$ |
|---|---|---|---|---|
| 309 | 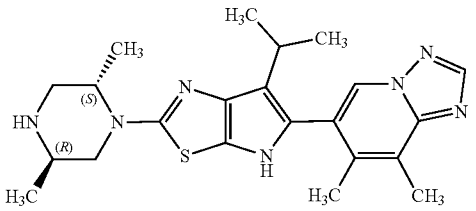 | A | 1.34 | 424.2 |
| 310 | 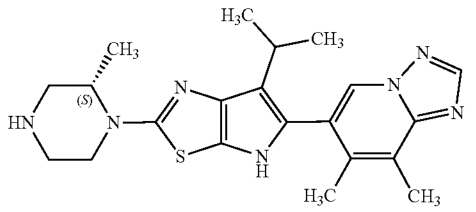 | A | 1.35 | 410.1 |

TABLE 34-continued

| Ex. No. | Structure | HPLC Method | Ret Time (min) | LCMS MH+ |
|---|---|---|---|---|
| 311 | 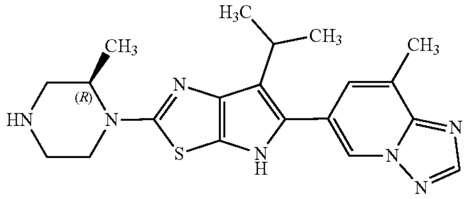 | A | 1.13 | 396.2 |

Example 312

(R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N,N-dimethylacetamide (312)

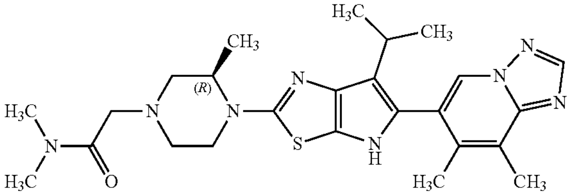

To a solution of (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (50 mg, 0.122 mmol) and 2-chloro-N,N-dimethylacetamide (14.84 mg, 0.122 mmol) in DMF (1 mL) and THE (2 mL) was added TEA (0.017 mL, 0.122 mmol). The resulting solution was stirred at room temperature for 12 h. The reaction mass was diluted with water (5 mL) and extracted with EtOAc (3×10 mL). The separated organic layer was dried over sodium sulphate, filtered and concentrated. The crude sample was purified by prep LCMS Method I to afford (R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N,N-dimethylacetamide (27 mg, 0.054 mmol, 44.3% yield) as a pale yellow solid. LCMS retention time 1.71 min [A]. MS ($E^-$) m/z: 495.3 (M+H). $^1$H NMR (400 MHz, DMSO-$d_6$) δ 10.94 (s, 1H) 8.66 (s, 1H) 8.43 (s, 1H) 3.99-4.10 (m, 1H) 3.51-3.62 (m, 1H) 3.12-3.28 (m, 3H) 3.08 (s, 3H) 2.89 (br d, J=11.49 Hz, 1H) 2.84 (s, 3H) 2.74 (br d, J=11.00 Hz, 1H) 2.63 (dt, J=13.63, 6.76 Hz, 1H) 2.56 (s, 3H) 2.39 (dd, J=11.25, 3.42 Hz, 1H) 2.19-2.29 (m, 1H) 2.19 (s, 2H) 1.24-1.31 (m, 9H).

The following Examples were prepared according to the general procedure described in Example 312.

TABLE 35

| Ex. No. | Structure | HPLC Method | Ret Time (min) | LCMS MH+ |
|---|---|---|---|---|
| 313 | 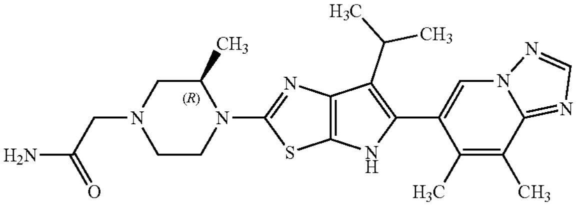 | A | 1.52 | 467.2 |
| 314 | 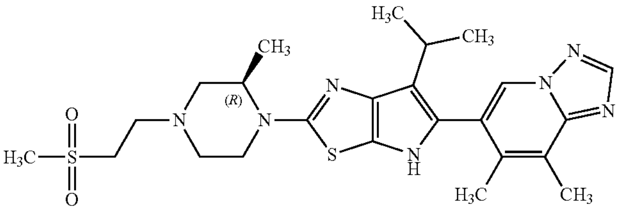 | A | 1.68 | 516.2 |

TABLE 35-continued

| Ex. No. | Structure | HPLC Method | Ret Time (min) | LCMS MH+ |
|---|---|---|---|---|
| 315 | 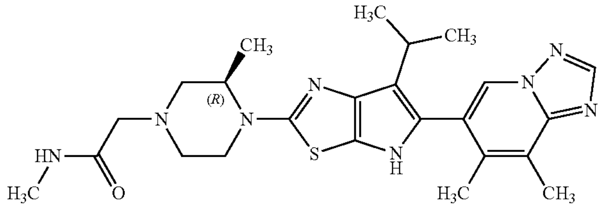 | A | 1.62 | 481.2 |

Example 316

(R)-5-(7,8-dimethyl-[1,2,4]triazolo[1,5-a]pyridin-6-yl)-6-isopropyl-2-(2-methyl-4-(oxetan-3-yl)piperazin-1-yl)-4H-pyrrolo[3,2-d]thiazole (316)

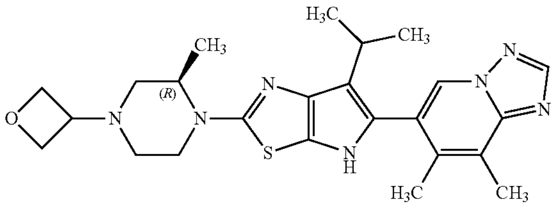

To a solution of (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (50 mg, 0.122 mmol) and oxetan-3-one (8.80 mg, 0.122 mmol) in methanol (1 mL) was added TEA (0.017 mL, 0.122 mmol) at 0° C. The resulting solution was stirred at room temperature for 12 h. Then sodium cyanoborohydride (15.34 mg, 0.244 mmol) was added at 0° C. and the reaction mixture was stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford (R)-5-(7,8-dimethyl-[1,2,4]triazolo[1,5-a]pyridin-6-yl)-6-isopropyl-2-(2-methyl-4-(oxetan-3-yl)piperazin-1-yl)-4H-pyrrolo[3,2-d]thiazole (22 mg, 0.043 mmol, 35.6% yield) as a pale yellow solid. LCMS retention time 1.78 min [A]. MS ($E^-$) m/z: 466.2 (M+H).

The following Examples were prepared according to the general procedure described in Example 316.

TABLE 36

| Ex. No. | Structure | HPLC Method | Ret Time (min) | LCMS MH+ |
|---|---|---|---|---|
| 317 | 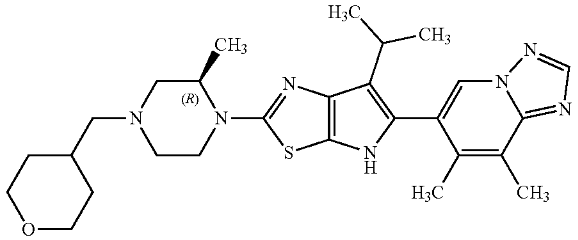 | A | 2.24 | 508.2 |
| 318 | 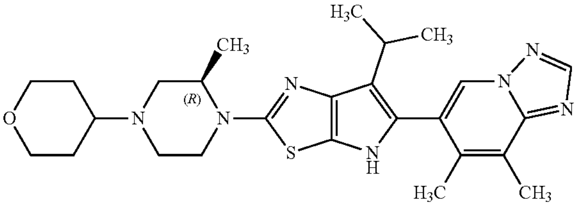 | A | 1.98 | 494.3 |

TABLE 36-continued
| Ex. No. | Structure | HPLC Method | Ret Time (min) | LCMS MH+ |
|---|---|---|---|---|
| 319 | 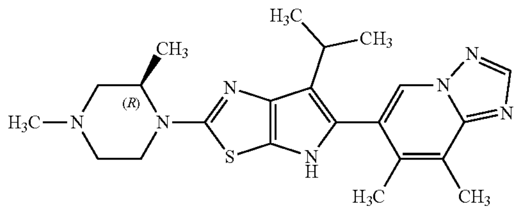 | A | 1.81 | 424.2 |
| 320 | 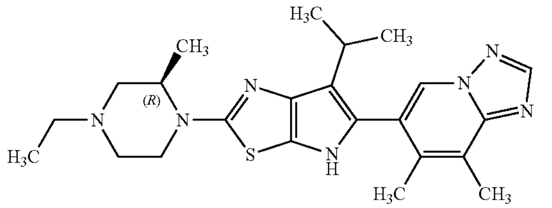 | A | 2.01 | 438.2 |
| 322 | 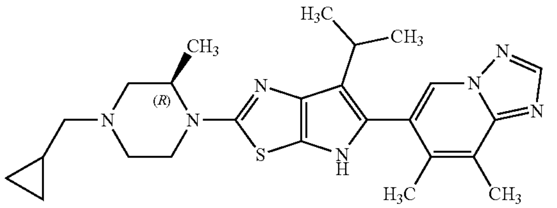 | A | 2.26 | 464.2 |
| 323 | 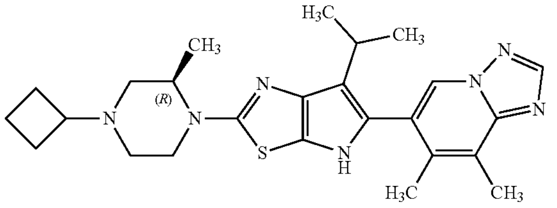 | A | 2.41 | 464.2 |
| 324 | 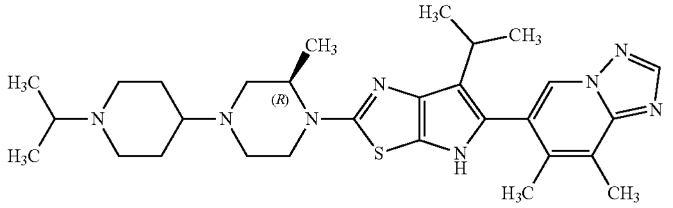 | A | 1.51 | 535.2 |

Example 325

(R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol

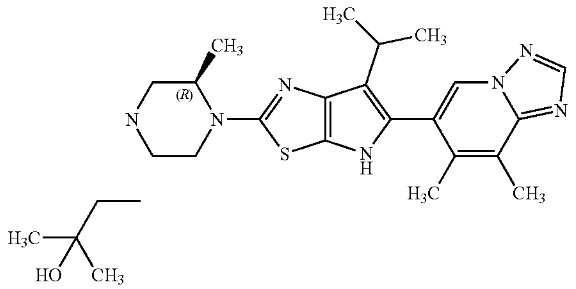

To a solution of (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (50 mg, 0.122 mmol) and 1-chloro-2-methylpropan-2-ol (13.25 mg, 0.122 mmol) in DMF (1 mL) was added potassium carbonate (16.87 mg, 0.122 mmol). The resulting solution was heated at 80° C. for 12 h. The reaction mass was diluted with water (5 mL) and extracted with EtOAc (3x10 mL). The separated organic layer was dried over sodium sulphate, filtered and concentrated. The crude sample was purified by prep LCMS using Method I, the fractions containing the product was combined and dried using Genevac centrifugal evaporator to afford (R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol (14.9 mg, 0.030 mmol, 24.83% yield) as a pale yellow solid. LCMS retention time 2.03 min [A]. MS ($E^-$) m/z: 482.2 (M+H). $^1H$ NMR (400 MHz, DMSO-$d_6$) δ ppm 10.92 (s, 1H) 8.66 (s, 1H) 8.43 (s, 1H) 4.16 (s, 1H) 3.95-4.04 (m, 1H) 3.52 (br d, J=12.23 Hz, 1H) 3.27 (td, J=12.10, 2.93 Hz, 1H) 3.18 (d, J=5.14 Hz, 1H) 2.99 (br d, J=11.00 Hz, 1H) 2.90 (br d, J=11.00 Hz, 2H) 2.59-2.67 (m, 1H) 2.56 (s, 2H) 2.43 (dd, J=11.37, 3.30 Hz, 1H) 2.16-2.32 (m, 4H) 2.08 (s, 2H) 1.24-1.36 (m, 6H) 1.14 (d, J=6.11 Hz, 6H).

Example 326

(R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(methylamino)ethan-1-one

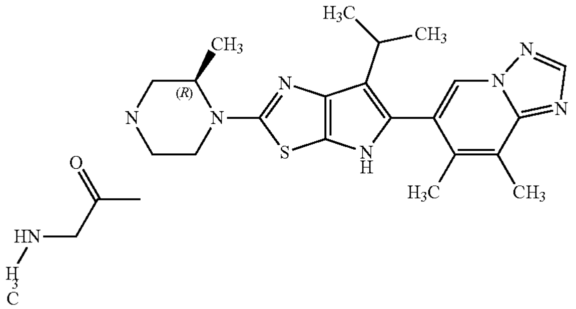

Intermediate 326A: Tert-butyl (R)-(2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-oxoethyl)(methyl) carbamate (326A)

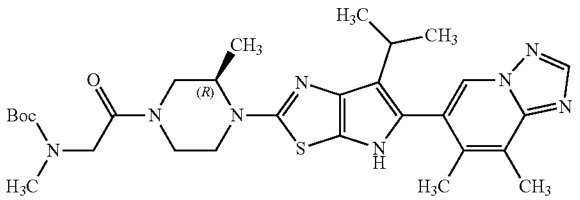

To a solution of (R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (50 mg, 0.122 mmol) and N-(tert-butoxycarbonyl)-N-methylglycine (23.10 mg, 0.122 mmol) in DMF (1 mL) was added HATU (46.4 mg, 0.122 mmol) followed by TEA (0.017 mL, 0.122 mmol). The resulting solution was stirred at room temperature for 12 h. The reaction mass was diluted with water (5 mL) and extracted with EtOAc (3x10 mL). The separated organic layer was dried over sodium sulphate, filtered and dried to afford tert-butyl (R)-(2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-oxoethyl)(methyl)carbamate (50 mg, 0.086 mmol, 70.5% yield) as a yellow solid. LCMS retention time 1.88 min [F]. MS ($E^-$) m/z: 581.2.

Example 326: (R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(methylamino)ethan-1-one To a solution tert-butyl (R)-(2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-oxoethyl)(methyl) carbamate (50 mg, 0.086 mmol) in DCM (2 mL) was added 4M hydrochloric acid in dioxane (1 mL, 32.9 mmol) dropwise and stirred at room temperature for 12 h. The reaction mass was diluted with water (5 mL) and extracted with EtOAc (3x10 mL). The separated organic layer was dried over sodium sulphate, filtered and concentrated. The crude sample was purified by prep LCMS using Method I, the fractions containing the product was combined and dried using Genevac centrifugal evaporator to afford (R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(methylamino)ethan-1-one (27 mg, 0.053 mmol, 61.3% yield) as a pale yellow solid. LCMS retention time 1.29 min [A]. MS ($E^-$) m/z: 481.2 (M+H). $^1H$ NMR (400 MHz, DMSO-$d_6$) δ ppm 10.96-11.03 (m, 1H) 8.64-8.84 (m, 3H) 8.45 (s, 1H) 6.96-7.27 (m, 1H) 3.96-4.44 (m, 5H) 3.65-3.80 (m, 3H) 3.33 (br d, J=9.54 Hz, 1H) 3.09-3.25 (m, 2H) 2.80-3.05 (m, 1H) 2.54-2.69 (m, 6H) 2.18 (s, 3H) 1.21-1.30 (m, 6H).

The following Example was prepared according to the general procedure described in Example 326:

| Ex. No. | Structure | HPLC Method | Ret Time (min) | LCMS MH+ |
|---|---|---|---|---|
| 327 | 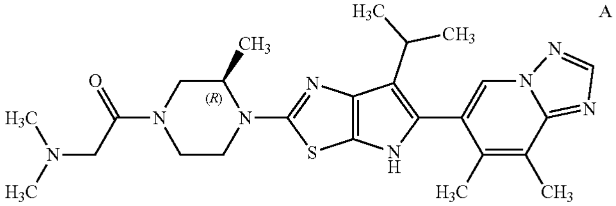 | A | 1.44 | 495.2 |

Example 328

2-((2S,5R)-2,5-dimethyl-4-(oxetan-3-yl)piperazin-1-yl)-5-(7,8-dimethyl-[1,2,4]triazolo[1,5-a]pyridin-6-yl)-6-isopropyl-4H-pyrrolo[3,2-d]thiazole (328)

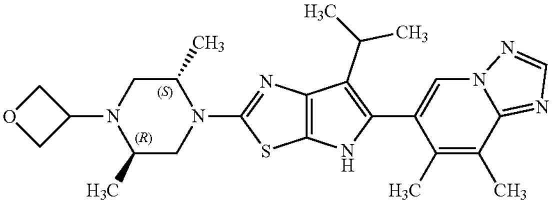

To a solution of 5-(7,8-dimethyl-[1,2,4]triazolo[1,5-a]pyridin-6-yl)-2-((2S,5R)-2,5-dimethylpiperazin-1-yl)-6-isopropyl-4H-pyrrolo[3,2-d]thiazole (50 mg, 0.118 mmol) and oxetan-3-one (8.51 mg, 0.118 mmol) in methanol (1 mL) was added acetic acid (6.76 μL, 0.118 mmol) at 0° C. The resulting solution was stirred at room temperature for 12 h. Then sodium cyanoborohydride (14.84 mg, 0.236 mmol) was added at 0° C. and stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford 2-((2S,5R)-2,5-dimethyl-4-(oxetan-3-yl)piperazin-1-yl)-5-(7,8-dimethyl-[1,2,4]triazolo[1,5-a]pyridin-6-yl)-6-isopropyl-4H-pyrrolo[3,2-d]thiazole) as a pale yellow solid. LCMS retention time 1.88 min [A]. MS ($E^-$) m/z: 480.2 (M+H).

The following Examples were prepared according to the general procedure described in Example 328.

TABLE 37

| Ex. No. | Structure | HPLC Method | Ret Time (min) | LCMS MH+ |
|---|---|---|---|---|
| 329 | 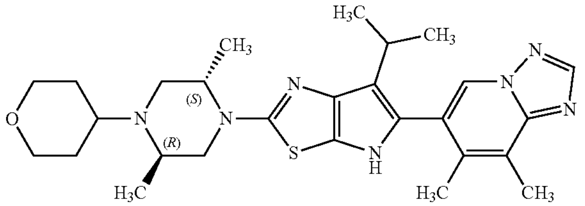 | A | 2.06 | 508.2 |
| 330 | 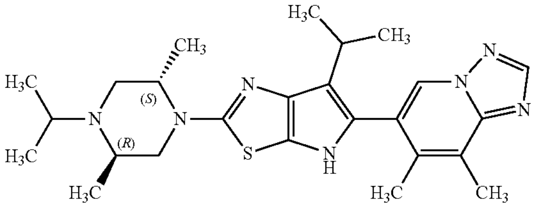 | A | 2.13 | 466.3 |
| 331 | 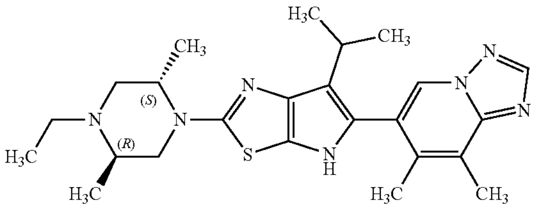 | A | 2.01 | 452.2 |

TABLE 37-continued

| Ex. No. | Structure | HPLC Method | Ret Time (min) | LCMS MH+ |
|---|---|---|---|---|
| 332 | 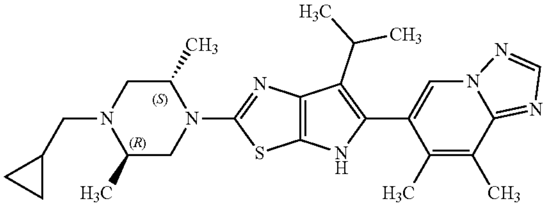 | A | 2.31 | 478.2 |
| 333 | 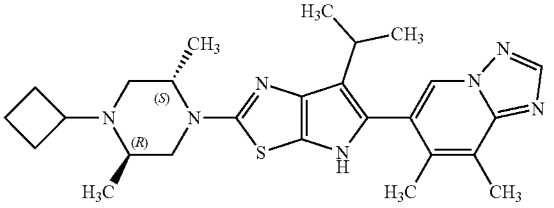 | A | 2.50 | 478.3 |
| 334 | 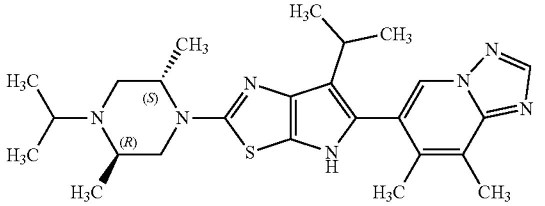 | A | 1.60 | 549.2 |

Example 335

2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-N,N-dimethylacetamide (335)

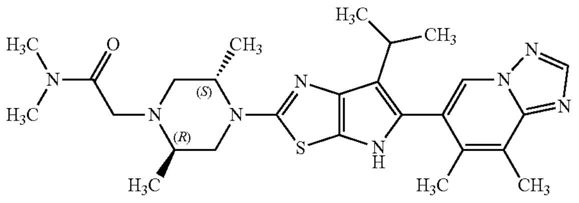

To a solution of 5-(7,8-dimethyl-[1,2,4]triazolo[1,5-a]pyridin-6-yl)-2-((2S,5R)-2,5-dimethylpiperazin-1-yl)-6-isopropyl-4H-pyrrolo[3,2-d]thiazole (50 mg, 0.118 mmol) and 2-chloro-N,N-dimethylacetamide (14.35 mg, 0.118 mmol) in DMF (1 mL) and THE (2 mL) was added TEA (0.016 mL, 0.118 mmol). The resulting solution was stirred at room temperature for 12 h. The reaction mass was diluted with water (5 mL) and extracted with EtOAc (3x10 mL). The separated organic layer was dried over sodium sulphate, filtered and concentrated. The crude sample was purified by prep LCMS using Method I, the fractions containing the product was combined and dried using Genevac centrifugal evaporator to afford 2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-N,N-dimethylacetamide (19 mg, 0.037 mmol, 31.3% yield) as a pale yellow solid. LCMS retention time 1.79 min [A]. MS ($E^-$) m/z: 509.2 (M+H).

The following Examples were prepared according to the general procedure described in Example 335.

TABLE 38

| Ex. No. | Structure | HPLC Method | Ret Time (min) | LCMS MH+ |
|---|---|---|---|---|
| 336 | 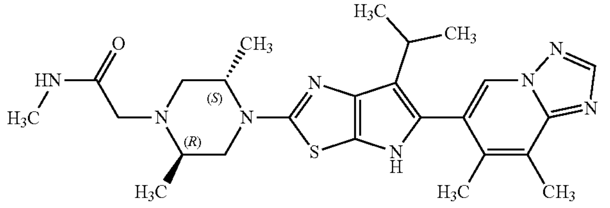 | A | 1.69 | 495.2 |
| 337 | 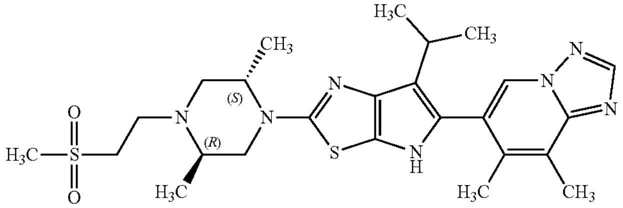 | A | 1.76 | 530.2 |
| 338 | 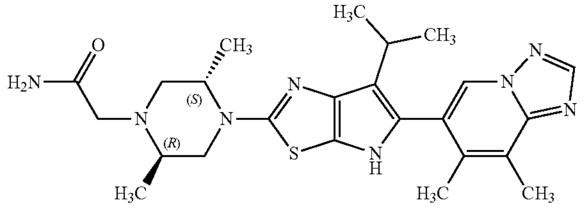 | A | 1.58 | 481.3 |

Example 339

1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-methylpropan-2-ol (339)

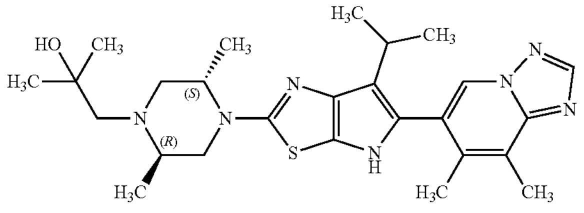

To a solution of 5-(7,8-dimethyl-[1,2,4]triazolo[1,5-a]pyridin-6-yl)-2-((2S,5R)-2,5-dimethylpiperazin-1-yl)-6-isopropyl-4H-pyrrolo[3,2-d]thiazole (50 mg, 0.118 mmol) and 1-chloro-2-methylpropan-2-ol (12.82 mg, 0.118 mmol) in DMF (1 mL) was added potassium carbonate (32.6 mg, 0.236 mmol). The resulting solution was heated at 80° C. for 12 h. The reaction mass was diluted with water (5 mL) and extracted with EtOAc (3x10 mL). The separated organic layer was dried over sodium sulphate, filtered and concentrated. The crude sample was purified by prep LCMS using Method I, the fractions containing the product was combined and dried using Genevac centrifugal evaporator to afford 1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-methylpropan-2-ol (14 mg, 0.027 mmol, 22.97% yield) as a pale yellow solid. LCMS retention time 2.13 min [A]. MS ($E^-$) m/z: 496.2 (M+H).

Example 340

1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(methylamino)ethan-1-one (340)

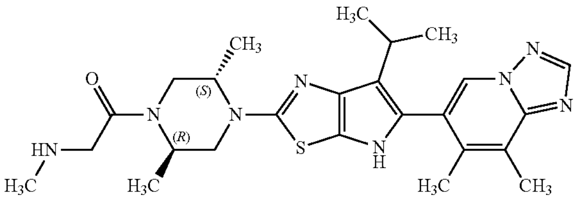

Intermediate 340A: Tert-butyl (2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-oxoethyl)(methyl)carbamate (340A)

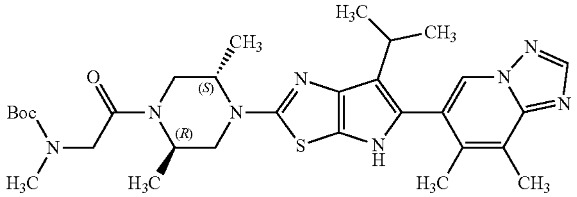

To a solution of 5-(7,8-dimethyl-[1,2,4]triazolo[1,5-a]pyridin-6-yl)-2-((2S,5R)-2,5-dimethylpiperazin-1-yl)-6-isopropyl-4H-pyrrolo[3,2-d]thiazole (50 mg, 0.118 mmol) and N-(tert-butoxycarbonyl)-N-methylglycine (22.33 mg, 0.118 mmol) in DMF (1 mL) was added HATU (44.9 mg, 0.118 mmol) followed by TEA (0.016 mL, 0.118 mmol). The resulting solution was stirred at room temperature for 12 h. The reaction mass was diluted with water (5 mL) and extracted with EtOAc (3×10 mL). The separated organic layer was dried over sodium sulphate, filtered and dried to afford tert-butyl (2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-oxoethyl)(methyl)carbamate (45 mg, 0.076 mmol, 64.1% yield) as a yellow solid. LCMS retention time 2.09 min [F]. MS ($E^-$) m/z: 595.2.

Example 340: 1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(methylamino)ethan-1-one To a solution tert-butyl (2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-oxoethyl)(methyl)carbamate (45 mg, 0.076 mmol) in DCM (2 mL) was added 4 M hydrochloric acid in dioxane (1 mL, 32.9 mmol) dropwise and stirred at room temperature for 12 h. The reaction mass was diluted with water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford 1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(methylamino)ethan-1-one (22 mg, 0.044 mmol, 58.2% yield) as a pale yellow solid. LCMS retention time 1.34 min [A]. MS ($E^-$) m/z: 495.2 (M+H).

The following Example was prepared according to the general procedure described in Example 340.

TABLE 39

| Ex. No. | Structure | HPLC Method | Ret Time (min) | LCMS $MH^+$ |
|---|---|---|---|---|
| 341 | 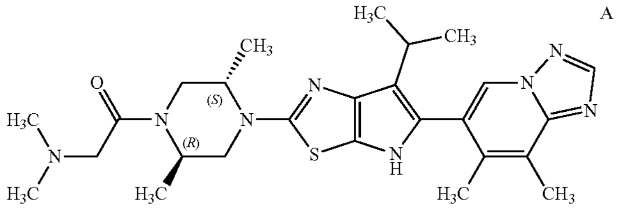 | A | 1.54 | 509.2 |

Example 342

(S)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N-methylacetamide

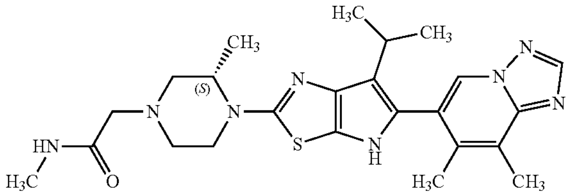

(342)

To a solution of (S)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (30 mg, 0.073 mmol) and 2-bromo-N-methylacetamide (11.13 mg, 0.073 mmol) in DMF (1 mL) and THE (2 mL) was added TEA (10.21 µl, 0.073 mmol). The resulting solution was stirred at room temperature for 12 h. The reaction mass was diluted with water (5 mL) and extracted with EtOAc (3x10 mL). The separated organic layer was dried over sodium sulphate, filtered and concentrated. The crude sample was purified by prep LCMS using Method I, the fractions containing the product was combined and dried using Genevac centrifugal evaporator to afford (S)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N-methylacetamide (8 mg, 0.017 mmol, 22.72% yield) as a pale yellow solid. LCMS retention time 1.60 min [A]. MS ($E^-$) m/z: 481.2 (M+H).

The following Examples were prepared according to the general procedure described in Example 342.

TABLE 40

| Ex. No. | Structure | HPLC Method | Ret Time (min) | LCMS MH+ |
|---|---|---|---|---|
| 343 | 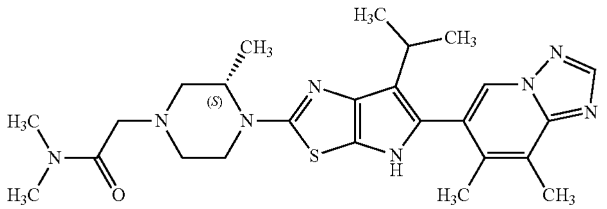 | A | 1.75 | 495.2 |
| 344 | 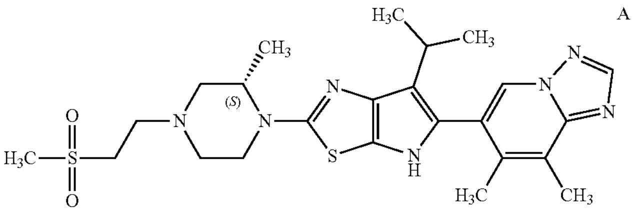 | A | 1.64 | 516.2 |

Example 345

(S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol

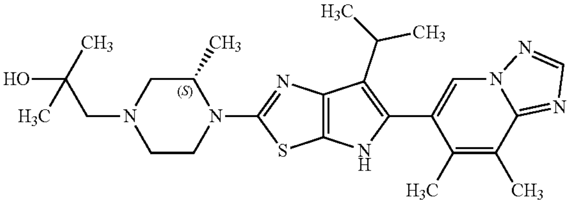

(345)

To a solution of (S)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (30 mg, 0.073 mmol) and 1-chloro-2-methylpropan-2-ol (11.21 mg, 0.073 mmol) in DMF (1 mL) was added potassium carbonate (10.12 mg, 0.073 mmol). The resulting solution was heated at 80° C. for 12 h. The reaction mass was diluted with water (5 mL) and extracted with EtOAc (3x10 mL). The separated organic layer was dried over sodium sulphate, filtered and concentrated. The crude sample was purified by prep LCMS using Method I, the fractions containing the product was combined and dried using Genevac centrifugal evaporator to afford (S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol (4.1 mg, 8.51 μmol, 11.62% yield) as a pale yellow solid. LCMS retention time 2.09 min [A]. MS ($E^-$) m/z: 482.2 (M+H).

Example 346

(S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(dimethylamino) ethan-1-one (346)

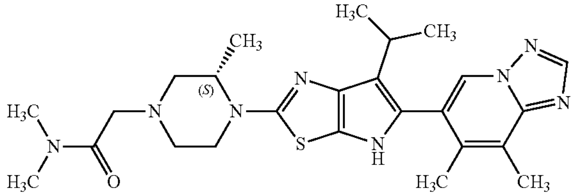

To a solution of (S)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (30 mg, 0.073 mmol) and dimethyl glycine (7.55 mg, 0.073 mmol) in DMF (1 mL) was added HATU (27.9 mg, 0.073 mmol) followed by TEA (10.21 μL, 0.073 mmol). The resulting solution was stirred at room temperature for 12 h. The reaction mass was diluted with water (5 mL) and extracted with EtOAc (3×10 mL). The crude sample was purified by prep LCMS using Method I, the fractions containing the product was combined and dried using Genevac centrifugal evaporator to afford (S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(dimethylamino)ethan-1-one (17 mg, 0.032 mmol, 44.1% yield) as a pale yellow solid. LCMS retention time 1.50 min [A]. MS ($E^-$) m/z: 495.2 (M+H).

The following Example was prepared according to the general procedure described in Example 346.

TABLE 41

| Ex. No. | Structure | HPLC Method | Ret Time (min) | LCMS $MH^+$ |
|---|---|---|---|---|
| 347 | 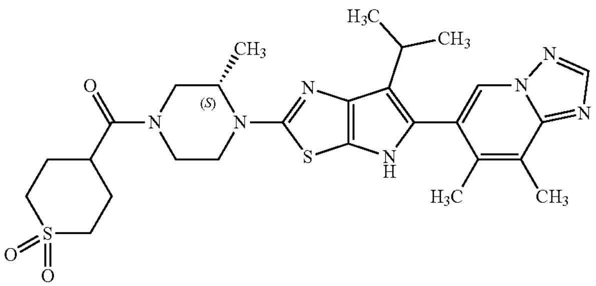 | A | 1.49 | 570.3 |

Example 348

(S)-5-(7,8-dimethyl-[1,2,4]triazolo[1,5-a]pyridin-6-yl)-6-isopropyl-2-(2-methyl-4-(oxetan-3-yl)piperazin-1-yl)-4H-pyrrolo[3,2-d]thiazole (348)

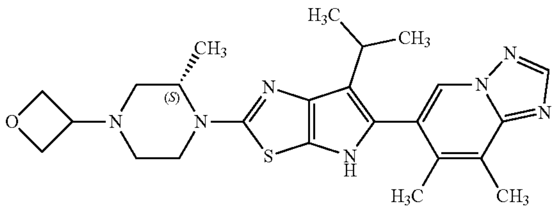

To a solution of (S)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (30 mg, 0.073 mmol) and oxetan-3-one (5.28 mg, 0.073 mmol) in methanol (1 mL) was added TEA (10.21 μL, 0.073 mmol) at 0° C. The resulting solution was stirred at room temperature for 12 h. Then sodium cyanoborohydride (9.21 mg, 0.147 mmol) was added at 0° C. and the reaction mixture was stirred for 2 h at room temperature. The reaction mass was concentrated, residue was dissolved in water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford (S)-5-(7,8-dimethyl-[1,2,4]triazolo[1,5-a]pyridin-6-yl)-6-isopropyl-2-(2-methyl-4-(oxetan-3-yl)piperazin-1-yl)-4H-pyrrolo[3,2-d]thiazole (15 mg, 0.032 mmol, 44.000 yield) as a pale yellow solid. LCMS retention time 1.78 min [A]. MS ($E^-$) m/z: 466.2 (M+H).

The following Examples were prepared according to the general procedure described in Example 348.

Example 353

To a solution of (R)-6-isopropyl-5-(8-methyl-[1,2,4]triazolo[1,5-a]pyridin-6-yl)-2-(2-methylpiperazin-1-yl)-4H-

TABLE 42

| Ex. No. | Structure | HPLC Method | Ret Time (min) | LCMS MH+ |
|---|---|---|---|---|
| 349 | 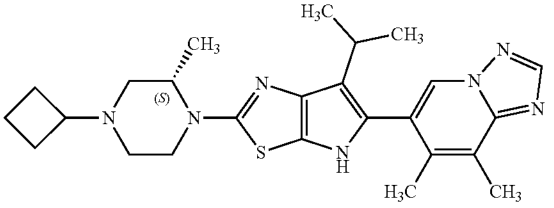 | A | 2.37 | 464.2 |
| 350 | 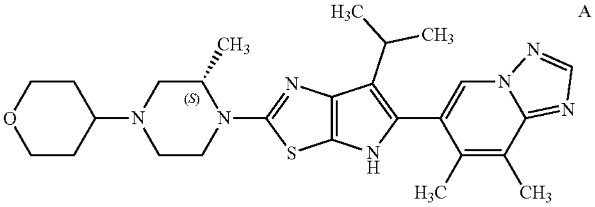 | A | 1.96 | 494.3 |
| 351 | 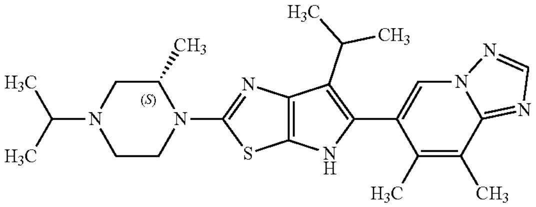 | A | 2.27 | 452.2 |
| 352 | 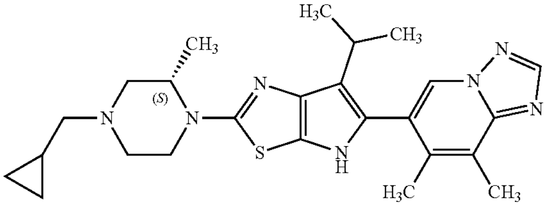 | A | 2.24 | 464.2 |

(R)-2-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-N-methylacetamide (353)

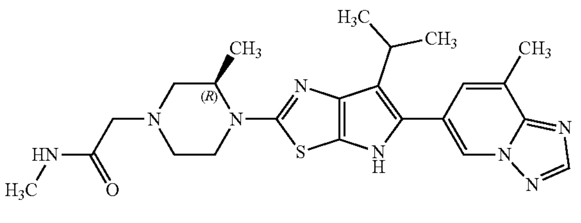

pyrrolo[3,2-d]thiazole (50 mg, 0.126 mmol) and 2-bromo-N-methylacetamide (19.21 mg, 0.126 mmol) in DMF (1 mL) and THF (2 mL) was added TEA (0.018 mL, 0.126 mmol). The resulting solution was stirred at room temperature for 12 h. The reaction mass was diluted with water (5 mL) and extracted with ethyl acetate (3×10 mL). The separated organic layer was dried over sodium sulphate, filtered and concentrated. The crude sample was purified by prep LCMS using Method I, the fractions containing the product was combined and dried using Genevac centrifugal evaporator to (R)-2-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-N-methylacetamide (24 mg, 0.047 mmol, 37.5% yield) as a pale yellow solid. LCMS retention time 1.45 min [A]. MS ($E^-$) m/z: 467.2 (M+H).

The following Examples were prepared according to the general procedure described in Example 353.

TABLE 43
| Ex. No. | Structure | HPLC Method | Ret Time (min) | LCMS MH+ |
|---|---|---|---|---|
| 354 | 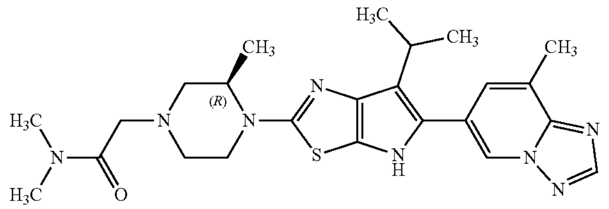 | A | 1.46 | 481.2 |
| 355 | 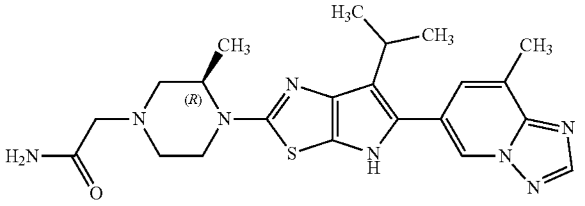 | A | 1.37 | 453.2 |
| 356 | 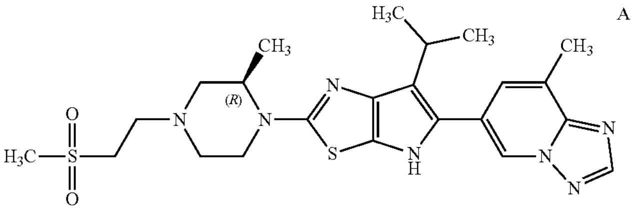 | A | 1.45 | 502.3 |
| 357 | 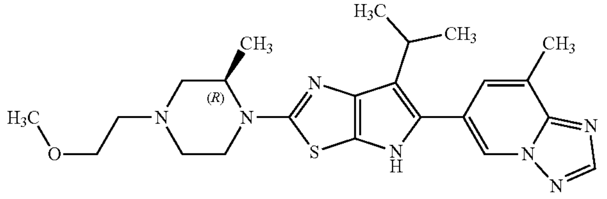 | A | 1.52 | 454.3 |
| 358 | 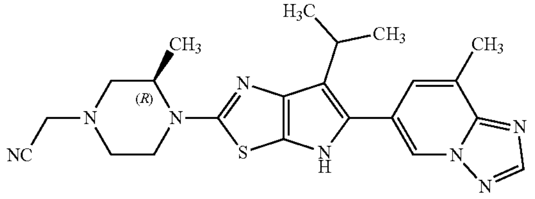 | A | 1.54 | 435.3 |

Example 359

(R)-1-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-2-methylpropan-2-ol (359)

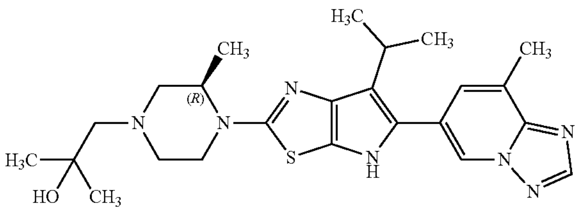

To a solution of (R)-6-isopropyl-5-(8-methyl-[1,2,4]triazolo[1,5-a]pyridin-6-yl)-2-(2-methylpiperazin-1-yl)-4H-pyrrolo[3,2-d]thiazole (50 mg, 0.126 mmol) and 1-chloro-2-methylpropan-2-ol (13.72 mg, 0.126 mmol) in DMF (1 mL) was added potassium carbonate (34.9 mg, 0.253 mmol). The resulting solution was heated at 80° C. for 12 h. The reaction mass was diluted with water (5 mL) and extracted with EtOAc (3×10 mL). The separated organic layer was dried over sodium sulphate, filtered and concentrated. The crude sample was purified by prep LCMS using Method I, the fractions containing the product was combined and dried using Genevac centrifugal evaporator to afford (R)-1-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)-2-methylpropan-2-ol (4.2 mg, 8.98 μmol, 7.10% yield) as a pale yellow solid. LCMS retention time 1.68 min [A]. MS ($E^-$) m/z: 468.2 (M+H).

Example 360

(R)-2-(dimethylamino)-1-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)ethan-1-one (360)

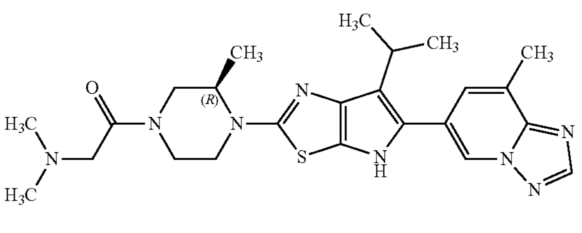

To a solution of (R)-6-isopropyl-5-(8-methyl-[1,2,4]triazolo[1,5-a]pyridin-6-yl)-2-(2-methylpiperazin-1-yl)-4H-pyrrolo[3,2-d]thiazole (50 mg, 0.126 mmol) and dimethylglycine (13.04 mg, 0.126 mmol) in DMF (1 mL) was added HATU (48.1 mg, 0.126 mmol) followed by TEA (0.018 mL, 0.126 mmol). The resulting solution was stirred at room temperature for 12 h. The reaction mass was diluted with water (5 mL) and extracted with EtOAc (3×10 mL). The crude sample was purified by prep LCMS using Method I, the fractions containing the product was combined and dried using Genevac centrifugal evaporator to afford (R)-2-(dimethylamino)-1-(4-(6-isopropyl-5-(8-methyl-[1,2,4]triazolo[1,5-a]pyridin-6-yl)-4H-pyrrolo[3,2-d]thiazol-2-yl)-3-methylpiperazin-1-yl)ethan-1-one (18 mg, 0.037 mmol, 29.3% yield) as a pale yellow solid. LCMS retention time 1.27 min [A]. MS ($E^-$) m/z: 481.2 (M+H).

Example 361

(R)-2-(4-isobutyl-2-methylpiperazin-1-yl)-6-isopropyl-5-(8-methyl-[1,2,4]triazolo[1,5-a]pyridin-6-yl)-4H-pyrrolo[3,2-d]thiazole (361)

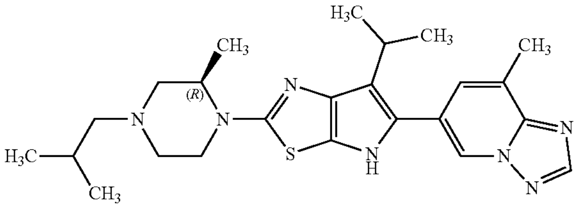

To a solution of (R)-6-isopropyl-5-(8-methyl-[1,2,4]triazolo[1,5-a]pyridin-6-yl)-2-(2-methylpiperazin-1-yl)-4H-pyrrolo[3,2-d]thiazole (50 mg, 0.126 mmol) and isobutyraldehyde (9.12 mg, 0.126 mmol) in methanol (1 mL) was added TEA (0.018 mL, 0.126 mmol) at 0° C. The resulting solution was stirred at room temperature for 12 h. Then sodium cyanoborohydride (15.89 mg, 0.253 mmol) was added at 0° C. and stirred for 2 h at room temperature. The reaction mass was concentrated, residue was dissolved in water (5 mL) and extracted with ethyl acetate (3×10 mL). The separated organic layer was dried over sodium sulphate, filtered and concentrated. The crude sample was purified by prep LCMS using Method I, the fractions containing the product was combined and dried using Genevac centrifugal evaporator to afford (R)-2-(4-isobutyl-2-methylpiperazin-1-yl)-6-isopropyl-5-(8-methyl-[1,2,4]triazolo[1,5-a]pyridin-6-yl)-4H-pyrrolo[3,2-d]thiazole (27 mg, 0.060 mmol, 47.3% yield) as a pale yellow solid. LCMS retention time 1.27 min [B]. MS ($E^-$) m/z: 452.2 (M+H).

The following Examples were prepared according to the general procedure described in Example 361.

TABLE 44
| Ex. No. | Structure | HPLC Method | Ret Time (min) | LCMS MH+ |
|---|---|---|---|---|
| 362 | 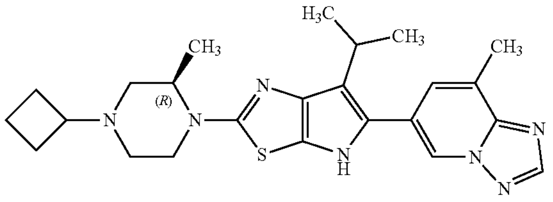 | A | 1.71 | 450.2 |
| 363 | 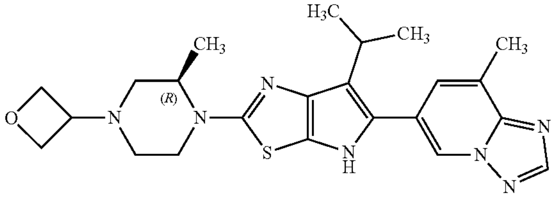 | A | 1.47 | 452.3 |
| 364 | 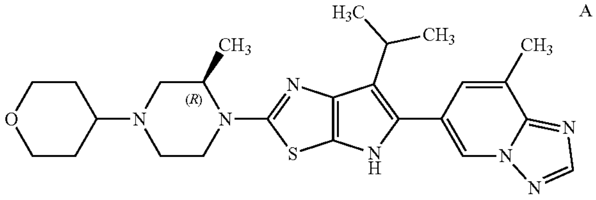 | A | 1.49 | 480.2 |
| 365 | 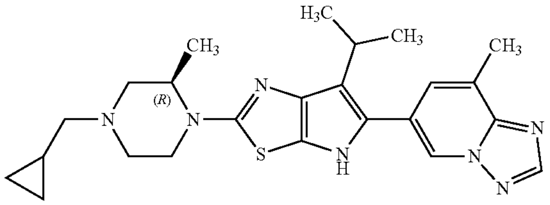 | A | 1.59 | 450.2 |
| 366 | 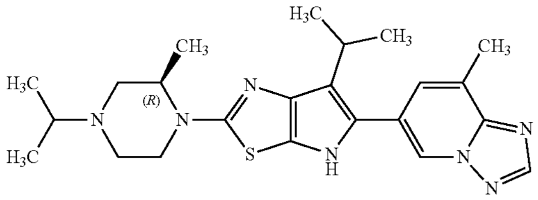 | A | 1.31 | 521.2 |
| 367 | 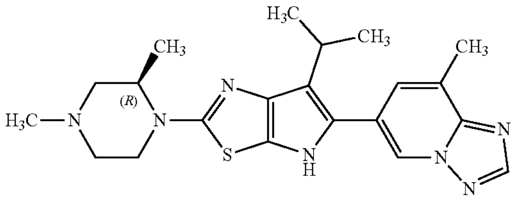 | A | 1.36 | 410.2 |

Examples 368 and 369

5-(7,8-dimethyl-[1,2,4]triazolo[1,5-a]pyridin-6-yl)-N-(4-(dimethylamino)cyclohexyl)-6-isopropyl-4H-pyrrolo[3,2-d]thiazole-2-carboxamide (368 and 369)

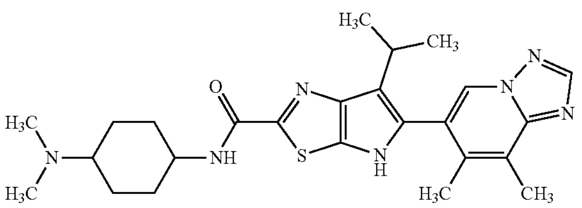

To a solution of 5-(7,8-dimethyl-[1,2,4]triazolo[1,5-a]pyridin-6-yl)-6-isopropyl-4H-pyrrolo[3,2-d]thiazole-2-carboxylic acid (20 mg, 0.056 mmol) and $N_1$,$N_1$-dimethylcyclohexane-1,4-diamine (8.00 mg, 0.056 mmol) in DMF (1 mL) was added DIPEA (9.83 μL, 0.056 mmol) followed by HATU (21.40 mg, 0.056 mmol). The resulting solution was stirred at room temperature for 4 h. The reaction mass was concentrated to afford crude product. The crude sample was purified by prep LCMS using Method I. After Preparative LCMS purification, fractions containing Isomers 1 and 2 were collected and dried separately using Genevac centrifugal evaporator to afford Example 368A (Isomer 1) (7.0 mg, 0.014 mmol, 25.7% yield) as a pale yellow solid and Example 368B (Isomer 2) (6.1 mg, 0.013 mmol, 22.60% yield) as a pale yellow solid. Example 368, Isomer 1: LCMS retention time 1.26 min [A]. MS ($E^-$) m/z: 480.2 (M+H). $^1$H NMR (400 MHz, DMSO-$d_6$) δ 11.66 (s, 1H), 8.83 (s, 1H), 8.53-8.42 (m, 1H), 8.12 (d, J=7.8 Hz, 1H), 3.94 (d, J=3.7 Hz, 1H), 2.86-2.71 (m, 1H), 2.59 (s, 3H), 2.23 (br. s., 5H), 2.17 (s, 3H), 2.14-1.97 (m, 2H), 1.93-1.73 (m, 4H), 1.54 (d, J=11.5 Hz, 4H), 1.37 (d, J=6.8 Hz, 5H).

Example 369, Isomer 2: LCMS retention time 1.29 min [A]. MS ($E^-$) m/z: 480.2 (M+H). 1H NMR (400 MHz, DMSO-$d_6$) δ 11.66 (s, 1H), 8.83 (s, 1H), 8.47 (s, 1H), 8.23 (d, J=9.3 HZ, 1H), 3.91 (s, 1H), 3.78 (br. s., 2H), 2.84-2.72 (m, 1H), 2.59 (s, 3H), 2.34 (br. s., 1H), 2.27 (br.s., 4H), 2.17 (s, 3H), 1.89 (br. s., 4H), 1.63-1.49 (m, 3H), 1.42-1.28 (m, 6H).

The following Examples were prepared according to the general procedure described in Example 368.

TABLE 45

| Ex. No. | Structure | HPLC Method | Ret Time (min) | LCMS MH+ |
|---|---|---|---|---|
| 370 | 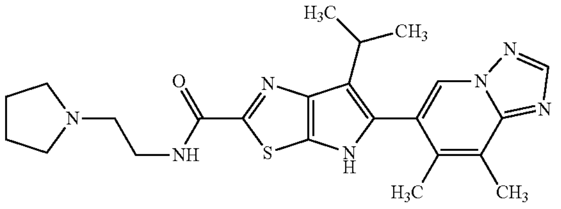 [SMILES: Cc1c(-c2[nH]c3sc(C(=O)NCCN4CCCC4)nc3c2C(C)C)cn2ncnc2c1C] | A | 1.30 | 452.2 |
| 371 | 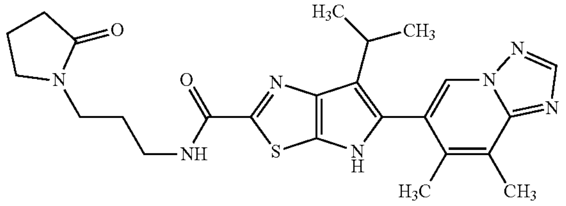 [SMILES: Cc1c(-c2[nH]c3sc(C(=O)NCCCN4CCCC4=O)nc3c2C(C)C)cn2ncnc2c1C] | A | 1.38 | 480.2 |
| 372 | 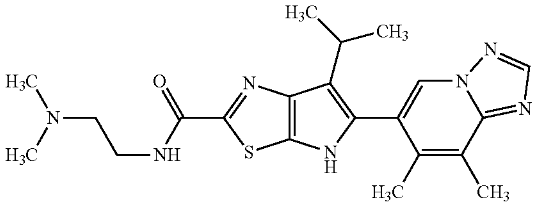 [SMILES: Cc1c(-c2[nH]c3sc(C(=O)NCCN(C)C)nc3c2C(C)C)cn2ncnc2c1C] | A | 1.28 | 426.2 |
| 373 | 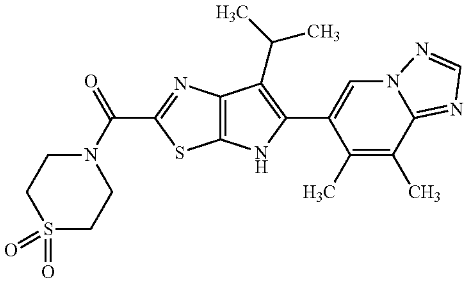 [SMILES: Cc1c(-c2[nH]c3sc(C(=O)N4CCS(=O)(=O)CC4)nc3c2C(C)C)cn2ncnc2c1C] | A | 1.42 | 473.2 |

TABLE 45-continued
| Ex. No. | Structure | HPLC Method | Ret Time (min) | LCMS MH+ |
|---|---|---|---|---|
| 374 | 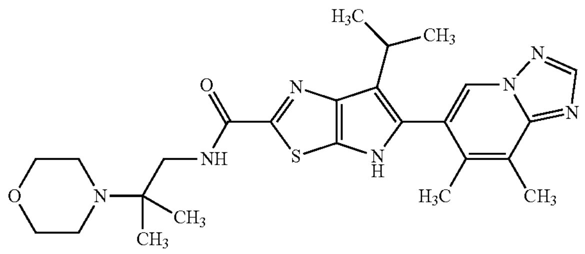 [SMILES: Cc1c(-c2[nH]c3sc(C(=O)NCC(C)(C)N4CCOCC4)nc3c2C(C)C)cn2ncnc2c1C] | A | 1.82 | 496.2 |
| 375 | 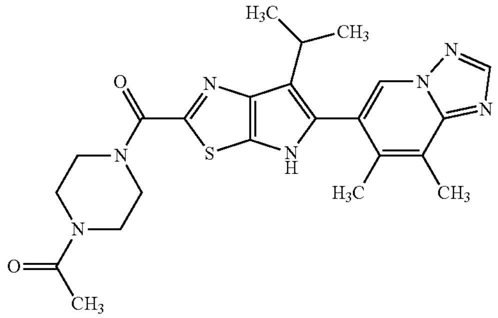 [SMILES: CC(=O)N1CCN(C(=O)c2nc3c(C(C)C)c(-c4cn5ncnc5c(C)c4C)[nH]c3s2)CC1] | A | 1.45 | 466.2 |
| 376 | 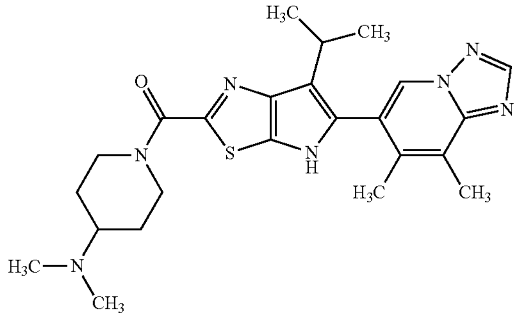 [SMILES: Cc1c(-c2[nH]c3sc(C(=O)N4CCC(N(C)C)CC4)nc3c2C(C)C)cn2ncnc2c1C] | A | 1.34 | 466.2 |
| 377 | 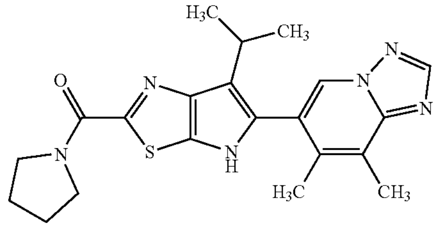 [SMILES: Cc1c(-c2[nH]c3sc(C(=O)N4CCCC4)nc3c2C(C)C)cn2ncnc2c1C] | A | 1.91 | 409.2 |
| 378 | 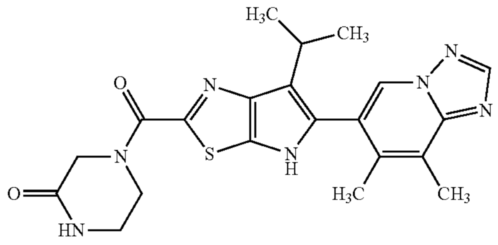 [SMILES: Cc1c(-c2[nH]c3sc(C(=O)N4CCNC(=O)C4)nc3c2C(C)C)cn2ncnc2c1C] | A | 1.30 | 438.2 |

TABLE 45-continued
| Ex. No. | Structure | HPLC Method | Ret Time (min) | LCMS $MH^+$ |
|---|---|---|---|---|
| 379 | 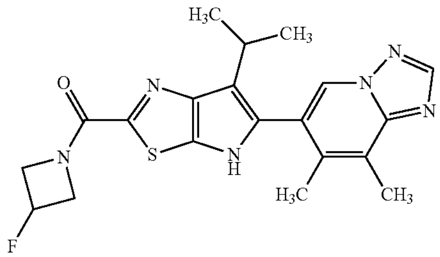 [SMILES: Cc1c(-c2[nH]c3sc(C(=O)N4CC(F)C4)nc3c2C(C)C)cn2ncnc2c1C] | A | 1.74 | 413.2 |
| 380 | 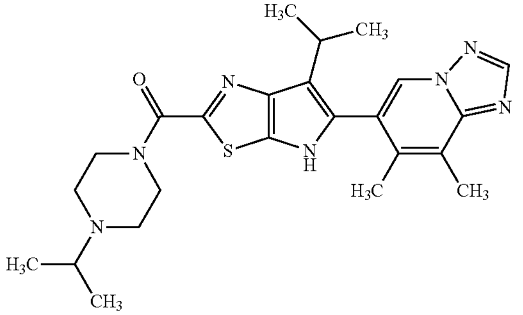 [SMILES: Cc1c(-c2[nH]c3sc(C(=O)N4CCN(C(C)C)CC4)nc3c2C(C)C)cn2ncnc2c1C] | A | 1.94 | 466.2 |
| 381 | 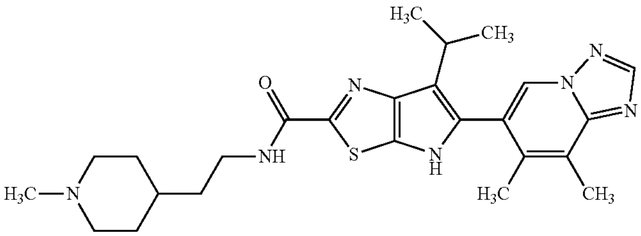 [SMILES: Cc1c(-c2[nH]c3sc(C(=O)NCCC4CCN(C)CC4)nc3c2C(C)C)cn2ncnc2c1C] | A | 1.40 | 480.3 |
| 382 | 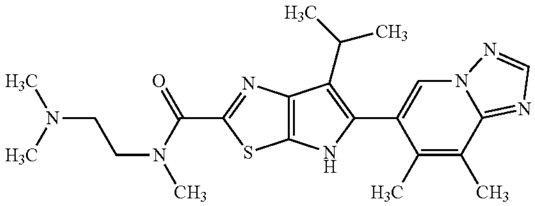 [SMILES: Cc1c(-c2[nH]c3sc(C(=O)N(C)CCN(C)C)nc3c2C(C)C)cn2ncnc2c1C] | A | 1.58 | 440.3 |
| 383 | 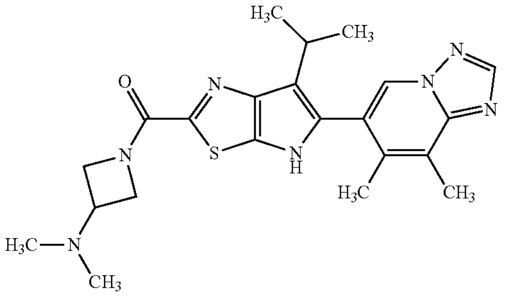 [SMILES: Cc1c(-c2[nH]c3sc(C(=O)N4CC(N(C)C)C4)nc3c2C(C)C)cn2ncnc2c1C] | A | 1.75 | 438.2 |

TABLE 45-continued
| Ex. No. | Structure | HPLC Method | Ret Time (min) | LCMS MH+ |
|---|---|---|---|---|
| 384 | 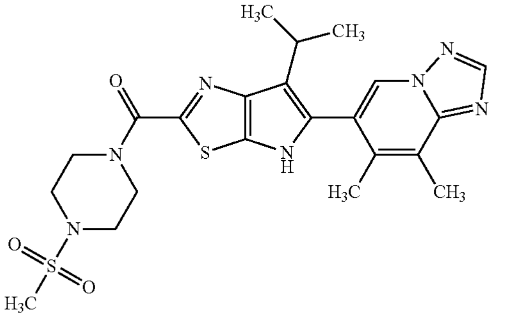 [SMILES: Cc1c(-c2[nH]c3sc(C(=O)N4CCN(S(C)(=O)=O)CC4)nc3c2C(C)C)cn2ncnc2c1C] | B | 1.67 | 502.3 |
| 385 | 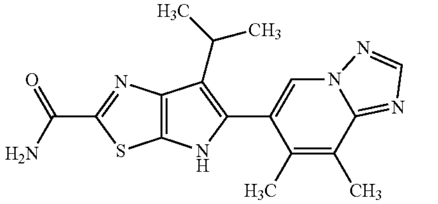 [SMILES: Cc1c(-c2[nH]c3sc(C(N)=O)nc3c2C(C)C)cn2ncnc2c1C] | A | 1.50 | 355.2 |
| 386 | 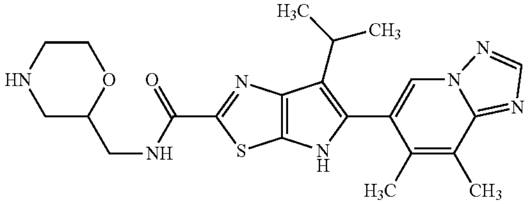 [SMILES: Cc1c(-c2[nH]c3sc(C(=O)NCC4CNCCO4)nc3c2C(C)C)cn2ncnc2c1C] | A | 1.36 | 454.3 |
| 387 | 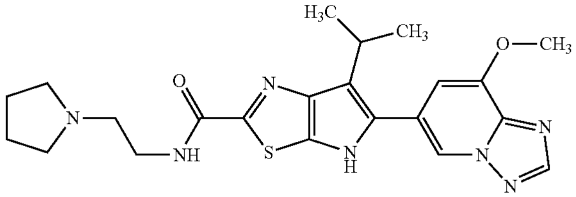 [SMILES: COc1cc(-c2[nH]c3sc(C(=O)NCCN4CCCC4)nc3c2C(C)C)cn2ncnc12] | D | 1.14 | 454.3 |
| 388 | 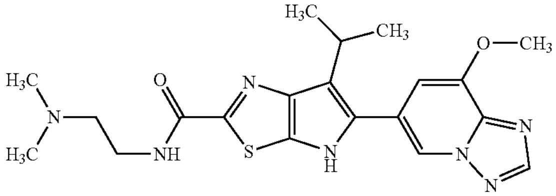 [SMILES: COc1cc(-c2[nH]c3sc(C(=O)NCCN(C)C)nc3c2C(C)C)cn2ncnc12] | D | 1.13 | 428.1 |
| 389 | 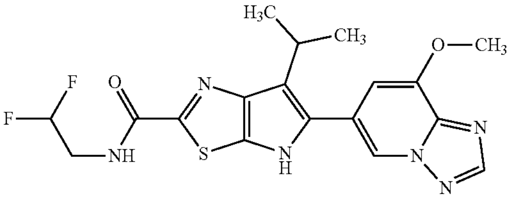 [SMILES: COc1cc(-c2[nH]c3sc(C(=O)NCC(F)F)nc3c2C(C)C)cn2ncnc12] | D | 1.58 | 421.1 |

TABLE 45-continued

| Ex. No. | Structure | HPLC Method | Ret Time (min) | LCMS MH+ |
|---|---|---|---|---|
| 390 | 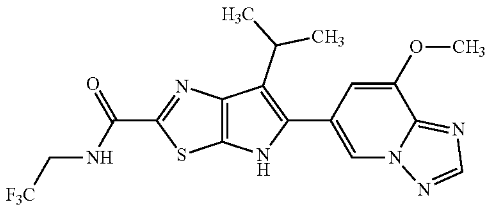 [SMILES: COc1cc(-c2[nH]c3sc(C(=O)NCC(F)(F)F)nc3c2C(C)C)cn2ncnc12] | D | 1.86 | 439.1 |

Example 391

6-isopropyl-5-(8-methyl-[1,2,4]triazolo[1,5-a]pyridin-6-yl)-4H-pyrrolo[3,2-d]thiazole-2-carboxamide (391)

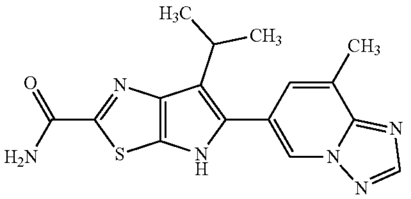

To a solution of 6-isopropyl-5-(8-methyl-[1,2,4]triazolo[1,5-a]pyridin-6-yl)-4H-pyrrolo[3,2-d]thiazole-2-carboxylic acid (30 mg, 0.088 mmol), ammonium acetate (33.9 mg, 0.439 mmol) and ammonium chloride (23.50 mg, 0.439 mmol) in DMF (1 mL) was added DIPEA (0.012 mL, 0.088 mmol) followed by HATU (33.4 mg, 0.088 mmol). The resulting solution was stirred at room temperature for 4 h. The reaction mass was concentrated to afford crude product. The crude sample was purified by prep LCMS using Method I, the fractions containing the product was combined and dried using Genevac centrifugal evaporator to afford 6-isopropyl-5-(8-methyl-[1,2,4]triazolo[1,5-a]pyridin-6-yl)-4H-pyrrolo[3,2-d]thiazole-2-carboxamide (2.9 mg, 8.52 μmol, 9.69% yield) as a pale yellow solid. LCMS retention time 1.37 min [A]. MS ($E^-$) m/z: 341.2 (M+H). $^1$H NMR (400 MHz, DMSO-$d_6$) δ 11.93 (s, 1H), 8.83 (s, 1H), 8.53 (s, 1H), 7.90 (br s, 1H), 7.61 (s, 2H), 3.22-3.13 (m, 1H), 2.63 (s, 3H), 1.48 (d, J=6.8 Hz, 6H).

The following Examples were prepared according to the general procedure described in Example 391.

TABLE 46

| Ex. No. | Structure | HPLC Method | Ret Time (min) | LCMS MH+ |
|---|---|---|---|---|
| 392 | 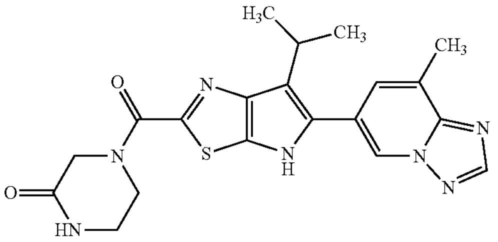 [SMILES: Cc1cc(-c2[nH]c3sc(C(=O)N4CCNC(=O)C4)nc3c2C(C)C)cn2ncnc12] | A | 1.20 | 424.2 |
| 393 | 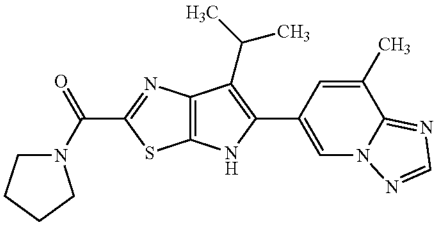 [SMILES: Cc1cc(-c2[nH]c3sc(C(=O)N4CCCC4)nc3c2C(C)C)cn2ncnc12] | A | 1.93 | 395.2 |

TABLE 46-continued
| Ex. No. | Structure | HPLC Method | Ret Time (min) | LCMS MH+ |
|---|---|---|---|---|
| 394 | 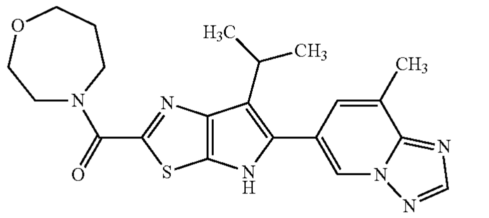 [SMILES: Cc1cc(-c2[nH]c3sc(C(=O)N4CCCOCC4)nc3c2C(C)C)cn2ncnc12] | A | 1.59 | 425.2 |
| 395 | 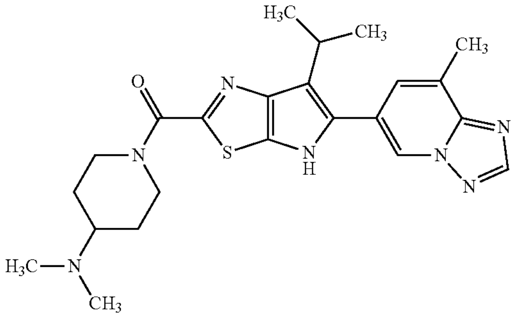 [SMILES: Cc1cc(-c2[nH]c3sc(C(=O)N4CCC(N(C)C)CC4)nc3c2C(C)C)cn2ncnc12] | A | 1.33 | 452.2 |
| 396 | 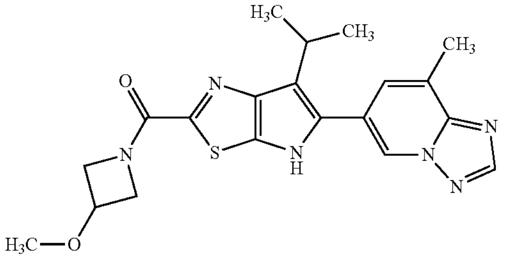 [SMILES: COC1CN(C(=O)c2nc3c(C(C)C)c(-c4cc(C)c5ncnn5c4)[nH]c3s2)C1] | A | 1.874 | 411.2 |
| 397 | 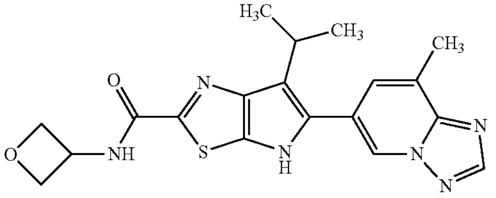 [SMILES: Cc1cc(-c2[nH]c3sc(C(=O)NC4COC4)nc3c2C(C)C)cn2ncnc12] | A | 1.48 | 397.2 |
| 398 | 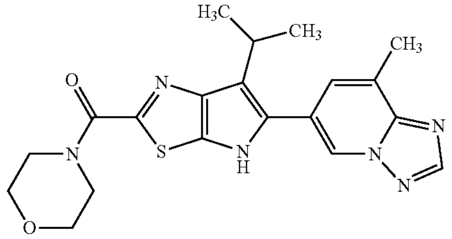 [SMILES: Cc1cc(-c2[nH]c3sc(C(=O)N4CCOCC4)nc3c2C(C)C)cn2ncnc12] | A | 1.54 | 411.2 |
| 399 | 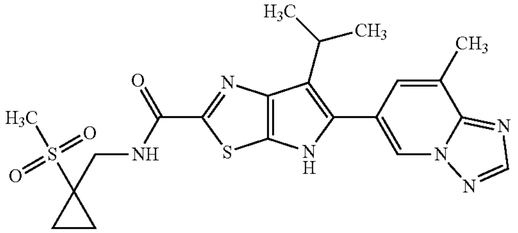 [SMILES: Cc1cc(-c2[nH]c3sc(C(=O)NCC4(S(C)(=O)=O)CC4)nc3c2C(C)C)cn2ncnc12] | A | 1.59 | 473.2 |

TABLE 46-continued

| Ex. No. | Structure | HPLC Method | Ret Time (min) | LCMS MH$^+$ |
|---|---|---|---|---|
| 400 | 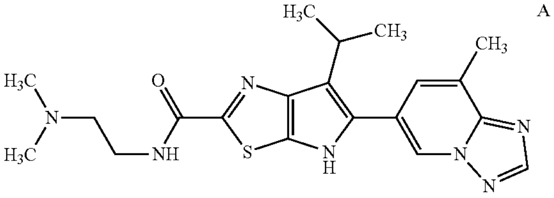 | A | 1.25 | 412.3 |

Example 401

N-((5-(7,8-dimethyl-[1,2,4]triazolo[1,5-a]pyridin-6-yl)-6-isopropyl-4H-pyrrolo[3,2-d]thiazol-2-yl)methyl)-1-isopropylpiperidin-4-amine (401)

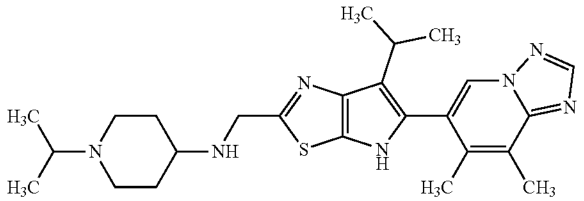

Intermediate 401A: Tert-butyl 5-(7,8-dimethyl-[1,2,4]triazolo[1,5-a]pyridin-6-yl)-2-(hydroxymethyl)-6-isopropyl-4H-pyrrolo[3,2-d]thiazole-4-carboxylate (401A)

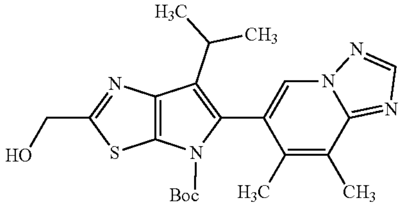

To a solution of 4-(tert-butyl) 2-methyl 5-(7,8-dimethyl-[1,2,4]triazolo[1,5-a]pyridin-6-yl)-6-isopropyl-4H-pyrrolo[3,2-d]thiazole-2,4-dicarboxylate (1.0 g, 2.130 mmol) in toluene (25 mL) was added diisobutylaluminium hydride (4.44 mL, 5.32 mmol) dropwise at −78° C. and the resulting reaction mixture was stirred at same temperature for 3 h. The reaction was quenched with 1.5 N HCl (15 mL) at −78° C. The reaction mass was extracted with EtOAc (3×50 mL). The separated organic layer was dried over sodium sulphate, filtered and concentrated to afford tert-butyl 5-(7,8-dimethyl-[1,2,4]triazolo[1,5-a]pyridin-6-yl)-2-(hydroxymethyl)-6-isopropyl-4H-pyrrolo[3,2-d]thiazole-4-carboxylate (0.9 g, 2.038 mmol, 96% yield) as a yellow solid. LCMS retention time 1.54 min [F]. MS (E$^-$) m/z: 442.2 (M+H).

Intermediate 401B: Tert-butyl 5-(7,8-dimethyl-[1,2,4]triazolo[1,5-a]pyridin-6-yl)-2-formyl-6-isopropyl-4H-pyrrolo[3,2-d]thiazole-4-carboxylate (401B)

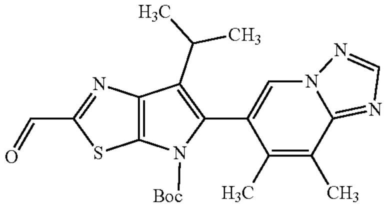

To a solution of tert-butyl 5-(7,8-dimethyl-[1,2,4]triazolo[1,5-a]pyridin-6-yl)-2-(hydroxymethyl)-6-isopropyl-4H-pyrrolo[3,2-d]thiazole-4-carboxylate (1.0 g, 2.265 mmol) in DCM (25 mL) was added Celite (0.488 g, 1.310 mmol) followed by portion wise addition of pyridinium chlorochromate (0.488 g, 2.265 mmol). The resulting solution was stirred at room temperature for 3 h. The reaction mass was filtered through celite bed, washed with additional DCM (60 mL). The filtrate was concentrated to afford crude product. The crude was purified by Combiflash using 24 g silica column by eluting with 40% ethyl acetate\Pet ether. Following concentration of fractions, collected tert-butyl 5-(7,8-dimethyl-[1,2,4]triazolo[1,5-a]pyridin-6-yl)-2-formyl-6-isopropyl-4H-pyrrolo[3,2-d]thiazole-4-carboxylate (0.65 g, 1.479 mmol, 65.3% yield) as a pale yellow solid. LCMS retention time 3.43 min [C]. MS (E$^-$) m/z: 44202 (M+H).

Intermediate 401C: 5-(7,8-dimethyl-[1,2,4]triazolo[1,5-a]pyridin-6-yl)-6-isopropyl-4H-pyrrolo[3,2-d]thiazole-2-carbaldehyde (401C)

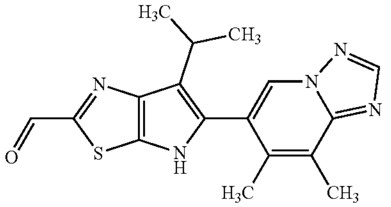

To a solution of tert-butyl 5-(7,8-dimethyl-[1,2,4]triazolo[1,5-a]pyridin-6-yl)-2-formyl-6-isopropyl-4H-pyrrolo[3,2-d]thiazole-4-carboxylate (0.65 g, 1.479 mmol) in DCM (10 mL) was added TFA (3 mL, 38.9 mmol) dropwise and stirred at room temperature for 12 h. The reaction mass was diluted with DCM (25 mL) and washed with cooled 10% sodium bicarbonate solution. The separated organic layer was dried over sodium sulphate, filtered and concentrated to afford 5-(7,8-dimethyl-[1,2,4]triazolo[1,5-a]pyridin-6-yl)-6-isopropyl-4H-pyrrolo[3,2-d]thiazole-2-carbaldehyde (0.42 g, 1.237 mmol, 84% yield) as a pale yellow solid. LCMS retention time 2.41 min [C]. MS ($E^-$) m/z: 440.2 (M+H).

Example 401: N-((5-(7,8-dimethyl-[1,2,4]triazolo[1,5-a]pyridin-6-yl)-6-isopropyl-4H-pyrrolo[3,2-d]thiazol-2-yl)methyl)-1-isopropylpiperidin-4-amine To a solution of 5-(7,8-dimethyl-[1,2,4]triazolo[1,5-a]pyridin-6-yl)-6-isopropyl-4H-pyrrolo[3,2-d]thiazole-2-carbaldehyde (30 mg, 0.088 mmol) in methanol (1 mL) was added 1-isopropylpiperidin-4-amine (12.57 mg, 0.088 mmol) followed by acetic acid (5.06 μL, 0.088 mmol) at 0° C. The resulting solution was stirred at room temperature for 12 h, then sodium cyanoborohydride (11.11 mg, 0.177 mmol) was added at 0° C. and continued stirring for 2 h at room temperature. The reaction mass was concentrated, residue was dissolved in water (5 mL) and extracted with ethyl acetate (3×10 mL). The separated organic layer was dried over sodium sulphate, filtered and concentrated. The crude sample was purified by prep LCMS using Method I, the fractions containing the product was combined and dried using Genevac centrifugal evaporator to afford N-((5-(7,8-dimethyl-[1,2,4]triazolo[1,5-a]pyridin-6-yl)-6-isopropyl-4H-pyrrolo[3,2-d]thiazol-2-yl)methyl)-1-isopropylpiperidin-4-amine (7.8 mg, 0.017 mmol, 18.70% yield) as a pale yellow solid. LCMS retention time 1.44 min [A]. MS ($E^-$) m/z: 466.3 (M+H). $^1$H NMR (400 MHz, DMSO-$d_6$) δ 11.27 (s, 1H), 8.72 (s, 1H), 8.45 (s, 1H), 4.06 (s, 2H), 2.79-2.64 (m, 4H), 2.57 (s, 3H), 2.47-2.38 (m, 1H), 2.18 (s, 3H), 2.13-2.03 (m, 2H), 1.90 (s, 2H), 1.88-1.79 (m, 2H), 1.30 (d, J=6.8 Hz, 6H), 0.95 (d, J=6.6 Hz, 6H).

The following Examples were prepared according to the general procedure described in Example 401.

TABLE 47

| Ex. No. | Structure | HPLC Method | Ret Time (min) | LCMS MH+ |
|---|---|---|---|---|
| 402 | 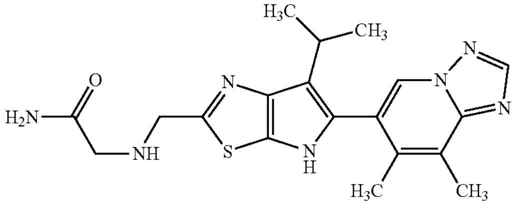 [SMILES: Cc1c(-c2[nH]c3sc(CNCC(N)=O)nc3c2C(C)C)cn2ncnc2c1C] | A | 1.15 | 398.2 |
| 403 | 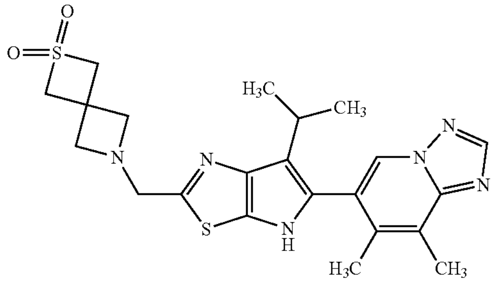 [SMILES: Cc1c(-c2[nH]c3sc(CN4CC5(C4)CS(=O)(=O)C5)nc3c2C(C)C)cn2ncnc2c1C] | A | 1.49 | 471.1 |
| 404 | 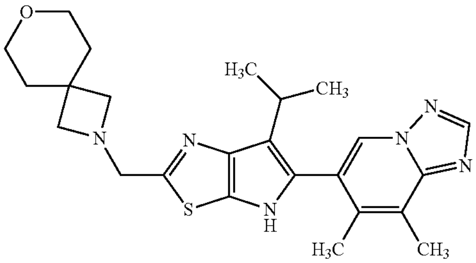 [SMILES: Cc1c(-c2[nH]c3sc(CN4CC5(CCOCC5)C4)nc3c2C(C)C)cn2ncnc2c1C] | A | 1.65 | 451.2 |
| 405 | 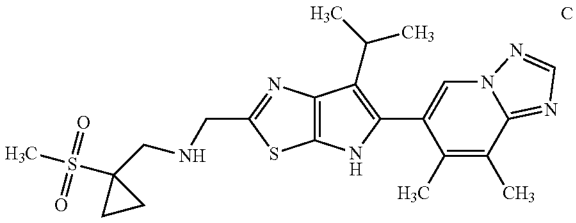 | C | 2.06 | 473.2 |

TABLE 47-continued

| Ex. No. | Structure | HPLC Method | Ret Time (min) | LCMS MH+ |
|---|---|---|---|---|
| 406 | 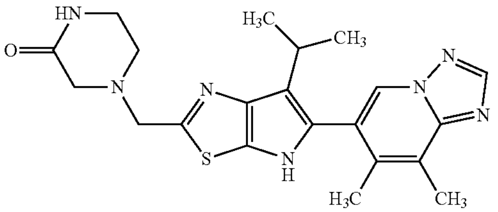 [SMILES: Cc1c(-c2[nH]c3sc(CN4CCNC(=O)C4)nc3c2C(C)C)cn2ncnc2c1C] | C | 1.58 | 424.2 |
| 407 | 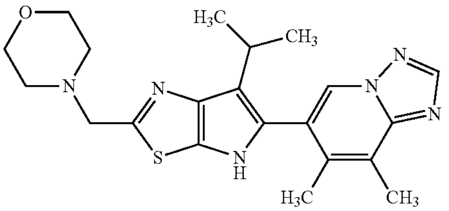 [SMILES: Cc1c(-c2[nH]c3sc(CN4CCOCC4)nc3c2C(C)C)cn2ncnc2c1C] | A | 1.62 | 411.2 |
| 408 | 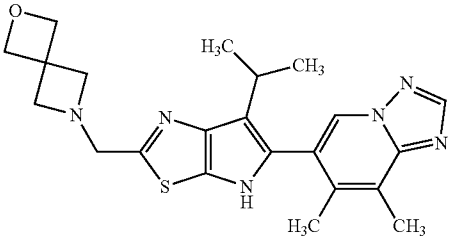 [SMILES: Cc1c(-c2[nH]c3sc(CN4CC5(COC5)C4)nc3c2C(C)C)cn2ncnc2c1C] | A | 1.45 | 423.2 |
| 409 | 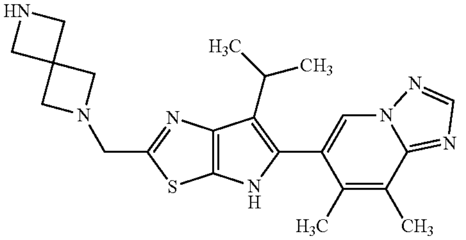 [SMILES: Cc1c(-c2[nH]c3sc(CN4CC5(CNC5)C4)nc3c2C(C)C)cn2ncnc2c1C] | A | 1.27 | 422.2 |

Example 410

6-isopropyl-5-(8-methoxy-[1, 2, 4]triazolo[1, 5-a]pyridin-6-yl)-2-(piperidin-4-yl)-4H-pyrrolo[2, 3-d]thiazole (410)

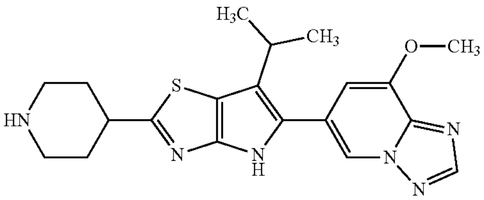

Intermediate 410A: Ethyl 2-bromothiazole-4-carboxylate (410A)

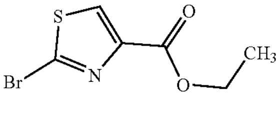

Tert-butyl nitrite (11.23 g, 109 mmol) was added dropwise to a solution of ethyl 2-aminothiazole-4-carboxylate (12.5 g, 72.6 mmol) and cupric bromide (24.32 g, 109 mmol) in acetonitrile (350 mL) at 0° C. The reaction mixture was stirred at 0° C. for 2 h. The reaction mass was diluted with water (150 mL) acidified to pH 1 with conc. HCl, and the aqueous layer was extracted with dichloromethane (3×150 mL). The combined organics were dried over sodium sulphate, filtered and the solvent was removed under reduced pressure. The crude material was purified by Combiflash using 80 g silica column by eluting with 10% EtOAc\Pet ether. Following concentration of fractions, tert-butyl ethyl 2-bromothiazole-4-carboxylate (10.5 g, 43.1 mmol, 59.4% yield) was collected as a white solid. LCMS retention time 1.79 min [F]. MS ($E^-$) m/z: 237.2 (M+H).

Intermediate 410B: 2-bromothiazole-4-carboxylic acid (410B)

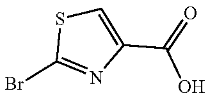

To a solution of ethyl 2-bromothiazole-4-carboxylate (10.5 g, 44.5 mmol) in methanol (150 mL) was added 10% NaOH (45 mL, 44.5 mmol) dropwise at 0° C. The reaction mixture was stirred at 0° C. for 2 h. The reaction mass was concentrated under vacuum to remove volatiles, aqueous layer was acidified with 1.5 N HCl to pH 4-5, the solid precipitated was filtered and dried to get 2-bromothiazole-4-carboxylic acid (8.7 g, 41.4 mmol, 93% yield) as a white solid product. LCMS retention time 0.33 min [C]. MS ($E^-$) m/z: 208.0 (M+2H).

Intermediate 410C: Tert-butyl (2-bromothiazol-4-yl) carbamate (410C)

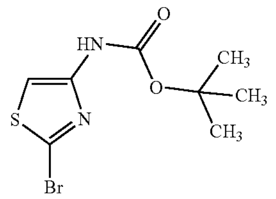

To a solution of 2-bromothiazole-4-carboxylic acid (8.7 g, 41.8 mmol) in t-BuOH (130 mL) were added TEA (6.99 mL, 50.2 mmol) and diphenylphosphoryl azide (10.13 mL, 46.0 mmol) at 0° C. The resulting solution was heated at 80° C. for 12 h. The reaction was quenched with water (250 mL. The mixture was concentrated under vacuum to remove volatiles and aqueous layer was extracted with DCM (3×200 mL). The separated organic layer was dried over sodium sulphate, filtered and concentrated to get crude product. The crude was purified by combiflash using 80 g silica column by eluting with 12% EtOAc/Pet. ether. Following concentration of fractions, collected tert-butyl (2-bromothiazol-4-yl) carbamate (7.2 g, 24.24 mmol, 58.0% yield) as a white solid. LCMS retention time 2.84 min [C]. MS ($E^-$) m/z: 278.2 (M−H).

Intermediate 410D: Tert-butyl 4-(4-((tert-butoxycarbonyl) amino) thiazol-2-yl)-3, 6-dihydropyridine-1 (2H)-carboxylate (410D)

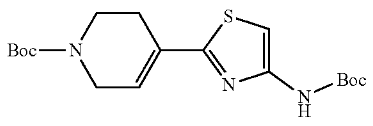

To a stirred solution of tert-butyl (2-bromothiazol-4-yl) carbamate (7.2 g, 25.8 mmol), tert-butyl 4-(4,4,5,5-tetramethyl-1,3,2-dioxaborolan-2-yl)-3,6-dihydropyridine-1 (2H)-carboxylate (11.96 g, 38.7 mmol) in dioxane (150 mL) and water (16.67 mL) was added potassium phosphate tribasic (16.42 g, 77 mmol). The resulting solution was degassed with nitrogen for 10 mins. Next, $PdCl_2(dppf)-CH_2Cl_2$ adduct (2.106 g, 2.58 mmol) was added and the reaction mixture was degassed again for 5 min. The resulting brown colored reaction mixture was heated to 110° C. for 12 h. The reaction was diluted with EtOAc (250 mL), washed with water (250 mL) and aqueous layer was extracted with ethyl acetate (2×200) mL. The combined organic layer was dried over sodium sulphate, filtered and concentrated to get crude product. The crude product was purified by Combiflash using 80 g silica column by eluting with 45% EtOAc/Pet. ether. Following concentration of fractions, tert-butyl 4-(4-((tert-butoxycarbonyl) amino) thiazol-2-yl)-3, 6-dihydropyridine-1 (2H)-carboxylate (7.8 g, 17.99 mmol, 69.8% yield) was collected as a yellow oil. LCMS retention time 3.31 min [C]. MS ($E^-$) m/z: 382.2 (M+H).

Intermediate 410E: Tert-butyl 4-(4-((tert-butoxycarbonyl) amino) thiazol-2-yl) piperidine-1-carboxylate (410E)

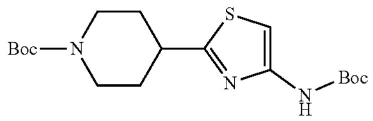

A solution of tert-butyl 4-(4-((tert-butoxycarbonyl) amino)thiazol-2-yl)-3,6-dihydropyridine-1 (2H)-carboxylate (7.8 g, 20.45 mmol) in ethyl acetate (150 mL) was purged with nitrogen gas and Pd/C (3.92 g, 3.68 mmol) was added. The reaction mixture was purged with $N_2$ three times. Hydrogen gas was introduced via a balloon to the mixture. The reaction mixture was stirred at room temperature for 8 h. The reaction mass was filtered through celite pad, rinsed with additional methanol and the filtrate was concentrated to dryness to give tert-butyl 4-(4-((tert-butoxycarbonyl) amino) thiazol-2-yl) piperidine-1-carboxylate (7.4 g, 19.30 mmol, 94% yield) as a yellow oil. LCMS retention time 3.44 min [C]. MS ($E^-$) m/z: 384.2 (M+H).

Intermediate 410F: Tert-butyl 4-(4-((tert-butoxycarbonyl) amino)-5-iodothiazol-2-yl) piperidine-1-carboxylate (410F)

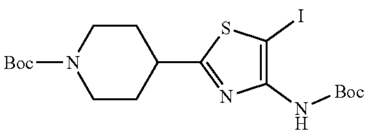

To a solution of tert-butyl 4-(4-((tert-butoxycarbonyl) amino)thiazol-2-yl)piperidine-1-carboxylate (1.0 g, 2.61 mmol) in acetonitrile (20 mL) was added NIS (0.587 g, 2.61 mmol) in acetonitrile (10 mL) dropwise at 0° C. The reaction mixture was stirred at 0° C. for 10 min. The reaction was quenched with the addition of sodium thiosulphate solution (50 mL). The reaction mixture was extracted with ethyl acetate (2×100 mL). The separated organic layer was dried over sodium sulphate, filtered and concentrated to get crude product. The crude product was purified by Combiflash using 24 g silica column by eluting with 16% EtOAc/Pet ether. Following concentration of fractions, tert-butyl 4-(4-((tert-butoxycarbonyl) amino)-5-iodothiazol-2-yl) piperidine-1-carboxylate (0.75 g, 1.458 mmol, 55.9% yield) was collected as a pale yellow solid. LCMS retention time 3.09 min [C]. MS ($E^-$) m/z: 510.1 (M+H).

Intermediate 410 G: Tert-butyl 4-(4-((tert-butoxycarbonyl)(3-methylbut-2-en-1-yl)amino)-5-iodothiazol-2-yl)piperidine-1-carboxylate (410G)

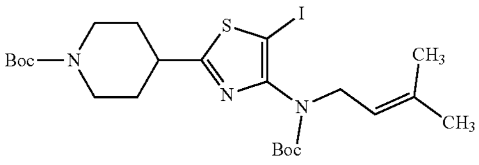

To a solution of tert-butyl 4-(4-((tert-butoxycarbonyl) amino)-5-iodothiazol-2-yl) piperidine-1-carboxylate (0.3 g, 0.589 mmol) in DMF (10 mL) was added NaH (0.024 g, 0.589 mmol) at 0° C. The reaction mixture was stirred at 0° C. for 10 min. Next, 1-bromo-3-methylbut-2-ene (0.069 mL, 0.589 mmol) was added dropwise and the reaction mixture was stirred at 0° C. for 10 min. The reaction was quenched with ice water (25 mL). The reaction mixture was extracted with DCM (2×50 mL). The separated organic layer was dried over sodium sulphate, filtered and concentrated to get tert-butyl 4-(4-((tert-butoxycarbonyl)(3-methylbut-2-en-1-yl) amino)-5-iodothiazol-2-yl) piperidine-1-carboxylate (0.25 g, 0.429 mmol, 72.8% yield) as a pale yellow oil. LCMS retention time 4.10 min [C]. MS ($E^-$) m/z: 578.1 (M+H).

Intermediate 41OH: Tert-butyl 2-(1-(tert-butoxycarbonyl) piperidin-4-yl)-6-isopropyl-4H-pyrrolo[2, 3-d]thiazole-4-carboxylate (410H)

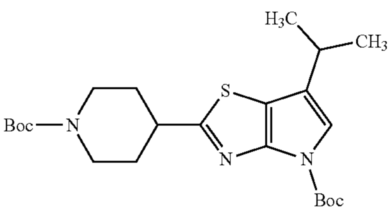

To a solution of tert-butyl 4-(4-((tert-butoxycarbonyl)(3-methylbut-2-en-1-yl)amino)-5-iodothiazol-2-yl)piperidine-1-carboxylate (3.0 g, 5.19 mmol) and potassium carbonate (0.790 g, 5.71 mmol) in DMF (25 mL) was added tetrabutylammonium bromide (5.02 g, 15.58 mmol). The mixture was degassed for 10 min and $PdOAc_2$ (0.117 g, 0.519 mmol) was added. The reaction mixture was degassed further for 5 min. The resulting reaction mixture was heated at 100° C. for 12 h. The reaction mass was filtered through celite bed to remove inorganics, washed with DCM (100 mL) and filtrate was concentrated to get crude product. The crude product was purified by Combiflash using 40 g silica column by eluting with 15% EtOAc\Pet ether. Following concentration of fractions, tert-butyl 2-(1-(tert-butoxycarbonyl) piperidin-4-yl)-6-isopropyl-4H-pyrrolo[2, 3-d]thiazole-4-carboxylate (0.72 g, 1.601 mmol, 30.8% yield) was collected as a yellow solid. LCMS retention time 4.24 min [C]. MS ($E^-$) m/z: 450.2 (M+H).

Intermediate 4101: Tert-butyl 5-bromo-2-(1-(tert-butoxycarbonyl) piperidin-4-yl)-6-isopropyl-4H-pyrrolo[2, 3-d]thiazole-4-carboxylate (410I)

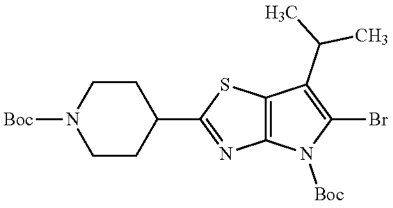

To a solution of tert-butyl 2-(1-(tert-butoxycarbonyl)piperidin-4-yl)-6-isopropyl-4H-pyrrolo[2,3-d]thiazole-4-carboxylate (0.9 g, 2.002 mmol) in DCE (2 mL) was added NBS (0.392 g, 2.202 mmol) in DCE (2 mL) at 0° C. The reaction mixture was stirred at 0° C. for 15 min. The reaction was quenched with water. The reaction mixture was extracted with DCM (2×10 mL). The separated organic layer was dried over sodium sulphate, filtered and concentrated to get crude product. The crude product was purified by Combiflash using 24 g silica column by eluting with 10% EtOAc/Pet ether. Following concentration of fractions, tert-butyl 5-bromo-2-(1-(tert-butoxycarbonyl) piperidin-4-yl)-6-isopropyl-4H-pyrrolo[2,3-d]thiazole-4-carboxylate (29 mg, 0.055 mmol, 49.3% yield) was collected as a pale yellow solid. LCMS retention time 4.66 min [C]. MS ($E^-$) m/z: 530.1 (M+H).

Intermediate 410J: Tert-butyl 2-(1-(tert-butoxycarbonyl)piperidin-4-yl)-6-isopropyl-5-(8-methoxy-[1,2,4]triazolo[1,5-a]pyridin-6-yl)-4H-pyrrolo[2,3-d]thiazole-4-carboxylate (410J)

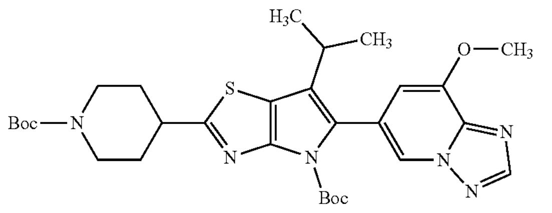

A mixture of tert-butyl 5-bromo-2-(1-(tert-butoxycarbonyl)piperidin-4-yl)-6-isopropyl-4H-pyrrolo[2,3-d]thiazole-4-carboxylate (25 mg, 0.047 mmol), 8-methoxy-6-(4,4,5,5-tetramethyl-1,3,2-dioxaborolan-2-yl)-[1,2,4]triazolo[1,5-a]pyridine (15.62 mg, 0.057 mmol) and potassium phosphate tribasic (24.72 mg, 0.142 mmol) in a dioxane (2 mL) and water (0.222 mL) was degassed for 10 min and then $PdCl_2$ (dppf)-$CH_2Cl_2$ adduct (1.931 mg, 2.365 μmol) was added. The reaction mixture was degassed again for 5 min. The reaction mixture was heated at 85° C. for 3 h. The reaction mass was filtered through celite bed to remove inorganics, washed with EtOAc (20 mL) and the filtrate was concentrated to get tert-butyl 2-(1-(tert-butoxycarbonyl)piperidin-4-yl)-6-isopropyl-5-(8-methoxy-[1,2,4]triazolo[1,5-a]pyridin-6-yl)-4H-pyrrolo[2,3-d]thiazole-4-carboxylate (22 mg, 0.037 mmol, 78% yield) as a brown solid product. LCMS retention time 1.80 min [F]. MS ($E^-$) m/z: 597.1 (M+H).

Example 410: 6-isopropyl-5-(8-methoxy-[1, 2, 4]triazolo [1, 5-a]pyridin-6-yl)-2-(piperidin-4-yl)-4H-pyrrolo[2, 3-d]thiazole To a solution of tert-butyl 2-(1-(tert-butoxycarbonyl)piperidin-4-yl)-6-isopropyl-5-(8-methoxy-[1,2,4]triazolo[1,5-a]pyridin-6-yl)-4H-pyrrolo[2,3-d]thiazole-4-carboxylate (21 mg, 0.035 mmol) in DCM (1 mL) was added 4 M hydrochloric acid in dioxane (1 ml, 32.9 mmol). The resulting solution was stirred at room temperature for 30 min. The reaction mass was concentrated under vacuum to remove volatiles. The crude product obtained was purified by prep LCMS using Method I. After Preparative LCMS purification, fractions containing product was collected and dried separately using Genevac centrifugal evaporator to afford 6-isopropyl-5-(8-methoxy-[1,2,4]triazolo[1,5-a]pyridin-6-yl)-2-(piperidin-4-yl)-4H-pyrrolo[2,3-d]thiazole (4.2 mg, 10.59 μmol, 30.1% yield) as a pale yellow solid. LCMS retention time 1.22 min [D]. MS ($E^-$) m/z: 397.1 (M+H). $^1H$ NMR (400 MHz, DMSO-$d_6$) δ 11.96 (br. s., 1H), 8.52 (d, J=1.2 Hz, 1H), 8.48 (s, 1H), 7.16 (d, J=1.2 Hz, 1H), 4.13-4.02 (m, 3H), 3.90 (s, 1H), 3.27-3.19 (m, 4H), 2.88-2.77 (m, 2H), 2.15-2.03 (m, 2H), 1.90 (s, 2H), 1.85-1.70 (m, 2H), 1.28 (d, J=6.6 Hz, 6H).

The following Example was prepared according to the general procedure described in Example 410.

TABLE 48

| Ex. No. | Structure | HPLC Method | Ret Time (min) | LCMS MH+ |
|---|---|---|---|---|
| 411 | 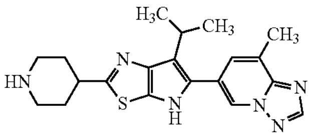 [SMILES: Cc1cc(-c2[nH]c3sc(C4CCNCC4)nc3c2C(C)C)cn2ncnc12] | D | 1.24 | 381.2 |

Example 412

6-isopropyl-5-(8-methyl-[1,2,4]triazolo[1,5-a]pyridin-6-yl)-2-(1-((3-methyloxetan-3-yl) methyl)piperidin-4-yl)-4H-pyrrolo[2,3-d]thiazole (412)

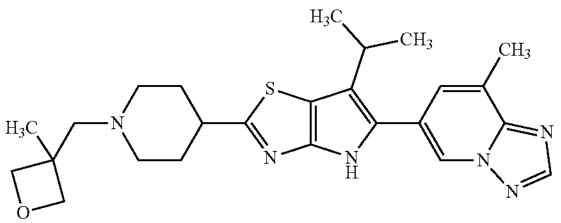

To a solution of 6-isopropyl-5-(8-methyl-[1,2,4]triazolo[1,5-a]pyridin-6-yl)-2-(piperidin-4-yl)-4H-pyrrolo[2,3-d]thiazole (30 mg, 0.079 mmol) in MeOH (2 mL) were added TEA (0.022 mL, 0.158 mmol), 3-methyloxetane-3-carbaldehyde (8.68 mg, 0.087 mmol) followed by acetic acid (0.451 μL, 7.88 μmol). The resulting light yellow solution was stirred under nitrogen at room temperature for 6 h. Next, sodium cyanoborohydride (9.91 mg, 0.158 mmol) was added and the mixture stirred at the same temperature for 2 h. The reaction mass was concentrated to remove volatiles, crude was diluted with DCM (30 mL) and washed with water (25 mL). The separated organic layer was dried over sodium sulphate, filtered and concentrated. After Preparative LCMS purification, fractions containing product was collected and dried separately using Genevac centrifugal evaporator to afford isopropyl-5-(8-methyl-[1,2,4]triazolo[1,5-a]pyridin-6-yl)-2-(1-((3-methyloxetan-3-yl)methyl)piperidin-4-yl)-4H-pyrrolo[2,3-d]thiazole (1.1 mg, 2.367 μmol, 3.00% yield) as a pale yellow solid. LCMS retention time 1.88 min [D]. MS ($E^-$) m/z: 465.2 (M+H). $^1H$ NMR (400 MHz, DMSO-$d_6$) δ 11.86 (s, 1H), 8.76 (s, 1H), 8.50 (s, 1H), 7.59 (s, 1H), 4.39 (d, J=5.1 Hz, 2H), 4.21 (d, J=5.4 Hz, 2H), 4.13 (q, J=5.1 Hz, 1H), 3.22-3.14 (m, 4H), 3.01 (br. s., 2H), 2.65-2.60 (m, 3H), 2.24-2.05 (m, 4H), 2.02 (br. s., 1H), 1.79 (br. s., 2H), 1.34 (s, 3H), 1.26 (d, J=6.8 Hz, 6H).

Example 413

6-isopropyl-5-(8-methoxy-[1,2,4]triazolo[1,5-a]pyridin-6-yl)-2-(piperidin-4-yl)-4H-thieno[3,2-b]pyrrole (413)

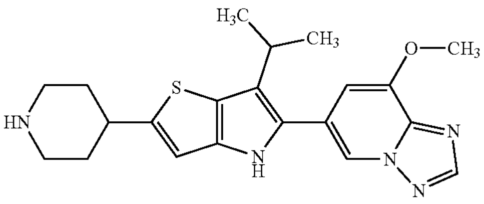

Intermediate 413A: (Z)-methyl 2-azido-3-(thiophen-2-yl)acrylate (413A)

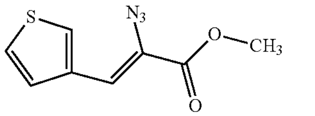

To a solution of thiophene-2-carbaldehyde (5.0 g, 44.6 mmol) and methyl-2-azidoacetate (20.52 g, 178 mmol) in MeOH (100 mL) was added sodium methoxide (38.5 g, 178 mmol) dropwise at −15° C. The reaction mixture was stirred at −15° C. for 4 h. The reaction mass was concentrated and partitioned between water and EtOAc. The organic layer was washed with water and brine solutions, dried over sodium sulphate, filtered and concentrated to afford (Z)-methyl 2-azido-3-(thiophen-2-yl)acrylate (2.5 g, 11.95 mmol, 26.8% yield) as a brown liquid. H NMR (400 MHz, DMSO-$d_6$) δ 7.81-7.80 (m, 1H), 7.57-7.55 (m, 1H), 7.30 (s, 1H), 7.16-7.14 (m, 1H), 3.84 (s, 3H).

Intermediate 413B: Methyl 4H-thieno[3,2-b]pyrrole-5-carboxylate (413B)

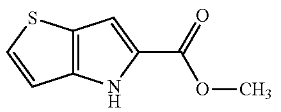

(Z)-methyl 2-azido-3-(thiophen-2-yl)acrylate (2.5 g, 11.95 mmol) was taken in toluene (15 mL) and refluxed for 2 h. Toluene was concentrated under high vacuum and the crude product was purified over silica gel chromatography by eluting with 15% ethyl acetate in hexane to afford methyl 4H-thieno[3,2-b]pyrrole-5-carboxylate (1.8 g, 9.93 mmol, 83% yield) as a pale yellow solid. LCMS retention time 1.07 min [H]. MS ($E^-$) m/z: 182.2 (M+H).

Intermediate 413C: Methyl 2-bromo-4H-thieno[3,2-b]pyrrole-5-carboxylate (413C)

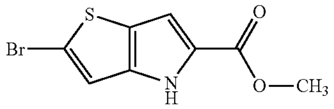

To a solution of methyl 4H-thieno[3,2-b]pyrrole-5-carboxylate (1.72 g, 9.49 mmol) in acetonitrile (20 mL) at 0° C. was added a solution of NBS (1.774 g, 9.97 mmol) in acetonitrile (4 mL). The resulting reaction mixture was stirred for 1 h at room temperature. Next, water (10 mL) was added to the reaction mass. A solid formed and was filtered. The crude product was purified over silica gel by eluting with 15% EA in hexane to afford methyl 2-bromo-4H-thieno[3,2-b]pyrrole-5-carboxylate (2.2 g, 8.46 mmol, 89% yield). LCMS retention time 1.32 min [F]. MS ($E^-$) m/z: 260.3 (M−H).

Intermediate 413D: Methyl 2-(1-(tert-butoxycarbonyl)-1,2,3,6-tetrahydropyridin-4-yl)-4H-thieno[3,2-b]pyrrole-5-carboxylate (413D)

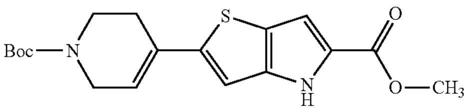

To a solution of tert-butyl 4-(4,4,5,5-tetramethyl-1,3,2-dioxaborolan-2-yl)-5,6-dihydropyridine-1 (2H)-carboxylate (2.64 g, 8.53 mmol) and methyl 2-bromo-4H-thieno[3,2-b]pyrrole-5-carboxylate (1.85 g, 7.11 mmol) in THE (20 mL) and water (4 mL) was added potassium phosphate tribasic (4.53 g, 21.34 mmol). The resulting solution was degassed with nitrogen for 10 mins. Then 1,1'-$PdCl_2$(dppf)-$CH_2Cl_2$ adduct (0.581 g, 0.711 mmol) was added and the reaction mixture was degassed again for 5 min. The resulting brown colored reaction mixture was heated to 80° C. for 12 h. The reaction mixture was diluted with EtOAc (100 mL), washed with water (100 mL) and aqueous layer was extracted with ethyl acetate (2×100 mL). The combined organic layer was dried over sodium sulphate, filtered and concentrated to get crude product. The crude product was purified by Combi-flash using 80 g silica column by eluting with 20% EtOAc/Pet. ether. Following concentration of fractions, methyl 2-(1-(tert-butoxycarbonyl)-1,2,3,6-tetrahydropyridin-4-yl)-4H-thieno[3,2-b]pyrrole-5-carboxylate (2.35 g, 6.48 mmol, 91% yield) was collected. LCMS retention time 1.50 min [F]. MS ($E^-$) m/z: 363.2 (M+H).

Intermediate 413E: methyl 2-(1-(tert-butoxycarbonyl)piperidin-4-yl)-4H-thieno[3,2-b]pyrrole-5-carboxylate (413E)

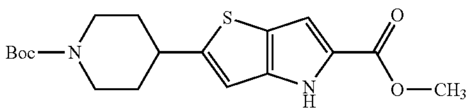

A solution of methyl 2-(1-(tert-butoxycarbonyl)-1,2,3,6-tetrahydropyridin-4-yl)-4H-thieno[3,2-b]pyrrole-5-carboxylate (0.44 g, 1.214 mmol) in MeOH (8 mL) was purged with nitrogen gas and Pd/C (0.039 g, 0.364 mmol) was added. The reaction mixture was purged with $N_2$ three times. Hydrogen gas was introduced via balloon to the mixture and the reaction mixture was stirred at room temperature for 8 h. The reaction mass was filtered through celite, rinsed with additional methanol and the filtrate was concentrated to dryness to give methyl 2-(1-(tert-butoxycarbonyl)piperidin-4-yl)-4H-thieno[3,2-b]pyrrole-5-carboxylate (0.31 g, 0.851 mmol, 70.1% yield). LCMS retention time 1.49 min [F]. MS ($E^-$) m/z: 365.4 (M+H).

Intermediate 413F: methyl 6-bromo-2-(1-(tert-butoxycarbonyl)piperidin-4-yl)-4H-thieno[3,2-b]pyrrole-5-carboxylate (413F)

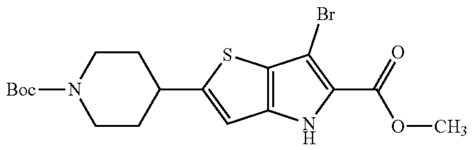

To a solution of methyl 2-(1-(tert-butoxycarbonyl)piperidin-4-yl)-4H-thieno[3,2-b]pyrrole-5-carboxylate (0.21 g, 0.576 mmol) in DMF (4 mL) was added a solution of NBS (0.103 g, 0.576 mmol) in DMF (0.5 ml) at 0° C. The reaction mixture was stirred for 1 h at room temperature. The reaction was quenched water (50 mL). The reaction mixture was extracted with ethyl acetate (2×50 mL). The separated organic layer was dried over sodium sulphate, filtered and concentrated to get methyl 6-bromo-2-(1-(tert-butoxycarbonyl) piperidin-4-yl)-4H-thieno[3,2-b]pyrrole-5-carboxylate (0.24 g, 0.541 mmol, 94% yield) LCMS retention time 1.60 min [F]. MS ($E^-$) m/z: 441.3 (M−2H).

Intermediate 413G: 4-(tert-butyl) 5-methyl 6-bromo-2-(1-(tert-butoxycarbonyl)piperidin-4-yl)-4H-thieno[3,2-b]pyrrole-4,5-dicarboxylate (413G)

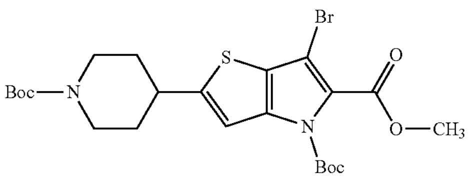

To a solution of methyl 6-bromo-2-(1-(tert-butoxycarbonyl)piperidin-4-yl)-4H-thieno[3,2-b]pyrrole-5-carboxylate (1.8 g, 4.06 mmol) in THE (20 mL) were added TEA (1.698 mL, 12.18 mmol), $Boc_2O$ (1.414 mL, 6.09 mmol) and DMAP (0.248 g, 2.030 mmol). The resulting reaction mixture was stirred at room temperature for 12 h. The reaction mass was partitioned between water (100 mL) and EtOAc (100 mL), the organic layer was washed with water and brine solution. The separated organic layer was dried over sodium sulphate, filtered and concentrated. The crude product was purified by Combiflash using silica column by eluting with 0-30% EtOAc/Pet ether. Following concentration of fractions, collected 4-tert-butyl 5-methyl 6-bromo-2-(1-(tert-butoxycarbonyl)piperidin-4-yl)-4H-thieno[3,2-b]pyrrole-4,5-dicarboxylate (1.4 g, 2.58 mmol, 63.4% yield). LCMS retention time 2.146 min [C]. MS ($E^-$) m/z: 431.0 (M+2H-2tBu).

Intermediate 413H: 4-(tert-butyl) 5-methyl 2-(1-(tert-butoxycarbonyl)piperidin-4-yl)-6-(prop-1-en-2-yl-4H-thieno[3,2-b]pyrrole-4,5-dicarboxylate (413H)

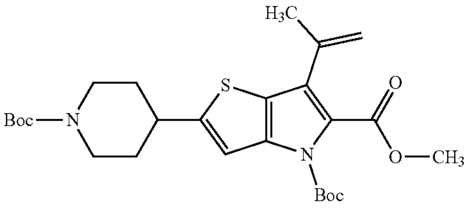

To a solution of 4-tert-butyl 5-methyl 6-bromo-2-(1-(tert-butoxycarbonyl)piperidin-4-yl)-4H-thieno[3,2-b]pyrrole-4,5-dicarboxylate (1.4 g, 2.58 mmol) and 4,4,5,5-tetramethyl-2-(prop-1-en-2-yl)-1,3,2-dioxaborolane (0.519 g, 3.09 mmol) in THE (15 mL) and water (1 mL) was added potassium phosphate tribasic (1.640 g, 7.73 mmol), The resulting solution was degassed with nitrogen for 10 mins. Then $2^{nd}$ G XPhos Precatalyst (0.203 g, 0.258 mmol) was added and the reaction mixture was degassed again for 5 min. The resulting brown colored reaction mixture was heated to 80° C. for 1 h. The reaction mixture was diluted with EtOAc (250 mL), washed with water (250 mL) and aqueous layer was extracted with ethyl acetate (2×200 mL). The combined organic layer was dried over sodium sulphate, filtered and concentrated to get crude product. The crude product was purified by Combiflash using silica column by eluting with 0-25% EtOAc/Pet. ether. Following concentration of fractions, 4-tert-butyl 5-methyl 2-(1-(tert-butoxycarbonyl)piperidin-4-yl)-6-(prop-1-en-2-yl)-4H-thieno[3,2-b]pyrrole-4,5-dicarboxylate (1.1 g, 2.180 mmol, 85% yield) was collected as a brown solid. LCMS retention time 4.59 min [C]. MS ($E^-$) m/z: 505.4 (M+H).

Intermediate 4131: 4-(tert-butyl) 5-methyl 2-(1-(tert-butoxycarbonyl)piperidin-4-yl)-6-isopropyl-4H-thieno[3,2-b]pyrrole-4,5-dicarboxylate (413I)

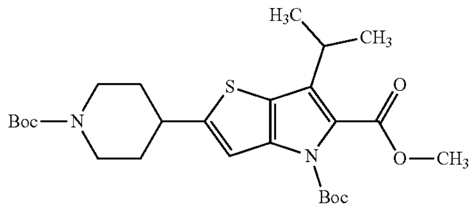

To a solution of 4-tert-butyl 5-methyl 2-(1-(tert-butoxycarbonyl)piperidin-4-yl)-6-(prop-1-en-2-yl)-4H-thieno[3,2-b]pyrrole-4,5-dicarboxylate (1.1 g, 2.180 mmol) in methanol (12 mL) was added Pd/C (0.232 g, 2.180 mmol). The reaction mixture was purged with $N_2$ three times. Hydrogen gas was introduced via a balloon to the mixture. The reaction mixture was stirred at room temperature for 16 h. The suspension was filtered through celite bed, the filtrate was collected and concentrated to afford 4-tert-butyl 5-methyl 2-(1-(tert-butoxycarbonyl)piperidin-4-yl)-6-isopropyl-4H-thieno[3,2-b]pyrrole-4,5-dicarboxylate (0.65 g, 1.283 mmol, 58.9% yield). LCMS retention time 2.26 min [F]. MS ($E^-$) m/z: 507.4 (M+H).

Intermediate 413J: 2-(1-(tert-butoxycarbonyl)piperidin-4-yl)-6-isopropyl-4H-thieno[3,2-b]pyrrole-5-carboxylic acid (413J)

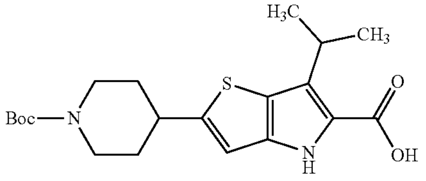

To a solution of 4-tert-butyl 5-methyl 2-(1-(tert-butoxycarbonyl)piperidin-4-yl)-6-isopropyl-4H-thieno[3,2-b]pyrrole-4,5-dicarboxylate (0.45 g, 0.888 mmol) in a mixture of methanol (10 mL) and water (1 mL) was added KOH (0.149 g, 2.66 mmol). The reaction mixture was stirred for 16 h at 60° C. The reaction mass was concentrated, aqueous layer was acidified to pH ~4-5, the resulting precipitate was filtered and dried to get 2-(1-(tert-butoxycarbonyl)piperidin-4-yl)-6-isopropyl-4H-thieno[3,2-b]pyrrole-5-carboxylic acid (0.32 g, 0.815 mmol, 92% yield) as a white solid. LCMS retention time 1.26 min [F]. MS ($E^-$) m/z: 391.4 (M−H).

Intermediate 413K: Tert-butyl 4-(5-bromo-6-isopropyl-4H-thieno[3,2-b]pyrrol-2-yl) piperidine-1-carboxylate (413K)

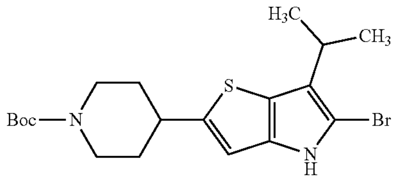

To a solution of 4-(tert-butoxycarbonyl)-2-(1-(tert-butoxycarbonyl)piperidin-4-yl)-6-isopropyl-4H-thieno[3,2-b]pyrrole-5-carboxylic acid (230 mg, 0.467 mmol) in DMF (6 mL) were added NBS (100 mg, 0.560 mmol) and iodobenzene diacetate (75 mg, 0.233 mmol). The reaction mixture was stirred for 24 h at room temperature. The reaction mass was partitioned between water and EtOAc. The organic layer was washed with water and brine solution, dried over sodium sulphate, filtered and concentrated. The crude product was purified over silica gel eluting 15% EA in hexane to afford tert-butyl 5-bromo-2-(1-(tert-butoxycarbonyl)piperidin-4-yl)-6-isopropyl-4H-thieno[3,2-b]pyrrole-4-carboxylate (50 mg, 0.117 mmol, 25.06% yield). LCMS retention time 1.88 min [F]. MS ($E^-$) m/z: 427.4 (M+2H).

Intermediate 413L: Tert-butyl 4-(6-isopropyl-5-(8-methoxy-[1,2,4]triazolo[1,5-a]pyridin-6-yl)-4H-thieno[3,2-b]pyrrol-2-yl)piperidine-1-carboxylate (413L)

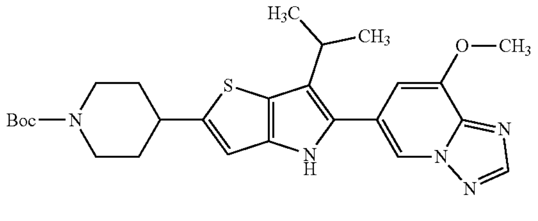

To a solution of tert-butyl 4-(5-bromo-6-isopropyl-4H-thieno[3,2-b]pyrrol-2-yl) piperidine-1-carboxylate (50 mg, 0.117 mmol) and 8-methoxy-6-(4,4,5,5-tetramethyl-1,3,2-dioxaborolan-2-yl)-[1,2,4]triazolo[1,5-a]pyridine (41.8 mg, 0.152 mmol) in a mixture of 1,4-dioxane (3 mL) and water (0.3 mL) was added tripotassium phosphate (74.5 mg, 0.351 mmol). The resulting solution was degassed with $N_2$ for 5 mins. Then $PdCl_2$(dppf)-$CH_2Cl_2$ adduct (9.55 mg, 0.012 mmol) was added and the reaction mixture was degassed for 2 mins. The resulting reaction mixture was heated at 105° C. for 2 h. The reaction mixture was filtered through celite, concentrated to get tert-butyl 4-(6-isopropyl-5-(8-methoxy-[1,2,4]triazolo[1,5-a]pyridin-6-yl)-4H-thieno[3,2-b]pyrrol-2-yl)piperidine-1-carboxylate (130 mg, 0.045 mmol, 38.1% yield). LCMS retention time 1.65 min [F]. MS ($E^-$) m/z: 496.6 (M+H).

Example 413: 6-isopropyl-5-(8-methoxy-[1,2,4]triazolo[1,5-a]pyridin-6-yl)-2-(piperidin-4-yl)-4H-thieno[3,2-b]pyrrole To a stirred solution of tert-butyl 4-(6-isopropyl-5-(8-methoxy-[1,2,4]triazolo[1,5-a]pyridin-6-yl)-4H-thieno[3,2-b]pyrrol-2-yl)piperidine-1-carboxylate (130 mg, 0.045 mmol) in DCM (1 mL) was added 4 M hydrochloric acid in dioxane (0.111 mL, 0.446 mmol) at 0° C. The reaction mixture was stirred at room temperature for 2 h. The reaction mass was concentrated under vacuum. After Preparative LCMS purification, fractions containing product was combined and dried using Genevac centrifugal evaporator to get 6-isopropyl-5-(8-methoxy-[1,2,4]triazolo[1,5-a]pyridin-6-yl)-2-(piperidin-4-yl)-4H-thieno[3,2-b]pyrrole (2.9 mg, 7.33 μmol, 16.44% yield). LCMS retention time 1.46 min [A]. MS ($E^-$) m/z: 396.0 (M+H). $^1$H NMR (400 MHz, DMSO-$d_6$) δ ppm 11.22 (s, 1H) 8.46 (s, 2H) 7.12 (s, 1H) 6.76-6.86 (m, 1H)) 4.01-4.14 (m, 3H) 3.17 (d, J=4.89 Hz, 4H) 3.09 (d, J=11.49 Hz, 1H) 2.96 (d, J=12.23 Hz, 2H) 2.33 (d, J=1.71 Hz, 2H) 1.86-2.14 (m, 2H) 1.22-1.35 (m, 6H).

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand ($R_{848}$ at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 48

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 1 | 2.01 | 8.14 | 760 |
| 2 | 2.27 | 5.82 | 6561 |
| 3 | 1.84 | 3.05 | 18524 |
| 4 | 5.52 | 33.9 | 287 |
| 6 | 2.05 | 20.9 | 1095 |
| 7 | 7.80 | 6.59 | 5474 |
| 8 | 2.47 | 5.42 | 30896 |
| 9 | >3125 | >3125 | 4157 |
| 10 | 1.37 | 1.90 | 1329 |
| 11 | 3.78 | 9.31 | 18465 |
| 12 | 1.59 | 0.86 | 2151 |
| 13 | 5.04 | 2.03 | 3332 |
| 14 | 1.92 | 0.94 | 3839 |
| 15 | 4.15 | 3.14 | 7813 |

TABLE 48-continued

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 16 | 3.09 | 2.74 | 43471 |
| 17 | 8.08 | 8.27 | 3433 |
| 18 | 5.69 | 2.57 | 3743 |
| 19 | 1.40 | 12.0 | 5943 |
| 20 | 3.69 | 8.06 | 16145 |
| 21 | 6.89 | 39.0 | >50,000 |
| 22 | 1.23 | 0.90 | 4851 |
| 23 | 1.27 | 1.01 | 4769 |
| 24 | 43.4 | 12.5 | 793 |
| 25 | 25.6 | 10.3 | 447 |
| 26 | 442 | 413 | 7208 |
| 27 | 29.7 | 2.87 | 388 |
| 28 | 39.0 | 265 | 645 |
| 29 | 18.4 | 1.91 | 216 |
| 30 | 4.37 | 2.07 | 14781 |
| 31 | 3.98 | 3.02 | >50,000 |
| 32 | 3.41 | 15.9 | >50,000 |
| 33 | 3.86 | 1.52 | >50,000 |
| 34 | 4.44 | 4.94 | >50,000 |
| 35 | 2.77 | 0.79 | 4348 |
| 36 | 1296 | 1545 | 25216 |
| 37 | 12.1 | 27.0 | 27925 |
| 38 | 7.93 | 4.43 | 2279 |
| 39 | 8.31 | 25.5 | 3560 |
| 40 | 29.9 | 31.1 | 18945 |
| 41 | 1.19 | 2.66 | 8427 |
| 42 | 2.99 | 6.77 | 19016 |
| 43 | 2.54 | 5.22 | >50,000 |
| 44 | 1.68 | 0.63 | 15060 |
| 45 | 1.84 | 19.5 | 45442 |
| 46 | 0.57 | 0.11 | 2500 |
| 47 | 2.92 | 0.56 | 6844 |
| 48 | 6.02 | 4.32 | 19485 |
| 49 | 0.97 | 0.48 | 9223 |
| 50 | 1.27 | 2.74 | 17297 |
| 51 | 1.59 | 1.03 | 8802 |
| 52 | 2.90 | 4.22 | 17961 |
| 53 | 0.94 | 0.79 | 5072 |
| 54 | 1.10 | 3.74 | 6670 |
| 55 | 2.99 | 1.15 | >50,000 |
| 56 | 4.36 | 3.43 | ND |
| 57 | 4.24 | 1.34 | 23122 |
| 58 | 3.01 | 1.43 | 32815 |
| 59 | 5.83 | 47.2 | >50,000 |
| 60 | 36.6 | 27.9 | >50,000 |
| 61 | 22.7 | 5.33 | >50,000 |
| 62 | 88.6 | 22.3 | >50,000 |
| 63 | 24.8 | 14.6 | >50,000 |
| 64 | 32.7 | 10.4 | >50,000 |
| 65 | 0.55 | 1.37 | 10099 |
| 66 | 3.59 | 16.9 | 5714 |
| 67 | 12.6 | 12.9 | 2249 |
| 68 | 0.81 | 0.58 | 3498 |
| 69 | 4.17 | 35.6 | 6322 |
| 70 | 0.58 | 1.46 | 6613 |
| 71 | 6.92 | 19.0 | 5810 |
| 72 | 1.23 | 4.75 | 7217 |
| 73 | 0.96 | 12.7 | 4275 |
| 74 | 0.71 | 3.44 | 1905 |
| 75 | 0.89 | 7.55 | 3392 |
| 76 | 0.90 | 2.62 | 1453 |
| 77 | 2.03 | 21.5 | 3268 |
| 78 | 0.59 | 1.64 | 2867 |
| 79 | 2.29 | 9.23 | 4115 |
| 82 | 4.69 | 43.6 | >50,000 |
| 83 | 6.33 | 238 | >50,000 |
| 84 | 0.90 | 0.84 | 9109 |
| 85 | 2.66 | 17.5 | 6907 |
| 86 | 1.34 | 0.70 | 6419 |
| 87 | 1.73 | 11.8 | 7794 |
| 88 | 0.81 | 1.84 | 4450 |
| 89 | 1.48 | 18.9 | 4097 |
| 90 | 0.80 | 1.13 | 11121 |
| 91 | 4.01 | 8.12 | 6720 |

TABLE 48-continued

| TLR7/8/9 Reporter Assay Data | | | |
|---|---|---|---|
| Ex. No. | TLR7 $IC_{50}$ (nM) | TLR8 $IC_{50}$ (nM) | TLR9 $IC_{50}$ (nM) |
| 92 | 0.31 | 2.34 | 4108 |
| 93 | 1.89 | 15.6 | 12020 |
| 94 | 1.94 | 3.14 | 40734 |
| 95 | 11.7 | 23.8 | 43167 |
| 96 | 1.53 | 0.98 | 7766 |
| 97 | 2.42 | 41.9 | 5491 |
| 98 | 0.12 | 1.37 | 2978 |
| 99 | 1.19 | 36.7 | 3610 |
| 100 | 78.9 | 114 | 6397 |
| 101 | 3.68 | 23.0 | 4788 |
| 102 | 0.37 | 14.0 | 3888 |
| 103 | 48.0 | 3.46 | 3600 |
| 104 | 1.98 | 2.81 | 5600 |
| 105 | 1.38 | 43.2 | 2181 |
| 106 | 2.25 | 90.9 | 14313 |
| 107 | 3.60 | 190 | 15381 |
| 108 | 1.34 | 4.49 | 5697 |
| 109 | 6.81 | 27.9 | 6089 |
| 110 | 2.21 | 0.93 | 5780 |
| 111 | 2.97 | 33.7 | 3926 |
| 112 | 11.4 | 28.3 | >50,000 |
| 113 | 1.09 | 27.1 | 7804 |
| 114 | 3.63 | 1.40 | 1460 |
| 115 | 11.7 | 17.0 | 1213 |
| 116 | 3.11 | 1.91 | 3879 |
| 117 | 5.72 | 22.9 | 7507 |
| 118 | 2.00 | 1.26 | 3300 |
| 119 | 3.33 | 54.2 | >50,000 |
| 120 | 4.19 | 16.7 | >50,000 |
| 121 | 8.51 | 57.3 | >50,000 |
| 122 | 1.95 | 3.34 | 9253 |
| 123 | 5.09 | 16.8 | 6292 |
| 124 | 7.72 | 31.5 | 28611 |
| 125 | 5.80 | 25.9 | 5401 |
| 126 | 0.98 | 6.83 | 13242 |
| 127 | 1.99 | 178 | >50,000 |
| 128 | 1.21 | 8.29 | 13442 |
| 129 | 1.34 | 7.36 | 14448 |
| 130 | 0.45 | 2.42 | 11470 |
| 131 | 7.48 | 32.6 | 10934 |
| 132 | 0.36 | 2.73 | 2140 |
| 134 | 1.23 | 1.28 | 16069 |
| 135 | 6.80 | 38.9 | 22365 |
| 136 | 1.69 | 4.36 | 42820 |
| 137 | 3.40 | 40.8 | 6731 |
| 138 | 0.93 | 3.96 | 14766 |
| 139 | 4.96 | 26.3 | 17548 |
| 140 | 0.59 | 0.89 | 10397 |
| 141 | 3.03 | 13.5 | 12807 |
| 142 | 2.08 | 2.70 | 6968 |
| 143 | 5.34 | 19.6 | 9282 |
| 144 | 7.26 | 3.56 | 15245 |
| 145 | 60.3 | 41.6 | >50,000 |
| 146 | 19.7 | 0.92 | 16339 |
| 147 | 90.1 | 5.67 | 18813 |
| 148 | 11.8 | 9.93 | >50,000 |
| 149 | 108 | 98.5 | >50,000 |
| 150 | 0.57 | 0.39 | 2825 |
| 151 | 49.2 | 60.0 | 23354 |
| 152 | 13.7 | 31.6 | 20871 |
| 153 | 27.8 | 6.62 | 22275 |
| 154 | 11.9 | 3.33 | 9308 |
| 155 | 41.5 | 21.5 | >50,000 |
| 156 | 1.72 | 0.09 | 10887 |
| 157 | 37.4 | 11.9 | 16381 |
| 158 | 8.95 | 31.0 | 14340 |
| 159 | 8.79 | 4.78 | 6872 |
| 160 | 0.61 | 0.06 | 5299 |
| 161 | 18.1 | 14.7 | 16956 |
| 162 | 2.60 | 15.7 | 20258 |
| 163 | 1.59 | 20.6 | 9403 |
| 164 | 1.32 | 4.43 | 15648 |
| 165 | 1.61 | 14.4 | 22808 |
| 166 | 0.88 | 0.87 | 383 |

TABLE 48-continued

| TLR7/8/9 Reporter Assay Data | | | |
|---|---|---|---|
| Ex. No. | TLR7 $IC_{50}$ (nM) | TLR8 $IC_{50}$ (nM) | TLR9 $IC_{50}$ (nM) |
| 167 | 7.37 | 34.8 | 1714 |
| 168 | 6.58 | 33.9 | >50,000 |
| 169 | 4.17 | 17.0 | 9815 |
| 170 | 2.38 | 4.65 | 1760 |
| 171 | 0.78 | 2.21 | 879 |
| 172 | 2.84 | 1.22 | 14808 |
| 173 | 8.56 | 7.58 | 7787 |
| 174 | 1.84 | 3.13 | 16045 |
| 175 | 3.76 | 6.23 | 6254 |
| 176 | 23.3 | 23.7 | 9581 |
| 177 | 3.23 | 5.63 | 9787 |
| 178 | 1.69 | 2.44 | 6711 |
| 179 | 9.72 | 13.5 | 7264 |
| 180 | 3.54 | 3.70 | 5281 |
| 181 | 9.92 | 36.0 | 5662 |
| 182 | 1.74 | 0.76 | 13524 |
| 183 | 8.89 | 9.41 | 6792 |
| 184 | 1.01 | 0.84 | 11393 |
| 185 | 7.42 | 3.38 | 23025 |
| 186 | 1.59 | 0.21 | 5924 |
| 187 | 10.4 | 4.25 | 8723 |
| 188 | 0.71 | 0.58 | 10798 |
| 189 | 3.35 | 5.18 | 10021 |
| 190 | 0.80 | 0.58 | 8347 |
| 191 | 1.50 | 1.79 | 9372 |
| 192 | 1.67 | 0.33 | 16153 |
| 193 | 1.97 | 4.45 | 7629 |
| 194 | 0.90 | 0.37 | 9218 |
| 195 | 2.24 | 1.66 | 5497 |
| 196 | 1.13 | 0.17 | 12741 |
| 197 | 5.35 | 2.08 | 13083 |
| 199 | 4.98 | 2.19 | 2951 |
| 200 | 0.92 | 0.39 | 10143 |
| 201 | 6.66 | 4.21 | 9247 |
| 204 | 1.50 | 0.63 | 17783 |
| 205 | 6.66 | 2.33 | 21543 |
| 206 | 2.27 | 0.64 | 12564 |
| 207 | 2.92 | 0.31 | 20699 |
| 208 | 1.00 | 0.52 | 19975 |
| 209 | 0.32 | 0.14 | 4172 |
| 210 | 1.80 | 1.24 | 23847 |
| 211 | 0.79 | 0.58 | 14287 |
| 212 | 0.62 | 0.63 | 7394 |
| 213 | 4.64 | 3.41 | 25506 |
| 214 | 1.37 | 0.39 | 10279 |
| 215 | 2.30 | 6.00 | 14960 |
| 216 | 0.72 | 1.02 | 6519 |
| 217 | 2.41 | 5.30 | 5867 |
| 218 | 1.44 | 18.6 | 35931 |
| 219 | 637 | 713 | 46250 |
| 220 | 1.40 | 4.38 | >50,000 |
| 221 | 3.08 | 33.3 | >50,000 |
| 222 | 0.75 | 1.94 | 30393 |
| 223 | 8.65 | 10.3 | 14267 |
| 224 | 0.56 | 0.63 | 9031 |
| 225 | 2.56 | 3.94 | 5492 |
| 226 | 0.35 | 0.41 | 6781 |
| 227 | 4.43 | 11.4 | 18152 |
| 228 | 2.18 | 1.46 | 8856 |
| 229 | 7.10 | 3.71 | 4956 |
| 230 | 4.92 | 1.50 | 43540 |
| 231 | 6.32 | 1.19 | 49483 |
| 232 | 4.19 | 7.87 | >50,000 |
| 233 | 2.30 | 0.59 | >50,000 |
| 234 | 15.1 | 59.8 | >50,000 |
| 235 | 1.05 | 1.01 | 16626 |
| 236 | 1.36 | 18.7 | 25422 |
| 237 | 4.87 | 0.29 | 5489 |
| 238 | 5.40 | 5.96 | 5373 |
| 239 | 1.96 | 0.27 | 9925 |
| 240 | 3.72 | 2.82 | 6228 |
| 241 | 8.06 | 3.19 | >50,000 |
| 242 | 47.1 | 16.1 | >50,000 |
| 243 | 16.4 | 2.10 | 29778 |

TABLE 48-continued

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 244 | 44.0 | 17.5 | 25345 |
| 245 | 2.60 | 0.65 | 22888 |
| 246 | 60.8 | 154 | >50,000 |
| 247 | 5.87 | 4.42 | 42481 |
| 248 | 8.33 | 12.0 | 13991 |
| 249 | 6.34 | 1.19 | 19782 |
| 250 | 46.8 | 43.6 | 43285 |
| 251 | 10.6 | 2.68 | 45256 |
| 252 | 67.9 | 35.8 | >50,000 |
| 253 | 4.70 | 3.01 | 23034 |
| 254 | 26.8 | 22.7 | 29154 |
| 255 | 6.86 | 4.88 | 15077 |
| 256 | 34.3 | 31.3 | 16919 |
| 257 | 13.6 | 0.86 | 34852 |
| 258 | 36.5 | 9.16 | 29352 |
| 259 | 23.5 | 13.8 | >50,000 |
| 260 | 170 | 138 | >50,000 |
| 261 | 8.43 | 2.26 | 17060 |
| 262 | 23.8 | 17.5 | 18343 |
| 263 | 4.74 | 4.48 | 18123 |
| 264 | 26.8 | 22.9 | 21966 |
| 265 | 14.0 | 3.29 | 47693 |
| 266 | 119 | 60.2 | >50,000 |
| 267 | 24.3 | 7.16 | >50,000 |
| 268 | 41.1 | 65.1 | >50,000 |
| 269 | 4.31 | 2.55 | 6277 |
| 270 | 8.99 | 14.0 | 3459 |
| 271 | 0.96 | 1.94 | 4561 |
| 272 | 137 | 122 | >50,000 |
| 273 | 13.7 | 26.5 | 5545 |
| 275 | 413 | 515 | >50,000 |
| 276 | 975 | >3125 | >50,000 |
| 278 | 1.43 | 0.33 | 10831 |
| 279 | 11.0 | 1.08 | 23868 |
| 280 | 1.26 | 0.73 | 4963 |
| 281 | 9.49 | 0.45 | 42605 |
| 282 | 29.8 | 5.33 | >50,000 |
| 283 | 18.8 | 1.70 | >50,000 |
| 284 | 9.60 | 5.12 | >50,000 |
| 285 | 7.70 | 2.71 | >50,000 |
| 286 | 25.6 | 14.6 | >50,000 |
| 287 | 13.3 | 0.54 | 29166 |
| 288 | 15.2 | 0.52 | 14160 |
| 289 | 5.19 | 0.97 | 19707 |
| 290 | 8.56 | 1.09 | 22075 |
| 291 | 7.65 | 0.39 | 16812 |
| 292 | 3.18 | 0.46 | 7518 |
| 293 | 2.98 | 0.38 | 6646 |
| 294 | 7.97 | 0.42 | 8988 |
| 295 | 4.94 | 0.28 | 9708 |
| 296 | 3.45 | 0.73 | 33812 |
| 297 | 2.25 | 0.27 | 8912 |
| 298 | 1.56 | 0.43 | 7406 |
| 299 | 1.42 | 0.72 | 12737 |
| 300 | 10.7 | 3.24 | 10058 |
| 301 | 7.77 | 1.53 | 12256 |
| 302 | 9.44 | 14.2 | >50,000 |
| 303 | 7.99 | 0.93 | 26352 |
| 304 | 8.20 | 19.2 | 35593 |
| 305 | 311 | 70.0 | >50,000 |
| 306 | 148 | 124 | >50,000 |
| 307 | 118 | 9.33 | >50,000 |
| 308 | 0.18 | 0.09 | 15839 |
| 309 | 6.67 | 4.19 | 14441 |
| 310 | 1.45 | 0.43 | 19250 |
| 311 | 1399 | >3125 | 18849 |
| 312 | 5.42 | 17.8 | >50,000 |
| 313 | 3.71 | 1.72 | >50,000 |
| 314 | 13.9 | 18.5 | >50,000 |
| 315 | 5.22 | 20.2 | >50,000 |
| 316 | 12.0 | 52.4 | >50,000 |
| 317 | 9.47 | 4.22 | 44385 |
| 318 | 6.23 | 0.83 | 21576 |
| 319 | 3.84 | 0.53 | 19426 |

TABLE 48-continued

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 320 | 4.38 | 1.30 | 21916 |
| 322 | 15.7 | 4.67 | 35830 |
| 323 | 22.4 | 3.86 | >50,000 |
| 324 | 6.96 | 2.26 | 6241 |
| 325 | 19.0 | 0.19 | >50,000 |
| 326 | 5.42 | 7.97 | 17597 |
| 327 | 7.50 | 7.11 | 15788 |
| 328 | 12.9 | 12.8 | 18825 |
| 329 | 414 | 60.3 | 14716 |
| 330 | 8.34 | 1.50 | 11379 |
| 331 | 4.29 | 0.49 | 6312 |
| 332 | 16.9 | 1.91 | 10223 |
| 333 | 34.9 | 2.19 | 37410 |
| 334 | 13.6 | 3.19 | 4833 |
| 335 | 15.5 | 11.1 | >50,000 |
| 336 | 13.5 | 39.7 | 38113 |
| 337 | 8.27 | 7.61 | 42352 |
| 338 | 10.1 | 31.1 | 45555 |
| 339 | 19.9 | 3.86 | 36585 |
| 340 | 4.64 | 3.38 | 5217 |
| 341 | 7.86 | 9.00 | 16469 |
| 342 | 19.6 | 12.6 | >50,000 |
| 343 | 24.1 | 3.30 | >50,000 |
| 344 | 39.0 | 12.7 | >50,000 |
| 345 | 23.4 | 3.12 | >50,000 |
| 346 | 6.30 | 7.94 | 19178 |
| 347 | 22.9 | 44.5 | >50,000 |
| 348 | 19.1 | 22.4 | >50,000 |
| 349 | 91.0 | 1.85 | >50,000 |
| 350 | 8.11 | 0.12 | 21733 |
| 351 | 8.23 | 0.98 | 19803 |
| 352 | 14.4 | 1.09 | 24469 |
| 357 | 1276 | >3125 | 38095 |
| 359 | 1116 | >3125 | >50,000 |
| 360 | 1219 | 1332 | >50,000 |
| 361 | 719 | >3125 | 45566 |
| 362 | >3125 | >3125 | 25136 |
| 366 | >3125 | >3125 | 6257 |
| 368 | 10.5 | 28.1 | 5465 |
| 369 | 18 | 33 | 46920 |
| 370 | 12.4 | 1.38 | 6439 |
| 371 | 72.1 | 29.4 | >50,000 |
| 372 | 10.7 | 2.49 | 8884 |
| 373 | 81.9 | 34.5 | 42120 |
| 374 | 11.7 | 9.33 | 41484 |
| 375 | 19.9 | 8.40 | 35613 |
| 376 | 4.54 | 2.80 | 6299 |
| 377 | 56.9 | 18.2 | >50,000 |
| 378 | 29.4 | 12.2 | >50,000 |
| 379 | 55.7 | 22.9 | 28012 |
| 380 | 11.5 | 5.07 | 6519 |
| 381 | 11.1 | 9.06 | 5882 |
| 382 | 2.32 | 2.33 | 9860 |
| 383 | 17.5 | 3.51 | 47044 |
| 384 | 39.5 | 20.1 | >50,000 |
| 385 | 58.8 | 31.4 | >50,000 |
| 386 | 10.3 | 3.56 | 9563 |
| 387 | 25.2 | 43.9 | 11523 |
| 388 | 22.4 | 37.4 | 16145 |
| 389 | 50.3 | 168 | 37137 |
| 390 | 93.6 | 481 | >50,000 |
| 391 | 102 | 118 | >50,000 |
| 392 | 241 | 404 | >50,000 |
| 393 | 77.6 | 140 | >50,000 |
| 394 | 154 | 529 | >50,000 |
| 395 | 7.89 | 6.75 | 4505 |
| 396 | 102 | 53.9 | >50,000 |
| 397 | 221 | 463 | >50,000 |
| 398 | 137 | 365 | >50,000 |
| 399 | 126 | 132 | >50,000 |
| 400 | 13.5 | 15.9 | 9251 |
| 401 | 36.9 | 35.7 | 13527 |
| 402 | 35.1 | 297 | >50,000 |
| 403 | 26.9 | 156 | >50,000 |

TABLE 48-continued

| TLR7/8/9 Reporter Assay Data | | | |
|---|---|---|---|
| Ex. No. | TLR7 $IC_{50}$ (nM) | TLR8 $IC_{50}$ (nM) | TLR9 $IC_{50}$ (nM) |
| 404 | 43.6 | 124 | >50,000 |
| 405 | 77.5 | 215 | 37668 |
| 406 | 2.74 | 142 | >50,000 |
| 407 | 28.6 | 279 | >50,000 |
| 408 | 47.4 | 168 | >50,000 |
| 409 | 48.2 | 345 | 9800 |
| 410 | 130 | 560 | 6800 |
| 411 | 1.8 | 200 | 3100 |
| 412 | 50 | 520 | 5000 |
| 413 | 5.3 | 9.3 | 3100 |

In Vivo Mouse TLR7 PD Model:

Adult male C57BL/6 mice were used for the experiments. Mice (7 to 10 per group) were randomized into different treatment groups based on body weight. Mice from the respective treatment groups were administered orally with vehicle or test compound. Thirty min after the oral administration of vehicle or test compound, mice were challenged with intraperitoneal injection of gardiquimod for TLR7 PD model. Ninety minutes after gardiquimod injection, mice were bled under isoflurane anaesthesia and plasma IL-6 and IFN-alpha levels were estimated by using commercially available ELISA kit (BD Biosciences, PBL Life Sciences). At the end of experiment, mean cytokine data was plotted and one way ANOVA with Dunnett's test was performed to calculate the significance of test compound treated group vs. vehicle control group. Percent inhibition of cytokine induction was calculated for test compound treated group vs vehicle control group. Data with Example 65 is shown in Table 49.

TABLE 49

| Percent inhibition of IL-6 and IFN-alpha in mouse TLR7 PD model TLR7 PD model | | | |
|---|---|---|---|
| Ex. No. | Dose (mg/kg) | % inhibition of IL6 | % inhibition of IFN-alpha |
| 65 | 0.001 | 21 | 50 |
| | 0.005 | 42 | 63 |
| | 0.025 | 78 | 97 |
| | 0.050 | 94 | 99 |

What is claimed is:

1. A compound of Formula (I)

(I)

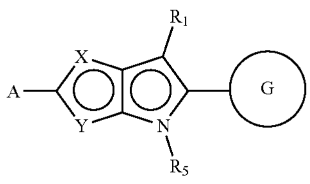

N-oxide, or a salt thereof, wherein:

X is N and Y is S; or X is S and Y is N;

$R_1$ is F, Cl, —CN, $C_{1-4}$ alkyl, $C_{1-3}$ fluoroalkyl, —$OCH_3$, or —$S(O)_2(C_{1-3}$ alkyl);

G is:

(i)

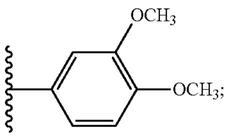 [SMILES: *c1ccc(OC)c(OC)c1]

(ii)

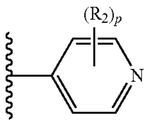

or

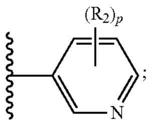

(iii)

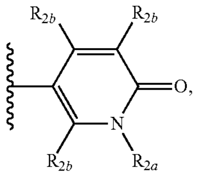

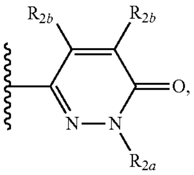

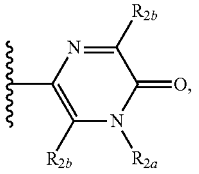

or

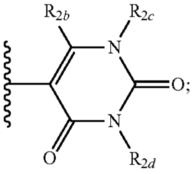

(iv) a 9-membered heterocyclic ring selected from:

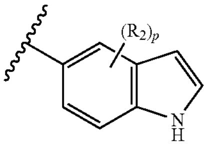

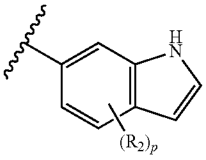

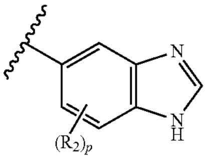

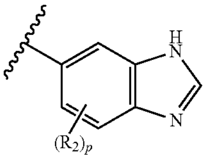

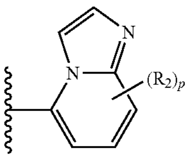

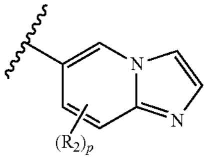

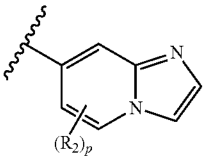

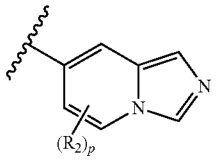

-continued
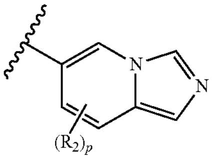
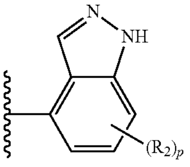
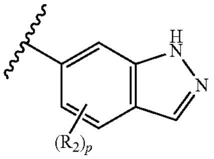
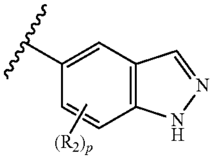
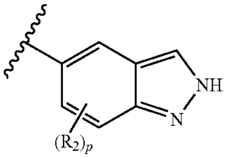
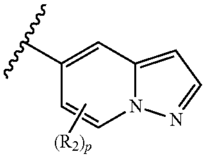
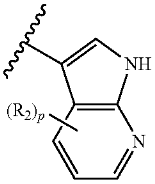
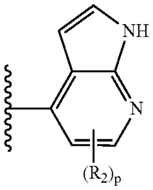
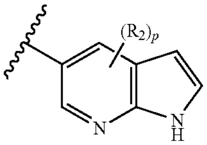
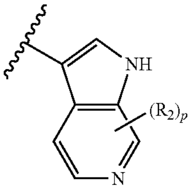
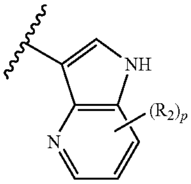
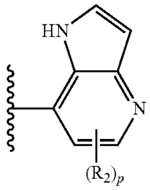
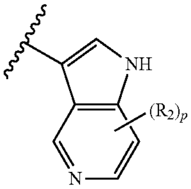
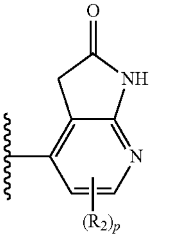
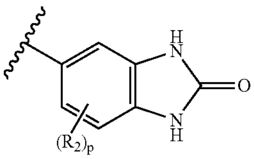
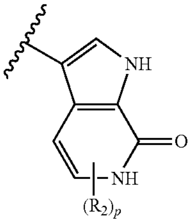
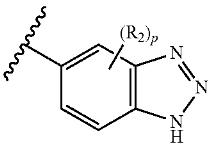
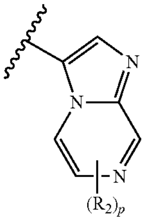
-continued
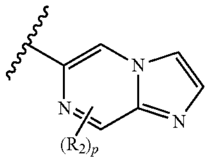
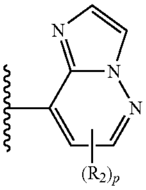
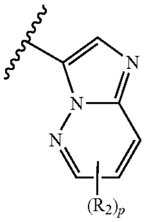
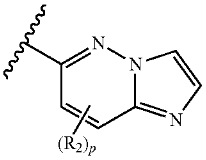
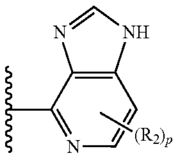
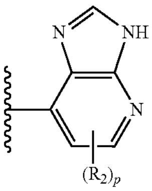
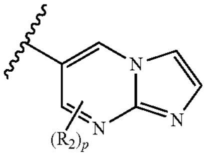
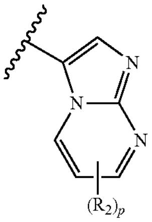
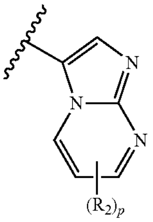
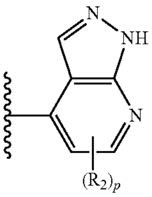
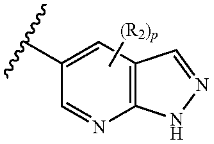
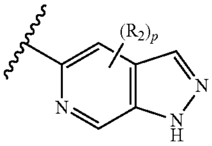
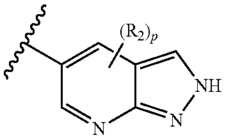
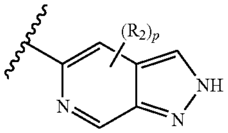
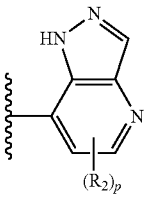
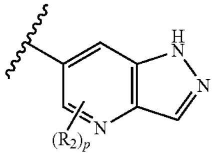
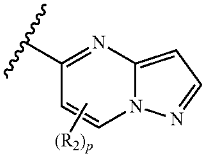
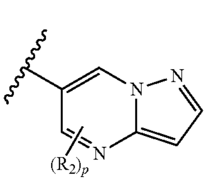
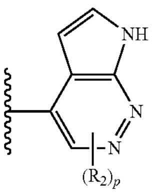
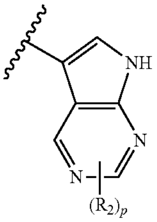

-continued
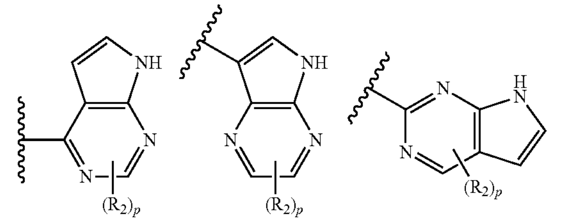
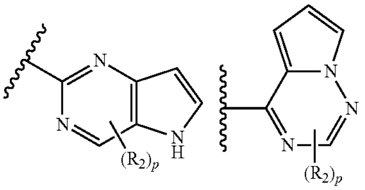
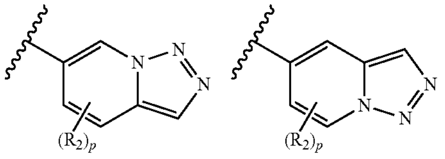
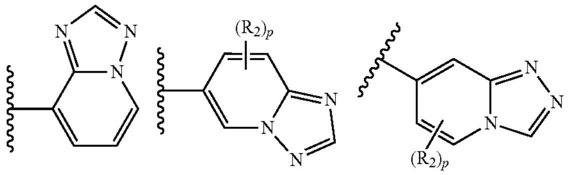
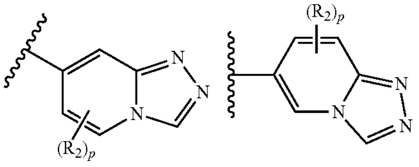
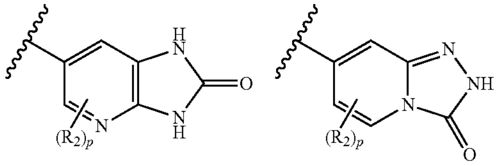
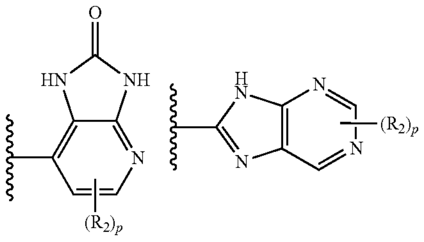
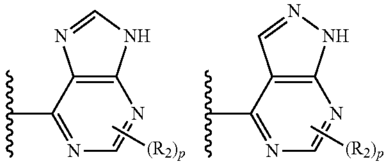
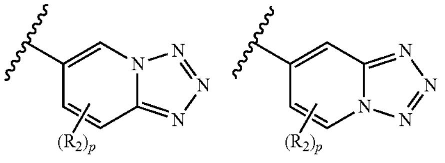
-continued
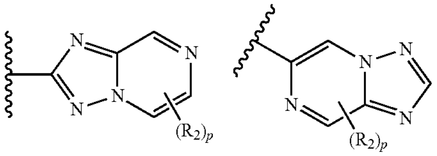
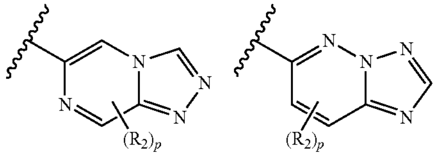
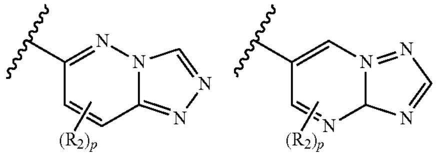
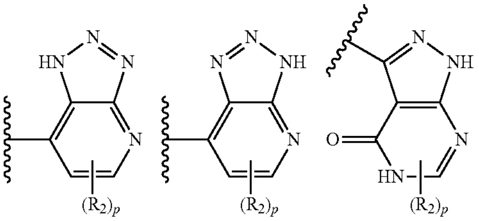
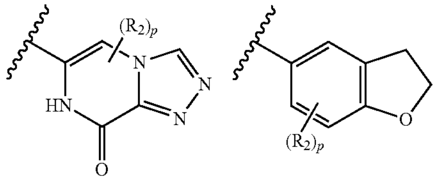
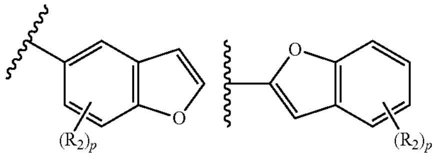
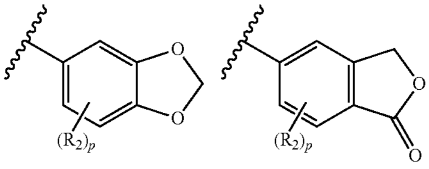
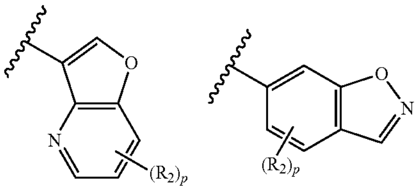
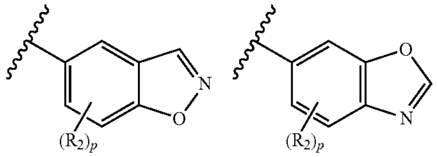
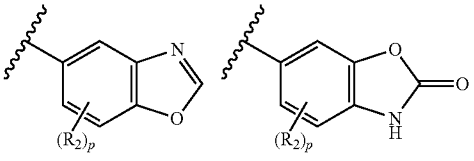

-continued

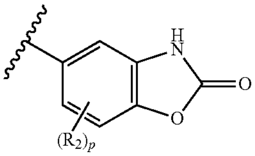

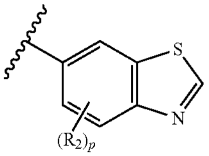

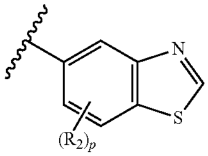

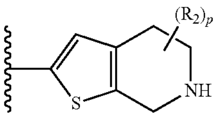

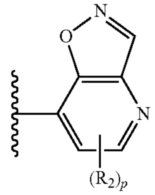

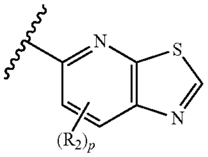

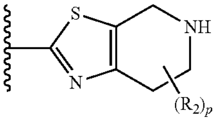

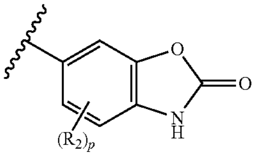

and

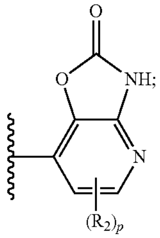

or (v) 10-membered heterocyclic ring selected from:

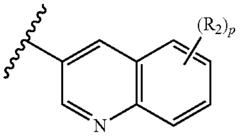

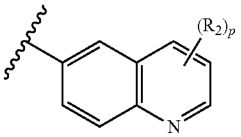

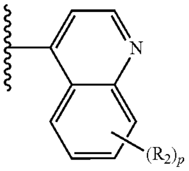

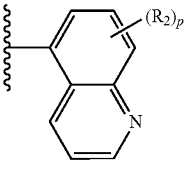

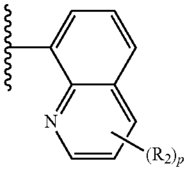

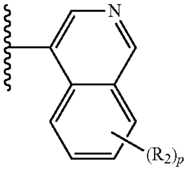

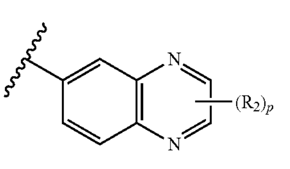

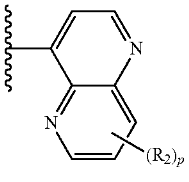

-continued

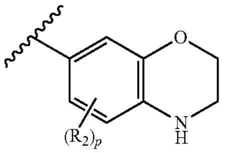

and

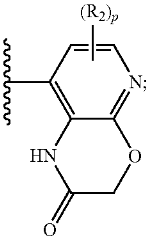

each $R_2$ is independently halo, —CN, —OH, —$NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —$O(CH_2)_{1-2}OH$, —$(CH_2)_{0-4}O(C_{1-4}$ alkyl), $C_{1-3}$ fluoroalkoxy, —$(CH_2)_{1-4}O(C_{1-3}$ alkyl), —$O(CH_2)_{1-2}OC(O)(C_{1-3}$ alkyl), —$O(CH_2)_{1-2}NR_xR_x$, —$C(O)O(C_{1-3}$ alkyl), —$(CH_2)_{0-2}C(O)NR_yR_y$, —C(O)NRx($C_{1-5}$ hydroxyalkyl), —$C(O)NR_x(C_{2-6}$ alkoxyalkyl), —$C(O)NR_x(C_{3-6}$ cycloalkyl), —$NR_yR_y$, —$NR_y(C_{1-3}$ fluoroalkyl), —$NR_y(C_{1-4}$ hydroxyalkyl), —$NR_xCH_2$(phenyl), —$NR_xS(O)_2(C_{3-6}$ cycloalkyl), —$NR_xC(O)(C_{1-3}$ alkyl), —$NR_xCH_2(C_{3-6}$ cycloalkyl), —$(CH_2)_{0-2}S(O)_2(C_{1-3}$ alkyl), —$(CH_2)_{0-2}(C_{3-6}$ cycloalkyl), —$(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, pyrimidinyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —$(CH_2)_{0-4}O(C_{1-3}$ alkyl), $C_{3-6}$ cycloalkyl, —$(CH_2)_{1-3}C(O)NR_yR_y$, —$CH_2(C_{3-6}$ cycloalkyl), —$CH_2$(phenyl), tetrahydrofuranyl, tetrahydropyranyl, or phenyl;

each $R_{2b}$ is independently H, halo, —CN, —$NR_xR_x$, $C_{1-6}$ alkyl, $C_{1-3}$ fluoroalkyl, $C_{1-3}$ hydroxyalkyl, $C_{1-3}$ fluoroalkoxy, —$(CH_2)_{0-2}O(C_{1-3}$ alkyl), —$(CH_2)_{0-3}C(O)NR_xR_x$, —$(CH_2)_{1-3}(C_{3-6}$ cycloalkyl), —$C(O)O(C_{1-3}$ alkyl), —$C(O)NR_x(C_{1-3}$ alkyl), —$CR_x$=$CR_xR_x$, or —$CR_x$=$CH(C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_2$ is $R_{2b}$;

A is:

(i) —$NR_yR_y$, or —$CH_2NHCH_2C(O)NR_xR_x$;

(ii) —$CR_xR_xR_3$, —$CR_xR_xNR_xR_3$, —$CR_xR_xNR_xCH_2R_3$, —$C(O)NR_xR_3$, —$C(O)NR_xR_4$, —$C(O)R_3$, or —$NR_xC(O)R_3$; or (iii) $R_3$;

$R_3$ is:

(i) $C_{3-5}$ cycloalkyl, azetidinyl, oxetanyl, pyrrolidinyl, pyrrolidinonyl, piperidinyl, piperazinyl, piperazinonyl, morpholinyl, dioxidothiomorpholinyl, oxazepanyl, diazaspiro[3.3]heptanyl, dioxidothiaazaspiro[3.3]heptanyl, oxaazaspiro[3.3]heptanyl, or oxaazaspiro[3.5]nonanyl, each substituted with zero to 2 $R_{3a}$ and zero to 2 $R_{3b}$;

(ii) cyclohexyl substituted with —$NR_yR_y$, —$NR_x(C_{1-6}$ hydroxyalkyl), —$NR_x(CR_xR_x)_{1-2}O(C_{1-3}$ alkyl), —$NR_x(C_{1-6}$ hydroxy-fluoroalkyl), —$NR_xCH_2C(O)NR_xR_x$, —$NR_x(CH_2)_{1-2}S(O)_2(C_{1-3}$ alkyl), —$NR_xC(O)(C_{1-3}$ alkyl), —$NR_xC(O)CH_2NR_xR_x$, —$NR_xC(O)CH_2NR_xR_y$, —$NR_x(CH_2)_{1-2}C(O)NR_xR_x$, —$NR_x(CH_2)_{1-2}NR_x$,$R_x$, —$NR_xS(O)_2(C_{1-3}$ alkyl), —$S(O)_2(C_{1-3}$ alkyl); —$NR_x$(cyanocyclopropyl), —$NR_x$(azetidinyl), —$NR_x$(oxetanyl), —$NR_x$(methyloxetanyl), —$NR_x$(ethyloxetanyl), —$NR_x$ (isopropyloxetanyl), —$NR_x$(tetrahydropyranyl), —$NR_x$(bicyclo[1.1.1]pentyl), —$NR_x$($CH_2$(methyloxetanyl)), —$NR_x$(dioxidotetrahydrothiophenyl), —$NR_xCH_2$(hydroxymethylcyclopropyl), —$NR_xCH_2$(methylsulfonylcyclopropyl), —$NR_xCH_2$(methylcyclobutyl), —$NR_xHCH_2C(O)$(morpholinyl), azetidinyl, fluoroazetidinyl, hydroxyazetidinyl, methoxyazetidinyl, hydroxy(trifluoromethyl)azetidinyl, bis(hydroxymethyl)azetidinyl, pyrrolidinyl, piperazinonyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl; or (iii) diazaspiro[3.3]heptanyl substituted with $C_{1-6}$ alkyl, $C_{1-6}$ hydroxyalkyl, —$(CH_2)_{1-3}S(O)_2(C_{1-6}$ alkyl), oxetanyl, or —$CH_2$(tetrahydropyranyl);

each $R_{3a}$ is independently F, Cl, $C_{1-6}$ alkyl, $C_{1-6}$ cyanoalkyl, $C_{1-6}$ fluoroalkyl, $C_{1-6}$ hydroxyalkyl, —$(CH_2)_{1-3}O(C_{1-3}$ alkyl), —$C(O)(C_{1-6}$ alkyl), —$CH_2C(O)NR_yR_y$, —$NR_yR_y$, —$NR_x(C_{1-4}$ hydroxyalkyl), —$C(O)(CH_2)_{1-3}NR_yR_y$, —$C(O)(C_{1-6}$ alkyl), —$(CH_2)_{0-2}S(O)_2(C_{1-3}$ alkyl), —$(CH_2)_{1-2}NR_xS(O)_2(C_{1-3}$ alkyl), —$NR_xCH_2C(O)NR_yR_y$, —$NR_x(CH_2)_{1-3}S(O)_2(C_{1-3}$ alkyl), —$NR_x(C_{3-6}$ cycloalkyl), —$NR_x$(oxetanyl), —$CH_2$(methyltriazolyl), $C_{3-6}$ cycloalkyl, oxetanyl, oxetanyl, pyrrolidinyl, morpholinyl, tetrahydropyranyl, —$CH_2(C_{3-6}$ cycloalkyl), —$CH_2$(oxetanyl), —$CH_2$(methyloxetanyl), —$CH_2$(tetrahydropyranyl), —$NR_x(C_{3-6}$ cycloalkyl), —$NR_x$(oxetanyl), —$NR_x$(methyloxetanyl), —$NR_xCH_2$(methyloxetanyl), or —C(O)(dioxidotetrahydrothiopyranyl);

each $R_{3b}$ is —$CH_3$;

$R_4$ is H, $C_{1-2}$ fluoroalkyl, —$(CR_xR_x)_{1-2}NR_yR_y$, or —$(CR_xR_x)_{1-3}R_3$;

$R_5$ is H, $C_{1-3}$ alkyl, or $C_{1-3}$ fluoroalkyl;

each $R_x$ is independently H or —$CH_3$;

each $R_y$ is independently H or $C_{1-6}$ alkyl; and p is zero, 1, or 2.

2. The compound according to claim 1, N-oxide, or a salt thereof, wherein X is N and Y is S.

3. The compound according to claim 1, N-oxide, or a salt thereof, wherein:

$R_1$ is —$CH_3$, —$CH_2CH_3$, —$CH(CH_3)_2$, —$CF_3$, —$OCH_3$, or —$S(O)_2(C_{1-2}$ alkyl);

G is:

(i)

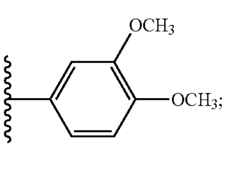 [SMILES: *c1ccc(OC)c(OC)c1]

(ii)

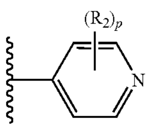

or

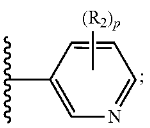

(iii)

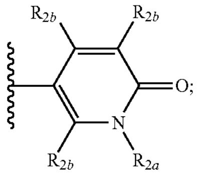

(iv) a 9-membered heterocyclic ring selected from:

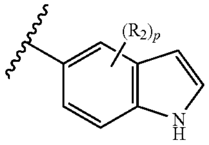
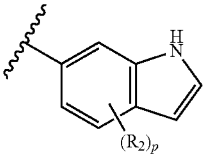
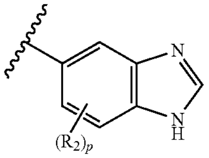
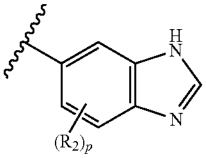
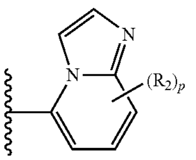
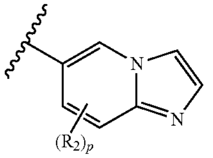
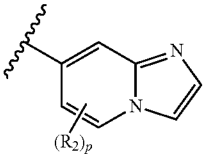
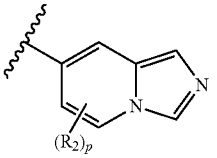
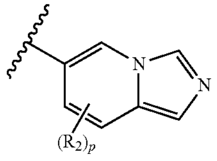
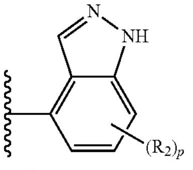
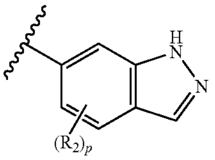
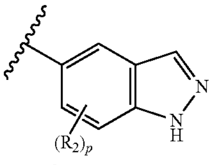
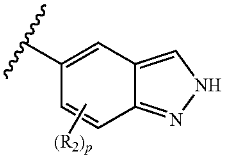
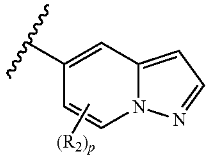
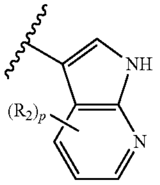
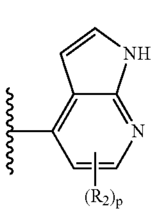
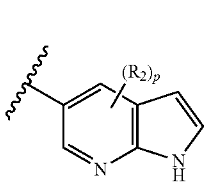

-continued
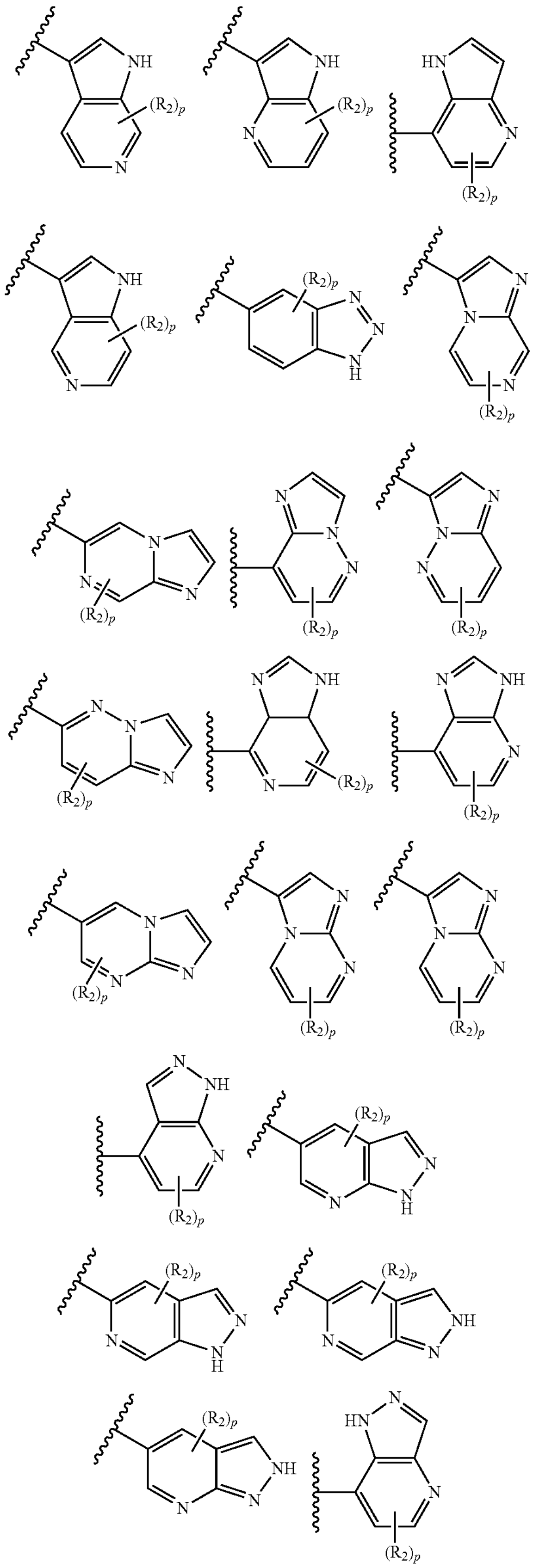
-continued
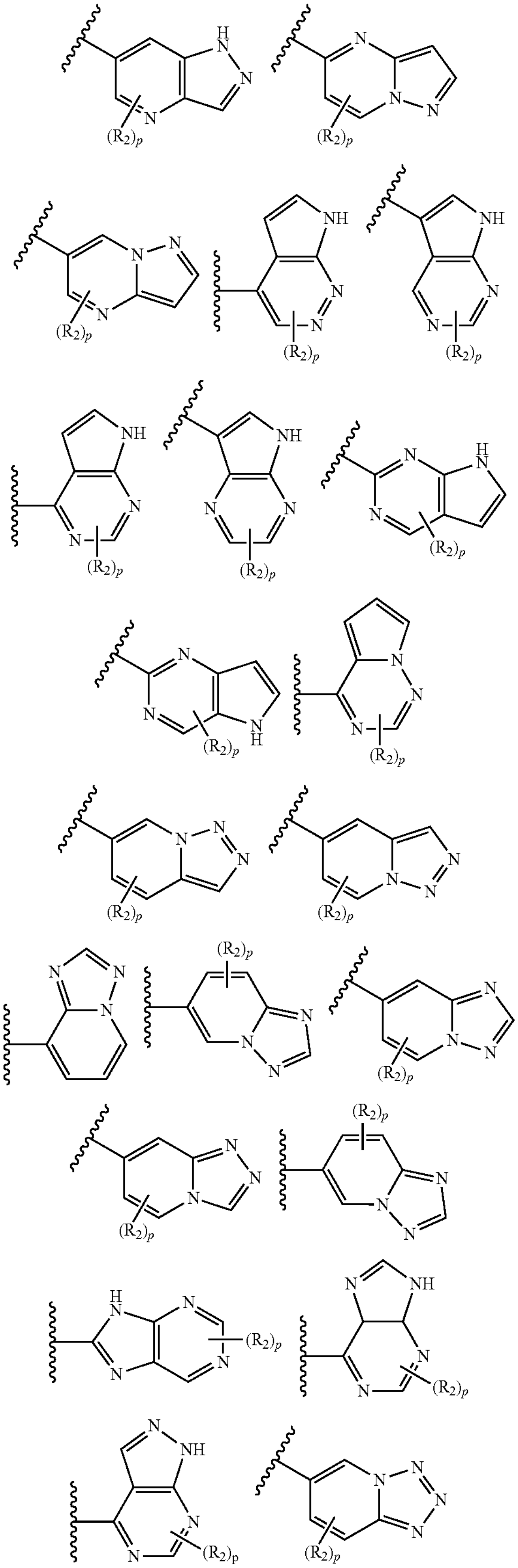

-continued

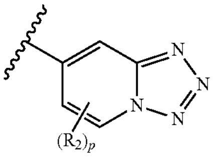
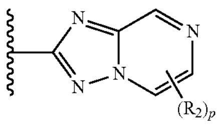
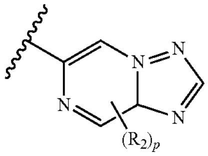
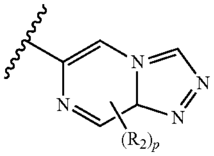
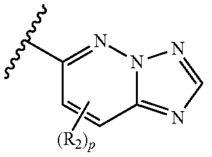
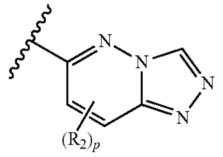
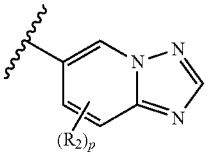
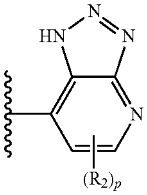
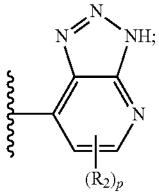

(v) 10-membered heterocyclic ring selected from:

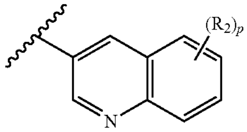
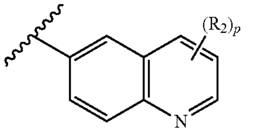
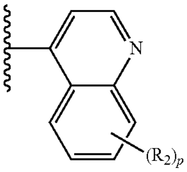
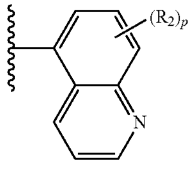
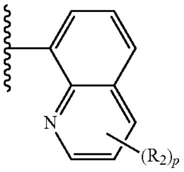
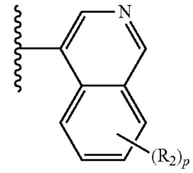
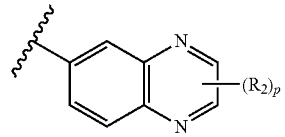
or
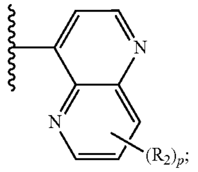

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$(CH_2)_{0-2}S(O)_2(C_{1-3}$ alkyl), —$CH_2(C_{3-6}$ cycloalkyl), —$CH_2$(phenyl), phenyl, pyrimidinyl, or triazolyl;

$R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl;

each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —$C(O)O(C_{1-2}$ alkyl), or —$C(O)NR_x(C_{1-3}$ alkyl);

A is:

(i) —$CH_2NHCH_2C(O)NR_xR_x$;

(ii) —$CR_xR_xR_3$, —$CH_2NR_xR_3$, —$CH_2NR_xCH_2R_3$, —$C(O)NR_xR_3$, —$C(O)NR_xR_4$, —$C(O)R_3$, or —$NR_xC(O)R_3$; or (iii) $R_3$; and $R_3$ is:

(i) azetidinyl, oxetanyl, cyclopropyl, pyrrolidinyl, pyrrolidinonyl, piperidinyl, piperazinyl, piperazinonyl, morpholinyl, dioxidothiomorpholinyl, oxazepanyl, diazaspiro[3.3]heptanyl, dioxidothiaazaspiro[3.3]heptanyl, oxaazaspiro[3.3]heptanyl, or oxaazaspiro[3.5]nonanyl, each substituted with zero to 1 $R_{3a}$ and zero to 2 $R_{3b}$;

(ii) cyclohexyl substituted with —$NR_yR_y$, —$NR_x(C_{1-4}$ hydroxyalkyl), —$NR_x(CR_xR_x)_{1-2}O(C_{1-2}$ alkyl), —$NR_x(C_{1-6}$ hydroxy-fluoroalkyl), —$NR_xCH_2C(O)NR_xR_x$, —$NR_x(CH_2)_{1-2}S(O)_2(C_{1-2}$ alkyl), —$NR_xC(O)(C_{1-2}$ alkyl), —$NR_xC(O)CH_2NR_xR_x$, —$NR_xC(O)CH_2NR_xR_y$, —$NR_x(CH_2)_{1-2}C(O)NR_xR_x$, —$NR_x(CH_2)_{1-2}NR_x,R_x$, —$NR_xS(O)_2(C_{1-2}$ alkyl), —$S(O)_2(C_{1-2}$ alkyl); —$NR_x$(cyanocyclopropyl), —$NR_x$(azetidinyl), —$NR_x$(oxetanyl), —$NR_x$(methyloxetanyl), —$NR_x$(ethyloxetanyl), —$NR_x$(isopropyloxetanyl), —$NR_x$(tetrahydropyranyl), —$NR_x$(bicyclo[1.1.1]pentyl), —$NR_x(CH_2$(methyloxetanyl)), —$NR_x$(dioxidotetrahydrothiophenyl), —$NR_xCH_2$(hydroxymethylcyclopropyl), —$NR_xCH_2$(methylsulfonylcyclopropyl), —$NR_xCH_2$(methylcyclobutyl), —$NR_xHCH_2C(O)$(morpholinyl), azetidinyl, fluoroazetidinyl, hydroxyazetidinyl, methoxyazetidinyl, hydroxy(trifluoromethyl)azetidinyl, bis(hydroxymethyl)azetidinyl, pyrrolidinyl, piperazinonyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl; or (iii) diazaspiro[3.3]heptanyl substituted with $C_{1-4}$ alkyl, $C_{1-4}$ hydroxyalkyl, —$(CH_2)_{1-2}S(O)_2(C_{1-3}$ alkyl), oxetanyl, or —$CH_2$(tetrahydropyranyl);

each $R_{3a}$ is independently F, Cl, $C_{1-5}$ alkyl, $C_{1-3}$ cyanoalkyl, $C_{1-3}$ fluoroalkyl, $C_{1-4}$ hydroxyalkyl, —$(CH_2)_{1-2}O(C_{1-2}$ alkyl), —$C(O)(C_{1-3}$ alkyl), —$CH_2C(O)NR_xR_x$, —$NR_yR_y$, —$NH(C_{1-4}$ hydroxyalkyl), —$C(O)(CH_2)_{1-3}NR_xR_x$, —$C(O)(C_{1-3}$ alkyl), —$(CH_2)_{0-2}S(O)_2(C_{1-2}$ alkyl), —$(CH_2)_{1-2}NR_xS(O)_2(C_{1-2}$ alkyl), —$NR_xCH_2C(O)NR_yR_y$, —$NR_xCH_2CH_2S(O)_2(C_{1-2}$ alkyl), —$NR_x(C_{3-6}$ cycloalkyl), —$NR_x$(oxetanyl), —$CH_2$(methyltriazolyl), cyclobutyl, oxetanyl, pyrrolidinyl, morpholinyl, tetrahydropyranyl, —$CH_2(C_{3-4}$ cycloalkyl), —$CH_2$(oxetanyl), —$CH_2$(methyloxetanyl), —$CH_2$(tetrahydropyranyl), —$NR_x$(cyclobutyl), —$NR_x$(oxetanyl), —$NR_x$(methyloxetanyl), —$NR_xCH_2$(methyloxetanyl), or —C(O)(dioxidotetrahydrothiopyranyl); and $R_x$ is H, —$CH_3$, —$CH_2CH_3$, —$CF_3$, —$CH_2CHF_2$, or —$CH_2CF_3$.

4. The compound according to claim 1, N-oxide, or a salt thereof, wherein:

$R_1$ is independently —$CH_3$, —$CH_2CH_3$, or —$CH(CH_3)_2$;

G is:

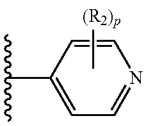

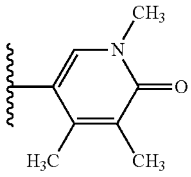

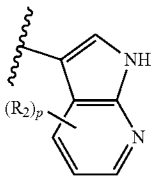

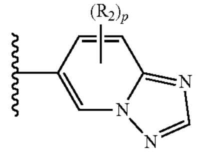

or

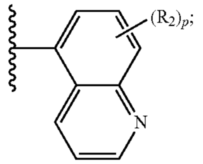

each $R_2$ is independently —CN, —$CH_3$, or —$OCH_3$;

A is:

(i) —$CH_2NHCH_2C(O)NH_2$;

(ii) —$CH_2R_3$, —$CH_2NHR_3$, —$CH_2NHCH_2R_3$, —C(O)$NHR_3$, —$C(O)NR_xR_4$, or —$C(O)R_3$; or (iii) cyclohexyl, piperidinyl, piperazinyl, methylpiperazinyl, dimethylpiperazinyl, or diazaspiro[3.3]heptanyl, each substituted with zero to 1 $R_{3a}$;

$R_3$ is azetidinyl, oxetanyl, cyclopropyl, cyclobutyl, pyrrolidinyl, pyrrolidinonyl, piperidinyl, piperazinyl, piperazinonyl, morpholinyl, dioxidothiomorpholinyl, oxazepanyl, diazaspiro[3.3]heptanyl, dioxidothiaazaspiro[3.3]heptanyl, oxaazaspiro[3.3]heptanyl, or oxaazaspiro[3.5]nonanyl, each substituted with zero to 1 $R_{3a}$ and zero to 2 $R_{3b}$;

$R_{3a}$ is F —$CH_3$, —$CH_2CH_3$, —$CH_2CH_2CH_3$, —$CH(CH_3)_2$, —$CH_2CH(CH_3)_2$, —$CH_2C(CH_3)_3$, —$CH_2CH(CH_2CH_3)_2$, —$CH_2CF_3$, —$CH_2CN$, —$CH_2C(CH_3)_2OH$, —$CH_2CH_2OCH_3$, —$CH_2CH_2S(O)_2CH_3$, —$CH_2C(O)NR_xR_x$, —$OCH_3$, —$C(O)CH_3$, —$C(O)CH_2N(CH_3)_2$, —$NH_2$, —$NH(CH_3)$, —$NH(CH(CH_3)_2)$, —$NH(CH_2C(CH_3)_3)$, —$NH(CH_2C(CH_3)_2OH)$, —$NH(CH_2CHFC(CH_3)_2OH)$, —$NH(CH_2C(CH_3)_2OCH_3)$, —$N(CH_3)(CH_2CH_3)$, —$N(CH_3)(CH(CH_3)_2)$, —$N(CH_3)CH_2CH(CH_3)_2$, —$N(CH_3)CH_2C(O)N(CH_3)_2$, —$N(CH_3)CH_2CH_2S(O)_2CH_3$, —$NHC(O)CH_2N(CH_3)_2$, —$NHC(O)CH_2N(CH_3)(CH_2CH_3)$, —$NHC(O)CH_2NH(CH_2CH(CH_3)_2)$, —$NHCH_2C(O)NH_2$, —$NHCH_2C(O)NH(CH_3)$, —$NHCH_2C(O)N(CH_3)_2$, —$NHCH_2CH_2NH(CH_3)$, —$NHS(O)_2CH_3$, —$S(O)_2CH_3$, —$CH_2$(cyclopropyl), —$CH_2$(methyloxetanyl), —$CH_2$(tetrahydropyranyl), —C(O)(dioxidotetrahydrothiopyranyl), —NH(cyanocyclopropyl), —NH(cyclobutyl), —NH(methylcyclobutyl), —NH(oxetanyl), —NH(methyloxetanyl), —NH(ethyloxetanyl), —NH(isopropylpiperidinyl), —NH(tetrahydropyranyl), —NH(bicyclo[1.1.1]pentyl), —$NHCH_2$(methyloxetanyl), —NH(dioxidotetrahydrothiophenyl), —$NHCH_2$(hydroxymethylcyclopropyl), —$NHCH_2$(methylsulfonylcyclopropyl), —$NHCH_2$(methylcyclobutyl), —$NHCH_2C(O)$(morpholinyl), cyclobutyl, azetidinyl, fluoroazetidinyl, difluoroazetidinyl, hydroxyazetidinyl, methoxyazetidinyl, hydroxy(trifluoromethyl)azetidinyl, bis(hydroxymethyl)azetidinyl, oxetanyl, pyrrolidinyl, acetamidopyrrolidinyl, piperazinonyl, tetrahydropyranyl, morpholinyl, dioxothiomorpholinyl, oxazepanyl, bicyclo[1.1.1]pentanyl, azaspiro[3.3]heptanyl, oxaazaspiro[3.3]heptanyl, dioxidothiaazaspiro[3.3]heptanyl, oxaazabicyclo[3.2.1]octanyl, oxaazaspiro[3.5]nonanyl, or diazaspiro[4.4]nonanyl;

$R_4$ is H, —$CH_2CHF_2$, —$CH_2CF_3$, —$CH_2CH_2N(CH_3)_2$, —$CH_2R_3$, —$CH_2CR_xR_xR_3$, or —$(CH_2)_3R_3$;

$R_5$ is H or —$CH_2CF_3$; and p is zero, 1, or 2.

5. The compound according to claim 1, N-oxide, or a salt thereof, wherein A is cyclohexyl, piperidinyl, piperazinyl, methylpiperazinyl, dimethylpiperazinyl, or diazaspiro[3.3]heptanyl, each substituted with zero to 1 $R_{3a}$.

6. The compound according to claim 1, N-oxide, or a salt thereof, wherein A is —$CH_2R_3$, —$CH_2NHR_3$, —$CH_2NHCH_2R_3$, or —$CH_2NHCH_2C(O)NH_2$.

7. The compound according to claim 1, N-oxide, or a salt thereof, wherein A is —$C(O)NHR_3$ or —$C(O)NR_xR_4$.

8. The compound according to claim 1, N-oxide, or a salt thereof, wherein A is —$C(O)R_3$.

9. The compound according to claim 1, N-oxide, or a salt thereof, wherein X is S and Y is N.

10. A pharmaceutical composition comprising a compound according to claim 1 or a pharmaceutically-acceptable salt thereof, and a pharmaceutically acceptable carrier.

11. A method of treating an autoimmune disease or a chronic inflammatory disease, comprising administering to a mammalian patent a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

12. The compound according to claim 1, N-oxide, or a salt thereof, wherein said compound is:

6-isopropyl-5-(8-methoxy-[1,2,4]triazolo[1,5-a]pyridin-6-yl)-2-(piperidin-4-yl)-4H-pyrrolo[3,2-d]thiazole (1);

6-isopropyl-5-(8-methyl-[1,2,4]triazolo[1,5-a]pyridin-6-yl)-2-(piperidin-4-yl)-4H-pyrrolo[3,2-d]thiazole (2);

6-isopropyl-5-(1-methyl-1H-pyrrolo[2,3-b]pyridin-3-yl)-2-(piperidin-4-yl)-4H-pyrrolo[3,2-d]thiazole (3);

5-(2,6-dimethylpyridin-4-yl)-6-isopropyl-2-(piperidin-4-yl)-4H-pyrrolo[3,2-d]thiazole (4);

5-(6-isopropyl-2-(piperidin-4-yl)-4H-pyrrolo[3,2-d]thiazol-5-yl)quinoline-8-carbonitrile (5);

2-(dimethylamino)-1-(4-(6-isopropyl-5-(8-methoxy-[1,2,4]triazolo[1,5-a]pyridin-6-yl)-4H-pyrrolo[3,2-d]thiazol-2-yl)piperidin-1-yl)ethan-1-one (6);

2-(4-(6-isopropyl-5-(8-methoxy-[1,2,4]triazolo[1,5-a]pyridin-6-yl)-4H-pyrrolo[3,2-d]thiazol-2-yl)piperidin-1-yl)-N,N-dimethylacetamide (7);

2-(4-(6-isopropyl-5-(8-methoxy-[1,2,4]triazolo[1,5-a]pyridin-6-yl)-4H-pyrrolo[3,2-d]thiazol-2-yl)piperidin-1-yl)-N-methylacetamide (8);

6-isopropyl-5-(8-methoxy-[1,2,4]triazolo[1,5-a]pyridin-6-yl)-4-(2,2,2-trifluoroethyl)-2-(1-(2,2,2-trifluoroethyl)piperidin-4-yl)-4H-pyrrolo[3,2-d]thiazole (9);

6-isopropyl-2-(1-isopropylpiperidin-4-yl)-5-(8-methoxy-[1,2,4]triazolo[1,5-a]pyridin-6-yl)-4H-pyrrolo[3,2-d]thiazole (10);

6-isopropyl-5-(8-methoxy-[1,2,4]triazolo[1,5-a]pyridin-6-yl)-2-(1-(oxetan-3-yl) piperidin-4-yl)-4H-pyrrolo[3,2-d]thiazole (11);

6-isopropyl-5-(8-methoxy-[1,2,4]triazolo[1,5-a]pyridin-6-yl)-2-(1-(tetrahydro-2H-pyran-4-yl)piperidin-4-yl)-4H-pyrrolo[3,2-d]thiazole (12);

6-isopropyl-5-(8-methoxy-[1,2,4]triazolo[1,5-a]pyridin-6-yl)-2-(1-neopentylpiperidin-4-yl)-4H-pyrrolo[3,2-d]thiazole (13);

6-isopropyl-5-(8-methoxy-[1,2,4]triazolo[1,5-a]pyridin-6-yl)-2-(1-((3-methyloxetan-3-yl)methyl) piperidin-4-yl)-4H-pyrrolo[3,2-d]thiazole (14);

1-(4-(6-isopropyl-5-(8-methoxy-[1,2,4]triazolo[1,5-a]pyridin-6-yl)-4H-pyrrolo[3,2-d]thiazol-2-yl)piperidin-1-yl)-2-methylpropan-2-ol (15);

6-isopropyl-5-(8-methoxy-[1,2,4]triazolo[1,5-a]pyridin-6-yl)-2-(1-(2-(methylsulfonyl)ethyl)piperidin-4-yl)-4H-pyrrolo[3,2-d]thiazole (16);

2-(4-(6-isopropyl-5-(8-methyl-[1,2,4]triazolo[1,5-a]pyridin-6-yl)-4H-pyrrolo[3,2-d]thiazol-2-yl) piperidin-1-yl)-N,N-dimethylacetamide (17);

1-(4-(6-isopropyl-5-(8-methyl-[1,2,4]triazolo[1,5-a]pyridin-6-yl)-4H-pyrrolo[3,2-d]thiazol-2-yl)piperidin-1-yl)-2-methylpropan-2-ol (18);

2-(dimethylamino)-1-(4-(6-isopropyl-5-(8-methyl-[1,2,4]triazolo[1,5-a]pyridin-6-yl)-4H-pyrrolo[3,2-d]thiazol-2-yl)piperidin-1-yl)ethan-1-one (19);

6-isopropyl-5-(8-methyl-[1,2,4]triazolo[1,5-a]pyridin-6-yl)-2-(1-(oxetan-3-yl) piperidin-4-yl)-4H-pyrrolo[3,2-d]thiazole (20);

6-isopropyl-2-(1-isopropylpiperidin-4-yl)-5-(8-methyl-[1,2,4]triazolo[1,5-a]pyridin-6-yl)-4H-pyrrolo[3,2-d]thiazole (21);

6-isopropyl-5-(8-methyl-[1,2,4]triazolo[1,5-a]pyridin-6-yl)-2-(1-(tetrahydro-2H-pyran-4-yl)piperidin-4-yl)-4H-pyrrolo[3,2-d]thiazole (22);

6-isopropyl-5-(8-methyl-[1,2,4]triazolo[1,5-a]pyridin-6-yl)-2-(1-((3-methyloxetan-3-yl)methyl)piperidin-4-yl)-4H-pyrrolo[3,2-d]thiazole (23);

2-(4-(5-(2,6-dimethylpyridin-4-yl)-6-isopropyl-4H-pyrrolo[3,2-d]thiazol-2-yl) piperidin-1-yl)-N,N-dimethylacetamide (24);

5-(2,6-dimethylpyridin-4-yl)-6-isopropyl-2-(1-isopropylpiperidin-4-yl)-4H-pyrrolo[3,2-d]thiazole (25);

5-(2,6-dimethylpyridin-4-yl)-6-isopropyl-2-(1-(tetrahydro-2H-pyran-4-yl) piperidin-4-yl)-4H-pyrrolo[3,2-d]thiazole (26);

5-(2,6-dimethylpyridin-4-yl)-6-isopropyl-2-(1-((3-methyloxetan-3-yl)methyl) piperidin-4-yl)-4H-pyrrolo[3,2-d]thiazole (27);

2-(dimethylamino)-1-(4-(5-(2,6-dimethylpyridin-4-yl)-6-isopropyl-4H-pyrrolo[3,2-d]thiazol-2-yl)piperidin-1-yl)ethan-1-one (28);

1-(4-(5-(2,6-dimethylpyridin-4-yl)-6-isopropyl-4H-pyrrolo[3,2-d]thiazol-2-yl) piperidin-1-yl)-2-methylpropan-2-ol (29);

2-(4-(6-isopropyl-5-(1-methyl-1H-pyrrolo[2,3-b]pyridin-3-yl)-4H-pyrrolo[3,2-d]thiazol-2-yl) piperidin-1-yl)-N,N-dimethylacetamide (30);

2-(4-(6-isopropyl-5-(1-methyl-1H-pyrrolo[2,3-b]pyridin-3-yl)-4H-pyrrolo[3,2-d]thiazol-2-yl)piperidin-1-yl)acetamide (31);

2-(dimethylamino)-1-(4-(6-isopropyl-5-(1-methyl-1H-pyrrolo[2,3-b]pyridin-3-yl)-4H-pyrrolo[3,2-d]thiazol-2-yl)piperidin-1-yl)ethan-1-one (32);

6-isopropyl-5-(1-methyl-1H-pyrrolo[2,3-b]pyridin-3-yl)-2-(1-(2-(methylsulfonyl) ethyl)piperidin-4-yl)-4H-pyrrolo[3,2-d]thiazole (33);

6-isopropyl-5-(1-methyl-1H-pyrrolo[2,3-b]pyridin-3-yl)-2-(1-(oxetan-3-yl)piperidin-4-yl)-4H-pyrrolo[3,2-d]thiazole (34);

6-isopropyl-5-(1-methyl-1H-pyrrolo[2,3-b]pyridin-3-yl)-2-(1-(tetrahydro-2H-pyran-4-yl)piperidin-4-yl)-4H-pyrrolo[3,2-d]thiazole (35);

6-isopropyl-2-(1-isopropylpiperidin-4-yl)-5-(1-methyl-1H-pyrrolo[2,3-b]pyridin-3-yl)-4H-pyrrolo[3,2-d]thiazole (36);

5-(6-isopropyl-2-(1-(oxetan-3-yl)piperidin-4-yl)-4H-pyrrolo[3,2-d]thiazol-5-yl)quinoline-8-carbonitrile (37);

5-(6-isopropyl-2-(1-(tetrahydro-2H-pyran-4-yl)piperidin-4-yl)-4H-pyrrolo[3,2-d]thiazol-5-yl) quinoline-8-carbonitrile (38);

5-(2-(1-(dimethylglycyl)piperidin-4-yl)-6-isopropyl-4H-pyrrolo[3,2-d]thiazol-5-yl)quinoline-8-carbonitrile (39);

2-(4-(5-(8-cyanoquinolin-5-yl)-6-isopropyl-4H-pyrrolo[3,2-d]thiazol-2-yl)piperidin-1-yl)-N,N-dimethylacetamide (40);

5-(7,8-dimethyl-[1,2,4]triazolo[1,5-a]pyridin-6-yl)-6-isopropyl-2-(1-(oxetan-3-yl) piperidin-4-yl)-4H-pyrrolo[3,2-d]thiazole (41);

5-(6-isopropyl-2-(piperidin-4-yl)-4H-pyrrolo[3,2-d]thiazol-5-yl)-1,3,4-trimethylpyridin-2(1H)-one (42);

5-(7,8-dimethyl-[1,2,4]triazolo[1,5-a]pyridin-6-yl)-6-isopropyl-2-(1-(oxetan-3-yl) piperidin-4-yl)-4H-pyrrolo[3,2-d]thiazole (43);

5-(7,8-dimethyl-[1,2,4]triazolo[1,5-a]pyridin-6-yl)-6-isopropyl-2-(1-isopropylpiperidin-4-yl)-4H-pyrrolo[3,2-d]thiazole (44);

5-(7,8-dimethyl-[1,2,4]triazolo[1,5-a]pyridin-6-yl)-6-isopropyl-2-(1-(methylsulfonyl) piperidin-4-yl)-4H-pyrrolo[3,2-d]thiazole (45);

5-(7,8-dimethyl-[1,2,4]triazolo[1,5-a]pyridin-6-yl)-6-isopropyl-2-(1-(tetrahydro-2H-pyran-4-yl)piperidin-4-yl)-4H-pyrrolo[3,2-d]thiazole (46);

5-(7,8-dimethyl-[1,2,4]triazolo[1,5-a]pyridin-6-yl)-6-isopropyl-2-(1-((3-methyloxetan-3-yl)methyl)piperidin-4-yl)-4H-pyrrolo[3,2-d]thiazole (47);

5-(7,8-dimethyl-[1,2,4]triazolo[1,5-a]pyridin-6-yl)-6-isopropyl-2-(1-((tetrahydro-2H-pyran-4-yl)methyl) piperidin-4-yl)-4H-pyrrolo[3,2-d]thiazole (48);

5-(7,8-dimethyl-[1,2,4]triazolo[1,5-a]pyridin-6-yl)-6-isopropyl-2-(1-methylpiperidin-4-yl)-4H-pyrrolo[3,2-d]thiazole (49);

5-(7,8-dimethyl-[1,2,4]triazolo[1,5-a]pyridin-6-yl)-2-(1-ethylpiperidin-4-yl)-6-isopropyl-4H-pyrrolo[3,2-d]thiazole (50);

5-(7,8-dimethyl-[1,2,4]triazolo[1,5-a]pyridin-6-yl)-6-isopropyl-2-(1-propylpiperidin-4-yl)-4H-pyrrolo[3,2-d]thiazole (51);

5-(7,8-dimethyl-[1,2,4]triazolo[1,5-a]pyridin-6-yl)-2-(1-isobutylpiperidin-4-yl)-6-isopropyl-4H-pyrrolo[3,2-d]thiazole (52);

2-(1-(cyclopropylmethyl)piperidin-4-yl)-5-(7,8-dimethyl-[1,2,4]triazolo[1,5-a]pyridin-6-yl)-6-isopropyl-4H-pyrrolo[3,2-d]thiazole (53);

5-(7,8-dimethyl-[1,2,4]triazolo[1,5-a]pyridin-6-yl)-2-(1-(2-ethylbutyl)piperidin-4-yl)-6-isopropyl-4H-pyrrolo[3,2-d]thiazole (54);

5-(7,8-dimethyl-[1,2,4]triazolo[1,5-a]pyridin-6-yl)-6-isopropyl-2-(1-(2-(methylsulfonyl)ethyl)piperidin-4-yl)-4H-pyrrolo[3,2-d]thiazole (55);

2-(4-(5-(7,8-dimethyl-[1,2,4]triazolo[1,5-a]pyridin-6-yl)-6-isopropyl-4H-pyrrolo[3,2-d]thiazol-2-yl)piperidin-1-yl)-N-methylacetamide (56);

2-(4-(5-(7,8-dimethyl-[1,2,4]triazolo[1,5-a]pyridin-6-yl)-6-isopropyl-4H-pyrrolo[3,2-d]thiazol-2-yl) piperidin-1-yl)-N,N-dimethylacetamide (57);

2-(4-(5-(7,8-dimethyl-[1,2,4]triazolo[1,5-a]pyridin-6-yl)-6-isopropyl-4H-pyrrolo[3,2-d]thiazol-2-yl)piperidin-1-yl)acetamide (58);

1-(4-(5-(7,8-dimethyl-[1,2,4]triazolo[1,5-a]pyridin-6-yl)-6-isopropyl-4H-pyrrolo[3,2-d]thiazol-2-yl)piperidin-1-yl)ethan-1-one (59);

5-(6-isopropyl-2-(1-(oxetan-3-yl)piperidin-4-yl)-4H-pyrrolo[3,2-d]thiazol-5-yl)-1,3,4-trimethylpyridin-2(1H)-one (60);

5-(6-isopropyl-2-(1-(2-(methylsulfonyl)ethyl)piperidin-4-yl)-4H-pyrrolo[3,2-d]thiazol-5-yl)-1,3,4-trimethylpyridin-2(1H)-one (61);

2-(4-(6-isopropyl-5-(1,4,5-trimethyl-6-oxo-1,6-dihydropyridin-3-yl)-4H-pyrrolo[3,2-d]thiazol-2-yl)piperidin-1-yl)-N,N-dimethylacetamide (62);

2-(4-(6-isopropyl-5-(1,4,5-trimethyl-6-oxo-1,6-dihydropyridin-3-yl)-4H-pyrrolo[3,2-d]thiazol-2-yl)piperidin-1-yl)-N-methylacetamide (63);

2-(4-(6-isopropyl-5-(1,4,5-trimethyl-6-oxo-1,6-dihydropyridin-3-yl)-4H-pyrrolo[3,2-d]thiazol-2-yl)piperidin-1-yl)acetamide (64);

N-(4-(6-isopropyl-5-(8-methoxy-[1,2,4]triazolo[1,5-a]pyridin-6-yl)-4H-pyrrolo[3,2-d]thiazol-2-yl)cyclohexyl)oxetan-3-amine (65-66);

(1-(4-(6-isopropyl-5-(8-methoxy-[1,2,4]triazolo[1,5-a]pyridin-6-yl)-4H-pyrrolo[3,2-d]thiazol-2-yl)cyclohexyl)azetidine-3,3-diyl)dimethanol (67);

6-(4-(6-isopropyl-5-(8-methoxy-[1,2,4]triazolo[1,5-a]pyridin-6-yl)-4H-pyrrolo[3,2-d]thiazol-2-yl)cyclohexyl)-2-oxa-6-azaspiro[3.3]heptane (68-69);

N-(4-(6-isopropyl-5-(8-methoxy-[1,2,4]triazolo[1,5-a]pyridin-6-yl)-4H-pyrrolo[3,2-d]thiazol-2-yl)cyclohexyl)-3-methyloxetan-3-amine (70-71);

N-ethyl-4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (72-73);

4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (74-75);

2-(4-(azetidin-1-yl)cyclohexyl)-6-isopropyl-5-(8-methoxy-[1,2,4]triazolo[1,5-a]pyridin-6-yl)-4H-pyrrolo[3,2-d]thiazole (76-77);

N-isopropyl-4-(6-isopropyl-5-(8-methoxy-[1,2,4]triazolo[1,5-a]pyridin-6-yl)-4H-pyrrolo[3,2-d]thiazol-2-yl)cyclohexan-1-amine (78-79);

4-(4-(6-isopropyl-5-(8-methoxy-[1,2,4]triazolo[1,5-a]pyridin-6-yl)-4H-pyrrolo[3,2-d]thiazol-2-yl)cyclohexyl) thiomorpholine 1,1-dioxide (82-83);

1-((4-(6-isopropyl-5-(8-methoxy-[1,2,4]triazolo[1,5-a]pyridin-6-yl)-4H-pyrrolo[3,2-d]thiazol-2-yl)cyclohexyl)amino)-2-methylpropan-2-ol (84-85);

4-(6-isopropyl-5-(8-methoxy-[1,2,4]triazolo[1,5-a]pyridin-6-yl)-4H-pyrrolo[3,2-d]thiazol-2-yl)-N-(2-methoxy-2-methylpropyl)cyclohexan-1-amine (86-87);

N-isopropyl-4-(6-isopropyl-5-(8-methoxy-[1,2,4]triazolo[1,5-a]pyridin-6-yl)-4H-pyrrolo[3,2-d]thiazol-2-yl)-N-methylcyclohexan-1-amine (88-89);

(R)-3-fluoro-4-((4-(6-isopropyl-5-(8-methoxy-[1,2,4]triazolo[1,5-a]pyridin-6-yl)-4H-pyrrolo[3,2-d]thiazol-2-yl)cyclohexyl) amino)-2-methylbutan-2-ol (90-91);

4-(6-isopropyl-5-(8-methoxy-[1,2,4]triazolo[1,5-a]pyridin-6-yl)-4H-pyrrolo[3,2-d]thiazol-2-yl)cyclohexan-1-amine (92-93);

3-ethyl-N-(4-(6-isopropyl-5-(8-methoxy-[1,2,4]triazolo[1,5-a]pyridin-6-yl)-4H-pyrrolo[3,2-d]thiazol-2-yl)cyclohexyl)oxetan-3-amine (94-95);

6-(4-(6-isopropyl-5-(8-methoxy-[1,2,4]triazolo[1,5-a]pyridin-6-yl)-4H-pyrrolo[3,2-d]thiazol-2-yl)cyclohexyl)-2-thia-6-azaspiro[3.3]heptane 2,2-dioxide (96-97);

6-isopropyl-5-(8-methoxy-[1,2,4]triazolo[1,5-a]pyridin-6-yl)-2-(4-(pyrrolidin-1-yl) cyclohexyl)-4H-pyrrolo[3,2-d]thiazole (98-99);

(R)—N-(1-(4-(6-isopropyl-5-(8-methoxy-[1,2,4]triazolo[1,5-a]pyridin-6-yl)-4H-pyrrolo[3,2-d]thiazol-2-yl)cyclohexyl)pyrrolidin-3-yl)acetamide (100-101);

4-(4-(6-isopropyl-5-(8-methoxy-[1,2,4]triazolo[1,5-a]pyridin-6-yl)-4H-pyrrolo[3,2-d]thiazol-2-yl)cyclohexyl)-1,4-oxazepane (102-103);

(1R,5S)-8-(4-(6-isopropyl-5-(8-methoxy-[1,2,4]triazolo[1,5-a]pyridin-6-yl)-4H-pyrrolo[3,2-d]thiazol-2-yl)cyclohexyl)-3-oxa-8-azabicyclo[3.2.1]octane (104-105);

1-((4-(6-isopropyl-5-(8-methoxy-[1,2,4]triazolo[1,5-a]pyridin-6-yl)-4H-pyrrolo[3,2-d]thiazol-2-yl)cyclohexyl)amino)cyclopropane-1-carbonitrile (106-107);

4-(6-isopropyl-5-(8-methoxy-[1,2,4]triazolo[1,5-a]pyridin-6-yl)-4H-pyrrolo[3,2-d]thiazol-2-yl)-N-(1-methylcyclobutyl)cyclohexan-1-amine (108-109);

2-(4-(6-isopropyl-5-(8-methoxy-[1,2,4]triazolo[1,5-a]pyridin-6-yl)-4H-pyrrolo[3,2-d]thiazol-2-yl)cyclohexyl)-7-oxa-2-azaspiro[3.5]nonane (110-111);

7-(4-(6-isopropyl-5-(8-methoxy-[1,2,4]triazolo[1,5-a]pyridin-6-yl)-4H-pyrrolo[3,2-d]thiazol-2-yl)cyclohexyl)-2-oxa-7-azaspiro[3.5]nonane (112-113);

2-(4-(2,7-diazaspiro[4.4]nonan-2-yl)cyclohexyl)-6-isopropyl-5-(8-methoxy-[1,2,4]triazolo[1,5-a]pyridin-6-yl)-4H-pyrrolo[3,2-d]thiazole (114-115);

N-(4-(6-isopropyl-5-(8-methoxy-[1,2,4]triazolo[1,5-a]pyridin-6-yl)-4H-pyrrolo[3,2-d]thiazol-2-yl)cyclohexyl)-2-azaspiro[3.3]heptan-6-amine (116-117);

1-(4-(6-isopropyl-5-(8-methoxy-[1,2,4]triazolo[1,5-a]pyridin-6-yl)-4H-pyrrolo[3,2-d]thiazol-2-yl)cyclohexyl)-3-(trifluoromethyl)azetidin-3-ol (118-119);

4-(4-(6-isopropyl-5-(8-methoxy-[1,2,4]triazolo[1,5-a]pyridin-6-yl)-4H-pyrrolo[3,2-d]thiazol-2-yl)cyclohexyl) piperazin-2-one (120-121);

6-isopropyl-5-(8-methoxy-[1,2,4]triazolo[1,5-a]pyridin-6-yl)-2-(4-(3-methoxyazetidin-1-yl)cyclohexyl)-4H-pyrrolo[3,2-d]thiazole (122-123);

N-(4-(6-isopropyl-5-(8-methoxy-[1,2,4]triazolo[1,5-a]pyridin-6-yl)-4H-pyrrolo[3,2-d]thiazol-2-yl)cyclohexyl)-N-methyloxetan-3-amine (124-125);

2-(dimethylamino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (126);

N-(4-(6-isopropyl-5-(8-methoxy-[1,2,4]triazolo[1,5-a]pyridin-6-yl)-4H-pyrrolo[3,2-d]thiazol-2-yl)cyclohexyl)methanesulfonamide (127);

trans 2-(ethyl(methyl)amino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (128);

2-(isobutylamino)-N-(4-(6-isopropyl-5-(8-methoxy-[1,2,4]triazolo[1,5-a]pyridin-6-yl)-4H-pyrrolo[3,2-d]thiazol-2-yl)cyclohexyl)acetamide (129);

N-(4-(6-isopropyl-5-(8-methyl-[1,2,4]triazolo[1,5-a]pyridin-6-yl)-4H-pyrrolo[3,2-d]thiazol-2-yl)cyclohexyl) oxetan-3-amine (130-131);

N-ethyl-4-(6-isopropyl-5-(8-methyl-[1,2,4]triazolo[1,5-a]pyridin-6-yl)-4H-pyrrolo[3,2-d]thiazol-2-yl)-N-methylcyclohexan-1-amine (132);

4-(6-isopropyl-5-(8-methyl-[1,2,4]triazolo[1,5-a]pyridin-6-yl)-4H-pyrrolo[3,2-d]thiazol-2-yl)-N-((3-methyloxetan-3-yl)methyl)cyclohexan-1-amine (134-135);

6-(4-(6-isopropyl-5-(8-methyl-[1,2,4]triazolo[1,5-a]pyridin-6-yl)-4H-pyrrolo[3,2-d]thiazol-2-yl)cyclohexyl)-2-oxa-6-azaspiro[3.3]heptane (136-137);

N-(4-(6-isopropyl-5-(8-methyl-[1,2,4]triazolo[1,5-a]pyridin-6-yl)-4H-pyrrolo[3,2-d]thiazol-2-yl)cyclohexyl)bicyclo[1.1.1]pentan-1-amine (138-139);

1-((4-(6-isopropyl-5-(8-methyl-[1,2,4]triazolo[1,5-a]pyridin-6-yl)-4H-pyrrolo[3,2-d]thiazol-2-yl)cyclohexyl)amino)-2-methylpropan-2-ol (140-141);

(1-(((4-(6-isopropyl-5-(8-methyl-[1,2,4]triazolo[1,5-a]pyridin-6-yl)-4H-pyrrolo[3,2-d]thiazol-2-yl)cyclohexyl)amino)methyl)cyclopropyl)methanol (142-143);

N-(4-(6-isopropyl-5-(7-methyl-[1,2,4]triazolo[1,5-a]pyridin-6-yl)-4H-pyrrolo[3,2-d]thiazol-2-yl)cyclohexyl)-3-methyloxetan-3-amine (144-145);

4-(4-(6-isopropyl-5-(7-methyl-[1,2,4]triazolo[1,5-a]pyridin-6-yl)-4H-pyrrolo[3,2-d]thiazol-2-yl)cyclohexyl)-1,4-oxazepane (146-147);

4-(4-(6-isopropyl-5-(7-methyl-[1,2,4]triazolo[1,5-a]pyridin-6-yl)-4H-pyrrolo[3,2-d]thiazol-2-yl)cyclohexyl) piperazin-2-one (148-149);

6-isopropyl-2-(4-(3-methoxyazetidin-1-yl) cyclohexyl)-5-(7-methyl-[1,2,4]triazolo[1,5-a]pyridin-6-yl)-4H-pyrrolo[3,2-d]thiazole (150-151);

N-(4-(6-isopropyl-5-(7-methyl-[1,2,4]triazolo[1,5-a]pyridin-6-yl)-4H-pyrrolo[3,2-d]thiazol-2-yl)cyclohexyl) oxetan-3-amine (152-153);

6-isopropyl-5-(7-methyl-[1,2,4]triazolo[1,5-a]pyridin-6-yl)-2-(4-(pyrrolidin-1-yl)cyclohexyl)-4H-pyrrolo[3,2-d]thiazole (154-155);

1-((4-(6-isopropyl-5-(7-methyl-[1,2,4]triazolo[1,5-a]pyridin-6-yl)-4H-pyrrolo[3,2-d]thiazol-2-yl)cyclohexyl)amino)-2-methylpropan-2-ol (156-157);

N-isopropyl-4-(6-isopropyl-5-(7-methyl-[1,2,4]triazolo[1,5-a]pyridin-6-yl)-4H-pyrrolo[3,2-d]thiazol-2-yl)-N-methylcyclohexan-1-amine (158-159);

N-(4-(6-isopropyl-5-(7-methyl-[1,2,4]triazolo[1,5-a]pyridin-6-yl)-4H-pyrrolo[3,2-d]thiazol-2-yl) cyclohexyl) tetrahydro-2H-pyran-4-amine (160-161);

2-((4-(6-isopropyl-5-(8-methoxy-[1,2,4]triazolo[1,5-a]pyridin-6-yl)-4H-pyrrolo[3,2-d]thiazol-2-yl)cyclohexyl)(methyl) amino)-N,N-dimethylacetamide (162-163);

4-(6-isopropyl-5-(8-methoxy-[1,2,4]triazolo[1,5-a]pyridin-6-yl)-4H-pyrrolo[3,2-d]thiazol-2-yl)-N-methyl-N-(2-(methylsulfonyl)ethyl)cyclohexan-1-amine (164-165);

1-isopropyl-N-(4-(6-isopropyl-5-(8-methoxy-[1,2,4]triazolo[1,5-a]pyridin-6-yl)-4H-pyrrolo[3,2-d]thiazol-2-yl)cyclohexyl) piperidin-4-amine (166-167);

N-(4-(6-isopropyl-5-(8-methoxy-[1,2,4]triazolo[1,5-a]pyridin-6-yl)-4H-pyrrolo[3,2-d]thiazol-2-yl)cyclohexyl)bicyclo[1.1.1]pentan-1-amine (168-169);

N1-(4-(6-isopropyl-5-(8-methoxy-[1,2,4]triazolo[1,5-a]pyridin-6-yl)-4H-pyrrolo[3,2-d]thiazol-2-yl)cyclohexyl)-N2-methylethane-1,2-diamine (170-171);

4-(6-isopropyl-5-(1-methyl-1H-pyrrolo[2,3-b]pyridin-3-yl)-4H-pyrrolo[3,2-d]thiazol-2-yl)-N-((3-methyloxetan-3-yl)methyl)cyclohexan-1-amine (172-173);

N-ethyl-4-(6-isopropyl-5-(1-methyl-1H-pyrrolo[2,3-b]pyridin-3-yl)-4H-pyrrolo[3,2-d]thiazol-2-yl)-N-methylcyclohexan-1-amine (174-175);

N-(4-(6-isopropyl-5-(1-methyl-1H-pyrrolo[2,3-b]pyridin-3-yl)-4H-pyrrolo[3,2-d]thiazol-2-yl)cyclohexyl)bicyclo[1.1.1]pentan-1-amine (176-177);

N-(4-(6-isopropyl-5-(1-methyl-1H-pyrrolo[2,3-b]pyridin-3-yl)-4H-pyrrolo[3,2-d]thiazol-2-yl)cyclohexyl) oxetan-3-amine (178-179);

6-(4-(6-isopropyl-5-(1-methyl-1H-pyrrolo[2,3-b]pyridin-3-yl)-4H-pyrrolo[3,2-d]thiazol-2-yl)cyclohexyl)-2-oxa-6-azaspiro[3.3]heptane (180-181);

1-((4-(6-isopropyl-5-(1-methyl-1H-pyrrolo[2,3-b]pyridin-3-yl)-4H-pyrrolo[3,2-d]thiazol-2-yl)cyclohexyl) amino)-2-methylpropan-2-ol (182-183);

N-(4-(5-(7,8-dimethyl-[1,2,4]triazolo[1,5-a]pyridin-6-yl)-6-isopropyl-4H-pyrrolo[3,2-d]thiazol-2-yl)cyclohexyl)oxetan-3-amine (184-185);

4-(5-(7,8-dimethyl-[1,2,4]triazolo[1,5-a]pyridin-6-yl)-6-isopropyl-4H-pyrrolo[3,2-d]thiazol-2-yl)-N-(2-methoxy-2-methylpropyl)cyclohexan-1-amine (186-187);

5-(7,8-dimethyl-[1,2,4]triazolo[1,5-a]pyridin-6-yl)-6-isopropyl-2-(4-(3-methoxyazetidin-1-yl) cyclohexyl)-4H-pyrrolo[3,2-d]thiazole (188-189);

4-(5-(7,8-dimethyl-[1,2,4]triazolo[1,5-a]pyridin-6-yl)-6-isopropyl-4H-pyrrolo[3,2-d]thiazol-2-yl)-N-ethyl-N-methylcyclohexan-1-amine (190-191);

6-(4-(5-(7,8-dimethyl-[1,2,4]triazolo[1,5-a]pyridin-6-yl)-6-isopropyl-4H-pyrrolo[3,2-d]thiazol-2-yl)cyclohexyl)-2-oxa-6-azaspiro[3.3]heptane (192-193);

4-(5-(7,8-dimethyl-[1,2,4]triazolo[1,5-a]pyridin-6-yl)-6-isopropyl-4H-pyrrolo[3,2-d]thiazol-2-yl)-N-isopropylcyclohexan-1-amine (194-195);

1-((4-(5-(7,8-dimethyl-[1,2,4]triazolo[1,5-a]pyridin-6-yl)-6-isopropyl-4H-pyrrolo[3,2-d]thiazol-2-yl)cyclohexyl) amino)-2-methylpropan-2-ol (196-197);

4-(5-(7,8-dimethyl-[1,2,4]triazolo[1,5-a]pyridin-6-yl)-6-isopropyl-4H-pyrrolo[3,2-d]thiazol-2-yl)-N-neopentylcyclohexan-1-amine (198-199);

N-(4-(5-(7,8-dimethyl-[1,2,4]triazolo[1,5-a]pyridin-6-yl)-6-isopropyl-4H-pyrrolo[3,2-d]thiazol-2-yl)cyclohexyl)tetrahydro-2H-pyran-4-amine (200-201);

4-(5-(7,8-dimethyl-[1,2,4]triazolo[1,5-a]pyridin-6-yl)-6-isopropyl-4H-pyrrolo[3,2-d]thiazol-2-yl)-N-((1-methylcyclobutyl)methyl)cyclohexan-1-amine (202-203);

2-((4-(5-(7,8-dimethyl-[1,2,4]triazolo[1,5-a]pyridin-6-yl)-6-isopropyl-4H-pyrrolo[3,2-d]thiazol-2-yl)cyclohexyl) amino)-N,N-dimethylacetamide (204-205);

2-((4-(5-(7,8-dimethyl-[1,2,4]triazolo[1,5-a]pyridin-6-yl)-6-isopropyl-4H-pyrrolo[3,2-d]thiazol-2-yl)cyclohexyl)amino)-1-morpholinoethan-1-one (206-207);

2-((4-(5-(7,8-dimethyl-[1,2,4]triazolo[1,5-a]pyridin-6-yl)-6-isopropyl-4H-pyrrolo[3,2-d]thiazol-2-yl)cyclohexyl)amino)-N-methylacetamide (208-209);

2-((4-(5-(7,8-dimethyl-[1,2,4]triazolo[1,5-a]pyridin-6-yl)-6-isopropyl-4H-pyrrolo[3,2-d]thiazol-2-yl)cyclohexyl)amino)acetamide (210-211);

4-(4-(5-(7,8-dimethyl-[1,2,4]triazolo[1,5-a]pyridin-6-yl)-6-isopropyl-4H-pyrrolo[3,2-d]thiazol-2-yl)cyclohexyl) morpholine (212-213);

4-(5-(7,8-dimethyl-[1,2,4]triazolo[1,5-a]pyridin-6-yl)-6-isopropyl-4H-pyrrolo[3,2-d]thiazol-2-yl)-N-((1-(methylsulfonyl)cyclopropyl)methyl) cyclohexan-1-amine (214-215);

2-(4-(azetidin-1-yl)cyclohexyl)-5-(7,8-dimethyl-[1,2,4]triazolo[1,5-a]pyridin-6-yl)-6-isopropyl-4H-pyrrolo[3,2-d]thiazole (216-217);

2-(4-(3,3-difluoroazetidin-1-yl)cyclohexyl)-5-(7,8-dimethyl-[1,2,4]triazolo[1,5-a]pyridin-6-yl)-6-isopropyl-4H-pyrrolo[3,2-d]thiazole (218-219);

4-(4-(5-(7,8-dimethyl-[1,2,4]triazolo[1,5-a]pyridin-6-yl)-6-isopropyl-4H-pyrrolo[3,2-d]thiazol-2-yl)cyclohexyl) piperazin-2-one (220-221);

4-(5-(7,8-dimethyl-[1,2,4]triazolo[1,5-a]pyridin-6-yl)-6-isopropyl-4H-pyrrolo[3,2-d]thiazol-2-yl)-N-isopropyl-N-methylcyclohexan-1-amine (222-223);

1-(4-(5-(7,8-dimethyl-[1,2,4]triazolo[1,5-a]pyridin-6-yl)-6-isopropyl-4H-pyrrolo[3,2-d]thiazol-2-yl)cyclohexyl) azetidin-3-ol (224-225);

5-(7,8-dimethyl-[1,2,4]triazolo[1,5-a]pyridin-6-yl)-2-(4-(3-fluoroazetidin-1-yl) cyclohexyl)-6-isopropyl-4H-pyrrolo[3,2-d]thiazole (226-227);

4-(5-(7,8-dimethyl-[1,2,4]triazolo[1,5-a]pyridin-6-yl)-6-isopropyl-4H-pyrrolo[3,2-d]thiazol-2-yl)-N-isobutyl-N-methylcyclohexan-1-amine (228-229);

3-((4-(5-(7,8-dimethyl-[1,2,4]triazolo[1,5-a]pyridin-6-yl)-6-isopropyl-4H-pyrrolo[3,2-d]thiazol-2-yl)cyclohexyl)amino)tetrahydrothiophene 1,1-dioxide (230-232);

6-(4-(5-(7,8-dimethyl-[1,2,4]triazolo[1,5-a]pyridin-6-yl)-6-isopropyl-4H-pyrrolo[3,2-d]thiazol-2-yl)cyclohexyl)-2-thia-6-azaspiro[3.3]heptane 2,2-dioxide (233-234);

1-(4-(5-(7,8-dimethyl-[1,2,4]triazolo[1,5-a]pyridin-6-yl)-6-isopropyl-4H-pyrrolo[3,2-d]thiazol-2-yl)cyclohexyl)-3-(trifluoromethyl)azetidin-3-ol (235-236);

7-(4-(5-(7,8-dimethyl-[1,2,4]triazolo[1,5-a]pyridin-6-yl)-6-isopropyl-4H-pyrrolo[3,2-d]thiazol-2-yl) cyclohexyl)-2-oxa-7-azaspiro[3.5]nonane (237-238);

2-(4-(5-(7,8-dimethyl-[1,2,4]triazolo[1,5-a]pyridin-6-yl)-6-isopropyl-4H-pyrrolo[3,2-d]thiazol-2-yl) cyclohexyl)-7-oxa-2-azaspiro[3.5]nonane (239-240);

5-(6-isopropyl-2-(4-(oxetan-3-ylamino)cyclohexyl)-4H-pyrrolo[3,2-d]thiazol-5-yl)-1,3,4-trimethylpyridin-2(1H)-one (241-242);

5-(6-isopropyl-2-(4-((2-methoxy-2-methylpropyl)amino) cyclohexyl)-4H-pyrrolo[3,2-d]thiazol-5-yl)-1,3,4-trimethylpyridin-2(1H)-one (243-244);

5-(2-(4-(2-oxa-6-azaspiro[3.3]heptan-6-yl)cyclohexyl)-6-isopropyl-4H-pyrrolo[3,2-d]thiazol-5-yl)-1,3,4-trimethylpyridin-2(1H)-one (245-246);

5-(2-(4-(ethyl(methyl)amino)cyclohexyl)-6-isopropyl-4H-pyrrolo[3,2-d]thiazol-5-yl)-1,3,4-trimethylpyridin-2(1H)-one (247-248);

5-(6-isopropyl-2-(4-((tetrahydro-2H-pyran-4-yl)amino) cyclohexyl)-4H-pyrrolo[3,2-d]thiazol-5-yl)-1,3,4-trimethylpyridin-2(1H)-one (249-250);

5-(2-(4-((2-hydroxy-2-methylpropyl)amino)cyclohexyl)-6-isopropyl-4H-pyrrolo[3,2-d]thiazol-5-yl)-1,3,4-trimethylpyridin-2(1H)-one (251-252);

5-(6-isopropyl-2-(4-(isopropylamino)cyclohexyl)-4H-pyrrolo[3,2-d]thiazol-5-yl)-1,3,4-trimethylpyridin-2(1H)-one (253-254);

5-(2-(4-(azetidin-1-yl)cyclohexyl)-6-isopropyl-4H-pyrrolo[3,2-d]thiazol-5-yl)-1,3,4-trimethylpyridin-2(1H)-one (255-256);

5-(6-isopropyl-2-(4-(((1-(methylsulfonyl) cyclopropyl) methyl)amino)cyclohexyl)-4H-pyrrolo[3,2-d]thiazol-5-yl)-1,3,4-trimethylpyridin-2(1H)-one (257-258);

4-(4-(6-isopropyl-5-(1,4,5-trimethyl-6-oxo-1,6-dihydropyridin-3-yl)-4H-pyrrolo[3,2-d]thiazol-2-yl)cyclohexyl)piperazin-2-one (259-260);

5-(6-isopropyl-2-(4-(isopropyl(methyl)amino)cyclohexyl)-4H-pyrrolo[3,2-d]thiazol-5-yl)-1,3,4-trimethylpyridin-2(1H)-one (261-262);

5-(2-(4-(3-hydroxyazetidin-1-yl)cyclohexyl)-6-isopropyl-4H-pyrrolo[3,2-d]thiazol-5-yl)-1,3,4-trimethylpyridin-2(1H)-one (263-264);

5-(2-(4-(3-fluoroazetidin-1-yl)cyclohexyl)-6-isopropyl-4H-pyrrolo[3,2-d]thiazol-5-yl)-1,3,4-trimethylpyridin-2(1H)-one (265-266);

5-(2-(4-(3-hydroxy-3-(trifluoromethyl)azetidin-1-yl)cyclohexyl)-6-isopropyl-4H-pyrrolo[3,2-d]thiazol-5-yl)-1,3,4-trimethylpyridin-2(1H)-one (267-268);

6-(4-(6-ethyl-5-(8-methoxy-[1,2,4]triazolo[1,5-a]pyridin-6-yl)-4H-pyrrolo[3,2-d]thiazol-2-yl)cyclohexyl)-2-oxa-6-azaspiro[3.3]heptane (269-270);

N-(4-(6-ethyl-5-(8-methoxy-[1,2,4]triazolo[1,5-a]pyridin-6-yl)-4H-pyrrolo[3,2-d]thiazol-2-yl)cyclohexyl) oxetan-3-amine (271-272);

N-(4-(5-(8-methoxy-[1,2,4]triazolo[1,5-a]pyridin-6-yl)-6-methyl-4H-pyrrolo[3,2-d]thiazol-2-yl)cyclohexyl) oxetan-3-amine (273);

4-(4-(5-(8-methoxy-[1,2,4]triazolo[1,5-a]pyridin-6-yl)-6-methyl-4H-pyrrolo[3,2-d]thiazol-2-yl)cyclohexyl) piperazin-2-one (275-276);

5-(7,8-dimethyl-[1,2,4]triazolo[1,5-a]pyridin-6-yl)-6-isopropyl-2-(piperazin-1-yl)-4H-pyrrolo[3,2-d]thiazole (278);

5-(6-isopropyl-2-(piperazin-1-yl)-4H-pyrrolo[3,2-d]thiazol-5-yl)-1,3,4-trimethylpyridin-2(1H)-one (279);

1-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-2-(dimethylamino)ethan-1-one (280);

1-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-2-methylpropan-2-ol (281);

5-(7,8-dimethyl-[1,2,4]triazolo[1,5-a]pyridin-6-yl)-6-isopropyl-2-(4-(2-(methylsulfonyl) ethyl)piperazin-1-yl)-4H-pyrrolo[3,2-d]thiazole (282);

2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-N,N-dimethylacetamide (283);

2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)-N-methylacetamide (284);

2-(4-(5-(7,8-dimethyl-[1,2,4]triazolo[1,5-a]pyridin-6-yl)-6-isopropyl-4H-pyrrolo[3,2-d]thiazol-2-yl)piperazin-1-yl)acetamide (285);

5-(7,8-dimethyl-[1,2,4]triazolo[1,5-a]pyridin-6-yl)-6-isopropyl-2-(4-(oxetan-3-yl) piperazin-1-yl)-4H-pyrrolo [3,2-d]thiazole (286);

5-(7,8-dimethyl-[1,2,4]triazolo[1,5-a]pyridin-6-yl)-6-isopropyl-2-(4-(tetrahydro-2H-pyran-4-yl)piperazin-1-yl)-4H-pyrrolo[3,2-d]thiazole (287);

5-(7,8-dimethyl-[1,2,4]triazolo[1,5-a]pyridin-6-yl)-6-isopropyl-2-(4-isopropylpiperazin-1-yl)-4H-pyrrolo[3,2-d]thiazole (288);

5-(7,8-dimethyl-[1,2,4]triazolo[1,5-a]pyridin-6-yl)-6-isopropyl-2-(4-((3-methyloxetan-3-yl)methyl) piperazin-1-yl)-4H-pyrrolo[3,2-d]thiazole (289);

1-(5-(7,8-dimethyl-[1,2,4]triazolo[1,5-a]pyridin-6-yl)-6-isopropyl-4H-pyrrolo[3,2-d]thiazol-2-yl)-N-(3-methyloxetan-3-yl) piperidin-4-amine (290);

1-((1-(5-(7,8-dimethyl-[1,2,4]triazolo[1,5-a]pyridin-6-yl)-6-isopropyl-4H-pyrrolo[3,2-d]thiazol-2-yl)piperidin-4-yl)amino)-2-methylpropan-2-ol (291);

1-(5-(7,8-dimethyl-[1,2,4]triazolo[1,5-a]pyridin-6-yl)-6-isopropyl-4H-pyrrolo[3,2-d]thiazol-2-yl)-N-isopropyl-N-methylpiperidin-4-amine (292);

N-cyclobutyl-1-(5-(7,8-dimethyl-[1,2,4]triazolo[1,5-a]pyridin-6-yl)-6-isopropyl-4H-pyrrolo[3,2-d]thiazol-2-yl) piperidin-4-amine (293);

1-(5-(7,8-dimethyl-[1,2,4]triazolo[1,5-a]pyridin-6-yl)-6-isopropyl-4H-pyrrolo[3,2-d]thiazol-2-yl)-N-(2-methoxy-2-methylpropyl)piperidin-4-amine (294);

1-(5-(7,8-dimethyl-[1,2,4]triazolo[1,5-a]pyridin-6-yl)-6-isopropyl-4H-pyrrolo[3,2-d]thiazol-2-yl)-N-((3-methyloxetan-3-yl)methyl)piperidin-4-amine (295);

1-(5-(7,8-dimethyl-[1,2,4]triazolo[1,5-a]pyridin-6-yl)-6-isopropyl-4H-pyrrolo[3,2-d]thiazol-2-yl)-N-(oxetan-3-yl)piperidin-4-amine (296);

1-(5-(7,8-dimethyl-[1,2,4]triazolo[1,5-a]pyridin-6-yl)-6-isopropyl-4H-pyrrolo[3,2-d]thiazol-2-yl)-N-isopropylpiperidin-4-amine (297);

1-(5-(7,8-dimethyl-[1,2,4]triazolo[1,5-a]pyridin-6-yl)-6-isopropyl-4H-pyrrolo[3,2-d]thiazol-2-yl)-N-ethyl-N-methylpiperidin-4-amine (298);

1-(5-(7,8-dimethyl-[1,2,4]triazolo[1,5-a]pyridin-6-yl)-6-isopropyl-4H-pyrrolo[3,2-d]thiazol-2-yl)piperidin-4-amine (299);

5-(7,8-dimethyl-[1,2,4]triazolo[1,5-a]pyridin-6-yl)-2-(6-isobutyl-2,6-diazaspiro[3.3]heptan-2-yl)-6-isopropyl-4H-pyrrolo[3,2-d]thiazole (300);

5-(7,8-dimethyl-[1,2,4]triazolo[1,5-a]pyridin-6-yl)-6-isopropyl-2-(6-((tetrahydro-2H-pyran-4-yl)methyl)-2,6-diazaspiro[3.3]heptan-2-yl)-4H-pyrrolo[3,2-d]thiazole (301);

5-(7,8-dimethyl-[1,2,4]triazolo[1,5-a]pyridin-6-yl)-6-isopropyl-2-(6-(oxetan-3-yl)-2,6-diazaspiro[3.3]heptan-2-yl)-4H-pyrrolo[3,2-d]thiazole (302);

1-(6-(5-(7,8-dimethyl-[1,2,4]triazolo[1,5-a]pyridin-6-yl)-6-isopropyl-4H-pyrrolo[3,2-d]thiazol-2-yl)-2,6-diazaspiro[3.3]heptan-2-yl)-2-methylpropan-2-ol (303);

5-(7,8-dimethyl-[1,2,4]triazolo[1,5-a]pyridin-6-yl)-6-isopropyl-2-(6-(2-(methylsulfonyl)ethyl)-2,6-diazaspiro[3.3]heptan-2-yl)-4H-pyrrolo[3,2-d]thiazole (304);

5-(6-isopropyl-2-(6-(2-(methylsulfonyl)ethyl)-2,6-diazaspiro[3.3]heptan-2-yl)-4H-pyrrolo[3,2-d]thiazol-5-yl)-1,3,4-trimethylpyridin-2(1H)-one (305);

5-(6-isopropyl-2-(6-(oxetan-3-yl)-2,6-diazaspiro[3.3]heptan-2-yl)-4H-pyrrolo[3,2-d]thiazol-5-yl)-1,3,4-trimethylpyridin-2(1H)-one (306);

5-(6-isopropyl-2-(6-((tetrahydro-2H-pyran-4-yl)methyl)-2,6-diazaspiro[3.3]heptan-2-yl)-4H-pyrrolo[3,2-d]thiazol-5-yl)-1,3,4-trimethylpyridin-2(1H)-one (307);

(R)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole, HCl (308);

5-(7,8-dimethyl-[1,2,4]triazolo[1,5-a]pyridin-6-yl)-2-((2S,5R)-2,5-dimethylpiperazin-1-yl)-6-isopropyl-4H-pyrrolo[3,2-d]thiazole (309);

(S)-5-(7,8-dimethyl-[1,2,4]triazolo[1,5-a]pyridin-6-yl)-6-isopropyl-2-(2-methylpiperazin-1-yl)-4H-pyrrolo[3,2-d]thiazole (310);

(R)-6-isopropyl-5-(8-methyl-[1,2,4]triazolo[1,5-a]pyridin-6-yl)-2-(2-methylpiperazin-1-yl)-4H-pyrrolo[3,2-d]thiazole (311);

(R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N,N-dimethylacetamide (312);

(R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)acetamide (313);

(R)-5-(7,8-dimethyl-[1,2,4]triazolo[1,5-a]pyridin-6-yl)-6-isopropyl-2-(2-methyl-4-(2-(methylsulfonyl)ethyl)piperazin-1-yl)-4H-pyrrolo[3,2-d]thiazole (314);

(R)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N-methylacetamide (315);

(R)-5-(7,8-dimethyl-[1,2,4]triazolo[1,5-a]pyridin-6-yl)-6-isopropyl-2-(2-methyl-4-(oxetan-3-yl)piperazin-1-yl)-4H-pyrrolo[3,2-d]thiazole (316);

(R)-5-(7,8-dimethyl-[1,2,4]triazolo[1,5-a]pyridin-6-yl)-6-isopropyl-2-(2-methyl-4-((tetrahydro-2H-pyran-4-yl)methyl)piperazin-1-yl)-4H-pyrrolo[3,2-d]thiazole (317);

(R)-5-(7,8-dimethyl-[1,2,4]triazolo[1,5-a]pyridin-6-yl)-6-isopropyl-2-(2-methyl-4-(tetrahydro-2H-pyran-4-yl)piperazin-1-yl)-4H-pyrrolo[3,2-d]thiazole (318);

(R)-5-(7,8-dimethyl-[1,2,4]triazolo[1,5-a]pyridin-6-yl)-2-(2,4-dimethylpiperazin-1-yl)-6-isopropyl-4H-pyrrolo[3,2-d]thiazole (319);

(R)-5-(7,8-dimethyl-[1,2,4]triazolo[1,5-a]pyridin-6-yl)-2-(4-ethyl-2-methylpiperazin-1-yl)-6-isopropyl-4H-pyrrolo[3,2-d]thiazole (320);

(R)-2-(4-(cyclopropylmethyl)-2-methylpiperazin-1-yl)-5-(7,8-dimethyl-[1,2,4]triazolo[1,5-a]pyridin-6-yl)-6-isopropyl-4H-pyrrolo[3,2-d]thiazole (321);

(R)-2-(4-cyclobutyl-2-methylpiperazin-1-yl)-5-(7,8-dimethyl-[1,2,4]triazolo[1,5-a]pyridin-6-yl)-6-isopropyl-4H-pyrrolo[3,2-d]thiazole (322);

(R)-5-(7,8-dimethyl-[1,2,4]triazolo[1,5-a]pyridin-6-yl)-6-isopropyl-2-(4-(1-isopropylpiperidin-4-yl)-2-methylpiperazin-1-yl)-4H-pyrrolo[3,2-d]thiazole (323);

(R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol (325);

(R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(methylamino)ethan-1-one (326);

(R)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(dimethylamino)ethan-1-one (327);

2-((2S,5R)-2,5-dimethyl-4-(oxetan-3-yl)piperazin-1-yl)-5-(7,8-dimethyl-[1,2,4]triazolo[1,5-a]pyridin-6-yl)-6-isopropyl-4H-pyrrolo[3,2-d]thiazole (328);

2-((2S,5R)-2,5-dimethyl-4-(tetrahydro-2H-pyran-4-yl)piperazin-1-yl)-5-(7,8-dimethyl-[1,2,4]triazolo[1,5-a]pyridin-6-yl)-6-isopropyl-4H-pyrrolo[3,2-d]thiazole (329);

5-(7,8-dimethyl-[1,2,4]triazolo[1,5-a]pyridin-6-yl)-6-isopropyl-2-((2S,5R)-4-isopropyl-2,5-dimethylpiperazin-1-yl)-4H-pyrrolo[3,2-d]thiazole (330);

5-(7,8-dimethyl-[1,2,4]triazolo[1,5-a]pyridin-6-yl)-2-((2S,5R)-4-ethyl-2,5-dimethylpiperazin-1-yl)-6-isopropyl-4H-pyrrolo[3,2-d]thiazole (331);

2-((2S,5R)-4-(cyclopropylmethyl)-2,5-dimethylpiperazin-1-yl)-5-(7,8-dimethyl-[1,2,4]triazolo[1,5-a]pyridin-6-yl)-6-isopropyl-4H-pyrrolo[3,2-d]thiazole (332);

2-((2S,5R)-4-cyclobutyl-2,5-dimethylpiperazin-1-yl)-5-(7,8-dimethyl-[1,2,4]triazolo[1,5-a]pyridin-6-yl)-6-isopropyl-4H-pyrrolo[3,2-d]thiazole (333);

5-(7,8-dimethyl-[1,2,4]triazolo[1,5-a]pyridin-6-yl)-6-isopropyl-2-((2S,5R)-4-isopropyl-2,5-dimethylpiperazin-1-yl)-4H-pyrrolo[3,2-d]thiazole (334);

2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-N,N-dimethylacetamide (335);

2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-N-methylacetamide (336);
2-((2S,5R)-2,5-dimethyl-4-(2-(methylsulfonyl)ethyl)piperazin-1-yl)-5-(7,8-dimethyl-[1,2,4]triazolo[1,5-a]pyridin-6-yl)-6-isopropyl-4H-pyrrolo[3,2-d]thiazole (337);
2-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)acetamide (338);
1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-methylpropan-2-ol (339);
1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(methylamino)ethan-1-one (340);
1-((2R,5S)-4-(5-(7,8-dimethyl-[1,2,4]triazolo[1,5-a]pyridin-6-yl)-6-isopropyl-4H-pyrrolo[3,2-d]thiazol-2-yl)-2,5-dimethylpiperazin-1-yl)-2-(dimethylamino)ethan-1-one (341);
(S)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N-methylacetamide (342);
(S)-2-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-N,N-dimethylacetamide (343);
(S)-5-(7,8-dimethyl-[1,2,4]triazolo[1,5-a]pyridin-6-yl)-6-isopropyl-2-(2-methyl-4-(2-(methylsulfonyl)ethyl)piperazin-1-yl)-4H-pyrrolo[3,2-d]thiazole (344);
(S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-methylpropan-2-ol (345);
(S)-1-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)-2-(dimethylamino)ethan-1-one (346);
(S)-(4-(5-(7,8-dimethyl-[1,2,4]triazolo[1,5-a]pyridin-6-yl)-6-isopropyl-4H-pyrrolo[3,2-d]thiazol-2-yl)-3-methylpiperazin-1-yl)(1,1-dioxidotetrahydro-2H-thiopyran-4-yl)methanone (347);
(S)-5-(7,8-dimethyl-[1,2,4]triazolo[1,5-a]pyridin-6-yl)-6-isopropyl-2-(2-methyl-4-(oxetan-3-yl) piperazin-1-yl)-4H-pyrrolo[3,2-d]thiazole (348);
(S)-2-(4-cyclobutyl-2-methylpiperazin-1-yl)-5-(7,8-dimethyl-[1,2,4]triazolo[1,5-a]pyridin-6-yl)-6-isopropyl-4H-pyrrolo[3,2-d]thiazole (349);
(S)-5-(7,8-dimethyl-[1,2,4]triazolo[1,5-a]pyridin-6-yl)-6-isopropyl-2-(2-methyl-4-(tetrahydro-2H-pyran-4-yl) piperazin-1-yl)-4H-pyrrolo[3,2-d]thiazole (350);
(S)-5-(7,8-dimethyl-[1,2,4]triazolo[1,5-a]pyridin-6-yl)-6-isopropyl-2-(4-isopropyl-2-methylpiperazin-1-yl)-4H-pyrrolo[3,2-d]thiazole (351);
(S)-2-(4-(cyclopropylmethyl)-2-methylpiperazin-1-yl)-5-(7,8-dimethyl-[1,2,4]triazolo[1,5-a]pyridin-6-yl)-6-isopropyl-4H-pyrrolo[3,2-d]thiazole (352);
(R)-2-(4-(6-isopropyl-5-(8-methyl-[1,2,4]triazolo[1,5-a] pyridin-6-yl)-4H-pyrrolo[3,2-d]thiazol-2-yl)-3-methylpiperazin-1-yl)-N-methylacetamide (353);
(R)-2-(4-(6-isopropyl-5-(8-methyl-[1,2,4]triazolo[1,5-a] pyridin-6-yl)-4H-pyrrolo[3,2-d]thiazol-2-yl)-3-methylpiperazin-1-yl)-N,N-dimethylacetamide (354);
R)-2-(4-(6-isopropyl-5-(8-methyl-[1,2,4]triazolo[1,5-a] pyridin-6-yl)-4H-pyrrolo[3,2-d]thiazol-2-yl)-3-methylpiperazin-1-yl)acetamide (355);
(R)-6-isopropyl-2-(2-methyl-4-(2-(methylsulfonyl)ethyl) piperazin-1-yl)-5-(8-methyl-[1,2,4]triazolo[1,5-a]pyridin-6-yl)-4H-pyrrolo[3,2-d]thiazole (356);
(R)-6-isopropyl-2-(4-(2-methoxyethyl)-2-methylpiperazin-1-yl)-5-(8-methyl-[1,2,4]triazolo[1,5-a]pyridin-6-yl)-4H-pyrrolo[3,2-d]thiazole (357);
(R)-2-(4-(6-isopropyl-5-(8-methyl-[1,2,4]triazolo[1,5-a] pyridin-6-yl)-4H-pyrrolo[3,2-d]thiazol-2-yl)-3-methylpiperazin-1-yl)acetonitrile (358);
(R)-1-(4-(6-isopropyl-5-(8-methyl-[1,2,4]triazolo[1,5-a] pyridin-6-yl)-4H-pyrrolo[3,2-d]thiazol-2-yl)-3-methylpiperazin-1-yl)-2-methylpropan-2-ol (359);
(R)-2-(dimethylamino)-1-(4-(6-isopropyl-5-(8-methyl-[1,2,4]triazolo[1,5-a]pyridin-6-yl)-4H-pyrrolo[3,2-d] thiazol-2-yl)-3-methylpiperazin-1-yl)ethan-1-one (360);
(R)-2-(4-isobutyl-2-methylpiperazin-1-yl)-6-isopropyl-5-(8-methyl-[1,2,4]triazolo[1,5-a]pyridin-6-yl)-4H-pyrrolo[3,2-d]thiazole (361);
(R)-2-(4-cyclobutyl-2-methylpiperazin-1-yl)-6-isopropyl-5-(8-methyl-[1,2,4]triazolo[1,5-a]pyridin-6-yl)-4H-pyrrolo[3,2-d]thiazole (362);
(R)-6-isopropyl-2-(2-methyl-4-(oxetan-3-yl)piperazin-1-yl)-5-(8-methyl-[1,2,4]triazolo[1,5-a]pyridin-6-yl)-4H-pyrrolo[3,2-d]thiazole (363);
(R)-6-isopropyl-2-(2-methyl-4-(tetrahydro-2H-pyran-4-yl)piperazin-1-yl)-5-(8-methyl-[1,2,4]triazolo[1,5-a] pyridin-6-yl)-4H-pyrrolo[3,2-d]thiazole (364);
(R)-2-(4-(cyclopropylmethyl)-2-methylpiperazin-1-yl)-6-isopropyl-5-(8-methyl-[1,2,4]triazolo[1,5-a]pyridin-6-yl)-4H-pyrrolo[3,2-d]thiazole (365);
(R)-6-isopropyl-2-(4-isopropyl-2-methylpiperazin-1-yl)-5-(8-methyl-[1,2,4]triazolo[1,5-a]pyridin-6-yl)-4H-pyrrolo[3,2-d]thiazole (366);
(R)-2-(2,4-dimethylpiperazin-1-yl)-6-isopropyl-5-(8-methyl-[1,2,4]triazolo[1,5-a]pyridin-6-yl)-4H-pyrrolo [3,2-d]thiazole (367);
5-(7,8-dimethyl-[1,2,4]triazolo[1,5-a]pyridin-6-yl)-N-(4-(dimethylamino) cyclohexyl)-6-isopropyl-4H-pyrrolo [3,2-d]thiazole-2-carboxamide (368-369);
5-(7,8-dimethyl-[1,2,4]triazolo[1,5-a]pyridin-6-yl)-6-isopropyl-N-(2-(pyrrolidin-1-yl) ethyl)-4H-pyrrolo[3,2-d] thiazole-2-carboxamide (370);
5-(7,8-dimethyl-[1,2,4]triazolo[1,5-a]pyridin-6-yl)-6-isopropyl-N-(3-(2-oxopyrrolidin-1-yl)propyl)-4H-pyrrolo [3,2-d]thiazole-2-carboxamide (371);
5-(7,8-dimethyl-[1,2,4]triazolo[1,5-a]pyridin-6-yl)-N-(2-(dimethylamino)ethyl)-6-isopropyl-4H-pyrrolo[3,2-d] thiazole-2-carboxamide (372);
(5-(7,8-dimethyl-[1,2,4]triazolo[1,5-a]pyridin-6-yl)-6-isopropyl-4H-pyrrolo[3,2-d]thiazol-2-yl)(1,1-dioxidothiomorpholino)methanone (373);
5-(7,8-dimethyl-[1,2,4]triazolo[1,5-a]pyridin-6-yl)-6-isopropyl-N-(2-methyl-2-morpholinopropyl)-4H-pyrrolo [3,2-d]thiazole-2-carboxamide (374);
1-(4-(5-(7,8-dimethyl-[1,2,4]triazolo[1,5-a]pyridin-6-yl)-6-isopropyl-4H-pyrrolo[3,2-d]thiazole-2-carbonyl)piperazin-1-yl)ethan-1-one (375);
(5-(7,8-dimethyl-[1,2,4]triazolo[1,5-a]pyridin-6-yl)-6-isopropyl-4H-pyrrolo[3,2-d]thiazol-2-yl)(4-(dimethylamino)piperidin-1-yl)methanone (376);
(5-(7,8-dimethyl-[1,2,4]triazolo[1,5-a]pyridin-6-yl)-6-isopropyl-4H-pyrrolo[3,2-d]thiazol-2-yl)(pyrrolidin-1-yl)methanone (377);
4-(5-(7,8-dimethyl-[1,2,4]triazolo[1,5-a]pyridin-6-yl)-6-isopropyl-4H-pyrrolo[3,2-d]thiazole-2-carbonyl)piperazin-2-one (378);

(5-(7,8-dimethyl-[1,2,4]triazolo[1,5-a]pyridin-6-yl)-6-isopropyl-4H-pyrrolo[3,2-d]thiazol-2-yl)(3-fluoroazetidin-1-yl)methanone (379);

(5-(7,8-dimethyl-[1,2,4]triazolo[1,5-a]pyridin-6-yl)-6-isopropyl-4H-pyrrolo[3,2-d]thiazol-2-yl)(4-isopropylpiperazin-1-yl)methanone (380);

5-(7,8-dimethyl-[1,2,4]triazolo[1,5-a]pyridin-6-yl)-6-isopropyl-N-(2-(1-methylpiperidin-4-yl)ethyl)-4H-pyrrolo[3,2-d]thiazole-2-carboxamide (381);

5-(7,8-dimethyl-[1,2,4]triazolo[1,5-a]pyridin-6-yl)-N-(2-(dimethylamino)ethyl)-6-isopropyl-N-methyl-4H-pyrrolo[3,2-d]thiazole-2-carboxamide (382);

(5-(7,8-dimethyl-[1,2,4]triazolo[1,5-a]pyridin-6-yl)-6-isopropyl-4H-pyrrolo[3,2-d]thiazol-2-yl)(3-(dimethylamino)azetidin-1-yl)methanone (383);

(5-(7,8-dimethyl-[1,2,4]triazolo[1,5-a]pyridin-6-yl)-6-isopropyl-4H-pyrrolo[3,2-d]thiazol-2-yl)(4-(methylsulfonyl)piperazin-1-yl)methanone (384);

5-(7,8-dimethyl-[1,2,4]triazolo[1,5-a]pyridin-6-yl)-6-isopropyl-4H-pyrrolo[3,2-d]thiazole-2-carboxamide (385);

5-(7,8-dimethyl-[1,2,4]triazolo[1,5-a]pyridin-6-yl)-6-isopropyl-N-(morpholin-2-ylmethyl)-4H-pyrrolo[3,2-d]thiazole-2-carboxamide (386);

6-isopropyl-5-(8-methoxy-[1,2,4]triazolo[1,5-a]pyridin-6-yl)-N-(2-(pyrrolidin-1-yl) ethyl)-4H-pyrrolo[3,2-d]thiazole-2-carboxamide (387);

N-(2-(dimethylamino)ethyl)-6-isopropyl-5-(8-methoxy-[1,2,4]triazolo[1,5-a]pyridin-6-yl)-4H-pyrrolo[3,2-d]thiazole-2-carboxamide (388);

N-(2,2-difluoroethyl)-6-isopropyl-5-(8-methoxy-[1,2,4]triazolo[1,5-a]pyridin-6-yl)-4H-pyrrolo[3,2-d]thiazole-2-carboxamide (389);

6-isopropyl-5-(8-methoxy-[1,2,4]triazolo[1,5-a]pyridin-6-yl)-N-(2,2,2-trifluoroethyl)-4H-pyrrolo[3,2-d]thiazole-2-carboxamide (390);

6-isopropyl-5-(8-methyl-[1,2,4]triazolo[1,5-a]pyridin-6-yl)-4H-pyrrolo[3,2-d]thiazole-2-carboxamide (391);

4-(6-isopropyl-5-(8-methyl-[1,2,4]triazolo[1,5-a]pyridin-6-yl)-4H-pyrrolo[3,2-d]thiazole-2-carbonyl)piperazin-2-one (392);

(6-isopropyl-5-(8-methyl-[1,2,4]triazolo[1,5-a]pyridin-6-yl)-4H-pyrrolo[3,2-d]thiazol-2-yl)(pyrrolidin-1-yl)methanone (393);

(6-isopropyl-5-(8-methyl-[1,2,4]triazolo[1,5-a]pyridin-6-yl)-4H-pyrrolo[3,2-d]thiazol-2-yl)(1,4-oxazepan-4-yl)methanone (394);

(4-(dimethylamino)piperidin-1-yl)(6-isopropyl-5-(8-methyl-[1,2,4]triazolo[1,5-a]pyridin-6-yl)-4H-pyrrolo[3,2-d]thiazol-2-yl)methanone (395);

(6-isopropyl-5-(8-methyl-[1,2,4]triazolo[1,5-a]pyridin-6-yl)-4H-pyrrolo[3,2-d]thiazol-2-yl)(3-methoxyazetidin-1-yl)methanone (396);

6-isopropyl-5-(8-methyl-[1,2,4]triazolo[1,5-a]pyridin-6-yl)-N-(oxetan-3-yl)-4H-pyrrolo[3,2-d]thiazole-2-carboxamide (397);

(6-isopropyl-5-(8-methyl-[1,2,4]triazolo[1,5-a]pyridin-6-yl)-4H-pyrrolo[3,2-d]thiazol-2-yl)(morpholino)methanone (398);

6-isopropyl-5-(8-methyl-[1,2,4]triazolo[1,5-a]pyridin-6-yl)-N-((1-(methylsulfonyl) cyclopropyl)methyl)-4H-pyrrolo[3,2-d]thiazole-2-carboxamide (399);

N-(2-(dimethylamino)ethyl)-6-isopropyl-5-(8-methyl-[1,2,4]triazolo[1,5-a]pyridin-6-yl)-4H-pyrrolo[3,2-d]thiazole-2-carboxamide (400);

N-((5-(7,8-dimethyl-[1,2,4]triazolo[1,5-a]pyridin-6-yl)-6-isopropyl-4H-pyrrolo[3,2-d]thiazol-2-yl)methyl)-1-isopropylpiperidin-4-amine (401);

2-(((5-(7,8-dimethyl-[1,2,4]triazolo[1,5-a]pyridin-6-yl)-6-isopropyl-4H-pyrrolo[3,2-d]thiazol-2-yl) methyl) amino)acetamide (402);

6-((5-(7,8-dimethyl-[1,2,4]triazolo[1,5-a]pyridin-6-yl)-6-isopropyl-4H-pyrrolo[3,2-d]thiazol-2-yl)methyl)-2-thia-6-azaspiro[3.3]heptane 2,2-dioxide (403);

2-((5-(7,8-dimethyl-[1,2,4]triazolo[1,5-a]pyridin-6-yl)-6-isopropyl-4H-pyrrolo[3,2-d]thiazol-2-yl)methyl)-7-oxa-2-azaspiro[3.5]nonane (404);

1-(5-(7,8-dimethyl-[1,2,4]triazolo[1,5-a]pyridin-6-yl)-6-isopropyl-4H-pyrrolo[3,2-d]thiazol-2-yl)-N-((1-(methylsulfonyl)cyclopropyl)methyl)methanamine (405);

4-((5-(7,8-dimethyl-[1,2,4]triazolo[1,5-a]pyridin-6-yl)-6-isopropyl-4H-pyrrolo[3,2-d]thiazol-2-yl)methyl) piperazin-2-one (406);

4-((5-(7,8-dimethyl-[1,2,4]triazolo[1,5-a]pyridin-6-yl)-6-isopropyl-4H-pyrrolo[3,2-d]thiazol-2-yl)methyl)morpholine (407);

6-((5-(7,8-dimethyl-[1,2,4]triazolo[1,5-a]pyridin-6-yl)-6-isopropyl-4H-pyrrolo[3,2-d]thiazol-2-yl)methyl)-2-oxa-6-azaspiro[3.3]heptane (408); or 2-((2,6-diazaspiro[3.3]heptan-2-yl)methyl)-5-(7,8-dimethyl-[1,2,4]triazolo[1,5-a]pyridin-6-yl)-6-isopropyl-4H-pyrrolo[3,2-d]thiazole (409).

13. The compound according to claim 1, N-oxide, or a salt thereof, wherein said compound is:

6-isopropyl-5-(8-methoxy-[1, 2, 4]triazolo[1, 5-a]pyridin-6-yl)-2-(piperidin-4-yl)-4H-pyrrolo[2, 3-d]thiazole (410);

6-isopropyl-5-(8-methyl-[1,2,4]triazolo[1,5-a]pyridin-6-yl)-2-(piperidin-4-yl)-4H-pyrrolo[2,3-d]thiazole (411); or 6-isopropyl-5-(8-methyl-[1,2,4]triazolo[1,5-a]pyridin-6-yl)-2-(1-((3-methyloxetan-3-yl)methyl)piperidin-4-yl)-4H-pyrrolo[2,3-d]thiazole (412).

* * * * *